US011975025B2

(12) United States Patent
Mata et al.

(10) Patent No.: US 11,975,025 B2
(45) Date of Patent: May 7, 2024

(54) VIRAL VECTORS AND USE THEREOF IN ADOPTIVE CELLULAR THERAPY

(71) Applicant: Immatics US, Inc., Houston, TX (US)

(72) Inventors: Melinda Mata, Missouri City, TX (US); Yannick Bulliard, Sugar Land, TX (US); Mamta Kalra, Houston, TX (US)

(73) Assignee: IMMATICS US, INC., Houston, TX (US)

( * ) Notice: Subject to any disclaimer, the term of this patent is extended or adjusted under 35 U.S.C. 154(b) by 703 days.

(21) Appl. No.: 16/884,804

(22) Filed: May 27, 2020

(65) Prior Publication Data

US 2020/0376031 A1  Dec. 3, 2020

Related U.S. Application Data

(60) Provisional application No. 62/853,123, filed on May 27, 2019.

(51) Int. Cl.
| | |
|---|---|
| *A61K 35/17* | (2015.01) |
| *C07K 14/705* | (2006.01) |
| *C07K 14/725* | (2006.01) |
| *C12N 5/078* | (2010.01) |
| *C12N 5/0783* | (2010.01) |
| *C12N 15/62* | (2006.01) |
| *C12N 15/64* | (2006.01) |
| *C12N 15/86* | (2006.01) |

(52) U.S. Cl.
CPC .......... *A61K 35/17* (2013.01); *C07K 14/7051* (2013.01); *C07K 14/70517* (2013.01); *C12N 5/0634* (2013.01); *C12N 15/64* (2013.01); *C12N 15/86* (2013.01); *C12N 2501/2302* (2013.01); *C12N 2501/2315* (2013.01); *C12N 2740/16043* (2013.01)

(58) Field of Classification Search
CPC .......... C07K 14/7051; C07K 14/70517; C07K 2319/00; C12N 2501/515; C12N 5/0634; C12N 5/0636; C12N 15/62; A61K 35/17
See application file for complete search history.

(56) References Cited

U.S. PATENT DOCUMENTS

| | | | |
|---|---|---|---|
| 7,425,339 | B2 | 9/2008 | Jakobsen et al. |
| 10,538,574 | B2 | 1/2020 | Bleakley et al. |
| 10,556,969 | B2 | 2/2020 | Schönfeld et al. |
| 10,633,441 | B2 | 4/2020 | Adusumilli et al. |
| 10,975,137 | B2 | 4/2021 | Davila |
| 11,236,166 | B2 | 2/2022 | Kley et al. |
| 11,446,398 | B2 | 9/2022 | Barrett et al. |
| 11,648,268 | B2 | 5/2023 | Adusumilli |
| 2005/0118676 | A1 | 6/2005 | Qi et al. |
| 2011/0236966 | A1* | 9/2011 | Mostoslavsky ........ C12N 15/86 435/325 |
| 2018/0256644 | A1 | 9/2018 | Swanson et al. |
| 2019/0000878 | A1 | 1/2019 | Xiao et al. |
| 2019/0125798 | A1 | 5/2019 | Xiao et al. |
| 2019/0151363 | A1 | 5/2019 | Brentjens et al. |

FOREIGN PATENT DOCUMENTS

| | | | |
|---|---|---|---|
| EP | 2408934 B1 | 11/2014 | |
| WO | 2014090985 A1 | 6/2014 | |
| WO | 2018058002 A1 | 3/2018 | |
| WO | 2018148454 A1 | 8/2018 | |
| WO | WO-2018172533 A2 * | 9/2018 | ............. A61K 35/12 |
| WO | 2019070541 A1 | 4/2019 | |
| WO | WO-2019204662 A1 * | 10/2019 | ............. A61K 35/17 |
| WO | 2020049496 A1 | 3/2020 | |

OTHER PUBLICATIONS

Riley et al., Seminars in Cell & Developmental Biology, 2018, 84:30-41.*
International Search Report and Written Opinion dated Aug. 31, 2020 in International Application No. PCT/US2020/304639 (12 pages).
Morgan, Richard A. et al., "High Efficiency TCR Gene Transfer into Primary Human Lymphocytes Affords Avid Recognition of Melanoma Tumor Antigen Glycoprotein 100 and Does Not Alter the Recognition of Autologous Melanoma Antigens", The Journal of Immunology, Sep. 15, 2003, pp. 3287-3295, vol. 171, No. 6.
Cohen, Cyrille J. et al., "Recognition of Fresh Human Tumor by Human Peripheral Blood Lymphocytes Transduced with a Bicistronic Tetroviral Vector Encoding a Murine Anti-p53 TCR", The Journal of Immunology, Nov. 1, 2005, pp. 5799-5808, vol. 175, No. 9.
Hughes, Marybeth S. et al., "Transfer of a TOR Gene Derived from a Patient with a Marked Antitumor Response Conveys Highly Active T-Cell Effector Functions", Human Gene Therapy, Apr. 2005, pp. 457-472, vol. 16, No. 4.
Zhao, Yangbing et al., "Primary Human Lymphocytes Transduced with NY-ESO-1 Antigen-Specific TCR Genes Recognize and Kill Diverse Human Tumor Cell Lines", The Journal of Immunology, Apr. 1, 2005, pp. 4415-4423, vol. 174, No. 7.
Yang, S. et al., "Development of optimal bicistronic lentiviral vectors facilitates high-level TCR gene expression and robust tumor cell recognition", Gene Therapy, May 22, 2008, pp. 1411-1423, vol. 15, No. 21.
NCBI GenBank BC100911.1, *Homo sapiens* CD8b molecule, mRNA (cDNA clone MGC:119114 IMAGE:40003720), complete cds, 2 pages, Retrieved on Jun. 7, 2023 from URL: https://www.ncbi.nlm.nih.gov/nuccore/BC100911.1? from=51&to=782.

(Continued)

*Primary Examiner* — Hong Sang
(74) *Attorney, Agent, or Firm* — McBee, Moore & Vanik, IP, LLC

(57) ABSTRACT

A vector containing a first nucleotide sequence S1 encoding a protein Z1, a second nucleotide sequence S2 encoding a protein Z2, a third nucleotide sequence S3 encoding a protein Y1, and a fourth nucleotide sequence S4 encoding a protein Y2, in which Z1 and Z2 form a first dimer and Y1 and Y2 form a second dimer, in which the first dimer Z1Z2 is different from the second dimer Y1Y2.

16 Claims, 47 Drawing Sheets
Specification includes a Sequence Listing.

(56) References Cited

OTHER PUBLICATIONS

NCBI GenBank: JA738613.1, Sequence 65 from Patent EP2408934, 1 page, Retrieved on Jun. 7, 2023 from URL: https://www.ncbi.nlm.nih.gov/nuccore/JA738613.1?from=51&to=782.
NCBI GenBank: LT736917.1, Human ORFeome Gateway entry vector pENTR223-CD8B, complete sequence, 2 pages, Retrieved on Jun. 7, 2023 from URL: https://www.ncbi.nlm.nih.gov/nuccore/LT736917.1?from=488&to=1218.
UnitProt, P01732—CD8A_HUMAN, and first entry of the sequence into public domain (1988), 12 pages, Retrieved on Jun. 7, 2023 from URL: https://www.uniprot.org/uniprotkb/P01732/history.

* cited by examiner

FIG. 2
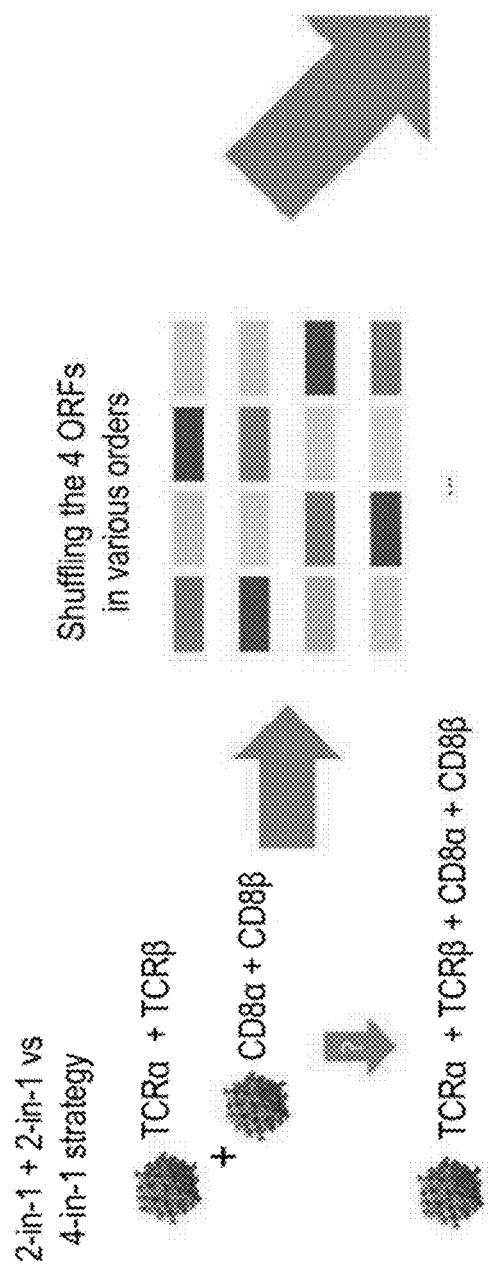
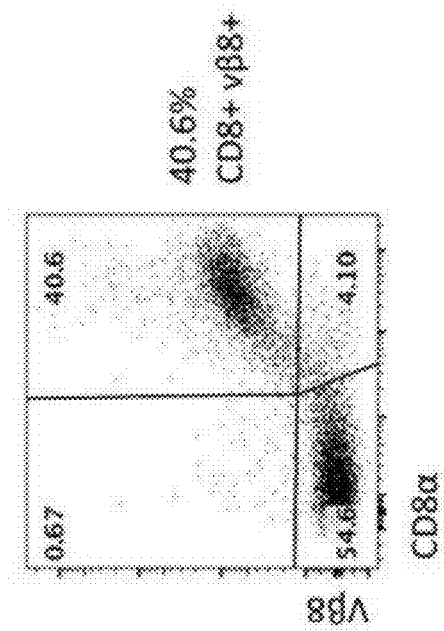

FIG. 3

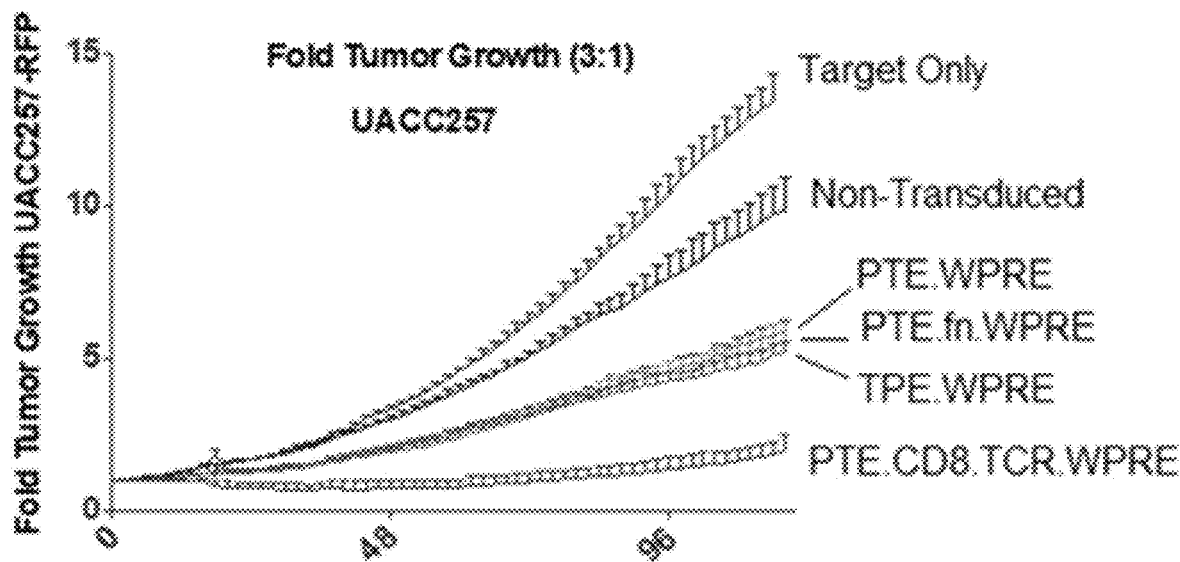
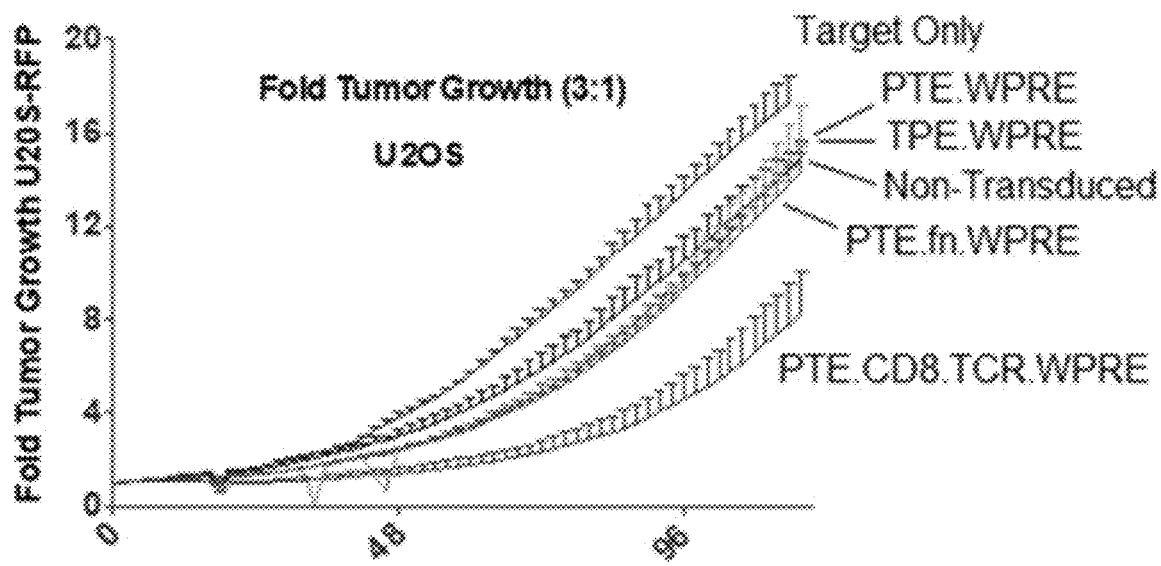
FIG. 12

Donor 4
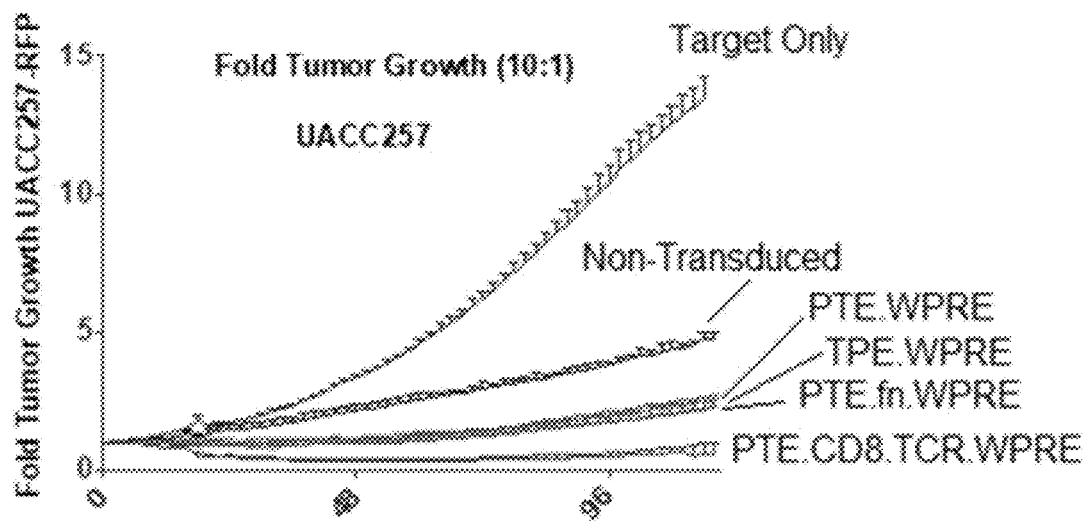
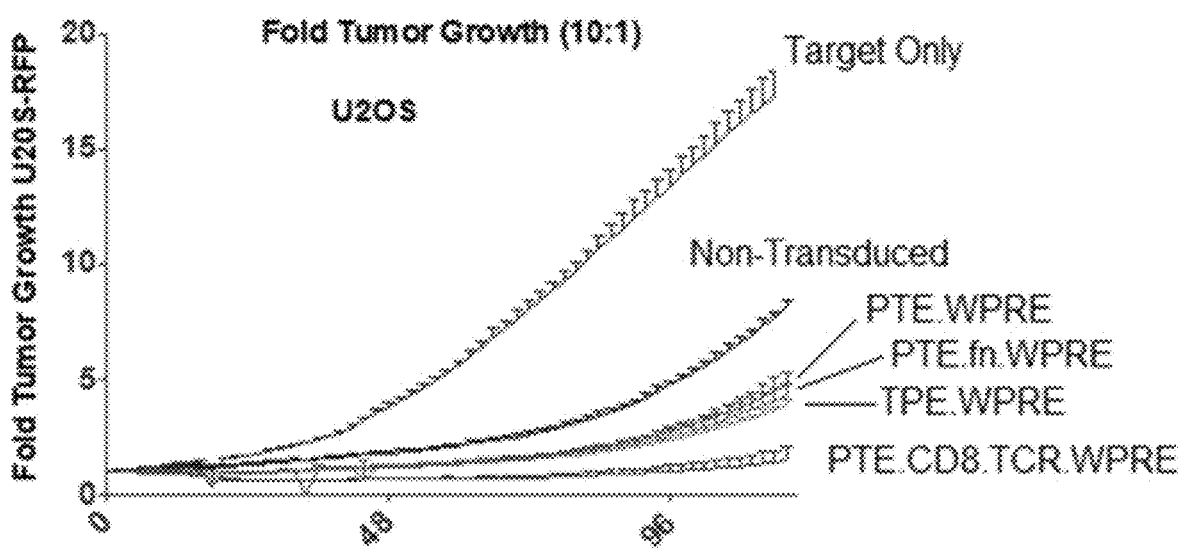
FIG. 14

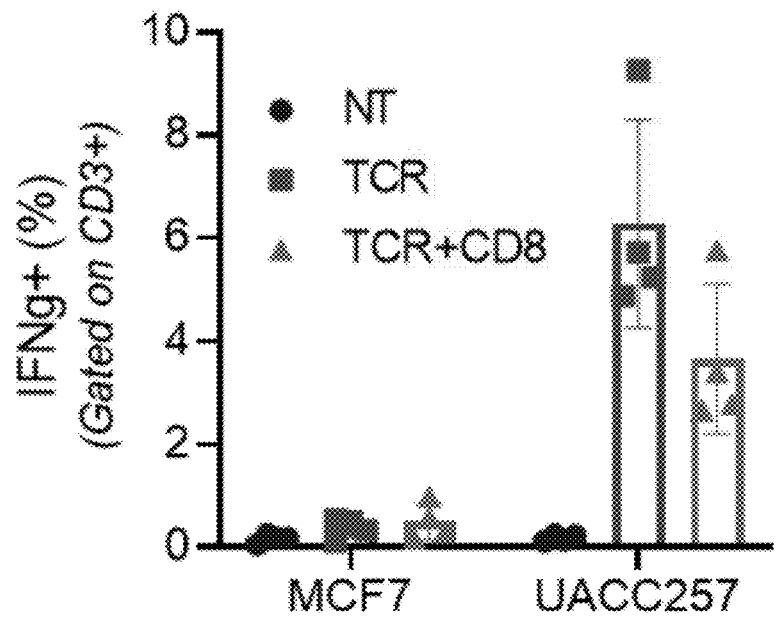
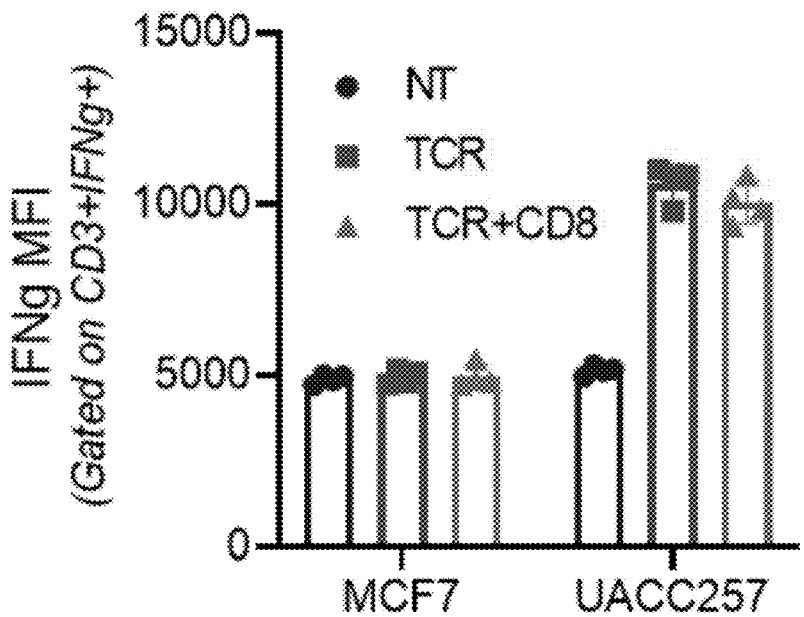
FIG. 30

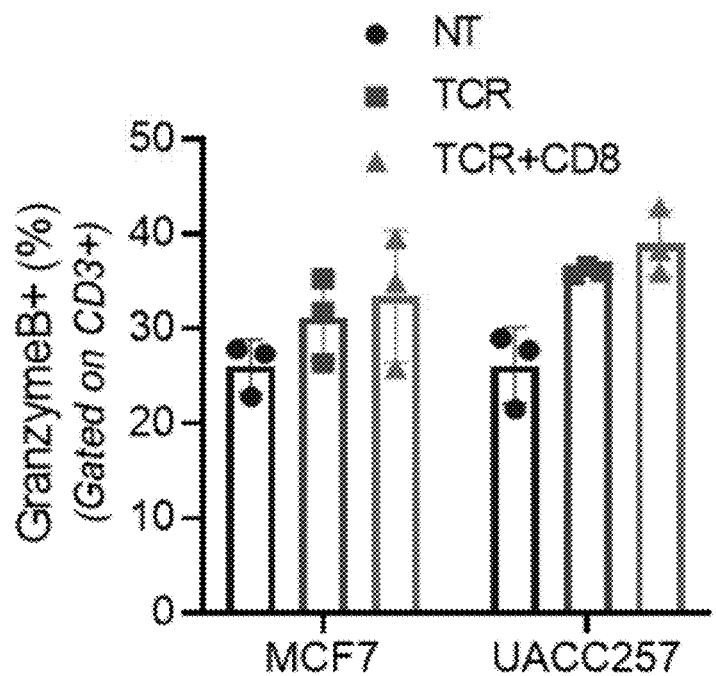
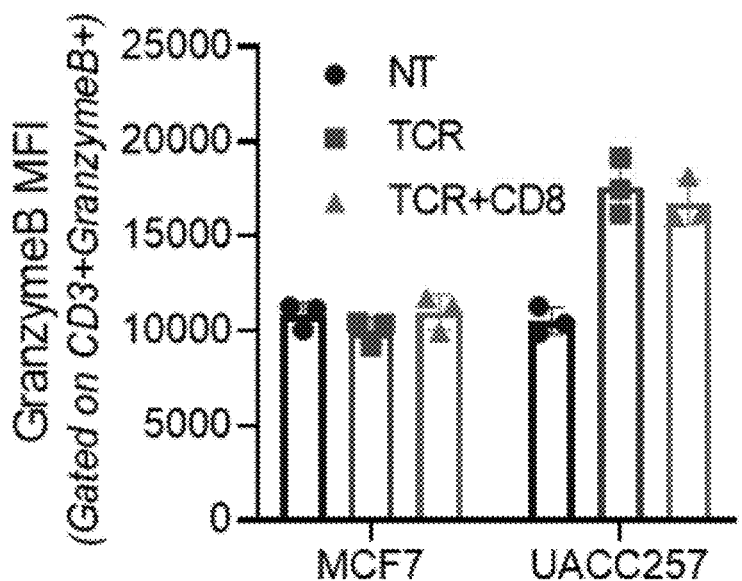
FIG. 31

VIRAL VECTORS AND USE THEREOF IN ADOPTIVE CELLULAR THERAPY

CROSS-REFERENCE TO RELATED APPLICATION

This U.S. Patent Application claims the benefit of U.S. Provisional Application No. 62/853,123, filed May 27, 2019, the contents of which are incorporated herein by reference in their entirety.

REFERENCE TO SEQUENCE LISTING SUBMITTED ELECTRONICALLY

The official copy of the sequence listing is submitted electronically via EFS-Web as an ASCII formatted sequence listing with a file named "Sequence_Listing_3000011-013001_ST25.txt", created on May 27, 2020, and having a size of 313,436 bytes and is filed concurrently with the specification. The sequence listing contained in this ASCII formatted document is part of the specification and is herein incorporated by reference in its entirety.

BACKGROUND

1. Field

The present disclosure relates to T cell manufacturing. In an aspect, the present disclosure relates to T cell manufacturing using a multi-cistronic cassette for expressing a plurality of proteins in a single vector. More specifically, the present disclosure relates to T cell manufacturing of T cells that co-express TCRαβ and CD8αβ and the use thereof in adoptive cellular therapy.

2. Background

The genetic engineering of human lymphocytes as a potential therapy for inherited, acquired or infectious disease requires efficient transfer and expression of the transgenes. In the case of adoptive immunotherapy for cancer, naturally-occurring and/or recombinant antitumor T-cell receptors (TCRs) have been used to endow normal T cells or tumor infiltrating lymphocytes with antitumor reactivity.

Morgan et al. (*J Immunol.* 2003 Sep. 15; 171(6): 3287-32percent) discloses an anti-gp100 TCR expressed by a bicistronic RNA, in which the expression of the first gene encoding the TCRβ chain is controlled by a long terminal repeat (LTR) and the second gene encoding the TCRα chain is governed by an internal ribosome entry site (IRES). CD4+ T cells engineered with this anti-gp100 TCR gene were antigen reactive.

Cohen et al. (*J Immunol.* 2005 Nov. 1; 175(9): 5799-5808) discloses a bicistronic retroviral vector for co-expression of both TCRα chain and TCRβ chain that bind a p53 epitope. The expression of the first gene encoding the TCRα chain is controlled by an LTR and the second gene encoding the TCRβ chain is governed by an IRES. The p53 TCR-transduced lymphocytes were able to specifically recognize, with high-avidity, peptide-pulsed APCs as well as HLA-A2.1+ cells transfected with either wild-type or mutant p53 protein.

Hughes et al. (*Hum Gene Ther.* 2005 April; 16(4): 457-472) discloses various bicistronic retroviral vectors for co-expression of an anti-MART-1 TCR. The expression of the first gene encoding the TCRα chain is controlled by an LTR and the second gene encoding the TCRβ chain is governed by an IRES, or vice versa. In addition, the expression of the first gene encoding the TCRα chain is controlled by an LTR and the second gene encoding the TCRβ chain is governed by a PGK promoter, or vice versa. T cells transduced with these vectors showed highly active T cell effector functions.

Zhao et al. (*J Immunol.* 2005 Apr. 1; 174(7): 4415-4423) discloses bicistronic retroviral vectors for co-expression of NY-ESO-1 TCR. The expression of the first gene encoding the TCRα chain is controlled by an LTR and the second gene encoding the TCRβ chain is governed by an IRES, or the expression of the first gene encoding the TCRα chain is controlled by an LTR and the second gene encoding the TCRβ chain is governed by a PGK promoter. The transduced lymphocytes could efficiently recognize and kill HLA-A2- and NY-ESO-1-positive melanoma cell lines.

Morgan et al. (*Gene Therapy* (2008) 15, 1411-1423) discloses bicistronic lentiviral vectors that combine a furin cleavage site and an amino acid spacer (GSG or SGSG (SEQ ID NO: 8)) followed by a 2A ribosomal skip peptide to express an anti-gp100 TCR or an anti-MART-1 TCR. When the spacer sequence was augmented by the addition of a synthetic V5 peptide tag sequence protein processing was boosted, which resulted in a lentiviral vector capable of mediating high-level TCR expression in transduced lymphocytes.

There remains a need for gene delivery systems for safe and efficient transgene expression in adoptive cellular therapy.

BRIEF SUMMARY

In an aspect, the disclosure provide for a gene delivery system including a vector comprising a first nucleotide sequence S1 encoding a protein Z1, a second nucleotide sequence S2 encoding a protein Z2, a third nucleotide sequence S3 encoding a protein Y1, and a fourth nucleotide sequence S4 encoding a protein Y2, in which Z1 and Z2 form a first dimer and Y1 and Y2 form a second dimer, in which the first dimer Z1Z2 is different from the second dimer Y1Y2 and wherein the gene delivery system is used in adaptive cellular therapy.

In another aspect, the S1, S2, S3, and S4 may be arranged in tandem in a 5' to 3' orientation selected from S1-S2-S3-S4, S1-S2-S4-S3, S1-S3-S2-S4, S1-S3-S4-S2, S1-S4-S3-S2, S1-S4-S2-S3, S2-S1-S3-S4, S2-S1-S4-S3, S2-S3-S1-S4, S2-S3-S4-S1, S2-S4-S3-S1, S2-S4-S1-S3, S3-S1-S2-S4, S3-S1-S4-S2, S3-S2-S1-S4, S3-S2-S4-S1, S3-S4-S1-S2, S3-S4-S2-S1, S4-S1-S2-S3, S4-S1-S3-S2, S4-S2-S1-S3, S4-S2-S3-S1, S4-S3-S1-S2, or S4-S3-S2-S1.

In another aspect, the vector may further include a fifth nucleotide sequence S5 encoding a 2A peptide and a sixth nucleotide sequence S6 encoding a linker peptide, wherein S5 and S6 are positioned between S1 and S2, S1 and S3, S1 and S4, S2 and S3, S2 and S4, and/or S3 and S4.

In another aspect, the 2A peptide may be selected from P2A (SEQ ID NO: 3), T2A (SEQ ID NO: 4), E2A (SEQ ID NO: 5), or F2A (SEQ ID NO: 6).

In another aspect, the linker peptide may be GSG or SGSG (SEQ ID NO: 8).

In another aspect, the vector may include a seventh nucleotide sequence S7 encoding a furin peptide (SEQ ID NO: 2), wherein S7 is positioned between S1 and S2, S1 and S3, S1 and S4, S2 and S3, S2 and S4, and/or S3 and S4.

In another aspect, the vector may further include a post-transcriptional regulatory element (PRE) sequence selected from a Woodchuck PRE (WPRE) or a hepatitis B virus (HBV) PRE (HPRE).

In another aspect, the vector may further include a promoter sequence that controls the transcription of S1, S2, S3, S4, S5, S6 and/or S7, wherein the promoter sequence is selected from cytomegalovirus (CMV) promoter, phosphoglycerate kinase (PGK) promoter, myelin basic protein (MBP) promoter, glial fibrillary acidic protein (GFAP) promoter, modified MoMuLV LTR containing myeloproliferative sarcoma virus enhancer (MNDU3), Ubiqitin C promoter, EF-1 alpha promoter, or Murine Stem Cell Virus (MSCV) promoter.

In another aspect, the first dimer Z1Z2 may be selected from SEQ ID NO: 13 and 14, 15 and 16, 17 and 18, 19 and 20, 21 and 22, 23 and 24, 25 and 26, 27 and 28, 29 and 30, 31 and 32, 33 and 34, 35 and 36, 37 and 38, 39 and 40, 41 and 42, 43 and 44, 45 and 46, 47 and 48, 49 and 50, 51 and 52, 53 and 54, 55 and 56, 57 and 58, 59 and 60, 61 and 62, 63 and 64, 65 and 66, 67 and 68, 69 and 70, 71 and 72, 73 and 74, 75 and 76, 77 and 78, 79 and 80, 81 and 82, 83 and 84, 85 and 86, 87 and 88, or 89 and 90.

In another aspect, the second dimer Y1 and Y2 is set forth in SEQ ID NO: 11 and 12.

In another aspect, the orientation is S2-S1-S4-S3.

In another aspect, the vector has the sequence selected from PTE WPRE (SEQ ID NO: 91), TPE WPRE (SEQ ID NO: 92), or PTE fn WPRE (SEQ ID NO: 93).

In another aspect, the orientation is S4-S3-S2-S1.

In another aspect, the vector has the sequence PTE CD8 TCR WPRE (SEQ ID NO: 94).

In another aspect, the viral vector is selected from adenoviruses, poxviruses, alphaviruses, arenaviruses, flaviviruses, rhabdoviruses, retroviruses, lentiviruses, herpesviruses, paramyxoviruses, or picornaviruses.

In another aspect, the vector is pseudotyped with an envelope protein of a virus selected from the native feline endogenous virus (RD114), a chimeric version of RD114 (RD114TR), gibbon ape leukemia virus (GALV), a chimeric version of GALV (GALV-TR), amphotropic murine leukemia virus (MLV 4070A), baculovirus (GP64), vesicular stomatitis virus (VSV-G), fowl plague virus (FPV), Ebola virus (EboV), baboon retroviral envelope glycoprotein (BaEV), or lymphocytic choriomeningitis virus (LCMV).

In another aspect, the vector is pseudotyped with an envelope protein of vesicular stomatitis virus (VSV-G).

In one aspect, the present disclosure relates to a method of preparing T cells for immunotherapy including isolating T cells from a blood sample of a human subject, activating the isolated T cells in the presence of an aminobisphosphonate, transducing the activated T cells with the vector described herein, and expanding the transduced T cells.

In another aspect, the T cells may be isolated from a leukapheresis human sample.

In another aspect, the aminobisphosphonate may be selected from pamidronic acid, alendronic acid, zoledronic acid, risedronic acid, ibandronic acid, incadronic acid, a salt thereof and/or a hydrate thereof.

In another aspect, the activating may be further in the presence of human recombinant interleukin 2 (IL-2) and human recombinant interleukin 15 (IL-15).

In another aspect, the expanding may be in the presence of IL-2 and IL-15.

In another aspect, the T cells may be γδ T cells.

In another aspect, the first dimer Z1Z2 and the second dimer Y1Y2 are co-expressed on the surface of the expanded T cells.

In another aspect, the present disclosure relates to a population of expanded T cells prepared by the method of the above aspects.

In one aspect, the present disclosure relates to a method of treating a patient who has cancer, comprising administering to the patient a composition comprising the population of expanded T cells described herein, in which the T cells kill cancer cells that present a peptide in a complex with an MHC molecule on the surface, wherein the peptide is selected from any of SEQ ID NO: 98-255, in which the cancer is selected from the group consisting of non-small cell lung cancer, small cell lung cancer, melanoma, liver cancer, breast cancer, uterine cancer, Merkel cell carcinoma, pancreatic cancer, gallbladder cancer, bile duct cancer, colorectal cancer, urinary bladder cancer, kidney cancer, leukemia, ovarian cancer, esophageal cancer, brain cancer, gastric cancer, and prostate cancer.

In another aspect, the composition further includes an adjuvant.

In another aspect, the adjuvant is selected from one or more of anti-CD40 antibody, imiquimod, resiquimod, GM-CSF, cyclophosphamide, sunitinib, bevacizumab, atezolizumab, interferon-alpha, interferon-beta, CpG oligonucleotides and derivatives, poly-(1:C) and derivatives, RNA, sildenafil, particulate formulations with poly(lactide co-glycolide) (PLG), virosomes, interleukin (IL)-1, IL-2, IL-4, IL-7, IL-12, IL-13, IL-15, IL-21, and IL-23.

In one aspect, the present disclosure relates to a method of eliciting an immune response in a patient who has cancer, comprising administering to the patient a composition comprising the population of expanded T cells described herein, in which the T cells kill cancer cells that present a peptide in a complex with an MHC molecule on the surface, wherein the peptide is selected from any of SEQ ID NO: 98-255, and in which the cancer is selected from the group consisting of non-small cell lung cancer, small cell lung cancer, melanoma, liver cancer, breast cancer, uterine cancer, Merkel cell carcinoma, pancreatic cancer, gallbladder cancer, bile duct cancer, colorectal cancer, urinary bladder cancer, kidney cancer, leukemia, ovarian cancer, esophageal cancer, brain cancer, gastric cancer, and prostate cancer.

In another aspect, the immune response comprises a cytotoxic T cell response.

In an aspect, the present disclosure provides for methods of preparing T cells by utilizing a statin in a method described herein. In another aspect, the present disclosure provides for methods of preparing T cells by activating the T cells in the presence of a statin.

In yet another aspect, the present disclosure relates to a method of preparing T cells for immunotherapy, including activating the T cells in the presence of a statin, transducing the activated T cells with the vector of the present disclosure, in which the vector may be pseudotyped with an envelope protein of vesicular stomatitis virus (VSV-G), and expanding the transduced T cells.

In another aspect, the T cells may include αβ T cells, γδ T cells, and/or natural killer T cells.

In another aspect, statin may be selected from atorvastatin, cerivastatin, dalvastatin, fluindostatin, fluvastatin, mevastatin, pravastatin, simvastatin, velostatin, and rosuvastatin.

In an aspect, the present disclosure relates to a method of preparing T cells for immunotherapy including activating the T cells, transducing the activated T cells with the vector of the present disclosure, and expanding the transduced T cells.

In another aspect, the activating may be in the presence of an anti-CD3 antibody and an anti-CD28 antibody.

In another aspect, the expanding may be in the presence of IL-7 and IL-15.

BRIEF DESCRIPTION OF THE DRAWINGS

FIG. 2 shows transduction strategies with open reading frames (ORFs) shuffling in accordance with some embodiments of the present disclosure.

FIG. 3 shows lentiviral constructs in accordance with some embodiments of the present disclosure. Linker sequences (GSG or SGSG (SEQ ID NO: 8)) are shown.

FIG. 12 shows tumor killing activity of γδ T cells obtained from Donor 3 transduced with viral vector containing PTE.CD8.TCR.WPRE, PTE.WPRE, PTE.Fn.WPRE, or TPE.WPRE in a high antigen expressing tumor cell line, e.g., UACC257 (top panel) or in a low antigen expressing tumor cell line, e.g., U2OS (bottom panel), as determined by Incucyte Cytotoxicity Assay. Target only and non-transduced cells serve as controls.

FIG. 14 shows tumor killing activity of γδ T cells obtained from Donor 4 transduced with viral vector containing PTE.CD8.TCR.WPRE, PTE.WPRE, PTE.Fn.WPRE, or TPE.WPRE in a high antigen expressing tumor cell line, e.g., UACC257 (top panel) or in a low antigen expressing tumor cell line, e.g., U2OS (bottom panel), as determined by Incucyte Cytotoxicity Assay. Target only and non-transduced cells serve as controls.

FIG. 30 shows increased % IFN-γ-positive cells (top panel) and increased IFN-γ MFI (bottom panel) in CD3+ T cells obtained from grouped donors transduced with LV-TCR (TCR) or LV-CD8.TCR (TCR+CD8) followed by co-culturing with high-target expressing UACC257 cells as compared with that co-culturing with non-target expressing MCF7. Non-transduced (NT) cells serve as control. (Effector to target cell ratio=2:1 and Donors grouped N=4).

FIG. 31 shows increased % Granzyme B-positive cells (top panel) and increased Granzyme B MFI (bottom panel) in CD3+ T cells obtained from grouped donors transduced with LV-TCR (TCR) or LV-CD8.TCR (TCR+CD8) followed by co-culturing with high-target expressing UACC257 cells as compared with that co-culturing with non-target expressing MCF7. Non-transduced (NT) cells serve as control. (Effector to target cell ratio=2:1 and Donors grouped N=3).

DETAILED DESCRIPTION

Figure 1:
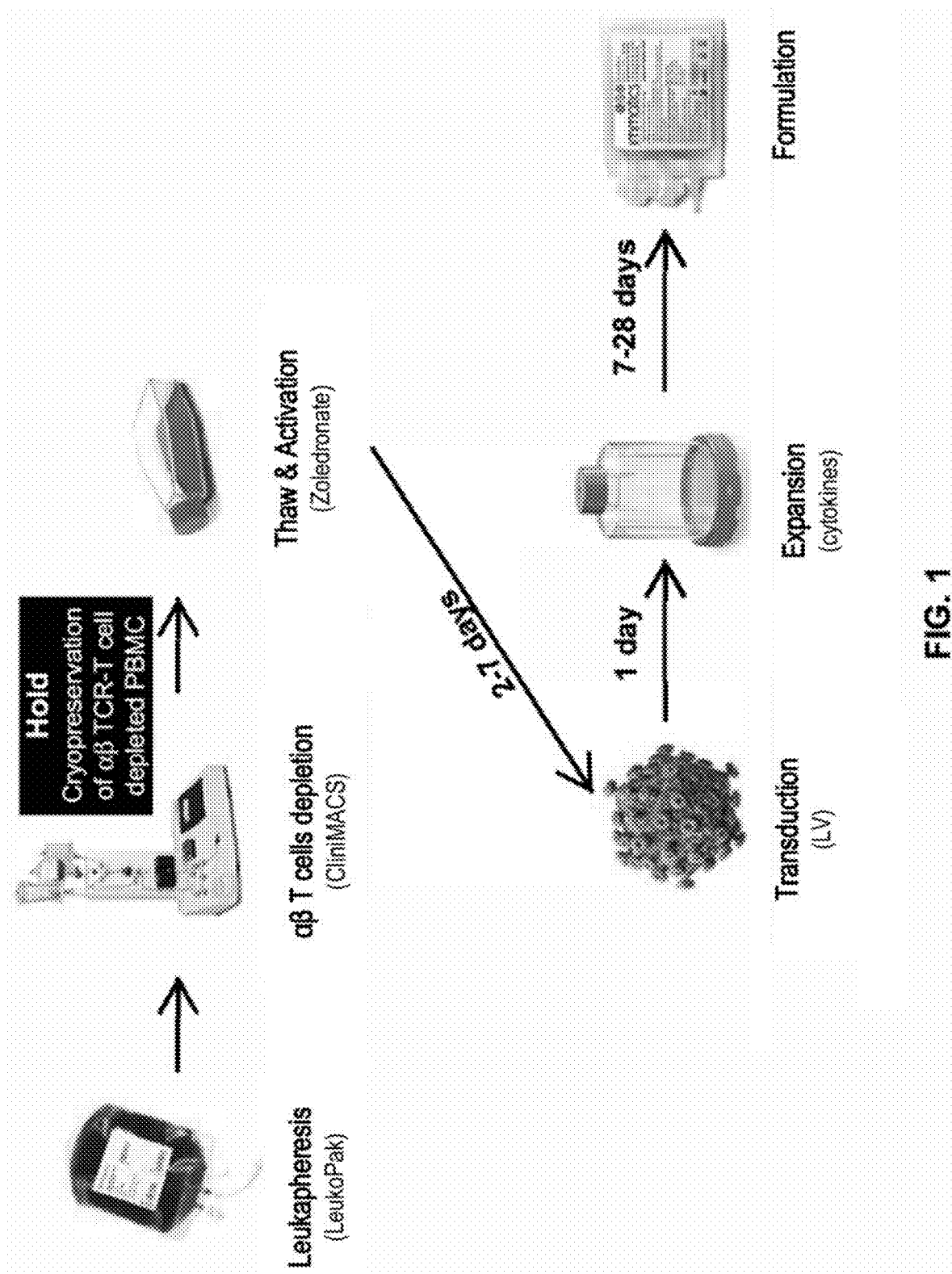
FIG. 1 shows a γδ T cell manufacturing process according to one embodiment of the present disclosure. γδ T cell manufacturing may include collecting or obtaining white blood cells or PBMC, e.g., leukapheresis product, depleting αβ T cells from PBMC or leukapheresis product, followed by activation, transduction, and expansion of γδ T cells.

As used herein, the term "self-cleaving 2A peptide" refers to relatively short peptides (of the order of 20 amino acids long, depending on the virus of origin) acting co-translationally, by preventing the formation of a normal peptide bond between the glycine and last proline, resulting in the ribosome skipping to the next codon, and the nascent peptide cleaving between the Gly and Pro. After cleavage, the short 2A peptide remains fused to the C-terminus of the 'upstream' protein, while the proline is added to the N-terminus of the 'downstream' protein. Self-cleaving 2A peptide may be selected from porcine teschovirus-1 (P2A), equine rhinitis A virus (E2A), Thosea asigna virus (T2A), foot-and-mouth disease virus (F2A), or any combination thereof (see, e.g., Kim et al., PLOS One 6:e18556, 2011, the content of which including 2A nucleic acid and amino acid sequences are incorporated herein by reference in their entireties). By adding the linker sequences (GSG or SGSG (SEQ ID NO: 8)) before the self-cleaving 2A sequence, this may enable efficient synthesis of biologically active proteins, e.g., TCRs.

As used herein, the term "promoter" refers to a regulatory region of DNA generally located upstream (towards the 5' region of the sense strand) of a gene that allows transcription of the gene. The promoter contains specific DNA sequences and response elements that are recognized by proteins known as transcription factors. These factors bind to the promoter sequences, recruiting RNA polymerase, the enzyme that synthesizes the RNA from the coding region of the gene. For example, the promoter sequence used herein may be selected from cytomegalovirus (CMV) promoter, phosphoglycerate kinase (PGK) promoter, myelin basic protein (MBP) promoter, glial fibrillary acidic protein (GFAP) promoter, modified MoMuLV LTR containing myeloproliferative sarcoma virus enhancer (MNDU3), Ubiqitin C promoter, EF-1 alpha promoter, or Murine Stem Cell Virus (MSCV) promoter.

The term "constitutive promoter" as used herein may include a regulatory sequence that directs transcription of a gene in most cells or tissues at most times. In some non-limiting embodiments, the constitutive promoter may be selected from the group consisting of a MSCV promoter, a Ubiqitin C (Ubc) promoter, a CMV promoter, an EF-1 alpha promoter, a PGK promoter, a beta-actin promoter, and a ROSA26 promoter.

In some embodiments, the promoter may be an inducible promoter. The activity of an inducible promoter may increase or decrease in response to a signal. For example, an inducible promoter may promote transcription in response to the presence of a signal, such as T cell activation or isopropyl β-D-1-thiogalactopyranoside (IPTG). An inducible promoter may promote transcription in response to the absence of a signal, such as phosphate. In either of these scenarios, the amount of transcription may or may not be proportional to the amount of signal, or the deficiency thereof. Examples of inducible promoters suitable for prokaryotic host cells may include, without limitation, NFAT, CD69, lac, tac, trc, trp, pho, recA, tetA, nar, phage PL, cspA, T7, and PBAD promoters (see Terpe K. 2006 Appl. Microbiol. Biotechnol. 72:211; the content of which is incorporated by reference in its entirety).

In some embodiments, the inducible promoter may include a nuclear factor of activated T cells (NFAT)/AP1 transcriptional response element (TRE). Upon recognition of the cognate peptide/MHC1 complex, NFAT may undergo Ca2+ dependent translocation to the nucleus, where it promotes transcription of genes that harbor an NFAT TRE. Suitable NFAT TREs are well-known in the art and include the human IL2 promoter NFAT TRE (Macian et al (2001) Oncogene, 2001 Apr. 30; 20(19):2476-89). Zhang et al. ("Tumor-Infiltrating Lymphocytes Genetically Engineered with an Inducible Gene Encoding Interleukin-12 for the Immunotherapy of Metastatic Melanoma," Clin. Cancer Res. 21:2278-2288, 2015) describes the use of human tumor-infiltrating lymphocytes (TILs) genetically engineered to secrete single-chain IL12, whose expression is driven by an inducible NFAT promoter, in a clinical trial. The contents of these cited references are incorporated by reference in their entireties.

In some embodiments, the inducible promoter may include a CD69 promoter, e.g., as disclosed in U.S. Pat. No. 5,759,805; the content of which is incorporated by reference in its entirety. CD69 may be among the earliest of these newly synthesized cell-surface activation molecules induced on activated T cells. CD69 expression can be observed within 60 minutes of T-cell stimulation, but may be absent on resting cells. CD69 expression may be also inducible on thymocytes, B cells, natural killer (NK) cells and neutrophils. Four non-coding regions referred to as CNS1-4 located within 50 kb upstream of the mouse CD69 promoter may contribute to the developmental and temporal control of CD69 activation in T- and B-cells. CNS2 region may function as a potent enhancer. Kulemzin et al. ("Design and analysis of stably integrated reporters for inducible transgene expression in human T cells and chimeric antigen receptor (CAR) NK cell lines," BMC Medical Genomics 2019, 12(Suppl 2):44, 88-95; the content of which is incorporated by reference in its entirety) describes, in the context of primary T cells, activation-inducible CD69 promoter variant provides the highest fold induction. This promoter therefore can be used for expressing proteins in the activated, but not resting human T or CAR T cells.

In some embodiments, the inducible promoter may be an IPTG-inducible promoter. An IPTG-inducible promoter may refer to any polynucleotide sequence that promotes transcription in a manner responsive to IPTG or any other lactose derivative that can promote transcription from the lac operon (e.g., allolactose). Many examples of IPTG-inducible promoters are known in the art, including, without limitation, tac (e.g., tacI, tacII, etc.) promoters, lac promoters, and derivatives thereof (e.g., lacUV5, taclac, and so forth).

Figure 5A:
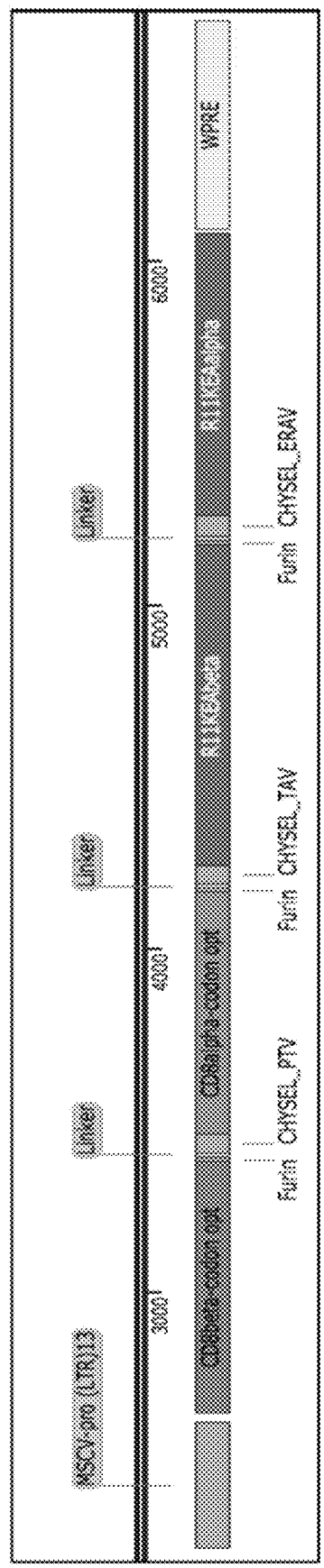
FIG. 5A shows a construct in accordance with an embodiment of the present disclosure.

In an aspect, expression of a 4-in-1 viral vector, e.g., lentiviral vector, containing sequences encoding CD8 alpha chains, CD8 beta chain, TCR alpha chain, and TCR beta chain may be driven by a constitutive or inducible promoter. For example, FIG. 5A shows a 4-in-1 viral vector containing PTE CD8 TCR WPRE (SEQ ID NO: 94) having codon-optimized sequences encoding CD8 alpha (SEQ ID NO: 12) and CD8 beta (SEQ ID NO: 13) located upstream from sequences encoding a TCR, e.g., TCR R11 KE alpha chain (SEQ ID NO: 13) and R11 KE beta chain (SEQ ID NO: 14) and driven by a constitutive MSCV promoter (SEQ ID NO: 1). The same coding sequences described above can also be driven by an inducible promote, e.g., NFAT, CD69, or IPTG promoter.

Figure 5B:
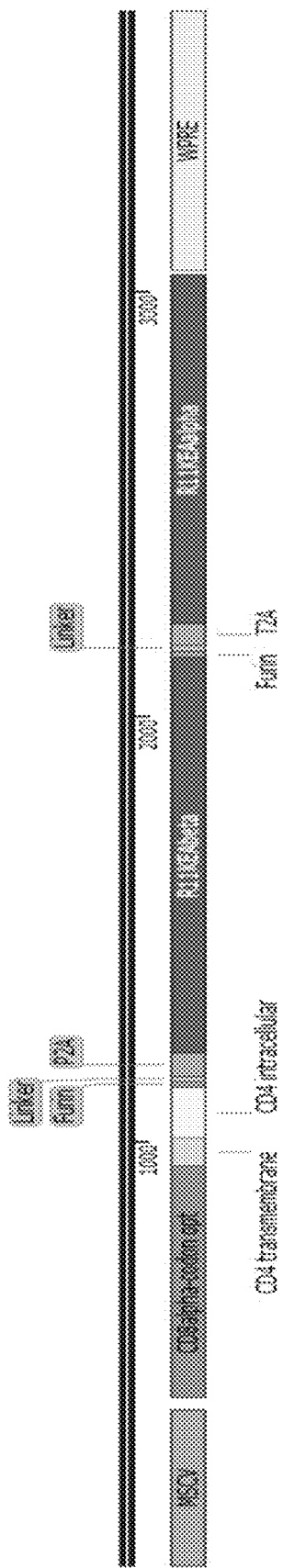
FIG. 5B shows a construct in accordance with another embodiment of the present disclosure.
Figure 5C:
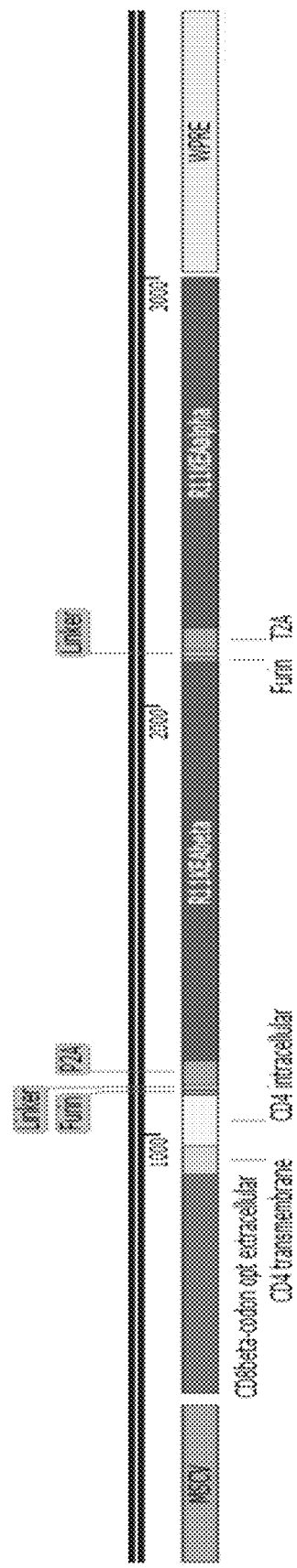
FIG. 5C shows a construct in accordance with another embodiment of the present disclosure.
Figure 5D:
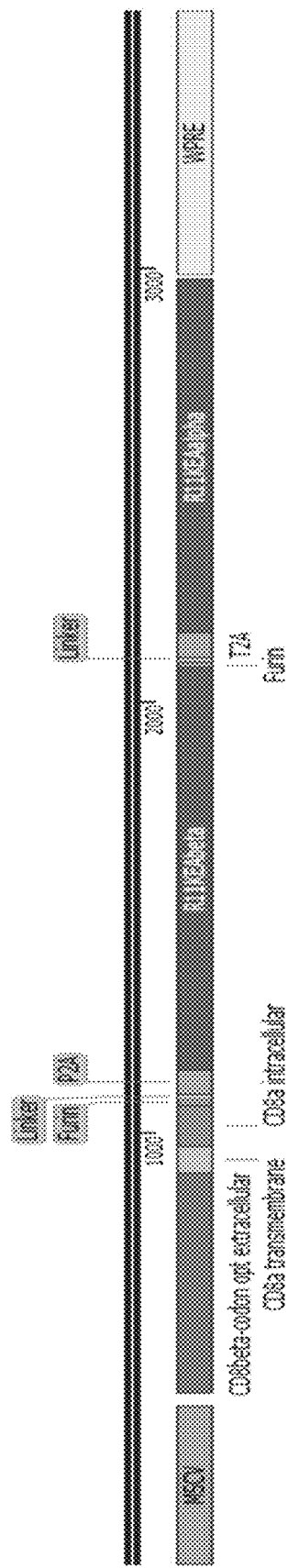
FIG. 5D shows a construct in accordance with another embodiment of the present disclosure.

In another aspect, expression of a 3-in-1 viral vector containing sequences encoding a fusion protein, TCR alpha chain, and TCR beta chain may be driven by a constitutive or inducible promoter. For example, FIG. 5B shows a viral vector containing CD8aCD4Fusion.TCR WPRE (SEQ ID NO: 256) having codon-optimized sequence encoding a fusion protein, in which CD8a extracellular domain is fused with CD4 transmembrane domain and CD4 intracellular domain, and sequences encoding TCR R11 KE alpha chain (SEQ ID NO: 13) and R11 KE beta chain (SEQ ID NO: 14) driven by MSCV promoter (SEQ ID NO: 1). FIG. 5C shows a viral vector containing CD8bCD4Fusion.TCR WPRE (SEQ ID NO: 257) having codon-optimized sequence encoding a fusion protein, in which CD8β extracellular domain is fused with CD4 transmembrane domain and CD4 intracellular domain, and sequences encoding TCR R11 KE alpha chain (SEQ ID NO: 13) and R11 KE beta chain (SEQ ID NO: 14) driven by MSCV promoter (SEQ ID NO: 1). FIG. 5D shows a viral vector containing CD8bCD8aFusion.TCR WPRE (SEQ ID NO: 258) having sequences encoding a fusion protein, in which CD8β extracellular domain is fused with CD8a transmembrane domain and CD8a intracellular domain, and sequences encoding TCR R11 KE alpha chain (SEQ ID NO: 13) and R11 KE beta chain (SEQ ID NO: 14) driven by MSCV promoter (SEQ ID NO: 1). The same coding sequences described above can also be driven by an inducible promote, e.g., NFAT, CD69, or IPTG promoter.

Figure 6A:
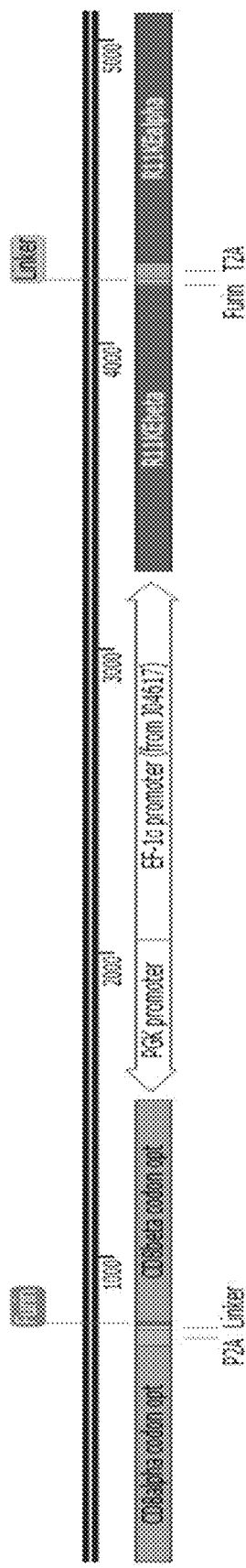
FIG. 6A shows a construct in accordance with another embodiment of the present disclosure.

In an aspect, expression of a 4-in-1 viral vector of the present disclosure may be driven by bidirectional constitutive and/or inducible promoters. For example, FIG. 6A shows a 4-in-1 viral vector containing PGK.CD8.EF1a.TCR (SEQ ID NO: 259) having codon-optimized sequences encoding CD8 alpha chain and CD8 beta chain located upstream from sequences encoding TCR R11 KE alpha chain and R11 KE beta chain, in which the sequences encoding CD8 alpha chain and CD8 beta chain and the sequences encoding TCR R11 KE alpha chain and R11 KE beta chain may be separated by bidirectional promoters, e.g., PGK promoter and EF-1 alpha promoter. PGK promoter may be positioned at the 3' end of the codon-optimized sequences encoding CD8 alpha chain and CD8 beta chain to drive the expression of CD8 alpha chain and CD8 beta chain. EF-1 alpha promoter may be positioned at the 5' end of the sequences encoding TCR R11 KE alpha chain and R11 KE beta chain to drive the expression of TCR R11 KE alpha chain and R11 KE beta chain.

Figure 6B:
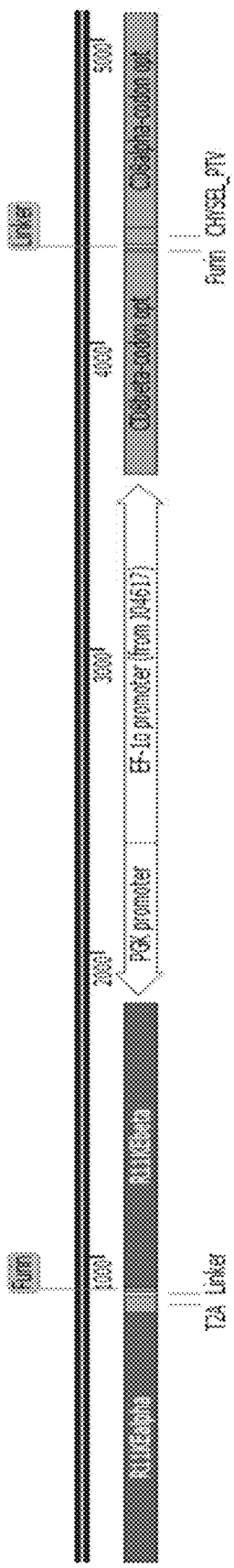
FIG. 6B shows a construct in accordance with another embodiment of the present disclosure.

FIG. 6B shows another 4-in-1 viral vector containing PGK.TCR.EF1a.CD8 (SEQ ID NO: 260) having sequences encoding TCR R11 KE alpha chain and R11 KE beta chain located upstream from codon-optimized sequences encoding CD8 alpha chain and CD8 beta chain, in which the sequences encoding TCR R11 KE alpha chain and R11 KE beta chain and the sequences encoding CD8 alpha chain and CD8 beta chain may be separated by bidirectional promoters, e.g., PGK promoter and EF-1 alpha promoter. PGK promoter may be positioned at the 3' end of the sequences encoding TCR R11 KE alpha chain and R11 KE beta chain to drive the expression of TCR R11 KE alpha chain and R11 KE beta chain. EF-1 alpha promoter may be positioned at the 5' end of the codon-optimized sequences encoding CD8 alpha chain and CD8 beta chain to drive the expression of CD8 alpha chain and CD8 beta chain.

Some embodiments of the present disclosure may include viral vectors containing sequences encoding TCR alpha chain and TCR beta chain and sequences encoding other proteins, such as cytokines (including, but not limited to, IL-1, IL-2, IL-6, IL-7, IL-10, IL-12, IL-15, IL-18, and IL-21), IL-15/IL-15 receptor (IL-15R) fusion protein, dominant-negative TGF beta receptor (DN TGFbRII), and/or extracellular domain of a transforming growth factor-beta receptor. In some embodiments, these coding sequences may be driven by a promotor or bidirectional promoters.

Figure 7:
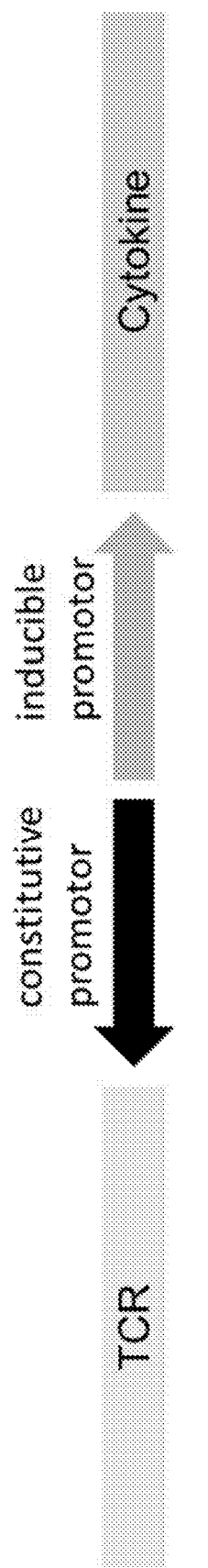
FIG. 7 shows a schematic of constructs in accordance with some embodiments of the present disclosure.
Figure 8A:
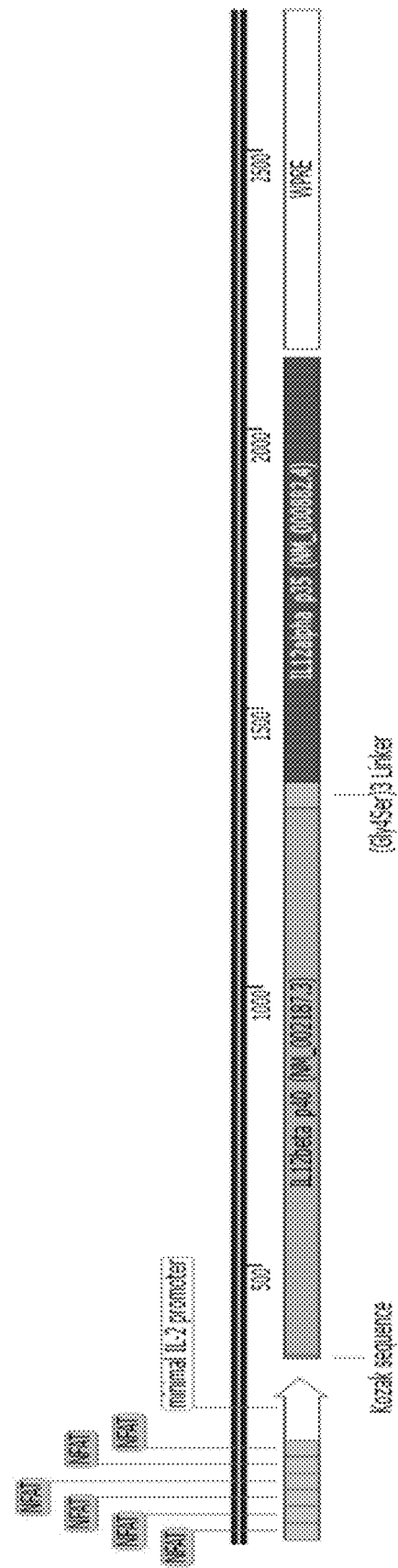
FIG. 8A shows a construct in accordance with an embodiment of the present disclosure.
Figure 8B:
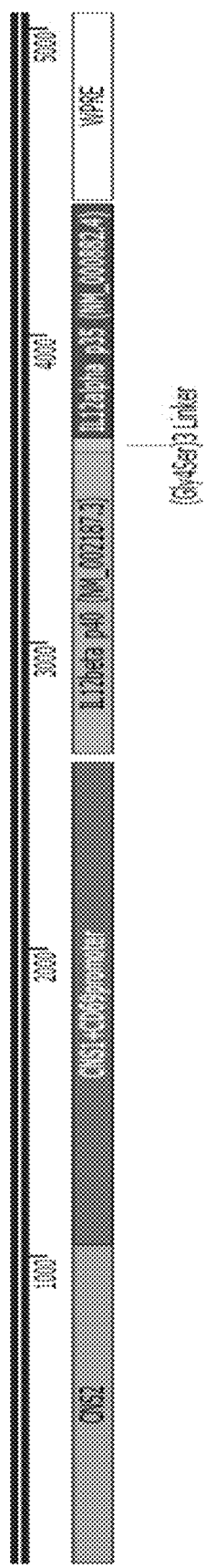
FIG. 8B shows a construct in accordance with another embodiment of the present disclosure.
Figure 8C:
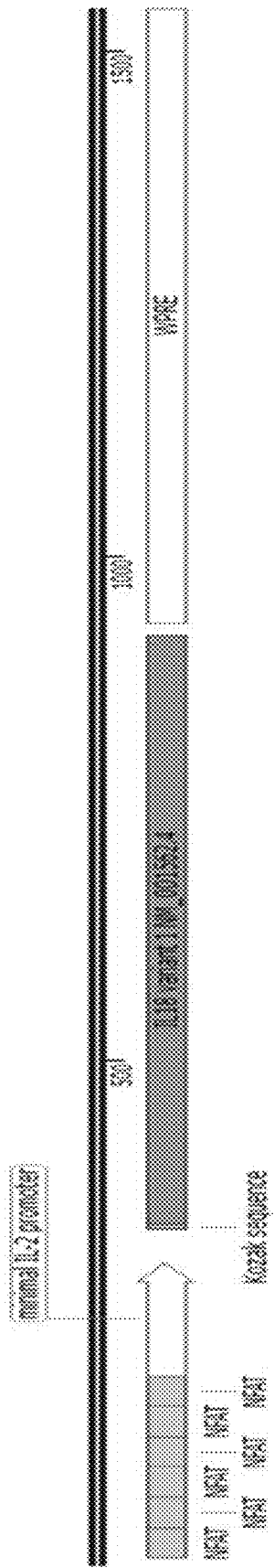
FIG. 8C shows a construct in accordance with another embodiment of the present disclosure.
Figure 8D:
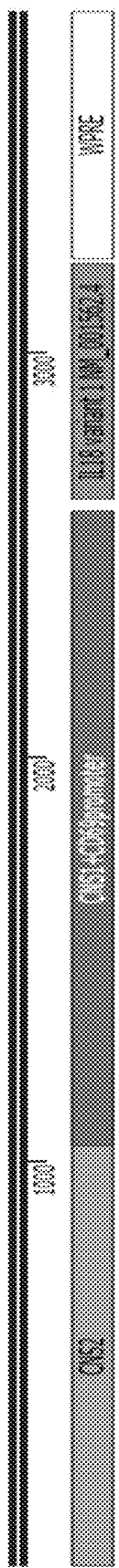
FIG. 8D shows a construct in accordance with another embodiment of the present disclosure.

FIG. 7 shows a viral vector containing sequences encoding TCR alpha chain and TCR beta chain located upstream from sequences encoding cytokines, in which the sequences encoding TCR alpha chain and TCR beta chain and sequences encoding cytokines may be separated by bidirectional promoters. Bidirectional promoters may be arranged in, from 5' to 3' direction, constitutive-constitutive, constitutive-inducible, inducible-constitutive, or inducible-inducible orientation. For example, a constitutive promoter, e.g., MSCV, PGK, or EF1 alpha promoter, may be positioned at the 3' end of the sequences encoding TCR alpha chain and TCR beta chain to drive the expression of TCR alpha chain and TCR beta chain. An inducible promote, e.g., NFAT, CD69, or IPTG promoter, may be positioned at the 5' end of the sequences encoding cytokines to drive the expression of cytokines. FIG. 8A shows an inducible NFAT promoter with minimal IL-2 promoter positioned at the 5' end of the sequences encoding IL-12, e.g., IL-12alpha(p35)/IL-12beta(p40) fusion protein (SEQ ID NO: 261) to drive the expression of 12alpha(p35)/IL-12beta(p40) fusion protein in a viral vector shown in FIG. 7. FIG. 8B shows an inducible CD69 promoter with CNS1 and CNS2 enhancer elements positioned at the 5' end of the sequences encoding IL-12, e.g., IL-12alpha(p35)/IL-12beta(p40) fusion protein (SEQ ID NO: 262) to drive the expression of 12alpha(p35)/IL-12beta (p40) fusion protein in a viral vector shown in FIG. 7. FIG. 8C shows an inducible NFAT promoter with minimal IL-2 promoter positioned at the 5' end of the sequences encoding IL-18, e.g., IL-18 variant 1 (SEQ ID NO: 263) to drive the expression of IL-18 variant 1 in a viral vector shown in FIG. 7. FIG. 8D shows an inducible CD69 promoter with CNS1 and CNS2 enhancer elements positioned at the 5' end of the sequences encoding IL-18, e.g., IL-18 variant 1 (SEQ ID NO: 264) to drive the expression of IL-18 variant 1 in a viral vector shown in FIG. 7.

In an aspect, the disclosure provides for 4-in-1 construct with a 5' end to 3' end direction orientation of CD8β-CD8α-TCRβ-TCRα. In another aspect, the disclosure provides for 4-in-1 construct with a 5' end to 3' end direction orientation of CD8β-CD8α-TCRα-TCRβ. In another aspect, the disclosure provides for 4-in-1 construct with a 5' end to 3' end direction orientation of CD8α-CD8β-TCRβ-TCRα. In another aspect, the disclosure provides for 4-in-1 construct with a 5' end to 3' end direction orientation of CD8α-CD8β-TCRα-TCRβ.

In an aspect, the disclosure provides for 4-in-1 construct with a 5' end to 3' end direction orientation does not include TCRβ-TCRα-CD8α-CD8β. In another aspect, the disclosure provides for 4-in-1 construct with a 5' end to 3' end direction orientation does not include TCRβ-TCRα-CD8β-CD8α. In another aspect, the disclosure provides for 4-in-1 construct with a 5' end to 3' end direction orientation does not include TCRα-TCRβ-CD8α-CD8β. In another aspect, the disclosure provides for 4-in-1 construct with a 5' end to 3' end direction orientation does not include TCRα-TCRβ-CD8β-CD8α.

In an aspect, the disclosure provides for 4-in-1 construct with a 5' end to 3' end direction orientation of CD8β-CD8α-TCRβ-TCRα. In a non-limiting aspect, the disclosure provides for 4-in-1 construct with a 5' end to 3' end direction orientation does not include TCRβ-TCRα-CD8α-CD8β.

Figures 9A, 9B:
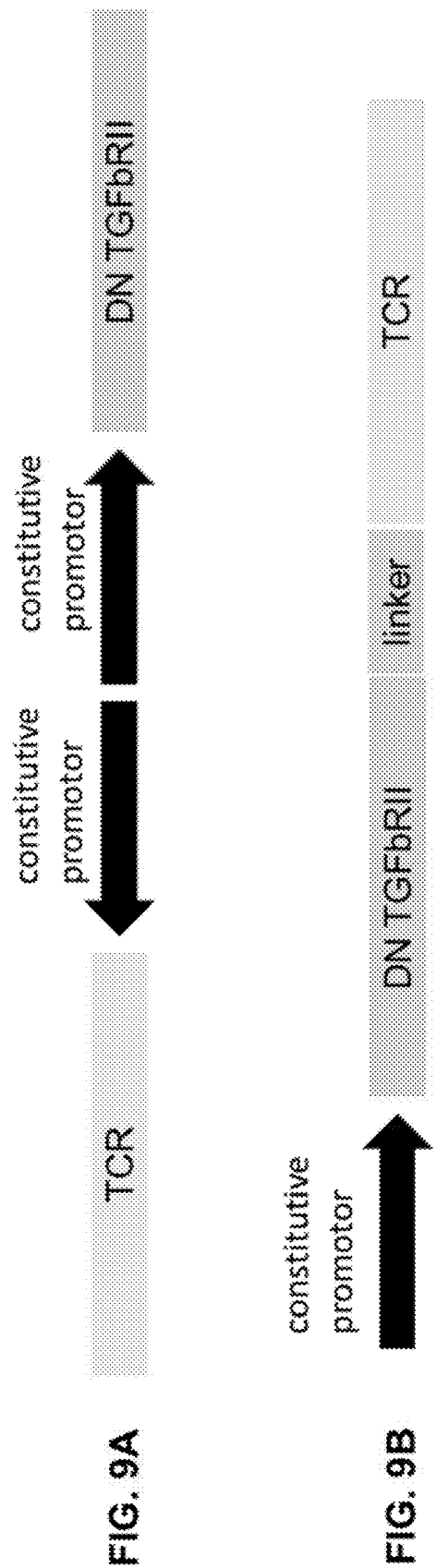
FIG. 9A shows a schematic of constructs in accordance with some embodiments of the present disclosure.
FIG. 9B shows a schematic of constructs in accordance with some embodiments of the present disclosure.

In some embodiments, viral vectors of the present disclosure may contain sequences encoding TCR alpha chain and TCR beta chain and sequences encoding a TGF-beta inhibitors, e.g., dominant-negative TGF beta receptor (DN TGFbRII), and/or extracellular domain of a transforming growth factor-beta receptor. FIG. 9A shows a viral vector containing sequences encoding TCR alpha chain and TCR beta chains located upstream from sequences encoding DN TGFbRII, in which the sequences encoding TCR alpha chain and TCR beta chains and the sequences encoding DN TGFbRII may be separated by bidirectional promoters. For example, FIG. 9A shows a constitutive promoter, e.g., MSCV, Ubc, CMV, EF-1 alpha, and PGK promoter, may be positioned at the 3' end of the sequences encoding TCR alpha chain and TCR beta chain to drive the expression of TCR alpha chain and TCR beta chain; and another constitutive promoter may be positioned at the 5' end of the sequences encoding DN TGFbRII to drive the expression of DN TGFbRII.

Alternatively, FIG. 9B shows a viral vector containing a constitutive promoter, e.g., MSCV, Ubc, CMV, EF-1 alpha, and PGK promoter, positioned at the 5' end of sequences encoding DN TGFbRII located upstream from sequences encoding TCR alpha chain and TCR beta chain to drive the expression of DN TGFbRII, TCR alpha chain, and TCR beta chain. The same coding sequences described above can also be driven by an inducible promote, e.g., NFAT, CD69, or IPTG promoter.

As used herein, the term "cistron" refers to a section of the DNA molecule that specifies the formation of one polypeptide chain, i.e. coding for one polypeptide chain. For example, "bi-cistron" refers to two sections of the DNA molecule that specify the formation of two polypeptide chains, i.e. coding for two polypeptide chains; "tri-cistron" refers to three sections of the DNA molecule that specify the formation of three polypeptide chains, i.e. coding for three polypeptide chains; etc.

As used herein, the term "multi-cistronic RNA" or "multi-cistronic RNA" refers to an RNA that contains the genetic information to translate to several proteins. In contrast, a mono-cistronic RNA contains the genetic information to translate only a single protein. In the context of the present disclosure, the multi-cistronic RNA transcribed from the lentivirus in the Examples 2-4 may be translated into four proteins (4-in-1): TCRα chain, TCRβ chain, CD8α chain, and CD8β chain; or translated to two proteins (2-in-1): TCRα chain and TCRβ chain or CD8α chain and CD8β chain.

As used herein, the term "arranged in tandem" refers to the arrangement of the genes contiguously, one following or behind the other, in a single file on a nucleic acid sequence. The genes are ligated together contiguously on a nucleic acid sequence, with the coding strands (sense strands) of each gene ligated together on a nucleic acid sequence.

As used herein, the term "sense strand" refers to the DNA strand of a gene that is translated or translatable into protein. When a gene is oriented in the "sense direction" with respect to the promoter in a nucleic acid sequence, the "sense strand" is located at the 5' end downstream of the promoter, wherein the first codon of the nucleic acid encoding the protein is proximal to the promoter and the last codon is distal from the promoter.

As used herein, the term "viral vector" refers to a nucleic acid vector construct that includes at least one element of viral origin and has the capacity to be packaged into a viral vector particle, and encodes at least an exogenous nucleic acid. The vector and/or particle can be utilized for the purpose of transferring any nucleic acids into cells either in vitro or in vivo. Numerous forms of viral vectors are known in the art. The term "virion" is used to refer to a single infective viral particle. "Viral vector", "viral vector particle" and "viral particle" also refer to a complete virus particle with its DNA or RNA core and protein coat as it exists outside the cell. For example, a viral vector may be selected from adenoviruses, poxviruses, alphaviruses, arenaviruses, flaviruses, rhabdoviruses, retroviruses, lentiviruses, herpesviruses, paramyxoviruses, or picornaviruses.

The terms "T cell" or "T lymphocyte" are art-recognized and are intended to include thymocytes, naïve T lymphocytes, immature T lymphocytes, mature T lymphocytes, resting T lymphocytes, or activated T lymphocytes. Illustrative populations of T cells suitable for use in particular embodiments include, but are not limited to, helper T cells (HTL; CD4+ T cell), a cytotoxic T cell (CTL; CD8+ T cell), CD4+CD8+ T cell, CD4−CD8− T cell, natural killer T cell, T cells expressing αβ TCR (ap T cells), T cells expressing γδ TCR (γδ T cells), or any other subset of T cells. Other illustrative populations of T cells suitable for use in particular embodiments include, but are not limited to, T cells expressing one or more of the following markers: CD3, CD4, CD8, CD27, CD28, CD45RA, CD45RO, CD62L, CD127, CD197, and HLA-DR and if desired, can be further isolated by positive or negative selection techniques.

The term "statin," "vastatin," or as used interchangeably herein "3-hydroxy-3-methylglutaryl coenzyme A (HMG-CoA) reductase inhibitor" refers to a pharmaceutical agent which inhibits the enzyme 3-hydroxy-3-methylglutaryl-coenzyme A (HMG-CoA) reductase. This enzyme is involved in the conversion of HMG-CoA to mevalonate, which is one of the steps in cholesterol biosynthesis. Such inhibition is readily determined according to standard assays well known to those skilled in the art.

Preferred statins which may be used in accordance with this present disclosure include atorvastatin, disclosed in U.S. Pat. No. 4,681,893; atorvastatin calcium, disclosed in U.S. Pat. No. 5,273,995; cerivastatin, disclosed in U.S. Pat. No. 5,502,199; dalvastatin, disclosed in U.S. Pat. No. 5,316,765; fluindostatin, disclosed in U.S. Pat. No. 4,915,954; fluvastatin, disclosed in U.S. Pat. No. 4,739,073; lovastatin, disclosed in U.S. Pat. No. 4,231,938; mevastatin, disclosed in U.S. Pat. No. 3,983,140; pravastatin, disclosed in U.S. Pat. No. 4,346,227; simvastatin, disclosed in U.S. Pat. No. 4,444,784; velostatin, disclosed in U.S. Pat. Nos. 4,448,784 and 4,450,171; and rosuvastatin, disclosed in U.S. Pat. Nos. 6,858,618 and 7,511,140, the contents of each of these references are herein incorporated by reference in their entireties. Representative 3-hydroxy-3-methylglutaryl coenzyme A reductase inhibitors may include atorvastatin, atorvastatin calcium, also known as Liptor®, lovastatin, also known as Mevacor®, pravastatin, also known as Pravachol®, simvastatin, also known as Zocor®, and rosuvastatin.

In one aspect, the present disclosure relates to activation, transduction, and/or expansion of T cells, e.g., tumor-infiltrating lymphocytes, CD8+ T cells, CD4+ T cells, and γδ T cells, that may be used for transgene expression. In another aspect, the disclosure relates to activation, transduction, and expansion of γδ T cells while depleting α- and/or β-TCR positive cells.

In an aspect, γδ T cells may be isolated from a complex sample that is cultured in vitro. In another aspect, whole PBMC population, without prior depletion of specific cell populations, such as monocytes, ap T-cells, B-cells, and NK cells, can be activated and expanded. In another aspect, enriched γδ T cell populations can be generated prior to their specific activation and expansion. In another aspect, activation and expansion of γδ T cells may be performed without the presence of native or engineered APCs. In another aspects, isolation and expansion of γδ T cells from tumor specimens can be performed using immobilized γδ T cell mitogens, including antibodies specific to γδ TCR, and other γδ TCR activating agents, including lectins. In another aspect, isolation and expansion of γδ T cells from tumor specimens can be performed in the absence of γδ T cell mitogens, including antibodies specific to γδ TCR, and other γδ TCR activating agents, including lectins.

In an aspect, γδ T cells are isolated from leukapheresis of a subject, for example, a human subject. In another aspect, γδ T cells are not isolated from peripheral blood mononuclear cells (PBMC).

In an aspect, the isolated γδ T cells can rapidly expand in response to contact with one or more antigens. Some γδ T cells, such as Vγ9Vδ2+ T cells, can rapidly expand in vitro in response to contact with some antigens, like prenyl-pyrophosphates, alkyl amines, and metabolites or microbial extracts during tissue culture. Stimulated γδ T-cells can exhibit numerous antigen-presentation, co-stimulation, and adhesion molecules that can facilitate the isolation of γδ T-cells from a complex sample. γδ T cells within a complex sample can be stimulated in vitro with at least one antigen for 1 day, 2 days, 3 days, 4 days, 5 days, 6 days, 7 days, or another suitable period of time. Stimulation of γδ T cells with a suitable antigen can expand γδ T cell population in vitro.

Non-limiting examples of antigens that may be used to stimulate the expansion of γδ T cells from a complex sample in vitro may include, prenyl-pyrophosphates, such as isopentenyl pyrophosphate (IPP), alkyl-amines, metabolites of human microbial pathogens, metabolites of commensal bacteria, methyl-3-butenyl-1-pyrophosphate (2M3B1 PP), (E)-4-hydroxy-3-methyl-but-2-enyl pyrophosphate (HMB-PP), ethyl pyrophosphate (EPP), farnesyl pyrophosphate (FPP), dimethylallyl phosphate (DMAP), dimethylallyl pyrophosphate (DMAPP), ethyl-adenosine triphosphate (EPPPA), geranyl pyrophosphate (GPP), geranylgeranyl pyrophosphate (GGPP), isopentenyl-adenosine triphosphate (IPPPA), monoethyl phosphate (MEP), monoethyl pyrophosphate (MEPP), 3-formyl-1-butyl-pyrophosphate (TUBAg 1), X-pyrophosphate (TUBAg 2), 3-formyl-1-butyl-uridine triphosphate (TUBAg 3), 3-formyl-1-butyl-deoxythymidine triphosphate (TUBAg 4), monoethyl alkylamines, allyl pyrophosphate, crotoyl pyrophosphate, dimethylallyl-γ-uridine triphosphate, crotoyl-γ-uridine triphosphate, allyl-γ-uridine triphosphate, ethylamine, isobutylamine, sec-butylamine, iso-amylamine and nitrogen containing bisphosphonates.

Activation and expansion of γδ T cells can be performed using activation and co-stimulatory agents described herein to trigger specific γδ T cell proliferation and persistence populations. In an aspect, activation and expansion of γδ T-cells from different cultures can achieve distinct clonal or mixed polyclonal population subsets. In another aspect, different agonist agents can be used to identify agents that provide specific γδ activating signals. In another aspect, agents that provide specific γδ activating signals can be different monoclonal antibodies (MAbs) directed against the γδ TCRs. In another aspect, companion co-stimulatory agents to assist in triggering specific γδ T cell proliferation without induction of cell energy and apoptosis can be used. These co-stimulatory agents can include ligands binding to receptors expressed on γδ cells, such as NKG2D, CD161, CD70, JAML, DNAX accessory molecule-1 (DNAM-1), ICOS, CD27, CD137, CD30, HVEM, SLAM, CD122, DAP, and CD28. In another aspect, co-stimulatory agents can be antibodies specific to unique epitopes on CD2 and CD3 molecules. CD2 and CD3 can have different conformation structures when expressed on αβ or γδ T-cells. In another aspect, specific antibodies to CD3 and CD2 can lead to distinct activation of γδ T cells.

A population of γδ T-cells may be expanded ex vivo prior to engineering of the γδ T-cells. Non-limiting example of reagents that can be used to facilitate the expansion of a γδ T-cell population in vitro may include anti-CD3 or anti-CD2, anti-CD27, anti-CD30, anti-CD70, anti-OX40 antibodies, IL-2, IL-15, IL-12, IL-9, IL-33, IL-18, or IL-21, CD70 (CD27 ligand), phytohaemagglutinin (PHA), concavalin A (ConA), pokeweed (PWM), protein peanut agglutinin (PNA), soybean agglutinin (SBA), Les *Culinaris* Agglutinin (LCA), *Pisum Sativum* Agglutinin (PSA), *Helix pomatia* agglutinin (HPA), *Vicia graminea* Lectin (VGA), or another suitable mitogen capable of stimulating T-cell proliferation.

The ability of γδ T cells to recognize a broad spectrum of antigens can be enhanced by genetic engineering of the γδ T cells. In an aspect, γδ T cells can be engineered to provide a universal allogeneic therapy that recognizes an antigen of choice in vivo. Genetic engineering of the γδ T-cells may include stably integrating a construct expressing a tumor recognition moiety, such as αβ TCR, γδ TCR, chimeric antigen receptor (CAR), which combines both antigen-binding and T-cell activating functions into a single receptor, an antigen binding fragment thereof, or a lymphocyte activation domain into the genome of the isolated γδ T-cell(s), a cytokine (for example, IL-15, IL-12, IL-2. IL-7. IL-21, IL-18, IL-19, IL-33, IL-4, IL-9, IL-23, or IL1β) to enhance T-cell proliferation, survival, and function ex vivo and in vivo. Genetic engineering of the isolated γδ T-cell may also include deleting or disrupting gene expression from one or more endogenous genes in the genome of the isolated γδ T-cells, such as the MHC locus (loci).

Engineered γδ T-cells may be generated with various methods. For example, a polynucleotide encoding an expression cassette that comprises a tumor recognition, or another type of recognition moiety, can be stably introduced into the γδ T-cell by a transposon/transposase system or a viral-based gene transfer system, such as a lentiviral or a retroviral system, or another suitable method, such as transfection, electroporation, transduction, lipofection, calcium phosphate ($CaPO_4$), nanoengineered substances, such as Ormosil, viral delivery methods, including adenoviruses, retroviruses, lentiviruses, adeno-associated viruses, or another suitable method. A number of viral methods have been used for human gene therapy, such as the methods described in WO 1993020221, the content of which is incorporated herein in its entirety. Non-limiting examples of viral methods that can be used to engineer γδ T cells may include γ-retroviral, adenoviral, lentiviral, herpes simplex virus, vaccinia virus, pox virus, or adeno-virus associated viral methods.

In an aspect, constructs and vectors described herein are used with the methodology described in U.S. Ser. No. 16/200,308, filed on Nov. 26, 2018, the contents of which are incorporated by reference in their entirety.

In an aspect, viruses refer to natural occurring viruses as well as artificial viruses. Viruses in accordance to some embodiments of the present disclosure may be either an enveloped or non-enveloped virus. Parvoviruses (such as AAVs) are examples of non-enveloped viruses. In a preferred embodiment, the viruses may be enveloped viruses. In preferred embodiments, the viruses may be retroviruses and in particular lentiviruses. Viral envelope proteins that can promote viral infection of eukaryotic cells may include HIV-1 derived lentiviral vectors (LVs) pseudotyped with envelope glycoproteins (GPs) from the vesicular stomatitis virus (VSV-G), the modified feline endogenous retrovirus (RD114TR) (SEQ ID NO: 97), and the modified gibbon ape leukemia virus (GALVTR). These envelope proteins can efficiently promote entry of other viruses, such as parvoviruses, including adeno-associated viruses (AAV), thereby demonstrating their broad efficiency. For example, other viral envelop proteins may be used including Moloney murine leukemia virus (MLV) 4070 env (such as described in Merten et al., *J. Virol.* 79:834-840, 2005; the content of which is incorporated herein by reference), RD114 env, chimeric envelope protein RD114pro or RDpro (which is an RD114-HIV chimera that was constructed by replacing the R peptide cleavage sequence of RD114 with the HIV-1 matrix/capsid (MA/CA) cleavage sequence, such as described in Bell et al. *Experimental Biology and Medicine* 2010; 235: 1269-1276; the content of which is incorporated herein by reference), baculovirus GP64 env (such as described in Wang et al. *J. Virol.* 81:10869-10878, 2007; the content of which is incorporated herein by reference), or GALV env (such as described in Merten et al., *J. Virol.* 79:834-840, 2005; the content of which is incorporated herein by reference), or derivatives thereof.

Embodiments of the present disclosure are based on the discovery that a single lentiviral cassette can be used to create a single lentiviral vector, expressing at least four individual monomer proteins of two distinct dimers from a single multi-cistronic mRNA so as to co-express the dimers on the cell surface. For example, the integration of a single copy of the lentiviral vector was sufficient to transform γδ T cells to co-express TCRαβ and CD8αβ.

In one aspect, the present disclosure relates to vectors containing a multi-cistronic cassette within a single vector capable of expressing more than one, more than two, more than three, more than four genes, more than five genes, or more than six genes, in which the polypeptides encoded by these genes may interact with one another, or may form dimers. The dimers may be homodimers, i.e., two identical proteins forming a dimer, or heterodimers, i.e., two structurally different proteins forming a dimer.

In one aspect, a lentiviral vector may contain a first nucleotide sequence S1 encoding a protein Z1, a second nucleotide sequence S2 encoding a protein Z2, a third nucleotide sequence S3 encoding a protein Y1, and a fourth nucleotide sequence S4 encoding a protein Y2, in which Z1 and Z2 form a first dimer and Y1 and Y2 form a second dimer, in which the first dimer Z1Z2 is different from the second dimer Y1Y2.

In one aspect, a first lentiviral vector may contain a bi-cistronic cassette (2-in-1) encoding a dimer Z1Z2, and a second lentiviral vector may contain a bi-cistronic cassette (2-in-1) encoding a dimer Y1Y2. In the 2-in-1 vectors, S1 and S2 may be arranged in tandem in a 5' to 3' orientation of S1-S2 or S2-S1. Likewise, In the 2-in-1 vectors, S3 and S4 may be arranged in tandem in a 5' to 3' orientation of S3-S4 or S4-S3. Z1 and Z2 or Y1 and Y2 may be separated by one or more self-cleaving 2A peptides.

In another aspect, a single lentiviral vector (4-in-1) may encode both distinct dimers Z1Z2 and Y1Y2, in which Z1, Z2, Y1, and Y2 may be separated by one or more self-cleaving 2A peptides. For example, the S1, S2, S3, and S4 may be arranged in tandem in a 5' to 3' orientation selected from S1-S2-S3-S4, S1-S2-S4-S3, S1-S3-S2-S4, S1-S3-S4-S2, S1-S4-S3-S2, S1-S4-S2-S3, S2-S1-S3-S4, S2-S1-S4-S3, S2-S3-S1-S4, S2-S3-S4-S1, S2-S4-S3-S1, S2-S4-S1-S3, S3-S1-S2-S4, S3-S1-S4-S2, S3-S2-S1-S4, S3-S2-S4-S1, S3-S4-S1-S2, S3-S4-S2-S1, S4-S1-S2-S3, S4-S1-S3-S2, S4-S2-S1-S3, S4-S2-S3-S1, S4-S3-S1-S2, or S4-S3-S2-S1.

In an aspect, the dimer Z1Z2 may be TCRs having a TCRα chain and a TCRβ chain.

In an aspect, TCRs and antigen binding proteins that are capable of use with the constructs, methods and embodiments described herein include, for example, those listed in Table 2 (SEQ ID NOs: 13-90) and those TCRs and antigen binding proteins described in U.S. Publication 20170267738, U.S. Publication 20170312350, U.S. Publication 20180051080, U.S. Publication 20180164315, U.S. Publication 20180161396, U.S. Publication 20180162922, U.S. Publication 20180273602, U.S. Publication 20190016801, U.S. Publication 20190002556, U.S. Publication 20190135914, U.S. Pat. Nos. 10,538,573, 10,626, 160, U.S. Publication 20190321478, U.S. Publication 20190256572, U.S. Pat. Nos. 10,550,182, 10,526,407, U.S. Publication 20190284276, U.S. Publication 20190016802, and U.S. Pat. No. 10,583,573, the contents of each of these publications and sequence listings described therein are herein incorporated by reference in their entireties.

In another aspect, the dimer Z1Z2 may be TCRα chain and TCRβ chain selected from R11 KEA (SEQ ID NO: 13 and 14), R20P1H7 (SEQ ID NO: 15 and 16), R7P1 D5 (SEQ ID NO: 17 and 18), R10P2G12 (SEQ ID NO: 19 and 20), R10P1A7 (SEQ ID NO: 21 and 22), R4P1 D10 (SEQ ID NO: 23 and 24), R4P3F9 (SEQ ID NO: 25 and 26), R4P3H3 (SEQ ID NO: 27 and 28), R36P3F9 (SEQ ID NO: 29 and 30), R52P2G11 (SEQ ID NO: 31 and 32), R53P2A9 (SEQ ID NO: 33 and 34), R26P1A9 (SEQ ID NO: 35 and 36), R26P2A6 (SEQ ID NO: 37 and 38), R26P3H1 (SEQ ID NO: 39 and 40), R35P3A4 (SEQ ID NO: 41 and 42), R37P1C9 (SEQ ID NO: 43 and 44), R37P1H1 (SEQ ID NO: 45 and 46), R42P3A9 (SEQ ID NO: 47 and 48), R43P3F2 (SEQ ID NO: 49 and 50), R43P3G5 (SEQ ID NO: 51 and 52), R59P2E7 (SEQ ID NO: 53 and 54), R11P3D3 (SEQ ID NO: 55 and 56), R16P1C10 (SEQ ID NO: 57 and 58), R16P1E8 (SEQ ID NO: 59 and 60), R17P1A9 (SEQ ID NO: 61 and 62), R17P1 D7 (SEQ ID NO: 63 and 64), R17P1 G3 (SEQ ID NO: 65 and 66), R17P2B6 (SEQ ID NO: 67 and 68), R11P3D3KE (SEQ ID NO: 69 and 70), R39P1C12 (SEQ ID NO: 71 and 72), R39P1F5 (SEQ ID NO: 73 and 74), R40P1C2 (SEQ ID NO: 75 and 76), R41P3E6 (SEQ ID NO: 77 and 78), R43P3G4 (SEQ ID NO: 79 and 80), R44P3B3 (SEQ ID NO: 81 and 82), R44P3E7 (SEQ ID NO: 83 and 84), R49P2B7 (SEQ ID NO: 85 and 86), R55P1G7 (SEQ ID NO: 87 and 88), or R59P2A7 (SEQ ID NO: 89 and 90). In an aspect, the sequences exhibit at least about 90%, at least about 95%, or at least about 98% to any of SEQ ID NO: 13-90.

Table 1 shows examples of the peptides to which TCRs bind when the peptide is in a complex with an MHC molecule.

TABLE 1

| TCR name | Peptide (name/sequence/SEQ ID NO:) |
| --- | --- |
| R20P1H7, R7P1D5, R10P2G12 | MAG-003 (KVLEHVVRV) (SEQ ID NO: 215) |
| R10P1A7 | IGF2BP3-001 (KIQEILTQV) (SEQ ID NO: 123) |
| R4P1D10, R4P3F9, R4P3H3 | COL6A3-002 (FLLDGSANV) (SEQ ID NO: 238) |
| R36P3F9, R52P2G11, R53P2A9 | DCAF4L2-001 (ILQDGQFLV) (SEQ ID NO: 193) |
| R26P1A9, R26P2A6, R26P3H1, R35P3A4, R37P1C9, R37P1H1, R42P3A9, R43P3F2, R43P3G5, R59P2E7 | MAGEA1-003 (KVLEYVIKV) (SEQ ID NO: 202) |
| R11KEA, R11P3D3, R16P1C10, R16P1E8, R17P1A9, R17P1D7, R17P1G3, R17P2B6, R11P3D3KE | PRAME-004 (SLLQHLIGL) (SEQ ID NO: 147) |
| R39P1C12, R39P1F5, R40P1C2, R41P3E6, R43P3G4, R44P3B3, R44P3E7, R49P2B7, R55P1G7, R59P2A7 | SPINK2-001 (ALSVLRLAL) (SEQ ID NO: 248) |

In an aspect, tumor associated antigen (TAA) peptides that are capable of use with the methods and embodiments described herein include, for example, those listed in Table 3 and those TAA peptides described in U.S. Publication 20160187351, U.S. Publication 20170165335, U.S. Publication 20170035807, U.S. Publication 20160280759, U.S. Publication 20160287687, U.S. Publication 20160346371, U.S. Publication 20160368965, U.S. Publication 20170022251, U.S. Publication 20170002055, U.S. Publication 20170029486, U.S. Publication 20170037089, U.S. Publication 20170136108, U.S. Publication 20170101473, U.S. Publication 20170096461, U.S. Publication 20170165337, U.S. Publication 20170189505, U.S. Publication 20170173132, U.S. Publication 20170296640, U.S. Publication 20170253633, U.S. Publication 20170260249, U.S. Publication 20180051080, U.S. Publication No. 20180164315, U.S. Publication 20180291082, U.S. Publication 20180291083, U.S. Publication 20190255110, U.S. Pat. Nos. 9,717,774, 9,895,415, U.S. Publication 20190247433, U.S. Publication 20190292520, U.S. Publication 20200085930, U.S. Pat. Nos. 10,336,809, 10,131,703, 10,081,664, 10,081,664, 10,093,715, 10,583,573, and US20200085930, the contents of each of these publications, sequences, and sequence listings described therein are herein incorporated by reference in their entireties.

In another aspect, the dimer Z1Z2 may be T cell dimeric signaling modules, such as CD3δ/ε, CD3γ/ε, and CD247 ζ/ζ or ζ/η, a dimer of a TCRα variable region (Vα) and a TCRβ variable region (Vβ), a dimer of immunoglobulin heavy chain variable region (VH) and immunoglobulin light chain variable region (VL), a dimer of Vα and VH, a dimer of Vα and VL, a dimer of Vβ and VH, or a dimer of Vβ and VL.

In another aspect, Y1Y2 may be CD8α chain and CD8β chain or any other suitable dimeric membrane receptors, preferably those expressed in the CD8+ T cells and/or in the CD4+ T cells.

Furin is a ubiquitous subtilisin-like proprotein convertase, whose natural substrates include certain serum proteins and growth factor receptors, such as the insulin-like growth factor receptor. The consensus sequence for furin cleavage is RXXR (SEQ ID NO: 7) but the potential for actual cleavage is dependent on substrate tertiary structure and the amino acids immediately surrounding the recognition site. Addition of a furin cleavage site plus the linker sequences (GSG or SGSG (SEQ ID NO: 8)) may enable highly efficient gene expression.

In one aspect, a nucleotide sequence of furin-linker-2A peptide arranged in tandem may be positioned between Z1 and Z2, between Z1 and Y1, between Z1 and Y2, between Z2 and Y1, between Z2 and Y2, and/or between Y1 and Y2. The furin may have a consensus sequence of RXXR (SEQ ID NO: 7), e.g., RAKR (SEQ ID NO: 2). The linker sequence may be GSG or SGSG (SEQ ID NO: 8). The 2A peptide may be selected from P2A (SEQ ID NO: 3), T2A (SEQ ID NO: 4), E2A (SEQ ID NO: 5), F2A (SEQ ID NO: 6), or any combination thereof.

In another aspect, a nucleotide sequence of linker-2A peptide arranged in tandem may be positioned between Z1 and Z2, between Z1 and Y1, between Z1 and Y2, between Z2 and Y1, between Z2 and Y2, and/or between Y1 and Y2. The linker sequence may be GSG or SGSG (SEQ ID NO: 8). The 2A peptide may be selected from P2A (SEQ ID NO: 3), T2A (SEQ ID NO: 4), E2A (SEQ ID NO: 5), F2A (SEQ ID NO: 6), or any combination thereof.

In an aspect, engineered (or transduced) γδ T cells can be expanded ex vivo without stimulation by an antigen presenting cell or aminobisphosphonate. Antigen reactive engineered T cells of the present disclosure may be expanded ex vivo and in vivo. In another aspect, an active population of engineered γδ T cells of the present disclosure may be expanded ex vivo without antigen stimulation by an antigen presenting cell, an antigenic peptide, a non-peptide molecule, or a small molecule compound, such as an aminobisphosphonate but using certain antibodies, cytokines, mitogens, or fusion proteins, such as IL-17 Fc fusion, MICA Fc fusion, and CD70 Fc fusion. Examples of antibodies that can be used in the expansion of a γδ T-cell population include anti-CD3, anti-CD27, anti-CD30, anti-CD70, anti-OX40, anti-NKG2D, or anti-CD2 antibodies, examples of cytokines may include IL-2, IL-15, IL-12, IL-21, IL-18, IL-9, IL-7, and/or IL-33, and examples of mitogens may include CD70 the ligand for human CD27, phytohaemagglutinin (PHA), concavalin A (ConA), pokeweed mitogen (PWM), protein peanut agglutinin (PNA), soybean agglutinin (SBA), les culinaris agglutinin (LCA), Pisum sativum agglutinin (PSA), Helix pomatia agglutinin (HPA), Vicia graminea Lectin (VGA) or another suitable mitogen capable of stimulating T-cell proliferation. In another aspect, a population of engineered γδ T cells can be expanded in less than 60 days, less than 48 days, less than 36 days, less than 24 days, less than 12 days, or less than 6 days. In another aspect, a population of engineered γδ T cells can be expanded from about 7 days to about 49 days, about 7 days to about 42 days, from about 7 days to about 35 days, from about 7 days to about 28 days, from about 7 days to about 21 days, or from about 7 days to about 14 days.

In another aspect, the present disclosure provides methods for the ex vivo expansion of a population of engineered γδ T-cells for adoptive transfer therapy. Engineered γδ T cells of the disclosure may be expanded ex vivo. Engineered γδ T cells of the disclosure can be expanded in vitro without activation by APCs, or without co-culture with APCs, and aminophosphates.

Methods of Treatment

Compositions containing engineered γδ T cells described herein may be administered for prophylactic and/or therapeutic treatments. In therapeutic applications, pharmaceutical compositions can be administered to a subject already suffering from a disease or condition in an amount sufficient to cure or at least partially arrest the symptoms of the disease or condition. An engineered γδ T-cell can also be administered to lessen a likelihood of developing, contracting, or worsening a condition. Effective amounts of a population of engineered γδ T-cells for therapeutic use can vary based on the severity and course of the disease or condition, previous therapy, the subject's health status, weight, and/or response to the drugs, and/or the judgment of the treating physician.

The composition of the present disclosure may also include one or more adjuvants. Adjuvants are substances that non-specifically enhance or potentiate the immune response (e.g., immune responses mediated by CD8-positive T cells and helper-T (TH) cells to an antigen and would thus be considered useful in the medicament of the present invention. Suitable adjuvants include, but are not limited to, 1018 ISS, aluminum salts, AMPLIVAX®, AS15, BCG, CP-870,893, CpG7909, CyaA, dSLIM, flagellin or TLR5 ligands derived from flagellin, FLT3 ligand, GM-CSF, IC30, IC31, Imiquimod (ALDARA®), resiquimod, ImuFact IMP321, Interleukins as IL-2, IL-13, IL-21, Interferon-alpha or -beta, or pegylated derivatives thereof, IS Patch, ISS, ISCOMATRIX, ISCOMs, JuvImmune®, LipoVac, MALP2, MF59, monophosphoryl lipid A, Montanide IMS 1312, Montanide ISA 206, Montanide ISA 50V, Montanide ISA-51, water-in-oil and oil-in-water emulsions, OK-432, OM-174, OM-197-MP-EC, ONTAK, OspA, PepTel® vector system, poly(lactide co-glycolide) [PLG]-based and dextran microparticles, talactoferrin SRL172, Virosomes and other Virus-like particles, YF-17D, VEGF trap, R848, beta-glucan, Pam3Cys, Aquila's QS21 stimulon, which is derived from saponin, mycobacterial extracts and synthetic bacterial cell wall mimics, and other proprietary adjuvants such as Ribi's Detox, Quil, or Superfos. Adjuvants such as Freund's or GM-CSF are preferred. Several immunological adjuvants (e.g., MF59) specific for dendritic cells and their preparation have been described previously (Allison and Krummel, 1995). Also cytokines may be used. Several cytokines have been directly linked to influencing dendritic cell migration to lymphoid tissues (e.g., TNF-), accelerating the maturation of dendritic cells into efficient antigen-presenting cells for T-lymphocytes (e.g., GM-CSF, IL-1 and IL-4) (U.S. Pat. No. 5,849,589, specifically incorporated herein by reference in its entirety) and acting as immunoadjuvants (e.g., IL-12, IL-15, IL-23, IL-7, IFN-alpha. IFN-beta) (Gabrilovich et al., 1996).

CpG immunostimulatory oligonucleotides have also been reported to enhance the effects of adjuvants in a vaccine setting. Without being bound by theory, CpG oligonucleotides act by activating the innate (non-adaptive) immune system via Toll-like receptors (TLR), mainly TLR9. CpG triggered TLR9 activation enhances antigen-specific humoral and cellular responses to a wide variety of antigens, including peptide or protein antigens, live or killed viruses, dendritic cell vaccines, autologous cellular vaccines and polysaccharide conjugates in both prophylactic and therapeutic vaccines. More importantly it enhances dendritic cell maturation and differentiation, resulting in enhanced activation of TH1 cells and strong cytotoxic T-lymphocyte (CTL) generation, even in the absence of CD4 T cell help. The TH1 bias induced by TLR9 stimulation is maintained even in the presence of vaccine adjuvants such as alum or incomplete Freund's adjuvant (IFA) that normally promote a TH2 bias. CpG oligonucleotides show even greater adjuvant activity when formulated or co-administered with other adjuvants or in formulations such as microparticles, nanoparticles, lipid emulsions or similar formulations, which are especially necessary for inducing a strong response when the antigen is relatively weak. They also accelerate the immune response and enable the antigen doses to be reduced by approximately two orders of magnitude, with comparable antibody responses to the full-dose vaccine without CpG in some experiments (Krieg, 2006). U.S. Pat. No. 6,406,705 B1 describes the combined use of CpG oligonucleotides, non-nucleic acid adjuvants and an antigen to induce an antigen-specific immune response. A CpG TLR9 antagonist is dSLIM (double Stem Loop Immunomodulator) by Mologen (Berlin, Germany) which is a preferred component of the pharmaceutical composition of the present invention. Other TLR binding molecules such as RNA binding TLR 7, TLR 8 and/or TLR 9 may also be used.

Other examples for useful adjuvants include, but are not limited to chemically modified CpGs (e.g. CpR, Idera), dsRNA analogues such as Poly(I:C) and derivates thereof (e.g. AmpliGen®, Hiltonol®, poly-(ICLC), poly(IC-R), poly(1:C12U), non-CpG bacterial DNA or RNA as well as immunoactive small molecules and antibodies such as cyclophosphamide, sunitinib, immune checkpoint inhibitors including ipilimumab, nivolumab, pembrolizumab, atezolizumab, avelumab, durvalumab, and cemiplimab, Bevacizumab®, celebrex, NCX-4016, sildenafil, tadalafil, vardenafil, sorafenib, temozolomide, temsirolimus, XL-999, CP-547632, pazopanib, VEGF Trap, ZD2171, AZD2171, anti-CTLA4, other antibodies targeting key structures of the immune system (e.g. anti-CD40, anti-TGFbeta, anti-TNFalpha receptor) and SC58175, which may act therapeutically and/or as an adjuvant. The amounts and concentrations of adjuvants and additives useful in the context of the present invention can readily be determined by the skilled artisan without undue experimentation.

Preferred adjuvants are anti-CD40, imiquimod, resiquimod, GM-CSF, cyclophosphamide, sunitinib, bevacizumab, atezolizumab, interferon-alpha, interferon-beta, CpG oligonucleotides and derivatives, poly-(I:C) and derivatives, RNA, sildenafil, and particulate formulations with poly (lactide co-glycolide) (PLG), virosomes, and/or interleukin (IL)-1, IL-2, IL-4, IL-7, IL-12, IL-13, IL-15, IL-21, and IL-23.

In a preferred embodiment, the pharmaceutical composition according to the invention the adjuvant is selected from the group consisting of colony-stimulating factors, such as Granulocyte Macrophage Colony Stimulating Factor (GM-CSF, sargramostim), cyclophosphamide, imiquimod, resiquimod, and interferon-alpha.

In a preferred embodiment, the pharmaceutical composition according to the invention the adjuvant is selected from the group consisting of colony-stimulating factors, such as Granulocyte Macrophage Colony Stimulating Factor (GM-CSF, sargramostim), cyclophosphamide, imiquimod and resiquimod. In a preferred embodiment of the pharmaceutical composition according to the invention, the adjuvant is cyclophosphamide, imiquimod or resiquimod. Even more preferred adjuvants are Montanide IMS 1312, Montanide ISA 206, Montanide ISA 50V, Montanide ISA-51, poly-ICLC (Hiltonol®) and anti-CD40 mAB, or combinations thereof.

Engineered γδ T cells of the present disclosure can be used to treat a subject in need of treatment for a condition, for example, a cancer described herein.

A method of treating a condition (e.g., ailment) in a subject with γδ T cells may include administering to the subject a therapeutically effective amount of engineered γδ T cells. γδ T cells of the present disclosure may be administered at various regimens (e.g., timing, concentration, dosage, spacing between treatment, and/or formulation). A subject can also be preconditioned with, for example, chemotherapy, radiation, or a combination of both, prior to receiving engineered γδ T cells of the present disclosure. A population of engineered γδ T cells may also be frozen or cryopreserved prior to being administered to a subject. A population of engineered γδ T cells can include two or more cells that express identical, different, or a combination of identical and different tumor recognition moieties. For instance, a population of engineered γδ T-cells can include several distinct engineered γδ T cells that are designed to recognize different antigens, or different epitopes of the same antigen.

γδ T cells of the present disclosure may be used to treat various conditions. In an aspect, engineered γδ T cells of the present disclosure may be used to treat a cancer, including solid tumors and hematologic malignancies. Non-limiting examples of cancers include: acute lymphoblastic leukemia, acute myeloid leukemia, adrenocortical carcinoma, AIDS-related cancers, AIDS-related lymphoma, anal cancer, appendix cancer, astrocytomas, neuroblastoma, basal cell carcinoma, bile duct cancer, bladder cancer, bone cancers, brain tumors, such as cerebellar astrocytoma, cerebral astrocytoma/malignant glioma, ependymoma, medulloblastoma, supratentorial primitive neuroectodermal tumors, visual pathway and hypothalamic glioma, breast cancer, bronchial adenomas, Burkitt lymphoma, carcinoma of unknown primary origin, central nervous system lymphoma, cerebellar astrocytoma, cervical cancer, childhood cancers, chronic lymphocytic leukemia, chronic myelogenous leukemia, chronic myeloproliferative disorders, colon cancer, cutaneous T-cell lymphoma, desmoplastic small round cell tumor, endometrial cancer, ependymoma, esophageal cancer, Ewing's sarcoma, germ cell tumors, gallbladder cancer, gastric cancer, gastrointestinal carcinoid tumor, gastrointestinal stromal tumor, gliomas, hairy cell leukemia, head and neck cancer, heart cancer, hepatocellular (liver) cancer, Hodgkin lymphoma, Hypopharyngeal cancer, intraocular melanoma, islet cell carcinoma, Kaposi sarcoma, kidney cancer, laryngeal cancer, lip and oral cavity cancer, liposarcoma, liver cancer, lung cancers, such as non-small cell and small cell lung cancer, lymphomas, leukemias, macroglobulinemia, malignant fibrous histiocytoma of bone/osteosarcoma, medulloblastoma, melanomas, mesothelioma, metastatic squamous neck cancer with occult primary, mouth cancer, multiple endocrine neoplasia syndrome, myelodysplastic syndromes, myeloid leukemia, nasal cavity and paranasal sinus cancer, nasopharyngeal carcinoma, neuroblastoma, non-Hodgkin lymphoma, non-small cell lung cancer, oral cancer, oropharyngeal cancer, osteosarcoma/malignant fibrous histiocytoma of bone, ovarian cancer, ovarian epithelial cancer, ovarian germ cell tumor, pancreatic cancer, pancreatic cancer islet cell, paranasal sinus and nasal cavity cancer, parathyroid cancer, penile cancer, pharyngeal cancer, pheochromocytoma, pineal astrocytoma, pineal germinoma, pituitary adenoma, pleuropulmonary blastoma, plasma cell neoplasia, primary central nervous system lymphoma, prostate cancer, rectal cancer, renal cell carcinoma, renal pelvis and ureter transitional cell cancer, retinoblastoma, rhabdomyosarcoma, salivary gland cancer, sarcomas, skin cancers, skin carcinoma merkel cell, small intestine cancer, soft tissue sarcoma, squamous cell carcinoma, stomach cancer, T-cell lymphoma, throat cancer, thymoma, thymic carcinoma, thyroid cancer, trophoblastic tumor (gestational), cancers of unknown primary site, urethral cancer, uterine sarcoma, vaginal cancer, vulvar cancer, Waldenstrm macroglobulinemia, and Wilms tumor.

In an aspect, engineered γδ T cells of the present disclosure may be used to treat an infectious disease. In another aspect, engineered γδ T cells of the present disclosure may be used to treat an infectious disease, an infectious disease may be caused a virus. In yet another aspect, engineered γδ T cells of the present disclosure may be used to treat an immune disease, such as an autoimmune disease.

Treatment with γδ T cells of the present disclosure may be provided to the subject before, during, and after the clinical onset of the condition. Treatment may be provided to the subject after 1 day, 1 week, 6 months, 12 months, or 2 years after clinical onset of the disease. Treatment may be provided to the subject for more than 1 day, 1 week, 1 month, 6 months, 12 months, 2 years, 3 years, 4 years, 5 years, 6 years, 7 years, 8 years, 9 years, 10 years or more after clinical onset of disease. Treatment may be provided to the subject for less than 1 day, 1 week, 1 month, 6 months, 12 months, or 2 years after clinical onset of the disease. Treatment may also include treating a human in a clinical trial. A treatment can include administering to a subject a pharmaceutical composition comprising engineered γδ T cells of the present disclosure.

In another aspect, administration of engineered γδ T cells of the present disclosure to a subject may modulate the activity of endogenous lymphocytes in a subject's body. In another aspect, administration of engineered γδ T cells to a subject may provide an antigen to an endogenous T-cell and may boost an immune response. In another aspect, the memory T cell may be a CD4+ T-cell. In another aspect, the memory T cell may be a CD8+ T-cell. In another aspect, administration of engineered γδ T cells of the present disclosure to a subject may activate the cytotoxicity of another immune cell. In another aspect, the other immune cell may be a CD8+ T-cell. In another aspect, the other immune cell may be a Natural Killer T-cell. In another aspect, administration of engineered γδ T-cells of the present disclosure to a subject may suppress a regulatory T-cell. In another aspect, the regulatory T-cell may be a FOX3+ Treg cell. In another aspect, the regulatory T-cell may be a FOX3– Treg cell. Non-limiting examples of cells whose activity can be modulated by engineered γδ T cells of the disclosure may include: hematopioietic stem cells; B cells; CD4; CD8; red blood cells; white blood cells; dendritic cells, including dendritic antigen presenting cells; leukocytes; macrophages; memory B cells; memory T-cells; monocytes; natural killer cells; neutrophil granulocytes; T-helper cells; and T-killer cells.

During most bone marrow transplants, a combination of cyclophosphamide with total body irradiation may be conventionally employed to prevent rejection of the hematopietic stem cells (HSC) in the transplant by the subject's immune system. In an aspect, incubation of donor bone marrow with interleukin-2 (IL-2) ex vivo may be performed to enhance the generation of killer lymphocytes in the donor marrow. Interleukin-2 (IL-2) is a cytokine that may be necessary for the growth, proliferation, and differentiation of wild-type lymphocytes. Current studies of the adoptive transfer of γδ T-cells into humans may require the co-administration of γδ T-cells and interleukin-2. However, both low- and high-dosages of IL-2 can have highly toxic side effects. IL-2 toxicity can manifest in multiple organs/systems, most significantly the heart, lungs, kidneys, and central nervous system. In another aspect, the disclosure provides a method for administrating engineered γδ T cells to a subject without the co-administration of a native cytokine or modified versions thereof, such as IL-2, IL-15, IL-12, IL-21. In another aspect, engineered γδ T cells can be administered to a subject without co-administration with IL-2. In another aspect, engineered γδ T cells may be administered to a subject during a procedure, such as a bone marrow transplant without the co-administration of IL-2.

Methods of Administration

One or multiple engineered γδ T cell populations may be administered to a subject in any order or simultaneously. If simultaneously, the multiple engineered γδ T cell can be provided in a single, unified form, such as an intravenous injection, or in multiple forms, for example, as multiple intravenous infusions, s.c, injections or pills. Engineered γδ T-cells can be packed together or separately, in a single package or in a plurality of packages. One or all of the engineered γδ T cells can be given in multiple doses. If not simultaneous, the timing between the multiple doses may vary to as much as about a week, a month, two months, three months, four months, five months, six months, or about a year. In another aspect, engineered γδ T cells can expand within a subject's body, in vivo, after administration to a subject. Engineered γδ T cells can be frozen to provide cells for multiple treatments with the same cell preparation. Engineered γδ T cells of the present disclosure, and pharmaceutical compositions comprising the same, can be packaged as a kit. A kit may include instructions (e.g., written instructions) on the use of engineered γδ T cells and compositions comprising the same.

In another aspect, a method of treating a cancer comprises administering to a subject a therapeutically-effective amount of engineered γδ T cells, in which the administration treats the cancer. In another embodiments, the therapeutically-effective amount of engineered γδ T cells may be administered for at least about 10 seconds, 30 seconds, 1 minute, 10 minutes, 30 minutes, 1 hour, 2 hours, 3 hours, 4 hours, 5 hours, 6 hours, 12 hours, 24 hours, 2 days, 3 days, 4 days, 5 days, 6 days, 1 week, 2 weeks, 3 weeks, 1 month, 2 months, 3 months, 4 months, 5 months, 6 months, or 1 year. In another aspect, the therapeutically-effective amount of the engineered γδ T cells may be administered for at least one week. In another aspect, the therapeutically-effective amount of engineered γδ T cells may be administered for at least two weeks.

Engineered γδ T-cells described herein can be administered before, during, or after the occurrence of a disease or condition, and the timing of administering a pharmaceutical composition containing an engineered γδ T-cell can vary. For example, engineered γδ T cells can be used as a prophylactic and can be administered continuously to subjects with a propensity to conditions or diseases in order to lessen the likelihood of occurrence of the disease or condition. Engineered γδ T-cells can be administered to a subject during or as soon as possible after the onset of the symptoms. The administration of engineered γδ T cells can be initiated immediately within the onset of symptoms, within the first 3 hours of the onset of the symptoms, within the first 6 hours of the onset of the symptoms, within the first 24 hours of the onset of the symptoms, within 48 hours of the onset of the symptoms, or within any period of time from the onset of symptoms. The initial administration can be via any route practical, such as by any route described herein using any formulation described herein. In another aspect, the administration of engineered γδ T cells of the present disclosure may be an intravenous administration. One or multiple dosages of engineered γδ T cells can be administered as soon as is practicable after the onset of a cancer, an infectious disease, an immune disease, sepsis, or with a bone marrow transplant, and for a length of time necessary for the treatment of the immune disease, such as, for example, from about 24 hours to about 48 hours, from about 48 hours to about 1 week, from about 1 week to about 2 weeks, from about 2 weeks to about 1 month, from about 1 month to about 3 months. For the treatment of cancer, one or multiple dosages of engineered γδ T cells can be administered years after onset of the cancer and before or after other treatments. In another aspect, engineered γδ T cells can be administered for at least about 10 minutes, 30 minutes, 1 hour, 2 hours, 3 hours, 4 hours, 5 hours, 6 hours, 12 hours, 24 hours, at least 48 hours, at least 72 hours, at least 96 hours, at least 1 week, at least 2 weeks, at least 3 weeks, at least 4 weeks, at least 1 month, at least 2 months, at least 3 months, at least 4 months, at least 5 months, at least 6 months, at least 7 months, at least 8 months, at least 9 months, at least 10 months, at least 11 months, at least 12 months, at least 1 year, at least 2 years at least 3 years, at least 4 years, or at least 5 years. The length of treatment can vary for each subject.

Preservation

In an aspect, γδ T cells may be formulated in freezing media and placed in cryogenic storage units such as liquid nitrogen freezers (−196° C.) or ultra-low temperature freezers (−65° C., −80° C., −120° C., or −150° C.) for long-term storage of at least about 1 month, 2 months, 3 months, 4 months, 5 months, 6 months, 1 year, 2 years, 3 years, or at least 5 years. The freeze media can contain dimethyl sulfoxide (DMSO), and/or sodium chloride (NaCl), and/or dextrose, and/or dextran sulfate and/or hydroyethyl starch (HES) with physiological pH buffering agents to maintain pH between about 6.0 to about 6.5, about 6.5 to about 7.0, about 7.0 to about 7.5, about 7.5 to about 8.0 or about 6.5 to about 7.5. The cryopreserved γδ T cells can be thawed and further processed by stimulation with antibodies, proteins, peptides, and/or cytokines as described herein. The cryopreserved γδ T-cells can be thawed and genetically modified with viral vectors (including retroviral, adeno-associated virus (AAV), and lentiviral vectors) or non-viral means (including RNA, DNA, e.g., transposons, and proteins) as described herein. The modified γδ T cells can be further cryopreserved to generate cell banks in quantities of at least about 1, 5, 10, 100, 150, 200, 500 vials at about at least 101, 102, 103, 104, 105, 106, 107, 108, 109, or at least about 1010 cells per mL in freeze media. The cryopreserved cell banks may retain their functionality and can be thawed and further stimulated and expanded. In another aspect, thawed cells can be stimulated and expanded in suitable closed vessels, such as cell culture bags and/or bioreactors, to generate quantities of cells as allogeneic cell product. Cryopreserved γδ T cells can maintain their biological functions for at least about 6 months, 7 months, 8 months, 9 months, 10 months, 11 months, 12 months, 13 months, 15 months, 18 months, 20 months, 24 months, 30 months, 36 months, 40 months, 50 months, or at least about 60 months under cryogenic storage condition. In another aspect, no preservatives may be used in the formulation. Cryopreserved γδ T-cells can be thawed and infused into multiple patients as allogeneic off-the-shelf cell product.

In an aspect, engineered γδ T-cell described herein may be present in a composition in an amount of at least $1 \times 10^3$ cells/ml, at least $2 \times 10^3$ cells/ml, at least $3 \times 10^3$ cells/ml, at least $4 \times 10^3$ cells/ml, at least $5 \times 10^3$ cells/ml, at least $6 \times 10^3$ cells/ml, at least $7 \times 10^3$ cells/ml, at least $8 \times 10^3$ cells/ml, at least $9 \times 10^3$ cells/ml, at least $1 \times 10^4$ cells/ml, at least $2 \times 10^4$ cells/ml, at least $3 \times 10^4$ cells/ml, at least $4 \times 10^4$ cells/ml, at least $5 \times 10^4$ cells/ml, at least $6 \times 10^4$ cells/ml, at least $7 \times 10^4$ cells/ml, at least $8 \times 10^4$ cells/ml, at least $9 \times 10^4$ cells/ml, at least $1 \times 10^5$ cells/ml, at least $2 \times 10^5$ cells/ml, at least $3 \times 10^5$ cells/ml, at least $4 \times 10^5$ cells/ml, at least $5 \times 10^5$ cells/ml, at least $6 \times 10^5$ cells/ml, at least $7 \times 10^5$ cells/ml, at least $8 \times 10^5$ cells/ml, at least $9 \times 10^5$ cells/ml, at least $1 \times 10^6$ cells/ml, at least $2 \times 10^6$ cells/ml, at least $3 \times 10^6$ cells/ml, at least $4 \times 10^6$ cells/ml, at least $5 \times 10^6$ cells/ml, at least $6 \times 10^6$ cells/ml, at least $7 \times 10^6$ cells/ml, at least $8 \times 10^6$ cells/ml, at least $9 \times 10^6$ cells/ml, at least $1 \times 10^7$ cells/ml, at least $2 \times 10^7$ cells/ml, at least $3 \times 10^7$ cells/ml, at least $4 \times 10^7$ cells/ml, at least $5 \times 10^7$ cells/ml, at least $6 \times 10^7$ cells/ml, at least $7 \times 10^7$ cells/ml, at least $8 \times 10^7$ cells/ml, at least $9 \times 10^7$ cells/ml, at least $1 \times 10^8$ cells/ml, at least $2 \times 10^8$ cells/ml, at least $3 \times 10^8$ cells/ml, at least $4 \times 10^8$ cells/ml, at least $5 \times 10^8$ cells/ml, at least $6 \times 10^8$ cells/ml, at least $7 \times 10^8$ cells/ml, at least $8 \times 10^8$ cells/ml, at least $9 \times 10^8$ cells/ml, at least $1 \times 10^9$ cells/ml, or more, from about $1 \times 10^3$ cells/ml to about at least $1 \times 10^8$ cells/ml, from about $1 \times 10^5$ cells/ml to about at least $1 \times 10^8$ cells/ml, or from about $1 \times 10^6$ cells/ml to about at least $1 \times 10^8$ cells/ml.

In an aspect, methods described herein may be used to produce autologous or allogenic products according to an aspect of the disclosure.

In an aspect, vectors, constructs, or sequences described herein may comprise about 80%, about 85%, about 90%, about 85%, about 96%, about 97%, about 98%, or about 99% to any of SEQ ID NO: 1-97 and 265-266. A sequence "at least 85% identical to a reference sequence" is a sequence having, on its entire length, 85%, or more, in particular 90%, 91%, 92%, 93%, 94%, 95%, 96%, 97%, 98% or 99% sequence identity with the entire length of the reference sequence.

In the context of the present application, the "percentage of identity" is calculated using a global pairwise alignment (i.e. the two sequences are compared over their entire length). Methods for comparing the identity of two or more sequences are well known in the art. The «needle» program, which uses the Needleman-Wunsch global alignment algorithm (Needleman and Wunsch, 1970 J. Mol. Biol. 48:443-453) to find the optimum alignment (including gaps) of two sequences when considering their entire length, may for example be used. The needle program is for example available on the ebi.ac.uk World Wide Web site and is further described in the following publication (*EMBOSS: The European Molecular Biology Open Software Suite* (2000) Rice, P. Longden, I. and Bleasby, A. Trends in Genetics 16, (6) pp. 276-277). The percentage of identity between two polypeptides, in accordance with the invention, is calculated using the EMBOSS: needle (global) program with a "Gap Open" parameter equal to 10.0, a "Gap Extend" parameter equal to 0.5, and a Blosum62 matrix.

Proteins consisting of an amino acid sequence "at least 80%, 85%, 90%, 95%, 96%, 97%, 98% or 99% identical" to a reference sequence may comprise mutations such as deletions, insertions and/or substitutions compared to the reference sequence. In case of substitutions, the protein consisting of an amino acid sequence at least 80%, 85%, 90%, 95%, 96%, 97%, 98% or 99% identical to a reference sequence may correspond to a homologous sequence derived from another species than the reference sequence.

"Amino acid substitutions" may be conservative or non-conservative. Preferably, substitutions are conservative substitutions, in which one amino acid is substituted for another amino acid with similar structural and/or chemical properties.

In an embodiment, conservative substitutions may include those, which are described by Dayhoff in "The Atlas of Protein Sequence and Structure. Vol. 5", Natl. Biomedical Research, the contents of which are incorporated by reference in their entirety. For example, in an aspect, amino acids, which belong to one of the following groups, can be exchanged for one another, thus, constituting a conservative exchange: Group 1: alanine (A), proline (P), glycine (G), asparagine (N), serine (S), threonine (T); Group 2: cysteine (C), serine (S), tyrosine (Y), threonine (T); Group 3: valine (V), isoleucine (I), leucine (L), methionine (M), alanine (A), phenylalanine (F); Group 4: lysine (K), arginine (R), histidine (H); Group 5: phenylalanine (F), tyrosine (Y), tryptophan (W), histidine (H); and Group 6: aspartic acid (D), glutamic acid (E). In an aspect, a conservative amino acid substitution may be selected from the following of T→A, G→A, A→I, T→V, A→M, T→I, A→V, T→G, and/or T→S.

In a further embodiment, a conservative amino acid substitution may include the substitution of an amino acid by another amino acid of the same class, for example, (1) nonpolar: Ala, Val, Leu, lie, Pro, Met, Phe, Trp; (2) uncharged polar: Gly, Ser, Thr, Cys, Tyr, Asn, Gin; (3) acidic: Asp, Glu; and (4) basic: Lys, Arg, His. Other conservative amino acid substitutions may also be made as follows: (1) aromatic: Phe, Tyr, His; (2) proton donor: Asn, Gin, Lys, Arg, His, Trp; and (3) proton acceptor: Glu, Asp, Thr, Ser, Tyr, Asn, Gin (see, for example, U.S. Pat. No. 10,106,805, the contents of which are incorporated by reference in their entirety).

In another embodiment, conservative substitutions may be made in accordance with Table 1. Methods for predicting tolerance to protein modification may be found in, for example, Guo et al., Proc. Natl. Acad. Sci., USA, 101(25): 9205-9210 (2004), the contents of which are incorporated by reference in their entirety.

TABLE A

Conservative Amino Acid substitution
Conservative Amino Acid Substitutions

| Amino Acid | Substitutions (others are known in the art) |
|---|---|
| Ala | Ser, Gly, Cys |
| Arg | Lys, Gln, His |
| Asn | Gln, His, Glu, Asp |
| Asp | Glu, Asn, Gln |
| Cys | Ser, Met, Thr |
| Gln | Asn, Lys, Glu, Asp, Arg |
| Glu | Asp, Asn, Gln |
| Gly | Pro, Ala, Ser |
| His | Asn, Gln, Lys |
| Ile | Leu, Val, Met, Ala |
| Leu | Ile, Val, Met, Ala |
| Lys | Arg, Gln, His |
| Met | Leu, Ile, Val, Ala, Phe |
| Phe | Met, Leu, Tyr, Trp, His |
| Ser | Thr, Cys, Ala |
| Thr | Ser, Val, Ala |
| Trp | Tyr, Phe |
| Tyr | Trp, Phe, His |
| Val | Ile, Leu, Met, Ala, Thr |

In an aspect, sequences described herein may include 1, 2, 3, 4, 5, 10, 15, 20, 25, or 30 amino acid or nucleotide mutations, substitutions, deletions. In an aspect, any one of SEQ ID NO: 1-97 and 265-266 may include 1, 2, 3, 4, 5, 10, 15, 20, 25, or 30 mutations, substitutions, or deletions. In yet another aspect, the mutations or substitutions are conservative amino acid substitutions.

In another embodiment, conservative substitutions may be those shown in Table B under the heading of "conservative substitutions." If such substitutions result in a change in biological activity, then more substantial changes, denominated "exemplary substitutions" in Table B, may be introduced and the products screened if needed.

TABLE B

Amino Acid substitution
Amino Acid Substitutions

| Original Residue (naturally occurring amino acid) | Conservative Substitutions | Exemplary Substitutions |
|---|---|---|
| Ala (A) | Val | Val; Leu; Ile |
| Arg (R) | Lys | Lys; Gln; Asn |
| Asn (N) | Gln | Gln; His; Asp, Lys; Arg |
| Asp (D) | Glu | Glu; Asn |
| Cys (C) | Ser | Ser; Ala |
| Gln (Q) | Asn | Asn; Glu |
| Glu (E) | Asp | Asp; Gln |
| Gly (G) | Ala | Ala |
| His (H) | Arg | Asn; Gln; Lys; Arg |
| Ile (I) | Leu | Leu; Val; Met; Ala; Phe; Norleucine |
| Leu (L) | Ile | Norleucine; Ile; Val; Met; Ala; Phe |
| Lys (K) | Arg | Arg; Gln; Asn |
| Met (M) | Leu | Leu; Phe; Ile |
| Phe (F) | Tyr | Leu; Val; Ile; Ala; Tyr |
| Pro (P) | Ala | Ala |
| Ser (S) | Thr | Thr |
| Thr (T) | Ser | Ser |
| Trp (W) | Tyr | Tyr; Phe |
| Tyr (Y) | Phe | Trp; Phe; Thr; Ser |
| Val (V) | Leu | Ile; Leu; Met; Phe; Ala; Norleucine |

Example 1

TABLE 2

DNA and protein sequences

| SEQ ID NO: | Description | Sequence |
|---|---|---|
| 1 | MSCV promoter | Tgaaagaccccacctgtaggtttggcaagctagcttaagtaacgccattttgcaaggc atggaaaatacataactgagaatagagaagttcagatcaaggttaggaacagagag acagcagaatatgggccaaacaggatatctgtggtaagcagttcctgccccggctca gggccaagaacagatggtccccagatgcggtcccgcccctcagcagtttctagaaac catcagatgtttccagggtgccccaaggacctgaaaatgaccctgtgccttatttgaact aaccaatcagttcgcttctcgcttctgttcgcgcgcttctgctccccgagctcaataaaag agcccacaacccctcact |
| 2 | Furin | RAKR |
| 3 | P2A | ATNFSLLKQAGDVEENPGP |
| 4 | T2A | EGRGSLLTCGDVEENPGP |
| 5 | E2A | QCTNYALLKLAGDVESNPGP |
| 6 | F2A | VKQTLNFDLLKLAGDVESNPGP |
| 7 | Furin consensus | RXXR |
| 8 | Linker | SGSG |
| 9 | WPRE | cagtctgacgtacgcgtaatcaacctctggattacaaaatttgtgaaagattgactggtat tcttaactatgttgctccttttacgctatgtggatacgctgctttaatgcctttgtatcatgctatt gcttcccgtatggctttcattttctcctccttgtataaatcctggttgctgtctctttatgaggagt tgtggcccgttgtcaggcaacgtggcgtggtgtgcactgtgtttgctgacgcaaccccca ctggttggggcattgccaccacctgtcagctcctttccgggactttcgctttccccctcccta ttgccacggcggaactcatcgccgcctgccttgcccgctgctggacaggggctcggct gtttgggcactgacaattccgtggtgttgtcggggaagctgacgtccttccatggctgctc gcctgtgttgccacctggattctgcgcgggacgtccttctgctacgtcccttcggccctca atccagcggaccttccttcccgcggcctgctgccggctctgcggcctcttccgcgtcttcg ccttcgccctcagacgagtcggatctccctttgggccgcctccccgcc |
| 10 | X protein promoter | Ggggaagctgacgtcctttcc |
| 11 | CD8 alpha chain | MALPVTALLLPLALLLHAARPSQFRVSPLDRTWNLGETVELKC QVLLSNPTSGCSWLFQPRGAAASPTFLLYLSQNKPKAAEGLD TQRFSGKRLGDTFVLTLSDFRRENEGYYFCSALSNSIMYFSH FVPVFLPAKPTTTPAPRPPTPAPTIASQPLSLRPEACRPAAGG AVHTRGLDFACDIYIWAPLAGTCGVLLLSLVITLYCNHRNRRR VCKCPRPVVKSGDKPSLSARYV |
| 12 | CD8 beta chain | MRPRLWLLLAAQLTVLHGNSVLQQTPAYIKVQTNKMVMLSCE AKISLSNMRIYWLRQRQAPSSDSHHEFLALWDSAKGTIHGEE VEQEKIAVFRDASRFILNLTSVKPEDSGIYFCMIVGSPELTFGK GTQLSVVDFLPTTAQPTKKSTLKKRVCRLPRPETQKGPLCSPI TLGLLVAGVLVLLSLGVAIHLCCRRRRARLRFMKQPQGEGIS GTFVPQCLHGYYSNTTTSQKLLNPWILKT |
| 13 | R11KEA alpha chain | MEKNPLAAPLLILWFHLDCVSSILNVEQSPQSLHVQEGDSTNF TCSFPSSNFYALHWYRKETAKSPEALFVMTLNGDEKKKGRIS ATLNTKEGYSYLYIKGSQPEDSATYLCALYNNNDMRFGAGTR LTVKPNIQNPDPAVYQLRDSKSSDKSVCLFTDFDSQTNVSQS KDSDVYITDKTVLDMRSMDFKSNSAVAWSNKSDFACANAFN NSIIPEDTFFPSPESSCDVKLVEKSFETDTNLNFQNLSVIGFRIL LLKVAGFNLLMTLRLWSS |
| 14 | R11KE beta chain | MDSWTFCCVSLCILVAKHTDAGVIQSPRHEVTEMGQEVTLRC KPISGHNSLFWYRETMMRGLELLIYFNNNVPIDDSGMPEDRF SAKMPNASFSTLKIQPSEPRDSAVYFCASSPGSTDTQYFGPG TRLTVLEDLKNVFPPEVAVFEPSEAEISHTQKATLVCLATGFY PDHVELSWWVNGKEVHSGVSTDPQPLKEQPALNDSRYCLSS RLRVSATFWQNPRNHFRCQVQFYGLSENDEWTQDRAKPVT QIVSAEAWGRADCGFTSESYQQGVLSATILYEILLGKATLYAV LVSALVLMAMVKRKDSRG |
| 15 | R20P1H7 alpha chain | MEKMLECAFIVLWLQLGWLSGEDQVTQSPEALRLQEGESSS LNCSYTVSGLRGLFWYRQDPGKGPEFLFTLYSAGEEKEKERL KATLTKKESFLHITAPKPEDSATYLCAVQGENSGYSTLTFGKG TMLLVSPDIQNPDPAVYQLRDSKSSDKSVCLFTDFDSQTNVS QSKDSDVYITDKTVLDMRSMDFKSNSAVAWSNKSDFACANA |

TABLE 2-continued

DNA and protein sequences

| SEQ ID NO: | Description | Sequence |
|---|---|---|
| | | FNNSIIPEDTFFPSPESSCDVKLVEKSFETDTNLNFQNLSVIGF RILLLKVAGFNLLMTLRLWSS |
| 16 | R20P1H7 beta chain | MGPQLLGYVVLCLLGAGPLEAQVTQNPRYLITVTGKKLTVTC SQNMNHEYMSWYRQDPGLGLRQIYYSMNVEVTDKGDVPEG YKVSRKEKRNFPLILESPSPNQTSLYFCASSLGPGLAAYNEQF FGPGTRLTVLEDLKNVFPPEVAVFEPSEAEISHTQKATLVCLA TGFYPDHVELSWWVNGKEVHSGVSTDPQPLKEQPALNDSR YCLSSRLRVSATFWQNPRNHFRCQVQFYGLSENDEWTQDR AKPVTQIVSAEAWGRADCGFTSESYQQGVLSATILYEILLGKA TLYAVLVSALVLMAMVKRKDSRG |
| 17 | R7P1D5 alpha chain | MKTFAGFSFLFLWLQLDCMSRGEDVEQSLFLSVREGDSSVIN CTYTDSSSTYLYWYKQEPGAGLQLLTYIFSNMDMKQDRLTV LLNKKDKHLSLRIADTQTGDSAIYFCAEYSSASKIIFGSGTRLSI RPNIQNPDDAVYQLRDSKSSDKSVCLFTDFDSQTNVSQSKDS DVYITDKTVLDMRSMDFKSNSAVAWSNKSDFACANAFNNSII PEDTFFPSPESSCDVKLVEKSFETDTNLNFQNLSVIGFRILLLK VAGFNLLMTLRLWSS |
| 18 | R7P1D5 beta chain | MGSWTLCCVSLCILVAKHTDAGVIQSPRHEVTEMGQEVTLRC KPISGHDYLFWYRQTMMRGLELLIYFNNNVPIDDSGMPEDRF SAKMPNASFSTLKIQPSEPRDSAVYFCASRANTGELFFGEGS RLTVLEDLKNVFPPEVAVFEPSEAEISHTQKATLVCLATGFYP DHVELSWWVNGKEVHSGVSTDPQPLKEQPALNDSRYCLSS RLRVSATFWQNPRNHFRCQVQFYGLSENDEWTQDRAKPVT QIVSAEAWGRADCGFTSESYQQGVLSATILYEILLGKATLYAV LVSALVLMAMVKRKDSRG |
| 19 | R10P2G12 alpha chain | MLTASLLRAVIASICVVSSMAQKVTQAQTEISVVEKEDVTLDC VYETRDTTYYLFWYKQPPSGELVFLIRRNSFDEQNEISGRYS WNFQKSTSSFNFTITASQVVDSAVYFCALSEGNSGNTPLVFG KGTRLSVIANIQNPDPAVYQLRDSKSSDKSVCLFTDFDSQTNV SQSKDSDVYITDKTVLDMRSMDFKSNSAVAWSNKSDFACAN AFNNSIIPEDTFFPSPESSCDVKLVEKSFETDTNLNFQNLSVIG FRILLLKVAGFNLLMTLRLWSS |
| 20 | R10P2G12 beta chain | MGIRLLCRVAFCFLAVGLVDVKVTQSSRYLVKRTGEKVFLEC VQDMDHENMFWYRQDPGLGLRLIYFSYDVKMKEKGDIPEGY SVSREKKERFSLILESASTNQTSMYLCASSLSSGSHQETQYF GPGTRLLVLEDLKNVFPPEVAVFEPSEAEISHTQKATLVCLAT GFYPDHVELSWWVNGKEVHSGVSTDPQPLKEQPALNDSRY CLSSRLRVSATFWQNPRNHFRCQVQFYGLSENDEWTQDRA KPVTQIVSAEAWGRADCGFTSESYQQGVLSATILYEILLGKAT LYAVLVSALVLMAMVKRKDSRG |
| 21 | R10P1A7 alpha chain | MKTFAGFSFLFLWLQLDCMSRGEDVEQSLFLSVREGDSSVIN CTYTDSSSTYLYWYKQEPGAGLQLLTYIFSNMDMKQDRLTV LLNKKDKHLSLRIADTQTGDSAIYFCAESKETRLMFGDGTQLV VKPNIQNPDDAVYQLRDSKSSDKSVCLFTDFDSQTNVSQSKD SDVYITDKTVLDMRSMDFKSNSAVAWSNKSDFACANAFNNSI IPEDTFFPSPESSCDVKLVEKSFETDTNLNFQNLSVIGFRILLL KVAGFNLLMTLRLWSS |
| 22 | R10P1A7 beta chain | MLLLLLLLGPGISLLLLPGSLAGSGLGAWSQHPSVWICKSGTSV KIECRSLDFQATTMFWYRQFPKQSLMLMATSNEGSKATYEQ GVEKDKFLINHASLTLSTLTVTSAHPEDSSFYICSARAGGHEQ FFGPGTRLTVLEDLKNVFPPEVAVFEPSEAEISHTQKATLVCL ATGFYPDHVELSWWVNGKEVHSGVSTDPQPLKEQPALNDS RYCLSSRLRVSATFWQNPRNHFRCQVQFYGLSENDEWTQD RAKPVTQIVSAEAWGRADCGFTSESYQQGVLSATILYEILLGK ATLYAVLVSALVLMAMVKRKDSRG |
| 23 | R4P1D10 alpha chain | MKSLRVLLVILWLQLSWVWSQQKEVEQNSGPLSVPEGAIASL NCTYSDRGSQSFFWYRQYSGKSPELIMFIYSNGDKEDGRFT AQLNKASQYVSLLIRDSQPSDSATYLCAVNFHDKIIFGKGTRL HILPNIQNPDDAVYQLRDSKSSDKSVCLFTDFDSQTNVSQSK DSDVYITDKTVLDMRSMDFKSNSAVAWSNKSDFACANAFNN SIIPEDTFFPSPESSCDVKLVEKSFETDTNLNFQNLSVIGFRILL LKVAGFNLLMTLRLWSS |
| 24 | R4P1D10 beta chain | MGFRLLCCVAFCLLGAGPVDSGVTQTPKHLITATGQRVTLRC SPRSGDLSVYWYQQSLDQGLQFLIHYYNGEERAKGNILERFS AQQFPDLHSELNLSSLELGDSALYFCASSVASAYGYTFGSGT RLTVVEDLKNVFPPEVAVFEPSEAEISHTQKATLVCLATGFFP |

TABLE 2-continued

DNA and protein sequences

| SEQ ID NO: | Description | Sequence |
|---|---|---|
| | | DHVELSWWVNGKEVHSGVSTDPQPLKEQPALNDSRYCLSS RLRVSATFWQNPRNHFRCQVQFYGLSENDEWTQDRAKPVT QIVSAEAWGRADCGFTSVSYQQGVLSATILYEILLGKATLYAV LVSALVLMAMVKRKDF |
| 25 | R4P3F9 alpha chain | MKSLRVLLVILWLQLSWVWSQQKEVEQNSGPLSVPEGAIASL NCTYSDRGSQSFFWYRQYSGKSPELIMFIYSNGDKEDGRFT AQLNKASQYVSLLIRDSQPSDSATYLCAAYSGAGSYQLTFGK GTKLSVIPNIQNPDDAVYQLRDSKSSDKSVCLFTDFDSQTNVS QSKDSDVYITDKTVLDMRSMDFKSNSAVAWSNKSDFACANA FNNSIIPEDTFFPSPESSCDVKLVEKSFETDTNLNFQNLSVIGF RILLLKVAGFNLLMTLRLWSS |
| 26 | R4P3F9 beta chain | MGFRLLCCVAFCLLGAGPVDSGVTQTPKHLITATGQRVTLRC SPRSGDLSVYWYQQSLDQGLQFLIQYYNGEERAKGNILERFS AQQFPDLHSELNLSSLELGDSALYFCASSVESSYGYTFGSGT RLTVVEDLNKVFPPEVAVFEPSEAEISHTQKATLVCLATGFFP DHVELSWWVNGKEVHSGVSTDPQPLKEQPALNDSRYCLSS RLRVSATFWQNPRNHFRCQVQFYGLSENDEWTQDRAKPVT QIVSAEAWGRADCGFTSVSYQQGVLSATILYEILLGKATLYAV LVSALVLMAMVKRKDF |
| 27 | R4P3H3 alpha chain | MKSLRVLLVILWLQLSWVWSQQKEVEQNSGPLSVPEGAIASL NCTYSDRGSQSFFWYRQYSGKSPELIMFIYSNGDKEDGRFT AQLNKASQYVSLLIRDSQPSDSATYLCAVKAGNQFYFGTGTS LTVIPNIQNPDDAVYQLRDSKSSDKSVCLFTDFDSQTNVSQSK DSDVYITDKTVLDMRSMDFKSNSAVAWSNKSDFACANAFNN SIIPEDTFFPSPESSCDVKLVEKSFETDTNLNFQNLSVIGFRILL LKVAGFNLLMTLRLWSS |
| 28 | R4P3H3 beta chain | MGTRLLCWVVLGFLGTDHTGAGVSQSPRYKVAKRGQDVALR CDPISGHVSLFWYQQALGQGPEFLTYFQNEAQLDKSGLPSD RFFAERPEGSVSTLKIQRTQQEDSAVYLCASSLLTSGGDNEQ FFGPGTRLTVLEDLKNVFPPEVAVFEPSEAEISHTQKATLVCL ATGFYPDHVELSWWVNGKEVHSGVSTDPQPLKEQPALNDS RYCLSSRLRVSATFWQNPRNHFRCQVQFYGLSENDEWTQD RAKPVTQIVSAEAWGRADCGFTSESYQQGVLSATILYEILLGK ATLYAVLVSALVLMAMVKRKDSRG |
| 29 | R36P3F9 alpha chain | METLLGVSLVILWLQLARVNSQQGEEDPQALSIQEGENATMN CSYKTSINNLQWYRQNSGRGLVHLILIRSNEREKHSGRLVTL DTSKKSSSLLITASRAADTASYFCATVSNYQLIWGAGTKLIIKP DIQNPDDAVYQLRDSKSSDKSVCLFTDFDSQTNVSQSKDSDV YITDKTVLDMRSMDFKSNSAVAWSNKSDFACANAFNNSIIPE DTFFPSPESSCDVKLVEKSFETDTNLNFQNLSVIGFRILLLKVA GFNLLMTLRLWSS |
| 30 | R36P3F9 beta chain | MGPQLLGYVVLCLLGAGPLEAQVTQNPRYLITVTGKKLTVTC SQNMNHEYMSWYRQDPGLGLRQIYYSMNVEVTDKGDVPEG YKVSRKEKRNFPLILESPSPNQTSLYFCASSSTGGLSGETQ YFGPGTRLLVLEDLKNVFPPEVAVFEPSEAEISHTQKATLVCL ATGFYPDHVELSWWVNGKEVHSGVSTDPQPLKEQPALNDS RYCLSSRLRVSATFWQNPRNHFRCQVQFYGLSENDEWTQD RAKPVTQIVSAEAWGRADCGFTSESYQQGVLSATILYEILLGK ATLYAVLVSALVLMAMVKRKDSRG |
| 31 | R52P2G11 alpha chain | MKKHLTTFLVILWLYFYRGNGKNQVEQSPQSLIILEGKNCTLQ CNYTVSPFSNLRWYKQDTGRGPVSLTIMTFSENTKSNGRYTA TLDADTKQSSLHITASQLSDSASYICVVSAYGKLQFGAGTQVV VTPDIQNPDDAVYQLRDSKSSDKSVCLFTDFDSQTNVSQSKD SDVYITDKTVLDMRSMDFKSNSAVAWSNKSDFACANAFNNSI IPEDTFFPSPESSCDVKLVEKSFETDTNLNFQNLSVIGFRILLL KVAGFNLLMTLRLWSS |
| 32 | R52P2G11 beta chain | MDSWTFCCVSLCILVAKHTDAGVIQSPRHEVTEMGQEVTLRC KPISGHNSLFWYRQTMMRGLELLIYFNNNVPIDDSGMPEDRF SAKMPNASFSTLKIQPSEPRDSAVYFCASSLGSPDGNQPQHF GDGTRLSILEDLNKVFPPEVAVFEPSEAEISHTQKATLVCLAT GFFPDHVELSWWVNGKEVHSGVSTDPQPLKEQPALNDSRY CLSSRLRVSATFWQNPRNHFRCQVQFYGLSENDEWTQDRA KPVTQIVSAEAWGRADCGFTSVSYQQGVLSATILYEILLGKAT LYAVLVSALVLMAMVKRKDF |
| 33 | R53 P2A9 alpha chain | MACPGFLWALVISTCLEFSMAQTVTQSQPEMSVQEAETVTLS CTYDTSESDYYLFWYKQPPSRQMILVIRQEAYKQQNATENRF |

TABLE 2-continued

DNA and protein sequences

| SEQ ID NO: | Description | Sequence |
|---|---|---|
| | | SVNFQKAAKSFSLKISDSQLGDAAMYFCAYNSYAGGTSYGKL TFGQGTILTVHPNIQNPDPAVYQLRDSKSSDKSVCLFTDFDS QTNVSQSKDSDVYITDKTVLDMRSMDFKSNSAVAWSNKSDF ACANAFNNSIIPEDTFFPSPESSCDVKLVEKSFETDTNLNFQN LSVIGFRILLLKVAGFNLLMTLRLWSS |
| 34 | R53P2A9 beta chain | MGPGLLCWVLLCLLGAGPVDAGVTQSPTHLIKTRGQQVTLRC SPISGHKSVSWYQQVLGQGPQFIFQYYEKEERGRGNFPDRF SARQFPNYSSELNVNALLLGDSALYLCASSLDGTSEQYFGPG TRLTVTEDLKNVFPPEVAVFEPSEAEISHTQKATLVCLATGFY PDHVELSWWVNGKEVHSGVSTDPQPLKEQPALNDSRYCLSS RLRVSATFWQNPRNHFRCQVQFYGLSENDEWTQDRAKPVT QIVSAEAWGRADCGFTSESYQQGVLSATILYEILLGKATLYAV LVSALVLMAMVKRKDSRG |
| 35 | R26P1A9 alpha chain | METLLGVSLVILWLQLARVNSQQGEEDPQALSIQEGENATMN CSYKTSINNLQWYRQNSGRGLVHLILIRSNEREKHSGRLRVTL DTSKKSSSLLITASRAADTASYFCLIGASGSRLTFGEGTQLTV NPDIQNPDPAVYQLRDSKSSDKSVCLFTDFDSQTNVSQSKDS DVYITDKTVLDMRSMDFKSNSAVAWSNKSDFACANAFNNSII PEDTFFPSPESSCDVKLVEKSFETDTNLNFQNLSVIGFRILLLK VAGFNLLMTLRLWSS |
| 36 | R26P1A9 beta chain | MGSWTLCCVSLCILVAKHTDAGVIQSPRHEVTEMGQEVTLRC KPISGHDYLFWYRQTMMRGLELLIYFNNNVPIDDSGMPEDRF SAKMPNASFSTLKIQPSEPRDSAVYFCASSYFGWNEKLFFGS GTQLSVLEDLNKVFPPEVAVFEPSEAEISHTQKATLVCLATGF FPDHVELSWWVNGKEVHSGVSTDPQPLKEQPALNDSRYCLS SRLRVSATFWQNPRNHFRCQVQFYGLSENDEWTQDRAKPV TQIVSAEAWGRADCGFTSVSYQQGVLSATILYEILLGKATLYA VLVSALVLMAMVKRKDF |
| 37 | R26P2A6 alpha chain | MMKSLRVLLVILWLQLSWVWSQQKEVEQDPGPLSVPEGAIV SLNCTYSNSAFQYFMWYRQYSRKGPELLMYTYSSGNKEDG RFTAQVDKSSKYISLFIRDSQPSDSATYLCAMSDVSGGYNKLI FGAGTRLAVHPYIQNPDPAVYQLRDSKSSDKSVCLFTDFDSQ TNVSQSKDSDVYITDKTVLDMRSMDFKSNSAVAWSNKSDFA CANAFNNSIIPEDTFFPSPESSCDVKLVEKSFETDTNLNFQNL SVIGFRILLLKVAGFNLLMTLRLWSS |
| 38 | R26P2A6 beta chain | MGPQLLGYVVLCLLGAGPLEAQVTQNPRYLITVTGKKLTVTC SQNMNHEYMSWYRQDPGLGLRQIYYSMNVEVTDKGDVPEG YKVSRKEKRNFPLILESPSPNQTSLYFCASTTPDGTDEQFFGP GTRLTVLEDLKNVFPPEVAVFEPSEAEISHTQKATLVCLATGF YPDHVELSWWVNGKEVHSGVSTDPQPLKEQPALNDSRYCLS SRLRVSATFWQNPRNHFRCQVQFYGLSENDEWTQDRAKPV TQIVSAEAWGRADCGFTSESYQQGVLSATILYEILLGKATLYA VLVSALVLMAMVKRKDSRG |
| 39 | R26P3H1 alpha chain | MASAPISMLAMLFTLSGLRAQSVAQPEDQVNVAEGNPLTVKC TYSVSGNPYLFWYVQYPNRGLQFLLKYITGDNLVKGSYGFEA EFNKSQTSFHLKKPSALVSDSALYFCAVRDMNRDDKIIFGKGT RLHILPNIQNPDPAVYQLRDSKSSDKSVCLFTDFDSQTNVSQS KDSDVYITDKTVLDMRSMDFKSNSAVAWSNKSDFACANAFN NSIIPEDTFFPSPESSCDVKLVEKSFETDTNLNFQNLSVIGFRIL LLKVAGFNLLMTLRLWSS |
| 40 | R26P3H1 beta chain | MSNQVLCCVVLCFLGANTVDGGITQSPKYLFRKEGQNVTLSC EQNLNHDAMYWYRQDPGQGLRLIYYSQIVNDFQKGDIAEGY SVSREKKESFPLTVTSAQKNPTAFYLCASSRAEGGEQYFGPG TRLTVTEDLKNVFPPEVAVFEPSEAEISHTQKATLVCLATGFY PDHVELSWWVNGKEVHSGVSTDPQPLKEQPALNDSRYCLSS RLRVSATFWQNPRNHFRCQVQFYGLSENDEWTQDRAKPVT QIVSAEAWGRADCGFTSESYQQGVLSATILYEILLGKATLYAV LVSALVLMAMVKRKDSRG |
| 41 | R35P3A4 alpha chain | MTSIRAVFIFLWLQLDLVNGENVEQHPSTLSVQEGDSAVIKCT YSDSASNYFPWYKQELGKRPQUIDIRSNVGEKKDQRIAVTLN KTAKHFSLHITETQPEDSAVYFCAASPTGGYNKLIFGAGTRLA VHPYIQNPDPAVYQLRDSKSSDKSVCLFTDFDSQTNVSQSKD SDVYITDKTVLDMRSMDFKSNSAVAWSNKSDFACANAFNNSI IPEDTFFPSPESSCDVKLVEKSFETDTNLNFQNLSVIGFRILLL KVAGFNLLMTLRLWSS |

TABLE 2-continued

DNA and protein sequences

| SEQ ID NO: | Description | Sequence |
|---|---|---|
| 42 | R35P3A4 beta chain | MSIGLLCCAALSLLWAGPVNAGVTQTPKFQVLKTGQSMTLQC AQDMNHEYMSWYRQDPGMGLRLIHYSVGAGITDQGEVPNG YNVSRSTTEDFPLRLLSAAPSQTSVYFCASSLGGASQEQYFG PGTRLTVTEDLKNVFPPEVAVFEPSEAEISHTQKATLVCLATG FYPDHVELSWWVNGKEVHSGVSTDPQPLKEQPALNDSRYCL SSRLRVSATFWQNPRNHFRCQVQFYGLSENDEWTQDRAKP VTQIVSAEAWGRADCGFTSESYQQGVLSATILYEILLGKATLY AVLVSALVLMAMVKRKDSRG |
| 43 | R37P1C9 alpha chain | MKLVTSITVLLSLGIMGDAKTTQPNSMESNEEEPVHLPCNHST ISGTDYIHWYRQLPSQGPEYVIHGLTSNVNNRMASLAIAEDRK SSTLILHRATLRDAAVYYCILFNFNKFYFGSGTKLNVKPNIQNP DPAVYQLRDSKSSDKSVCLFTDFDSQTNVSQSKDSDVYITDK TVLDMRSMDFKSNSAVAWSNKSDFACANAFNNSIIPEDTFFP SPESSCDVKLVEKSFETDTNLNFQNLSVIGFRILLLKVAGFNLL MTLRLWSS |
| 44 | R37P1C9 beta chain | MGPGLLHWMALCLLGTGHGDAMVIQNPRYQVTQFGKPVTLS CSQTLNHNVMYWYQQKSSQAPKLLFHYYDKDFNNEADTPDN FQSRRPNTSFCFLDIRSPGLGDAAMYLCATSSGETNEKLFFG SGTQLSVLEDLNKVFPPEVAVFEPSEAEISHTQKATLVCLATG FFPDHVELSWWVNGKEVHSGVSTDPQPLKEQPALNDSRYCL SSRLRVSATFWQNPRNHFRCQVQFYGLSENDEWTQDRAKP VTQIVSAEAWGRADCGFTSVSYQQGVLSATILYEILLGKATLY AVLVSALVLMAMVKRKDF |
| 45 | R37P1H1 alpha chain | MTRVSLLWAVVVSTCLESGMAQTVTQSQPEMSVQEAETVTL SCTYDTSESNYYLFWYKQPPSRQMILVIRQEAYKQQNATENR FSVNFQKAAKSFSLKISDSQLGDTAMYFCAFGYSGGGADGLT FGKGTHLIIQPYIQNPDDPAVYQLRDSKSSDKSVCLFTDFDSQT NVSQSKDSDVYITDKTVLDMRSMDFKSNSAVAWSNKSDFAC ANAFNNSIIPEDTFFPSPESSCDVKLVEKSFETDTNLNFQNLS VIGFRILLLKVAGFNLLMTLRLWSS |
| 46 | R37P1H1 beta chain | MGPGLLCWALLCLLGAGLVDAGVTQSPTHLIKTRGQQVTLRC SPKSGHDTVSWYQQALGQGPQFIFQYYEEEERQRGNFPDRF SGHQFPNYSSELNVNALLLGDSALYLCASSNEGQGWEAEAF FGQGTRLTVVEDLNKVFPPEVAVFEPSEAEISHTQKATLVCLA TGFFPDHVELSWWVNGKEVHSGVSTDPQPLKEQPALNDSRY CLSSRLRVSATFWQNPRNHFRCQVQFYGLSENDEWTQDRA KPVTQIVSAEAWGRADCGFTSVSYQQGVLSATILYEILLGKAT LYAVLVSALVLMAMVKRKDF |
| 47 | R42P3A9 alpha chain | MKRILGALLGLLSAQVCCVRGIQVEQSPPDLILQEGANSTLRC NFSDSVNNLQWFHQNPWGQLINLFYIPSGTKQNGRLSATTVA TERYSLLYISSSQTTDSGVYFCAVHNFNKFYFGSGTKLNVKP NIQNPDPAVYQLRDSKSSDKSVCLFTDFDSQTNVSQSKDSDV YITDKTVLDMRSMDFKSNSAVAWSNKSDFACANAFNNSIIPE DTFFPSPESSCDVKLVEKSFETDTNLNFQNLSVIGFRILLLKVA GFNLLMTLRLWSS |
| 48 | R42P3A9 beta chain | MLSPDLPDSAWNTRLLCHVMLCLLGAVSVAAGVIQSPRHLIK EKRETATLKCYPIPRHDTVYWYQQGPGQDPQFLISFYEKMQS DKGSIPDRFSAQQFSDYHSELNMSSLELGDSALYFCASSLLG QGYNEQFFGPGTRLTVLEDLKNVFPPEVAVFEPSEAEISHTQ KATLVCLATGFYPDHVELSWWVNGKEVHSGVSTDPQPLKEQ PALNDSRYCLSSRLRVSATFWQNPRNHFRCQVQFYGLSEND EWTQDRAKPVTQIVSAEAWGRADCGFTSESYQQGVLSATILY EILLGKATLYAVLVSALVLMAMVKRKDSRG |
| 49 | R43P3F2 alpha chain | MLTASLLRAVIASICVVSSMAQKVTQAQTEISVVEKEDVTLDC VYETRDTTYYLFWYKQPPSGELVFLIRRNSFDEQNEISGRYS WNFQKSTSSFNFTITASQVVDSAVYFCALSNNNAGNMLTFGG GTRLMVKPHIQNPDDPAVYQLRDSKSSDKSVCLFTDFDSQTNV SQSKDSDVYITDKTVLDMRSMDFKSNSAVAWSNKSDFACAN AFNNSIIPEDTFFPSPESSCDVKLVEKSFETDTNLNFQNLSVIG FRILLLKVAGFNLLMTLRLWSS |
| 50 | R43P3F2 beta chain | MLSPDLPDSAWNTRLLCHVMLCLLGAVSVAAGVIQSPRHLIK EKRETATLKCYPIPRHDTVYWYQQGPGQDPQFLISFYEKMQS DKGSIPDRFSAQQFSDYHSELNMSSLELGDSALYFCASSPTG TSGYNEQFFGPGTRLTVLEDLKNVFPPEVAVFEPSEAEISHTQ KATLVCLATGFYPDHVELSWWVNGKEVHSGVSTDPQPLKEQ PALNDSRYCLSSRLRVSATFWQNPRNHFRCQVQFYGLSEND |

TABLE 2-continued

DNA and protein sequences

| SEQ ID NO: | Description | Sequence |
|---|---|---|
| | | EWTQDRAKPVTQIVSAEAWGRADCGFTSESYQQGVLSATILY EILLGKATLYAVLVSALVLMAMVKRKDSRG |
| 51 | R43P3G5 alpha chain | MEKNPLAAPLLILWFHLDCVSSILNVEQSPQSLHVQEGDSTNF TCSFPSSNFYALHWYRWETAKSPEALFVMTLNGDEKKKGRIS ATLNTKEGYSYLYIKGSQPEDSATYLCALNRDDKIIFGKGTRL HILPNIQNPDPAVYQLRDSKSSDKSVCLFTDFDSQTNVSQSK DSDVYITDKTVLDMRSMDFKSNSAVAWSNKSDFACANAFNN SIIPEDTFFPSPESSCDVKLVEKSFETDTNLNFQNLSVIGFRILL LKVAGFNLLMTLRLWSS |
| 52 | R43P3G5 beta chain | MGIRLLCRVAFCFLAVGLVDVKVTQSSRYLVKRTGEKVFLEC VQDMDHENMFWYRQDPGLGLRLIYFSYDVKMKEKGDIPEGY SVSREKKERFSLILESASTNQTSMYLCASRLPSRTYEQYFGP GTRLTVTEDLKNVFPPEVAVFEPSEAEISHTQKATLVCLATGF YPDHVELSWWVNGKEVHSGVSTDPQPLKEQPALNDSRYCLS SRLRVSATFWQNPRNHFRCQVQFYGLSENDEWTQDRAKPV TQIVSAEAWGRADCGFTSESYQQGVLSATILYEILLGKATLYA VLVSALVLMAMVKRKDSRG |
| 53 | R59P2E7 alpha chain | METLLGLLILWLQLQWVSSKQEVTQIPAALSVPEGENLVLNCS FTDSAIYNLQWFRQDPGKGLTSLLLIQSSQREQTSGRLNASL DKSSGRSTLYIAASQPGDSATYLCAVNSDYKLSFGAGTTVTV RANIQNPDPAVYQLRDSKSSDKSVCLFTDFDSQTNVSQSKDS DVYITDKTVLDMRSMDFKSNSAVAWSNKSDFACANAFNNSII PEDTFFPSPESSCDVKLVEKSFETDTNLNFQNLSVIGFRILLLK VAGFNLLMTLRLWSS |
| 54 | R59P2E7 beta chain | MLSPDLPDSAWNTRLLCHVMLCLLGAVSVAAGVIQSPRHLIK EKRETATLKCYPIPRHDTVYWYQQGPGQDPQFLISFYEKMQS DKGSIPDRFSAQQFSDYHSELNMSSLELGDSALYFCASSLGL GTGDYGYTFGSGTRLTVVEDLNKVFPPEVAVFEPSEAEISHT QKATLVCLATGFFPDHVELSWWVNGKEVHSGVSTDPQPLKE QPALNDSRYCLSSRLRVSATFWQNPRNHFRCQVQFYGLSEN DEWTQDRAKPVTQIVSAEAWGRADCGFTSVSYQQGVLSATI LYEILLGKATLYAVLVSALVLMAMVKRKDF |
| 55 | R11P3D3 alpha chain | MEKNPLAAPLLILWFHLDCVSSILNVEQSPQSLHVQEGDSTNF TCSFPSSNFYALHWYRWETAKSPEALFVMTLNGDEKKKGRIS ATLNTKEGYSYLYIKGSQPEDSATYLCALYNNNDMRFGAGTR LTVKPNIQNPDPAVYQLRDSKSSDKSVCLFTDFDSQTNVSQS KDSDVYITDKTVLDMRSMDFKSNSAVAWSNKSDFACANAFN NSIIPEDTFFPSPESSCDVKLVEKSFETDTNLNFQNLSVIGFRIL LLKVAGFNLLMTLRLWSS |
| 56 | R11P3D3 beta chain | MDSWTFCCVSLCILVAKHTDAGVIQSPRHEVTEMGQEVTLRC KPISGHNSLFWYRQTMMRGLELLIYFNNNVPIDDSGMPEDRF SAKMPNASFSTLKIQPSEPRDSAVYFCASSPGSTDTQYFGPG TRLTVLEDLKNVFPPEVAVFEPSEAEISHTQKATLVCLATGFY PDHVELSWWVNGKEVHSGVSTDPQPLKEQPALNDSRYCLSS RLRVSATFWQNPRNHFRCQVQFYGLSENDEWTQDRAKPVT QIVSAEAWGRADCGFTSESYQQGVLSATILYEILLGKATLYAV LVSALVLMAMVKRKDSRG |
| 57 | R16P1C10 alpha chain | MKSLRVLLVILWLQLSWVWSQQKEVEQNSGPLSVPEGAIASL NCTYSDRGSQSFFWYRQYSGKSPELIMFIYSNGDKEDGRFT AQLNKASQYVSLLIRDSQPSDSATYLCAAVISNFGNEKLTFGT GTRLTIIPNIQNPDPAVYQLRDSKSSDKSVCLFTDFDSQTNVS QSKDSDVYITDKTVLDMRSMDFKSNSAVAWSNKSDFACANA FNNSIIPEDTFFPSPESSCDVKLVEKSFETDTNLNFQNLSVIGF RILLLKVAGFNLLMTLRLWSS |
| 58 | R16P1C10 beta chain | MGSRLLCWVLLCLLGAGPVKAGVTQTPRYLIKTRGQQVTLSC SPISGHRSVSWYQQTPGQGLQFLFEYFSETQRNKGNFPGRF SGRQFSNSRSEMNVSTLELGDSALYLCASSPWDSPNEQYFG PGTRLTVTEDLKNVFPPEVAVFEPSEAEISHTQKATLVCLATG FYPDHVELSWWVNGKEVHSGVSTDPQPLKEQPALNDSRYCL SSRLRVSATFWQNPRNHFRCQVQFYGLSENDEWTQDRAKP VTQIVSAEAWGRADCGFTSESYQQGVLSATILYEILLGKATLY AVLVSALVLMAMVKRKDSRG |
| 59 | R16P1E8 alpha chain | MMKSLRVLLVILWLQLSWVWSQQKEVEQDPGPLSVPEGAIV SLNCTYSNSAFQYFMWYRQYSRKGPELLMYTYSSGNKEDG RFTAQVDKSSKYISLFIRDSQPSDSATYLCAMSEAAGNKLTFG GGTRVLVKPNIQNPDPAVYQLRDSKSSDKSVCLFTDFDSQTN |

TABLE 2-continued

DNA and protein sequences

| SEQ ID NO: | Description | Sequence |
|---|---|---|
| | | VSQSKDSDVYITDKTVLDMRSMDFKSNSAVAWSNKSDFACA NAFNNSIIPEDTFFPSPESSCDVKLVEKSFETDTNLNFQNLSVI GFRILLLKVAGFNLLMTLRLWSS |
| 60 | R16P1E8 beta chain | MGTRLLCWAALCLLGAELTEAGVAQSPRYKIIEKRQSVAFWC NPISGHATLYWYQQILGQGPKLLIQFQNNGVVDDSQLPKDRF SAERLKGVDSTLKIQPAKLEDSAVYLCASSYTNQGEAFFGQG TRLTVVEDLNKVFPPEVAVFEPSEAEISHTQKATLVCLATGFF PDHVELSWWVNGKEVHSGVSTDPQPLKEQPALNDSRYCLSS RLRVSATFWQNPRNHFRCQVQFYGLSENDEWTQDRAKPVT QIVSAEAWGRADCGFTSVSYQQGVLSATILYEILLGKATLYAV LVSALVLMAMVKRKDF |
| 61 | R17P1A9 alpha chain | MKSLRVLLVILWLQLSWVWSQQKEVEQNSGPLSVPEGAIASL NCTYSDRGSQSFFWYRQYSGKSPELIMSIYSNGDKEDGRFT AQLNKASQYVSLLIRDSQPSDSATYLCAVLNQAGTALIFGKGT TLSVSSNIQNPDPAVYQLRDSKSSDKSVCLFTDFDSQTNVSQ SKDSDVYITDKTVLDMRSMDFKSNSAVAWSNKSDFACANAF NNSIIPEDTFFPSPESSCDVKLVEKSFETDTNLNFQNLSVIGFR ILLLKVAGFNLLMTLRLWSS |
| 62 | R17P1A9 beta chain | MGFRLLCCVAFCLLGAGPVDSGVTQTPKHLITATGQRVTLRC SPRSGDLSVYWYQQSLDQGLQFLIQYYNGEERAKGNILERFS AQQFPDLHSELNLSSLELGDSALYFCASSAETGPWLGNEQFF GPGTRLTVLEDLKNVFPPEVAVFEPSEAEISHTQKATLVCLAT GFYPDHVELSWWVNGKEVHSGVSTDPQPLKEQPALNDSRY CLSSRLRVSATFWQNPRNHFRCQVQFYGLSENDEWTQDRA KPVTQIVSAEAWGRADCGFTSESYQQGVLSATILYEILLGKAT LYAVLVSALVLMAMVKRKDSRG |
| 63 | R17P1D7 alpha chain | MACPGFLWALVISTCLEFSMAQTVTQSQPEMSVQEAETVTLS CTYDTSESDYYLFWYKQPPSRQMILVIRQEAYKQQNATENRF SVNFQKAAKSFSLKISDSQLGDAAMYFCAYRWAQGGSEKLV FGKGTKLTVNPYIQKPDPAVYQLRDSKSSDKSVCLFTDFDSQ TNVSQSKDSDVYITDKTVLDMRSMDFKSNSAVAWSNKSDFA CANAFNNSIIPEDTFFPSPESSCDVKLVEKSFETDTNLNFQNL SVIGFRILLLKVAGFNLLMTLRLWSS |
| 64 | R17P1D7 beta chain | MTIRLLCYMGFYFLGAGLMEADIYQTPRYLVIGTGKKITLECSQ TMGHDKMYWYQQDPGMELHLIHYSYGVNSTEKGDLSSESTV SRIRTEHFPLTLESARPSHTSQYLCATELWSSGGTGELFFGE GSRLTVLEDLKNVFPPEVAVFEPSEAEISHTQKATLVCLATGF YPDHVELSWWVNGKEVHSGVSTDPQPLKEQPALNDSRYCLS SRLRVSATFWQNPRNHFRCQVQFYGLSENDEWTQDRAKPV TQIVSAEAWGRADCGFTSESYQQGVLSATILYEILLGKATLYA VLVSALVLMAMVKRKDSRG |
| 65 | R17P1G3 alpha chain | IMSIYSNGDKEDGRFTAQLNKASQYVSLLIRDSQPSDSATYLC AVGPSGTYKYIFGTGTRLKVLANIQNPDPAVYQLRDSKSSDK SVCLFTDFDSQTNVSQSKDSDVYITDKTVLDMRSMDFKSNSA VAWSNKSDFACANAFNNSIIPEDTFFPSPESSCDVKLVEKSFE TDTNLNFQNLSVIGFRILLLKVAGFNLLMTLRLWSS |
| 66 | R17P1G3 beta chain | MGPQLLGYVVLCLLGAGPLEAQVTQNPRYLITVTGKKLTVTC SQNMNHEYMSWYRQDPGLGLRQIYYSMNVEVTDKGDVPEG YKVSRKEKRNFPLILESPSPNQTSLYFCASSPGGSGNEQFFG PGTRLTVLEDLKNVFPPEVAVFEPSEAEISHTQKATLVCLATG FYPDHVELSWWVNGKEVHSGVSTDPQPLKEQPALNDSRYCL SSRLRVSATFWQNPRNHFRCQVQFYGLSENDEWTQDRAKP VTQIVSAEAWGRADCGFTSESYQQGVLSATILYEILLGKATLY AVLVSALVLMAMVKRKDSRG |
| 67 | R17P2B6 alpha chain | MKSLRVLLVILWLQLSWVWSQQKEVEQNSGPLSVPEGAIASL NCTYSDRGSQSFFWYRQYSGKSPELIMFIYSNGDKEDGRFT AQLNKASQYVSLLIRDSQPSDSATYLCAVVSGGGADGLTFGK GTHLLIQPYIQKPDPAVYQLRDSKSSDKSVCLFTDFDSQTNVS QSKDSDVYITDKTVLDMRSMDFKSNSAVAWSNKSDFACANA FNNSIIPEDTFFPSPESSCDVKLVEKSFETDTNLNFQNLSVIGF RILLLKVAGFNLLMTLRLWSS |
| 68 | R17P2B6 beta chain | MLSPDLPDSAWNTRLLCHVMLCLLGAVSVAAGVIQSPRHLIK EKRETATLKCYPIPRHDTVYWYQQGPGQDPQFLISFYEKMQS DKGSIPDRFSAQQFSDYHSELNMSSLELGDSALYFCASSLGR GGQPQHFGDGTRLSILEDLKNVFPPEVAVFEPSEAEISHTQK ATLVCLATGFFPDHVELSWWVNGKEVHSGVSTDPQPLKEQP |

TABLE 2-continued

DNA and protein sequences

| SEQ ID NO: | Description | Sequence |
|---|---|---|
| | | ALNDSRYCLSSRLRVSATFWQNPRNHFRCQVQFYGLSENDE WTQDRAKPVTQIVSAEAWGRADCGFTSVSYQQGVLSATILYE ILLGKATLYAVLVSALVLMAMVKRKDF |
| 69 | R11P3D3KE alpha chain | MEKNPLAAPLLILWFHLDCVSSILNVEQSPQSLHVQEGDSTNF TCSFPSSNFYALHWYRKETAKSPEALFVMTLNGDEKKKGRIS ATLNTKEGYSYLYIKGSQPEDSATYLCALYNNNDMRFGAGTR LTVKPNIQNPDPAVYQLRDSKSSDKSVCLFTDFDSQTNVSQS KDSDVYITDKTVLDMRSMDFKSNSAVAWSNKSDFACANAFN NSIIPEDTFFPSPESSCDVKLVEKSFETDTNLNFQNLSVIGFRIL LLKVAGFNLLMTLRLWSS |
| 70 | R11P3D3KE beta chain | NNNVPIDDSGMPEDRFSAKMPNASFSTLKIQPSEPRDSAVYF CASSPGSTDTQYFGPGTRLTVLEDLKNVFPPEVAVFEPSEAEI SHTQKATLVCLATGFYPDHVELSWWVNGKEVHSGVSTDPQP LKEQPALNDSRYCLSSRLRVSATFWQNPRNHFRCQVQFYGL SENDEWTQDRAKPVTQIVSAEAWGRADCGFTSESYQQGVLS ATILYEILLGKATLYAVLVSALVLMAMVKRKDSRG |
| 71 | R39P1C12 alpha chain | TYLYWYKQEPGAGLQLLTYIFSNMDMKQDQRLTVLLNKKDKH LSLRIADTQTGDSAIYFCAEIDNQGGKLIFGQGTELSVKPNIQN PDPAVYQLRDSKSSDKSVCLFTDFDSQTNVSQSKDSDVYITD KTVLDMRSMDFKSNSAVAWSNKSDFACANAFNNSIIPEDTFF PSPESSCDVKLVEKSFETDTNLNFQNLSVIGFRILLLKVAGFNL LMTLRLWSS |
| 72 | R39P1C12 beta chain | MGPGLLCWALLCLLGAGLVDAGVTQSPTHLIKTRGQQVTLRC SPKSGHDTVSWYQQALGQGPQFIFQYYEEEERQRGNFPDRF SGHQFPNYSSELNVNALLLGDSALYLCASSQLNTEAFFGQGT RLTVVEDLNKVFPPEVAVFEPSEAEISHTQKATLVCLATGFFP DHVELSWWVNGKEVHSGVSTDPQPLKEQPALNDSRYCLSS RLRVSATFWQNPRNHFRCQVQFYGLSENDEWTQDRAKPVT QIVSAEAWGRADCGFTSVSYQQGVLSATILYEILLGKATLYAV LVSALVLMAMVKRKDF |
| 73 | R39P1F5 alpha chain | MKSLRVLLVILWLQLSWVWSQQKEVEQNSGPLSVPEGAIASL NCTYSDRGSQSFFWYRQYSGKSPELIMFIYSNGDKEDGRFT AQLNKASQYVSLLIRDSQPSDSATYLCAVNNARLMFGDGTQL VVKPNIQNPDPAVYQLRDSKSSDKSVCLFTDFDSQTNVSQSK DSDVYITDKTVLDMRSMDFKSNSAVAWSNKSDFACANAFNN SIIPEDTFFPSPESSCDVKLVEKSFETDTNLNFQNLSVIGFRILL LKVAGFNLLMTLRLWSS |
| 74 | R39P1F5 beta chain | MDTWLVCWAIFSLLKAGLTEPEVTQTPSHQVTQMGQEVILRC VPISNHLYFYWYRQILGQKVEFLVSFYNNEISEKSEIFDDQFSV ERPDGSNFTLKIRSTKLEDSAMYFCASSGQGANEQYFGPGT RLTVTEDLKNVFPPEVAVFEPSEAEISHTQKATLVCLATGFYP DHVELSWWVNGKEVHSGVSTDPQPLKEQPALNDSRYCLSS RLRVSATFWQNPRNHFRCQVQFYGLSENDEWTQDRAKPVT QIVSAEAWGRADCGFTSESYQQGVLSATILYEILLGKATLYAV LVSALVLMAMVKRKDSRG |
| 75 | R40P1C2 alpha chain | MACPGFLWALVISTCLEFSMAQTVTQSQPEMSVQEAETVTLS CTYDTSESDYYLFWYKQPPSRQMILVIRQEAYKQQNATENRF SVNFQKAAKSFSLKISDSQLGDAAMYFCAYLNYQLIWGAGTK LIIKPDIQNPDPAVYQLRDSKSSDKSVCLFTDFDSQTNVSQSK DSDVYITDKTVLDMRSMDFKSNSAVAWSNKSDFACANAFNN SIIPEDTFFPSPESSCDVKLVEKSFETDTNLNFQNLSVIGFRILL LKVAGFNLLMTLRLWSS |
| 76 | R40P1C2 beta chain | MDTWLVCWAIFSLLKAGLTEPEVTQTPSHQVTQMGQEVILRC VPISNHLYFYWYRQILGQKVEFLVSFYNNEISEKSEIFDDQFSV ERPDGSNFTLKIRSTKLEDSAMYFCASSEMTAVGQYFGPGTR LTVTEDLKNVFPPEVAVFEPSEAEISHTQKATLVCLATGFYPD HVELSWWVNGKEVHSGVSTDPQPLKEQPALNDSRYCLSSRL RVSATFWQNPRNHFRCQVQFYGLSENDEWTQDRAKPVTQIV SAEAWGRADCGFTSESYQQGVLSATILYEILLGKATLYAVLVS ALVLMAMVKRKDSRG |
| 77 | R41P3E6 alpha chain | MKSLRVLLVILWLQLSWVWSQQKEVEQNSGPLSVPEGAIASL NCTYSDRGSQSFFWYRQYSGKSPELIMFIYSNGDKEDGRFT AQLNKASQYVSLLIRDSQPSDSATYLCAAFSGYALNFGKGTS LLVTPHIQNPDPAVYQLRDSKSSDKSVCLFTDFDSQTNVSQS KDSDVYITDKTVLDMRSMDFKSNSAVAWSNKSDFACANAFN |

TABLE 2-continued

DNA and protein sequences

| SEQ ID NO: | Description | Sequence |
|---|---|---|
| | | NSIIPEDTFFPSPESSCDVKLVEKSFETDTNLNFQNLSVIGFRIL LLKVAGFNLLMTLRLWSS |
| 78 | R41P3E6 beta chain | MDTWLVCWAIFSLLKAGLTEPEVTQTPSHQVTQMGQEVILRC VPISNHLYFWYRQILGQKVEFLVSFYNNEISEKSEIFDDQFSV ERPDGSNFTLKIRSTKLEDSAMYFCASSQYTGELFFGEGSRL TVLEDLKNVFPPEVAVFEPSEAEISHTQKATLVCLATGFYPDH VELSWWVNGKEVHSGVSTDPQPLKEQPALNDSRYCLSSRLR VSATFWQNPRNHFRCQVQFYGLSENDEWTQDRAKPVTQIVS AEAWGRADCGFTSESYQQGVLSATILYEILLGKATLYAVLVSA LVLMAMVKRKDSRG |
| 79 | R43P3G4 alpha chain | MKSLRVLLVILWLQLSWVWSQQKEVEQNSGPLSVPEGAIASL NCTYSDRGSQSFFWYRQYSGKSPELIMFIYSNGDKEDGRFT AQLNKASQYVSLLIRDSQPSDSATYLCAVNGGDMRFGAGTRL TVKPNIQNPDPAVYQLRDSKSSDKSVCLFTDFDSQTNVSQSK DSDVYITDKTVLDMRSMDFKSNSAVAWSNKSDFACANAFNN SIIPEDTFFPSPESSCDVKLVEKSFETDTNLNFQNLSVIGFRILL LKVAGFNLLMTLRLWSS |
| 80 | R43P3G4 beta chain | MDTWLVCWAIFSLLKAGLTEPEVTQTPSHQVTQMGQEVILRC VPISNHLYFWYRQILGQKVEFLVSFYNNEISEKSEIFDDQFSV ERPDGSNFTLKIRSTKLEDSAMYFCASSGQGALEQYFGPGTR LTVTEDLKNVFPPEVAVFEPSEAEISHTQKATLVCLATGFYPD HVELSWWVNGKEVHSGVSTDPQPLKEQPALNDSRYCLSSRL RVSATFWQNPRNHFRCQVQFYGLSENDEWTQDRAKPVTQIV SAEAWGRADCGFTSESYQQGVLSATILYEILLGKATLYAVLVS ALVLMAMVKRKDSRG |
| 81 | R44P3B3 alpha chain | MAMLLGASVLILWLQPDWVNSQQKNDDQQVKQNSPSLSVQ EGRISILNCDYTNSMFDYFLWYKKYPAEGPTFLISISSIKDKNE DGRFTVFLNKSAKHLSLHIVPSQPGDSAVYFCAASGLYNQGG KLIFGQGTELSVKPNIQNPDPAVYQLRDSKSSDKSVCLFTDFD SQTNVSQSKDSDVYITDKTVLDMRSMDFKSNSAVAWSNKSD FACANAFNNSIIPEDTFFPSPESSCDVKLVEKSFETDTNLNFQ NLSVIGFRILLLKVAGFNLLMTLRLWSS |
| 82 | R44P3B3 beta chain | MGCRLLCCVVFCLLQAGPLDTAVSQTPKYLVTQMGNDKSIKC EQNLGHDTMYWYKQDSKKFLKIMFSYNNKELIINETVPNRFSP KSPDKAHLNLHINSLELGDSAVYFCASSLGDRGYEQYFGPGT RLTVTEDLKNVFPPEVAVFEPSEAEISHTQKATLVCLATGFYP DHVELSWWVNGKEVHSGVSTDPQPLKEQPALNDSRYCLSS RLRVSATFWQNPRNHFRCQVQFYGLSENDEWTQDRAKPVT QIVSAEAWGRADCGFTSESYQQGVLSATILYEILLGKATLYAV LVSALVLMAMVKRKDSRG |
| 83 | R44P3E7 alpha chain | MKTFAGFSFLFLWLQDCMSRGEDVEQSLFLSVREGDSSVIN CTYTDSSSTYLYWYKQEPGAGLQLLTYIFSNMDMKQDQRLTV LLNKKDKHLSLRIADTQTGDSAIYFCAEINNNARLMFGDGTQL VVKPNIQNPDPAVYQLRDSKSSDKSVCLFTDFDSQTNVSQSK DSDVYITDKTVLDMRSMDFKSNSAVAWSNKSDFACANAFNN SIIPEDTFFPSPESSCDVKLVEKSFETDTNLNFQNLSVIGFRILL LKVAGFNLLMTLRLWSS |
| 84 | R44P3E7 beta chain | MLSPDLPDSAWNTRLLCHVMLCLLGAVSVAAGVIQSPRHLIK EKRETATLKCYPIPRHDTVYWYQQGPGQDPQFLISFYEKMQS DKGSIPDRFSAQQFSDYHSELNMSSLELGDSALYFCASSPPD QNTQYFGPGTRLTVLEDLKNVFPPEVAVFEPSEAEISHTQKAT LVCLATGFYPDHVELSWWVNGKEVHSGVSTDPQPLKEQPAL NDSRYCLSSRLRVSATFWQNPRNHFRCQVQFYGLSENDEW TQDRAKPVTQIVSAEAWGRADCGFTSESYQQGVLSATILYEIL LGKATLYAVLVSALVLMAMVKRKDSRG |
| 85 | R49P2B7 alpha chain | MLLLLVPVLEVIFTLGGTRAQSVTQLGSHVSVSEGALVLLRCN YSSSVPPYLFWYVQYPNQGLQLLLKYTTGATLVKGINGFEAE FKKSETSFHLTKPSAHMSDAAEYFCAVRIFGNEKLTFGTGTRL TIIPNIQNPDPAVYQLRDSKSSDKSVCLFTDFDSQTNVSQSKD SDVYITDKTVLDMRSMDFKSNSAVAWSNKSDFACANAFNNSI IPEDTFFPSPESSCDVKLVEKSFETDTNLNFQNLSVIGFRILLL KVAGFNLLMTLRLWSS |
| 86 | R49P2B7 beta chain | MGIRLLCRVAFCFLAVGLVDVKVTQSSRYLVKRTGEKVFLEC VQDMDHENMFWYRQDPGLGLRLIYFSYDVKMKEKGDIPEGY SVSREKKERFSLILESASTNQTSMYLCASSLMGELTGELFFGE GSRLTVLEDLKNVFPPEVAVFEPSEAEISHTQKATLVCLATGF |

TABLE 2-continued

DNA and protein sequences

| SEQ ID NO: | Description | Sequence |
|---|---|---|
| | | YPDHVELSWWVNGKEVHSGVSTDPQPLKEQPALNDSRYCLS SRLRVSATFWQNPRNHFRCQVQFYGLSENDEWTQDRAKPV TQIVSAEAWGRADCGFTSESYQQGVLSATILYEILLGKATLYA VLVSALVLMAMVKRKDSRG |
| 87 | R55P1G7 alpha chain | MMKSLRVLLVILWLQLSWVWSQQKEVEQDPGPLSVPEGAIV SLNCTYSNSAFQYFMWYRQYSRKGPELLMYTYSSGNKEDG RFTAQVDKSSKYISLFIRDSQPSDSATYLCAMMGDTGTASKLT FGTGTRLQVTLDIQNPDDPAVYQLRDSKSSDKSVCLFTDFDSQ TNVSQSKDSDVYITDKTVLDMRSMDFKSNSAVAWSNKSDFA CANAFNNSIIPEDTFFPSPESSCDVKLVEKSFETDTNLNFQNL SVIGFRILLLKVAGFNLLMTLRLWSS |
| 88 | R55P1G7 beta chain | MGIRLLCRVAFCFLAVGLVDVKVTQSSRYLVKRTGEKVFLEC VQDMDHENMFWYRQDPGLGLRLIYFSYDVKMKEKGDIPEGY SVSREKKERFSLILESASTNQTSMYLCASSFGGYEQYFGPGT RLTVTEDLKNVFPPEVAVFEPSEAEISHTQKATLVCLATGFYP DHVELSWWVNGKEVHSGVSTDPQPLKEQPALNDSRYCLSS RLRVSATFWQNPRNHFRCQVQFYGLSENDEWTQDRAKPVT QIVSAEAWGRADCGFTSESYQQGVLSATILYEILLGKATLYAV LVSALVLMAMVKRKDSRG |
| 89 | R59P2A7 alpha chain | VKPNIQNPDPAVYQLRDSKSSDKSVCLFTDFDSQTNVSQSKD SDVYITDKTVLDMRSMDFKSNSAVAWSNKSDFACANAFNNSI IPEDTFFPSPESSCDVKLVEKSFETDTNLNFQNLSVIGFRILLL KVAGFNLLMTLRLWSS |
| 90 | R59P2A7 beta chain | MLCSLLALLLGTFFGVRSQTIHQWPATLVQPVGSPLSLECTVE GTSNPNLYWYRQAAGRGLQLLFYSVGIGQISSEVPQNLSASR PQDRQFILSSKKLLLLSDSGFYLCAWSGLVAEQFFGPGTRLTV LEDLKNVFPPEVAVFEPSEAEISHTQKATLVCLATGFYPDHVE LSWWVNGKEVHSGVSTDPQPLKEQPALNDSRYCLSSRLRVS ATFWQNPRNHFRCQVQFYGLSENDEWTQDRAKPVTQIVSAE AWGRADCGFTSESYQQGVLSATILYEILLGKATLYAVLVSALV LMAMVKRKDSRG |
| 91 | PTE WPRE | tgaaagaccccacctgtaggtttggcaagctagcttaagtaacgccattttgcaaggca tggaaaatacataactgagaatagagaagttcagatcaaggttaggaacagagaga cagcagaatatgggccaaacaggatatctgtggtaagcagttcctgccccggctcag ggccaagaacagatggtccccagatgcggtcccgccctcagcagtttctagagaacc atcagatgtttccagggtgccccaaggacctgaaaatgaccctgtgccttatttgaacta accaatcagttcgcttctcgcttctgttcgcgcgcttctgctccccgagctcaataaaaga gcccacaaccctcactcagcggccgccccgggtcgacgctaccaccatggactctt ggaccttctgctgcgtgagcctgtgcatcctggtggccaagcacacagacgccggcgt gatccagtcccctaggcacgaggtgaccgagatgggccaggaggtgacactgcgct gtaagccaatctctggccacaacagcctgttttggtataggggagaccatgatgcgcgg cctggagctgctgatctacttcaataacaatgtgcccatcgacgattccggcatgcctga ggatcggttttctgccaagatgcccaatgccagcttctccacactgaagatccagccta gcgagccaagagactccgccgtgtattttgcgcctctagcccaggcagcaccgatac acagtacttcggaccaggaaccaggctgacagtgctggaggtgacctgaagaacgtgtt ccccccctgaggtggccgtgtttgagccctctgaggccgagatcagccacacccagaa ggccaccctggtgtgcctggcaaccggcttctatcctgatcacgtggagctgtcctggtg ggtgaacggcaaggaggtgcacagcggcgtgtccacagacccacagcccctgaag gagcagccagccctgaatgatagccggtattgcctgtcctctcggctgagagtgtccgc cacctttggcagaaccccggaatcacttcagatgtcaggtgcagttttacggcctgtc cgagaacgatgagtggacccaggaccgggccaagctgtgacacagatcgtgtctg ccgaggcatggggaagagcagactgtggcttcacctctgagagctaccagcagggc gtgctgagcgccaccatcctgtatgagatcctgctgggcaaggccacactgtacgccg tcctggtctccgctctggtgctgatggcaatggtcaaaagaaaagatagtcgggacg ggccaagagatctggcagcggcgccaccaatttcagcctgctgaaacaggccggcg acgtggaagagaacctggccccatggagaagaatcccctggctgcccccctgctg atcctgtggtttcacctggactgctgtcctctatcctgaatgtggaacagagcccacag agcctgcacgtgcaggagggcgactccaccaacttcacatgctcttttcctagctccaa cttctacgccctgcactggtacagaaaggagaccgcaaagtccccagaggccctgtt cgtgatgacactgaacggcgatgagaagaagaagggccgcatcagcgccaccctg aatacaaaggagggctactcctatctgtacatcaagggctcccagctgaggactctg ccacctatctgtgcgccctgtacaacaataacgatatgcggtttggcgccggcaccag actgacagtgaagccaaacatccagaatccagacccccgccgtgtatcagctgcggg acagcaagtctagcgataagagcgtgtgcctgttcaccgactttgattctcagacaaac gtgagccagtccaaggacagcgacgtgtacatcaccgacaagacagtgctggatat gagaagcatggacttcaagtctaacagcgccgtggcctggtccaataagtctgatttcg cctgcgccaatgccttttaataactccatcatccccgaggataccttcttccttctccagag tcctcttgtgacgtgaagctggtggagaagtcttcgagaccgatacaaacctgaattttc agaacctgagcgtgatcggcttcaggatcctgctgctgaaggtggccggctttaatctg ctgatgaccctgaggctgtggagctcccgggccaagagatctggcagcggcgaggg |

TABLE 2-continued

DNA and protein sequences

| SEQ ID NO: | Description | Sequence |
|---|---|---|
| | | cagaggcagcctgctgacctgcggcgacgtggaggagaaccccggccccatgcgc ccgagactgtggcttctgctcgccgcgcaactgactgtcctgcacggaaacagcgtgc tgcagcagacaccggcctacatcaaagtgcagaccaacaagatggtcatgctgtcct gcgaggccaagatttccctctccaacatgcggatctattggttgcggcagagacaggc gccttcctcggactcccaccatgagttcttggccctgtgggactccgccaagggaactat tcacggcgaagaagtggaacaggagaagatcgccgtgtttcgcgatgcctcccgcttt atactgaatctgacctccgtgaagcccgaagatagcgggatctacttttgcatgattgtg ggctcacccgaactgaccttcgggaagggcactcagctgagcgtggtggacttcctcc ccactaccgcccaacccactaagaagtcaaccctgaagaagcgggtttgcagactcc cacggccgaaaacgcagaagggtccgctgtgttcccgatcaccctggggctcctgt ggctggagtgctggtccttctggtgtcccttggcgtcgccattcacctctgctgccggaga aggagggccagactgaggttcatgaagcagcctcagggagaggggatcagtggca ctttcgtgccacaatgcctccatggctactattccaacaccaccacctcgcaaaagctg ctgaaccctggatcctgaaaacccgggccaagagatctggcagcggcagtgcac caactacgccctgctgaagctggccggcgacgtggagagcaaccccggccccatgg cgcttcccgtgaccgcactcctgttgcccctgccctgctgttgcacgccggcacgaccttc ccaattccgggtgtccctctggatcgcacctggaacctcggggaaacggtggagctc aagtgtcaagtcctcctgtcgaacccgaccagcggatgcagctggctgttccagccga gaggagctgccgcctcacccaccttcctcctgtacttgagcagaacaagccgaagg ccgctgagggtctggacacccagcgcttctcgggcaaacggctgggagacactttttgt gctgactctctccgacttccggcgggagaacgagggctactacttctgctctgcgctctc caattcaatcatgtacttctcacacttcgtgccggtgttcctgcctgccaagcccaccact actccggcacccagacctccaactcccgctcccaccatcgcgtcccaaccccMcgct gcgccctgaagcgtgtcggcctgctgctggaggagccgtgcataccgcggtctgga cttcgcgtgcgacatctacatttgggcccctttggctggcacctgtggagtgctgctcctgt cccttgtgatcaccctgtactgcaaccaccggaataggcggagagtctgcaagtgtcc gcggcctgtcgtgaagtcaggagataagccgagcctgtccgcacgctacgtgtgaac cggtccgcagtctgacgtacgcgtaatcaacctctggattacaaaatttgtgaaagattg actggtattcttaactatgttgctccttttacgctatgtggatacgctgctttaatgcctttgtat catgctattgcttcccgtatggctttcattttctcctccttgtataaatcctggttgctgtctcttta tgaggagttgtggcccgttgtcaggcaacgtggcgtggtgtgcactgtgtttgctgacgc aaccccccactggttgggcattgccaccacctgtcagctcctttccgggactttcgctttc ccctccctattgccacggcggaactcatcgccgcctgccttgcccgctgctgacagg ggctcggctgttgggcactgacaattccgtggtgttgtcggggaagctgacgtccttcc atgctgctcgcctgtgttgccacctggattctgcgcgggacgtccttctgctacgtccctt cggccctcaatccagcggaccttccttcccgcggcctgctgccggctctgcggcctcttc cgcgtcttcgccttcgccctcagacgagtcggatctcccttgggccgcctccccgcc |
| 92 | TPE WPRE | tgaaagaccccacctgtaggtttggcaagctagcttaagtaacgccattttgcaaggca tggaaaatacataactgagaatagagaagttcagatcaaggttaggaacagagaga cagcagaatatgggccaaacaggatatctgtggtaagcagttcctgccccggctcag ggccaagaacagatggtccccagatgcggtcccgccctcagcagtttctagagaacc atcagatgtttccaggtgccccaaggacctgaaaatgaccctgtgccttatttgaacta accaatcagttcgcttctcgcttctgttcgcgcgcttctgctccccgagctcaataaaaga gcccacaaccccctcactcagcggccgccccgggtcgacgctaccaccatggactctt ggaccttctgctgcgtgagcctgtgcatcctggtggccaagcacacagacgccggcgt gatccagtcccctaggcacgaggtgaccgagatgggccaggaggtgacactgcgct gtaagccaatctctggccacaacagcctgtttggtatagggagaccatgatgcgcgg cctgggagctgctgatctacttcaataacaatgtgcccatcgacgattccggcatgcctga ggatcggttttctgccaagatgcccaatgccagcttctccacactgaagatccagccta gcgagccaagagactccgccgtgtatttttgcgcctctagcccaggcagcaccgatac acagtacttcggaccaggaaccaggctgacagtgctggaggacctgaagaacgtgtt ccccccctgaggtggccgtgtttgagccctctgaggccgagatcagccacacccagaa ggccaccctggtgtgcctggcaaccggcttctatcctgatcacgtggagctgtcctggtg ggtgaacggcaaggaggtgcacagcggcgtgtccacagacccacagcccctgaag gagcagccagcccctgaatgatagccggtattgcctgtcctctcggctgagagtgtccgc cacctttggcagaaccccggaatcacttcagatgtcaggtgcagttttacggcctgtc cgagaacgatgagtggaccaggacccgggccaagcctgtgacacagatcgtgtctg ccgaggcatggggaagagcagactgtggcttcacctctgagagctaccagcagggc gtgctgagcgccaccatcctgtatgagatcctgctgggcaaggccacactgtacgccg tcctggtctccgctctggtgctgatggcaatggtcaaaagaaaagatagtcggggacg ggccaagagatctggcagcggcgagggcagaggcagcctgctgacctgcggcgac gtggaggagaaccccggccccatggagaagaatcccctggctgccccctgctgatc ctgtggtttcacctggactgcgtgtcctctatcctgaatgtggaacagagcccacagagc ctgcacgtgcaggagggcgactccaccaacttcacatgctcttttcctagctccaacttct acgccctgcactggtacagaaaggagaccgcaaagtcccagaggccctgttcgtg atgacactgaacggcgatgagaagaagaagggccgcatcagcgccaccctgaata caaaggagggctactcctatctgtacatcaagggctcccagcctgaggactctgccac ctatctgtgcgccctgtacaacaataacgatatgcggtttggcgccggcaccagactga cagtgaagcccaaacatccagaatccagaccccgcgtgtatcagctgcgggacagc aagtctagcgataagagcgtgtgcctgttcaccgactttgattctcagacaaacgtgag ccagtccaaggacagcgacgtgtacatcaccgacaagacagtgctggatatgagaa gcatggacttcaagtctaacagcgccgtggcctggtccaataagtctgatttcgcctgcg ccaatgcctttaataaactccatcatccccgaggatacccttctttccttctccagagtcctctt gtgacgtgaagctggtggagaagtctttcgagaccgatacaaacctgaattttcagaac |

TABLE 2-continued

DNA and protein sequences

| SEQ ID NO: | Description | Sequence |
|---|---|---|
|  |  | ctgagcgtgatcggcttcaggatcctgctgctgaaggtggccggctttaatctgctgatg<br>accctgaggctgtggagctcccgggccaagagatctggcagcggcgccaccaatttc<br>agcctgctgaaacaggccggcgacgtggaagagaaccctggccccatgcgcccga<br>gactgtggcttctgctcgccgcgcaactgactgtcctgcacggaaacagcgtgctgca<br>gcagacaccggcctacatcaaagtgcagaccaacaagatggtcatgctgtcctgcga<br>ggccaagatttccctctccaacatgcggatctattggttgcggcagagacaggcgcctt<br>cctcggactcccaccatgagttcttggcctgtgggactccgccaagggaactattcac<br>ggcgaagaagtggaacaggagaagatcgccgtgtttcgcgatgcctcccgctttatac<br>tgaatctgacctccgtgaagcccgaagatagcgggatctacttttgcatgattgtgggct<br>cacccgaactgaccttcgggaagggcactcagctgagcgtggtggacttcctccccac<br>taccgcccaacccactaagaagtcaaccctgaagaagcgggtttgcagactcccac<br>ggccggaaacgcagaagggtccgctgtgttccccgatcaccctggggctccttgtggc<br>tggagtgctggtccttctggtgtcccttggcgtcgccattcacctctgctgccggagaagg<br>agggccagactgaggttcatgaagcagcctcagggagaggggatcagtggcactttc<br>gtgccacaatgcctccatggctactattccaacaccaccacctcgcaaaagctgctga<br>acccctggatcctgaaaacccgggccaagagatctggcagcggccagtgcaccaa<br>ctacgccctgctgaagctggccggcgacgtggagagcaaccccggccccatggcgc<br>ttcccgtgaccgcactcctgttgcccccttgccctgctgttgcacgccgcacgaccttccca<br>attccgggtgtcccctctggatcgcacctggaacctcggggaaacggtggagctcaag<br>tgtcaagtcctcctgtcgaacccgaccagcgatgcagctggctgttccagccgagag<br>gagctgccgcctcacccaccttcctcctgtacttgagccagaacaagccgaaggccg<br>ctgagggtctggacacccagcgcttctcgggcaaacggctgggagacacttttgtgctg<br>actctctccgacttccggcgggagaacgagggctactacttctgctctgcgctctccaatt<br>caatcatgtacttctcacacttcgtgccggtgttcctgcctgccaagcccaccactactcc<br>ggcacccagacctccaactcccgctcccaccatcgcgtcccaacccctttcgctgcgc<br>cctgaagcgtgtcggcctgctgctggaggagccgtgcatacccgcggtctggacttcg<br>cgtgcgacatctacatttgggcccctttggctggcacctgtggagtgctgctcctgtcccttt<br>gtgatcaccctgtactgcaaccaccggaataggcggagagtctgcaagtgtccgcgg<br>cctgtcgtgaagtcaggagataagccgagcctgtccgcacgctacgtgtgaaccggtc<br>cgcagtctgacgtacgcgtaatcaacctctggattacaaaatttgtgaaagattgactgg<br>tattcttaactatgttgctccttttacgctatgtggatacgctgctttaatgcctttgtatcatgct<br>attgcttcccgtatggctttcattttctcctccttgtataaatcctggttgctgtctctttatgagg<br>agttgtggcccgttgtcaggcaacgtggcgtggtgtgcactgtgtttgctgacgcaaccc<br>ccactggttggggcattgccaccacctgtcagctcctttccgggactttcgctttcccctc<br>cctattgccacggcggaactcatcgccgcctgccttgcccgctgctggacaggggctc<br>ggctgttggcactgacaattccgtggtgttgtcggggaagctgacgtcctttccatggct<br>gctcgcctgtgttgccacctggattctgcgcgggacgtccttctgctacgtcccttcggcc<br>ctcaatccagcggaccttccttcccgcggcctgctgccggctctgcgggcctcttccgcgt<br>cttcgccttcgccctcagacgagtcggatctcccttttgggccgcctccccgcc |
| 93 | PTE fn WPRE | tgaaagacccccacctgtaggtttggcaagctagcttaagtaacgccattttgcaaggca<br>tggaaaatacataactgagaatagagaagttcagatcaaggttaggaacagagaga<br>cagcagaatatgggccaaacaggatatctgtggtaagcagttcctgccccggctcag<br>ggccaagaacagatggtccccagatgcggtcccgccctcagcagtttctagagaacc<br>atcagatgtttccagggtgccccaaggacctgaaaatgaccctgtgccttatttgaacta<br>accaatcagttcgcttctcgcttctgttcgcgcgcttctgctccccgagctcaataaaaga<br>gcccacaacccctcactcagcggccgccccgggtcgacgctaccaccatggactctt<br>ggaccttctgctgcgtgagcctgtgcatcctggtggccaagcacacagacgccggcgt<br>gatccagtcccctaggcacgaggtgaccgagatgggccaggaggtgacactgcgct<br>gtaagccaatctctggccacaacagcctgttttggtatagggagaccatgatgcgcgg<br>cctggagctgctgatctacttcaataacaatgtgcccatcgacgattccggcatgcctga<br>ggatcggttttctgccaagatgcccaatgccagcttctccacactgaagatccagccta<br>gcgagccaagagactccgccgtgtattttgcgcctctagcccaggcagcaccgatac<br>acagtacttcggaccaggaaccaggctgacagtgctggaggacgtcaagaacgtgtt<br>cccccctgaggtggccgtgtttgagccctctgaggccgagatcagccacacccagaa<br>ggccaccctggtgtgcctggcaaccggcttctatcctgatcacgtggagctgtcctggtg<br>ggtgaacggcaaggaggtgcacagcggcgtgtccacagacccacagcccctgaag<br>gagcagccagccctgaatgatagccggtattgcctgtcctctcggctgagagtgtccgc<br>cacctttggcagaaccccggaatcacttcagatgtcaggtgcagttttacggcctgtc<br>cgagaacgatgagtggacccaggaccgggccaagcctgtgacacagatcgtgtctg<br>ccgaggcatggggaagagcagactgtggcttcacctctgagagctaccagcagggc<br>gtgctgagcgccaccatcctgtatgagatcctgctgggcaaggccacactgtacgccg<br>tcctggtctccgctctggtgctgatggcaatggtcaaaagaaaagatagtcggggatct<br>ggcagcggcgccaccaatttcagcctgctgaaacaggccggcgacgtggaagaga<br>accctggccccatggagaagaatccctggctgccccctgctgatcctgtggtttcac<br>ctggactgcgtgtcctctatcctgaatgtggaacagagcccacagagcctgcacgtgc<br>aggagggcgactccaccaacttcacatgctcttttcctagctccaacttctacgccctgc<br>actggtacagaaaggagaccgcaaagtccccagaggccctgttcgtgatgacactg<br>aacggcgatgagaagaagggccgcatcagcgccaccctgaatacaaaggag<br>ggctactcctatctgtacatcaagggctccgcctgcgaggactgtccacctatctgtgc<br>gccctgtacaacaataacgatatgggttttggcgccggcaccagactgacagtgaag<br>ccaaacatccagaatccagaccccgcgtgtatcagctgcgggacagcaagtctag<br>cgataagagcgtgtgcctgttcaccgactttgattctcagacaaacgtgagccagtcca<br>aggacagcgacgtgtacatcaccgacaagacagtgctggatatgagaagcatggac<br>ttcaagtctaacagcgccgtggcctggtccaataagtctgatttcgcctgcgccaatgcc |

TABLE 2-continued

DNA and protein sequences

| SEQ ID NO: | Description | Sequence |
|---|---|---|
| | | tttaataactccatcatccccgaggatacct tctttccttctccagagtcctcttgtgacgtga<br>agctggtggagaagtcttt cgagaccgatacaaacctgaattttcagaacctgagcgtg<br>atcggcttcaggatcctgctgctgaaggtggccggctttaatctgctgatgaccctgagg<br>ctgtggagctcccgggccaagagaggcagcggcgagggcagaggcagcctgctg<br>acctgcggcgacgtggaggagaaccccggccccatgcgcccgagactgtggcttct<br>gctcgccgcgcaactgactgtcctgcacggaaacagcgtgctgcagcagacaccgg<br>cctacatcaaagtgcagaccaacaagatggtcatgctgtcctgcgaggccaagatttc<br>cctctccaacatgcggatctattggttgcggcagagacaggcgccttcctcggactccc<br>accatgagttcttggccctgtgggactccgccaagggaactattcacggcgaagaagt<br>ggaacaggagaagatcgccgtgtttcgcgatgcctcccgctttatactgaatctgacctc<br>cgtgaagcccgaagatagcgggatctactttgcatgattgtgggctcacccgaactga<br>ccttcgggaagggcactcagctgagcgtggtggacttcctccccactaccgcccaacc<br>cactaagaagtcaaccctgaagaagcgggtttgcagactcccacggccggaaacgc<br>agaagggtccgctgtgttccccgatcaccctgggctccttgtggctggagtgctggtcc<br>ttctggtgtcccttggcgtcgccattcacctctgctgccggagaaggagggccagactg<br>aggttcatgaagcagcctcagggagaggggatcagtggcactttcgtgccacaatgc<br>ctccatggctactattccaacaccaccacctcgcaaaagctgctgaaccctggatcct<br>gaaaacccgggccaagagatctggcagcggccagtgcaccaactacgccctgctg<br>aagctggccggcgacgtggagagcaaccccggccccatggcgcttcccgtgaccgc<br>actcctgttgccccttgcctgctgttgcacgccgcacgaccttcccaattccgggtgtcc<br>cctctggatcgcacctggaacctcggggaaacggtggagctcaagtgtcaagtcctcc<br>tgtcgaacccgaccagcggatgcagctggctgttccagccgagaggagctgccgcct<br>cacccaccttcctcctgtacttgagccagaacaagccgaaggccgctgagggtctgg<br>acacccagcgcttctcgggcaaacggctgggagacacttttgtgctgactctctccgact<br>tccggcggagaacgagggctactacttctgctctgcgctctccaattcaatcatgtactt<br>ctcacacttcgtgccggtgttcctgcctgccaagcccaccactactccggcacccagac<br>ctccaactcccgctcccaccatcgcgtcccaaccccttcgctgcgccctgaagcgtgtc<br>ggcctgctgctggaggagccgtgcatacccgcggtctggacttcgcgtgcgacatcta<br>catttgggccccttt ggctggcacctgtggagtgctgctcctgtcccttgtgatcaccctgta<br>ctgcaaccaccggaataggcggagagtctgcaagtgtccgcggcctgtcgtgaagtc<br>aggagataagccgagcctgtccgcacgctacgtgtgaaccggtccgcagtctgacgt<br>acgcgtaatcaacctctgattacaaaatttgtgaaagattgactggtattcttaactatgt<br>tgctccttttacgctatgtggatacgctgcttttaatgcctttgtatcatgctattgcttcccgtat<br>ggctttcattttctcctccttgtataaatcctggttgctgtctctttatgaggagttgtggcccgtt<br>gtcaggcaacgtggcgtggtgtgcactgtgtttgctgacgcaaccccactggttgggg<br>cattgccaccacctgtcagctcctttccgggactttcgctttcccctcctattgccacgg<br>cggaactcatcgccgctgccttgccgctgctggacaggggctcggctgttgggcact<br>gacaattccgtggtgttgtcggggaagctgacgtccttttccatggctgctcgcctgtgttgc<br>cacctggattctgcgcgggacgtccttctgctacgtcccttcggccctcaatccagcgga<br>ccttccttcccgcggcctgctgccggctctgcggcctcttccgcgtcttcgccttcgccctc<br>agacgagtcggatctccctttgggccgcctcccgcc |
| 94 | PTE CD8 TCR WPRE | tgaaagaccccacctgtaggtttggcaagctagcttaagtaacgccattttgcaaggca<br>tggaaaatacataactgagaatagagaagttcagatcaaggttaggaacagagaga<br>cagcagaatatgggccaaacaggatatctgtggtaagcagttcctgccccggctcag<br>ggccaagaacagatggtccccagatgcggtcccgccctcagcagtttctagagaacc<br>atcagatgtttccagggtgccccaaggacctgaaaatgaccctgtgccttatttgaacta<br>accaatcagttcgcttctcgcttctgttcgcgcgcttctgctccccgagctcaataaaaga<br>gcccacaaccctcactcagcggccgcccccgggtcgacgctaccaccatgcgcccg<br>agactgtggcttctgctcgccgcgcaactgactgtcctgcacggaaacagcgtgctgc<br>agcagacaccggcctacatcaaagtgcagaccaacaagatggtcatgctgtcctgcg<br>aggccaagatttccctctccaacatgcggatctattggttgcggcagagacaggcgcct<br>tcctcggactcccaccatgagttcttggccctgtgggactccgccaagggaactattcac<br>ggcgaagaagtggaacaggagaagatcgccgtgtttcgcgatgcctcccgctttatac<br>tgaatctgacctccgtgaagcccgaagatagcgggatctactttgcatgattgtgggct<br>cacccgaactgaccttcgggaagggcactcagctgagcgtggtggacttcctccccac<br>taccgcccaacccactaagaagtcaaccctgaagaagcgggtttgcagactcccac<br>ggccggaaacgcagaagggtccgctgtgttccccgatcaccctgggctccttgtggc<br>tggagtgctggtccttctggtgtcccttggcgtcgccattcacctctgctgccggagaagg<br>agggccagactgaggttcatgaagcagcctcagggagaggggatcagtggcactttc<br>gtgccacaatgcctccatggctactattccaacaccaccacctcgcaaaagctgctga<br>accctggatcctgaaaacccgggccaagagatctggcagcggccaccaatttc<br>agcctgctgaaacaggccggcgacgtggaagagaaccctggccccatggcgcttcc<br>cgtgaccgcactcctgttgccccttgcctgctgttgcacgccgcacgaccttcccaattc<br>cgggtgtccctctggatcgcacctggaacctcggggaaacggtggagctcaagtgtc<br>aagtcctcctgtcgaacccgaccagcggatgcagctggctgttccagccgagaggag<br>ctgccgcctcacccaccttcctcctgtacttgagccagaacaagccgaaggccgctga<br>gggtctggacacccagcgcttctcgggcaaacggctgggagacacttttgtgctgactc<br>tctccgacttccggcgggagaacgagggctactacttctgctctgcgctctccaattcaat<br>catgtacttctcacacttcgtgccggtgttcctgcctgccaagcccaccactactccggca<br>cccagacctccaactcccgctcccaccatcgcgtcccaaccccttcgctgcgccctga<br>agcgtgtcggcctgctgctggaggagccgtgcatacccgcggtctggacttcgcgtgc<br>gacatctacatttgggccccttt ggctggcacctgtggagtgctgctcctgtcccttgtgat<br>caccctgtactgcaaccaccggaataggcggagagtctgcaagtgtccgcggcctgt<br>cgtgaagtcaggagataagccgagcctgtccgcacgctacgtgcgggccaagagat |

TABLE 2-continued

DNA and protein sequences

| SEQ ID NO: | Description | Sequence |
|---|---|---|
|  |  | ctggcagcggcgagggcagaggcagcctgctgacctgcggcgacgtggaggaga<br>accccggccccatggactcttggaccttctgctgcgtgagcctgtgcatcctggtggcca<br>agcacacagacgccggcgtgatccagtcccctaggcacgaggtgaccgagatggg<br>ccaggaggtgacactgcgctgtaagccaatctctggccacaacagcctgttttggtata<br>gggagaccatgatgcgcggcctggagctgctgatctacttcaataacaatgtgcccatc<br>gacgattccggcatgcctgaggatcggttttctgccaagatgcccaatgccagcttctcc<br>acactgaagatccagcctagcgagccaagagactccgccgtgtattttttgcgcctctag<br>cccaggcagcaccgatacacagtacttcggaccaggaaccaggctgacagtgctgg<br>aggacctgaagaacgtgttccccccctgaggtggccgtgtttgagccctctgaggccga<br>gatcagccacacccagaaggccaccctggtgtgcctggcaaccggcttctatcctgat<br>cacgtggagctgtcctggtgggtgaacggcaaggaggtgcacagcggcgtgtccac<br>agacccacagccccctgaaggagcagccagccctgaatgatagccggtattgcctgtc<br>ctctcggctgagagtgtccgccacctttggcagaaccccggaatcacttcagatgtca<br>ggtgcagttttacggcctgtccgagaacgatgagtggacccaggaccgggccaagcc<br>tgtgacacagatcgtgtctgccgaggcatggggaagagcagactgtggcttcacctct<br>gagagctaccagcagggcgtgctgagcgccaccatcctgtatgagatcctgctgggc<br>aaggccacactgtacgccgtcctggtctccgctctggtgctgatggcaatggtcaaaag<br>aaaagatagtcggggacgggccaagagatctggcagcggccagtgcaccaactac<br>gccctgctgaagctggccggcgacgtggagagcaaccccggccccatggagaaga<br>tcccctggctgcccccctgctgatcctgtggtttcacctggactgcgtgtcctctatcctg<br>aatgtggaacagagcccacagagcctgcacgtgcaggagggcgactccaccaactt<br>cacatgctcttttcctagctccaacttctacgccctgcactggtacagaaaggagaccgc<br>aaagtccccagaggccctgttcgtgatgacactgaacggcgatgagaagaagaagg<br>gccgcatcagcgccaccctgaatacaaaggagggctactcctatctgtacatcaagg<br>gctcccagcctgaggactctgccacctatctgtgcgccctgtacaacaataacgatatg<br>cggtttggcgccggcaccagactgacagtgaagccaaacatccagaatccagaccc<br>cgccgtgtatcagctgcgggacagcaagtctagcgataagagcgtgtgcctgttcacc<br>gactttgattctcagacaaacgtgagccagtccaaggacagcgacgtgtacatcaccg<br>acaagacagtgctggatatgagaagcatggacttcaagtctaacagcgccgtggcct<br>ggtccaataagtctgatttcgcctgcgccaatgcctttaataactccatcatccccgagg<br>ataccttctttccttctccagagtcctcttgtgacgtgaagctggtggagaagtctttcgag<br>accgatacaaacctgaattttcagaacctgagcgtgatcggcttcaggatcctgctgctg<br>aaggtggccggctttaatctgctgatgacccctgaggctgtggagctcctgaaccggtcc<br>gcagtctgacgtacgcgtaatcaacctctggattacaaaatttgtgaaagattgactggt<br>attcttaactatgttgctccttttacgctatgtggatacgctgctttaatgcctttgtatcatgct<br>attgcttcccgtatggctttcattttctcctccttgtataaatcctggttgctgtctctttatgagg<br>agttgtggcccgttgtcaggcaacgtggcgtggtgtgcactgtgtttgctgacgcaaccc<br>ccactggttggggcattgccaccacctgtcagctcctttccgggactttcgctttccccctc<br>cctattgccacggcggaactcatcgccgcctgccttgcccgctgctggacaggggctc<br>ggctgttgggcactgacaattccgtggtgttgtcggggaagctgacgtcctttccatggct<br>gctcgcctgtgttgccacctggattctgcgcgggacgtccttctgctacgtcccttcggcc<br>ctcaatccagcggaccttccttcccgcggcctgctgccggctctgcgggcctcttccgcgt<br>cttcgccttcgccctcagacgagtcggatctccctttgggccgcctccccgcc |
| 95 | R11KE WPRE | tgaaagaccccacctgtaggtttggcaagctagcttaagtaacgccatttgcaaggca<br>tggaaaatacataactgagaatagagaagttcagatcaaggttaggaacagagaga<br>cagcagaatatgggccaaacaggatatctgtggtaagcagttcctgccccggctcag<br>ggccaagaacagatggtcccagatgcggtccccgccctcagcagtttctagagaacc<br>atcagatgtttccagggtgccccaaggacctgaaaatgaccctgtgccttatttgaacta<br>accaatcagttcgcttctcgcttctgttcgcgcgcttctgctccccgagctcaataaaaga<br>gcccacaacccctcactcagcggccgcccgggtcgacgctaccaccatggactctt<br>ggaccttctgctgcgtgagcctgtgcatcctggtggccaagcacacagacgccggcgt<br>gatccagtcccctaggcacgaggtgaccgagatgggccaggaggtgacactgcgct<br>gtaagccaatctctggccacaacagcctgttttggtataggagaccatgatgcgcgg<br>cctggagctgctgatctacttcaataacaatgtgcccatcgacgattccggcatgcctga<br>ggatcggttttctgccaagatgcccaatgccagcttctccacactgaagatccagccta<br>gcgagccaagagactccgccgtgtattttttgcgcctctagcccaggcagcaccgatac<br>acagtacttcggaccaggaaccaggctgacagtgctggaggacctgaagaacgtgtt<br>ccccccctgaggtggccgtgtttgagccctctgaggccgagatcagccacacccagaa<br>ggccaccctggtgtgcctggcaaccggcttctatcctgatcacgtggagctgtcctggtg<br>ggtgaacggcaaggaggtgcacagcggcgtgtccacagacccacagcccctgaag<br>gagcagccagccctgaatgatagccggtattgcctgtcctctcggctgagagtgtccgc<br>cacctttggcagaaccccggaatcacttcagatgtcaggtgcagttttacggcctgtc<br>cgagaacgatgagtggacccaggaccgggccaagcctgtgacacagatcgtgtctg<br>ccgaggcatggggaagagcagactgtggcttcacctctgagagctaccagcagggc<br>gtgctgagcgccaccatcctgtatgagatcctgctgggcaaggccacactgtacgccg<br>tcctggtctccgctctggtgctgatggcaatggtcaaaagaaaagatagtcggggacg<br>ggccaagagatctggcagcggcgccaccaatttcagcctgctgaaacaggccggcg<br>acgtggaagagaaccctggccccatggagaagaatcccctggctgcccccctgctg<br>atcctgtggtttcacctggactgcgtgtcctctatcctgaatgtggaacagagcccacag<br>agcctgcacgtgcaggagggcgactccaccaacttcacatgctcttttcctagctccaa<br>cttctacgccctgcactggtacagaaaggagaccgcaaagtccccagaggccctgtt<br>cgtgatgacactgaacggcgatgagaagaagaagggccgcatcagcgccaccctg<br>aatacaaaggagggctactcctatctgtacatcaagggctcccagcctgaggactctg<br>ccacctatctgtgcgccctgtacaacaataacgatatgcggtttggcgccggcaccag |

TABLE 2-continued

DNA and protein sequences

| SEQ ID NO: | Description | Sequence |
|---|---|---|
|  |  | actgacagtgaagccaaacatccagaatccagaccccgccgtgtatcagctgcggg acagcaagtctagcgataagagcgtgtgcctgttcaccgactttgattctcagacaaac gtgagccagtccaaggacagcgacgtgtacatcaccgacaagacagtgctggatat gagaagcatggacttcaagtctaacagcgccgtggcctggtccaataagtctgatttcg cctgcgccaatgcctttaataactccatcatccccgaggataccttcttccttctccagag tcctcttgtgacgtgaagctggtggagaagtctttcgagaccgatacaaacctgaattttc agaacctgagcgtgatcggcttcaggatcctgctgctgaaggtggccggctttaatctg ctgatgaccctgaggctgtggagctcctgaaccggtccgcgactctgacgtacgcgtaat caacctctggattacaaaatttgtgaaagattgactggtattcttaactatgttgctccttttta cgctatgtggatacgctgctttaatgcctttgtatcatgctattgcttcccgtatggctttcatttt ctcctccttgtataaatcctggttgctgtctctttatgaggagttgtggcccgttgtcaggca acgtggcgtggtgtgcactgtgtttgctgacgcaaccccactggttggggcattgccac cacctgtcagctccttccgggactttcgctttcccctccctattgccacggcggaactca tcgccgcctgccttgcccgctgctggacaggggctcggctgttgggcactgacaattcc gtggtgttgtcggggaagctgacgtccttcctatggctgctcgcctgtgttgccacctggat tctgcgcgggacgtccttctgctacgtcccttcggccctcaatccagcggaccttccttcc cgcggcctgctgccggctctgcggcctcttccgcgtcttcgccttcgccctcagacgagt cggatctccctttgggccgcctccccgcc |
| 96 | CD8 WPRE | tgaaagaccccacctgtaggtttggcaagctagcttaagtaacgccatttgcaaggca tggaaaatacataactgagaatagagaagttcagatcaaggttaggaacagagaga cagcagaatatgggccaaacaggatatctgtggtaagcagttcctgccccggctcag ggccaagaacagatggtccccagatgcggtcccgccctcagcagtttctagagaacc atcagatgtttccagggtgccccaaggacctgaaaatgaccctgtgccttatttgaacta accaatcagttcgcttctcgcttctgttcgcgcgcttctgctccccgagctcaataaaaga gcccacaaccccctcactcagcggccgccccgggtcgacgctaccaccatgcgcccg agactgtggctctgctcgccgcgcaactgactgtcctgcacgaaacagcgtgctgc agcagacaccggcctacatcaaagtcagaccaacaagatggtcatgctgtcctgcg aggccaagattcctctcaacatgcggatcattggttgcggcagagacaggcgcct tcctcggactccaccatgagttcttggccctgtgggactccgccaagggaactattcac ggcgaagaagtggaacaggagaagatcgccgtgtttcgcgatgcctcccgcttatac tgaatctgacctccgtgaagcccaagatagcgggatctacttttgcatgattgtgggct caccgaactgaccttcgggaagggcactcagctgagcgtggtggacttcctcccac taccgcccaacccactaagaagtcaaccctgaagaagcgggtttgcagactcccac ggccggaaacgcagaagggtccgctgtgttccccgatcaccctgggggctccttgtggc tggagtgctggtccttctggtgtcccttggcgtcgccattcacctctgctgccggagaagg agggccagactgaggttcatgaagcagcctcagggagaggggatcagtggcactttc gtgccacaatgcctccatggctactattccaacaccaccacctcgcaaaagctgctga accccctggatcctgaaaaccccggggccaagagatctggcagcggcgccaccaatttc agcctgctgaaacaggccggcgacgtggaagagaaccctggccccatgcgcttcc cgtgaccgcactcctgttgcccccttgccctgctgttgcacgccgcacgaccttcccaattc cgggtgtcccctctggatcgcaccctggaacctcggggaaacggtggagctcaagtgtc aagtcctcctgtcgaacccgaccagcggatcagctggctgttccagccgagaggag ctgccgcctcacccaccttcctcctgtacttgagccagaacaagccgaaggccgctga gggtctggacacccagcgctctcgggcaaacggctgggagacacttttgtgctgactc tctccgacttccggcgggagaacgagggctactacttctgctctgcgctctccaattcaat catgtactttctcacacttcgtgccggtgttcctgcctgccaagcccaccactactccggca cccagacctccaactcccgctccaccatcgcgtcccaaccccttcgctgcgccctga agcgtgtcggcctgctgctggaggagccgtgcataccgcggtctggacttcgcgtgc gacatctacatttgggcccctttggctggcacctgtggagtgctgctcctgtcccttgtgat caccctgtactgcaaccaccggaataggcggagagtctgcaagtgtccgcggcctgt cgtgaagtcaggagataagccgagcctgtccgcacgctacgtgtgaaccggtccgca gtctgacgtacgcgtaatcaacctctggattacaaaatttgtgaaagattgactggtattct taactatgttgctccttttacgctatgtggatacgctgctttaatgcctttgtatcatgctattgc ttcccgtatggctttcattttctcctccttgtataaatcctggttgctgtctctttatgaggagttgt ggcccgttgtcaggcaacgtggcgtggtgtgcactgtgtttgctgacgcaaccccact ggttggggcattgccaccacctgtcagctccttccgggactttcgctttcccctcctatt gccacggcggaactcatcgccgcctgccttgcccgctgctggacaggggctcggctgt tgggcactgacaattccgtggtgttgtcggggaagctgacgtccttccatggctgctcgc ctgtgttgccacctggattctgcgcgggacgtccttctgctacgtcccttcggccctcaatc cagcggaccttccttcccgcggcctgctgccggctctgcggcctcttccgcgtcttcgcct tcgccctcagacgagtcggatctccctttgggccgcctccccgcc |
| 97 | RD114TR | MKLPTGMVILCSLIIVRAGFDDPRKAIALVQKQHGKPCECSGG QVSEAPPNSIQQVTCPGKTAYLMTNQKWKCRVTPKISPSGG ELQNCPCNTFQDSMHSSCYTEYRQCRRINKTYYTATLLKIRS GSLNEVQILQNPNQLLQSPCRGSINQPVCWSATAPIHISDGG GPLDTKRVWTVQKRLEQIHKAMTPELQYHPLALPKVRDDLSL DARTFDILNTTFFRLLQMSNFSLAQDCWLCLKLGTPTPLAIPTP SLTYSLADSLANASCQIIPPLLVQPMQFSNSSCLSSPFINDTEQ IDLGAVTFTNCTSVANVSSPLCALNGSVFLCGNNMAYTYLPQ NWTRLCVQASLLPDIDINPGDEPVPIPAIDHYIHRPKRAVQFIP LLAGLGITAAFTTGATGLGVSVTQYTKLSHQLISDVQVLSGTIQ DLQDQVDSLAEVVLQNRRGLDLLTAEQGGICLALQEKCCFYA |

TABLE 2-continued

DNA and protein sequences

| SEQ ID NO: | Description | Sequence |
|---|---|---|
| | | NKSGIVRNKIRTLQEELQKRRESLASNPLWTGLQGFLPYLLPL<br>LGPLLTLLLILTIGPCVFNRLVQFVKDRISVVQALVLTQQYHQL<br>KPL |
| 265 | WPREmut1 | cagtctgacgtacgcgtaatcaacctctggattacaaaatttgtgaaagattgactggtat<br>tcttaactatgttgctccttttacgctatgtggatacgctgctttaatgcctttgtatcatgctatt<br>gcttcccgtatggctttcattttctcctccttgtataaatcctggttgctgtctctttatgaggagt<br>tgtggcccgttgtcaggcaacgtggcgtggtgtgcactgtgtttgctgacgcaaccccca<br>ctggttggggcattgccaccacctgtcagctcctttccgggactttcgctttcccccctccccta<br>ttgccacggcggaactcatcgccgcctgccttgcccgctgctggacaggggctcggct<br>gttgggcactgacaattccgtggtgttgtcggggaaatcatcgtcctttccttggctgctcg<br>cctgtgttgccacctggattctgcgcgggacgtcctctgctacgtcccttcggccctcaat<br>ccagcggaccttccttcccgcggcctgctgccggctctgcggcctcttccgcgtcttcgc<br>cttcgccctcagacgagtcggatctccctttgggccgcctccccgcc |
| 266 | WPREmut2 | gagcatcttaccgccatttataccccatatttgttctgtttttcttgatttgggtatacatttaaatg<br>ttaataaaacaaaatggtggggcaatcatttacattttttgggatatgtaattactagttcag<br>gtgtattgccacaagacaaacttgttaagaaactttcccgttatttacgctctgttcctgtta<br>atcaacctctggattacaaaatttgtgaaagattgactgatattcttaactttgttgctccttttt<br>acgctgtgtggatttgctgctttattgcctctgtattcccgtacggctttcgttttt<br>ctcctccttgtataaatcctggttgctgtctcttttgaggagttgtggcccgttgtccgtcaac<br>gtggcgtggtgtgctctgtgtttgctgacgcaaccccactggctggggcattgccacca<br>cctgtcaactccttttctgggactttcgctttccccctcccgatcgccacggcagaactcatc<br>gccgcctgccttgcccgctgctggacaggggctaggttgctgggcactgataattccgt<br>ggtgttgtc |

TABLE 3

TAA Peptide sequences

| SEQ ID NO: | Amino Acid Sequence |
|---|---|
| 98 | YLYDSETKNA |
| 99 | HLMDQPLSV |
| 100 | GLLKKINSV |
| 101 | FLVDGSSAL |
| 102 | FLFDGSANLV |
| 103 | FLYKIIDEL |
| 104 | FILDSAETTTL |
| 105 | SVDVSPPKV |
| 106 | VADKIHSV |
| 107 | IVDDLTINL |
| 108 | GLLEELVTV |
| 109 | TLDGAAVNQV |
| 110 | SVLEKEIYSI |
| 111 | LLDPKTIFL |
| 112 | YTFSGDVQL |
| 113 | YLMDDFSSL |
| 114 | KVWSDVTPL |
| 115 | LLWGHPRVALA |
| 116 | KIWEELSVLEV |
| 117 | LLIPFTIFM |

TABLE 3-continued

TAA Peptide sequences

| SEQ ID NO: | Amino Acid Sequence |
|---|---|
| 118 | FLIENLLAA |
| 119 | LLWGHPRVALA |
| 120 | FLLEREQLL |
| 121 | SLAETIFIV |
| 122 | TLLEGISRA |
| 123 | KIQEILTQV |
| 124 | VIFEGEPMYL |
| 125 | SLFESLEYL |
| 126 | SLLNQPKAV |
| 127 | GLAEFQENV |
| 128 | KLLAVIHEL |
| 129 | TLHDQVHLL |
| 130 | TLYNPERTITV |
| 131 | KLQEKIQEL |
| 132 | SVLEKEIYSI |
| 133 | RVIDDSLVVGV |
| 134 | VLFGELPAL |
| 135 | GLVDIMVHL |
| 136 | FLNAIETAL |

TABLE 3-continued

TAA Peptide sequences

| SEQ ID NO: | Amino Acid Sequence |
|---|---|
| 137 | ALLQALMEL |
| 138 | ALSSSQAEV |
| 139 | SLITGQDLLSV |
| 140 | QLIEKNWLL |
| 141 | LLDPKTIFL |
| 142 | RLHDENILL |
| 143 | YTFSGDVQL |
| 144 | GLPSATTTV |
| 145 | GLLPSAESIKL |
| 146 | KTASINQNV |
| 147 | SLLQHLIGL |
| 148 | YLMDDFSSL |
| 149 | LMYPYIYHV |
| 150 | KVWSDVTPL |
| 151 | LLWGHPRVALA |
| 152 | VLDGKVAVV |
| 153 | GLLGKVTSV |
| 154 | KMISAIPTL |
| 155 | GLLETTGLLAT |
| 156 | TLNTLDINL |
| 157 | VIIKGLEEI |
| 158 | YLEDGFAYV |
| 159 | KIWEELSVLEV |
| 160 | LLIPFTIFM |
| 161 | ISLDEVAVSL |
| 162 | KISDFGLATV |
| 163 | KLIGNIHGNEV |
| 164 | ILLSVLHQL |
| 165 | LDSEALLTL |
| 166 | VLQENSSDYQSNL |
| 167 | HLLGEGAFAQV |
| 168 | SLVENIHVL |
| 169 | YTFSGDVQL |
| 170 | SLSEKSPEV |
| 171 | AMFPDTIPRV |
| 172 | FLIENLLAA |
| 173 | FTAEFLEKV |
| 174 | ALYGNVQQV |
| 175 | LFQSRIAGV |
| 176 | ILAEEPIYIRV |
| 177 | FLLEREQLL |
| 178 | LLLPLELSLA |
| 179 | SLAETIFIV |
| 180 | AILNVDEKNQV |
| 181 | RLFEEVLGV |
| 182 | YLDEVAFML |
| 183 | KLIDEDEPLFL |
| 184 | KLFEKSTGL |
| 185 | SLLEVNEASSV |
| 186 | GVYDGREHTV |
| 187 | GLYPVTLVGV |
| 188 | ALLSSVAEA |
| 189 | TLLEGISRA |
| 190 | SLIEESEEL |
| 191 | ALYVQAPTV |
| 192 | KLIYKDLVSV |
| 193 | ILQDGQFLV |
| 194 | SLLDYEVSI |
| 195 | LLGDSSFFL |
| 196 | VIFEGEPMYL |
| 197 | ALSYILPYL |
| 198 | FLFVDPELV |
| 199 | SEWGSPHAAVP |
| 200 | ALSELERVL |
| 201 | SLFESLEYL |
| 202 | KVLEYVIKV |
| 203 | VLLNEILEQV |
| 204 | SLLNQPKAV |
| 205 | KMSELQTYV |
| 206 | ALLEQTGDMSL |
| 207 | VIIKGLEEITV |
| 208 | KQFEGTVEI |
| 209 | KLQEEIPVL |
| 210 | GLAEFQENV |
| 211 | NVAEIVIHI |

TABLE 3-continued

TAA Peptide sequences

| SEQ ID NO: | Amino Acid Sequence |
|---|---|
| 212 | ALAGIVTNV |
| 213 | NLLIDDKGTIKL |
| 214 | VLMQDSRLYL |
| 215 | KVLEHVVRV |
| 216 | LLWGNLPEI |
| 217 | SLMEKNQSL |
| 218 | KLLAVIHEL |
| 219 | ALGDKFLLRV |
| 220 | FLMKNSDLYGA |
| 221 | KLIDHQGLYL |
| 222 | GPGIFPPPPPQP |
| 223 | ALNESLVEC |
| 224 | GLAALAVHL |
| 225 | LLLEAVWHL |
| 226 | SIIEYLPTL |
| 227 | TLHDQVHLL |
| 228 | SLLMWITQC |
| 229 | FLLDKPQDLSI |
| 230 | YLLDMPLWYL |
| 231 | GLLDCPIFL |
| 232 | VLIEYNFSI |
| 233 | TLYNPERTITV |
| 234 | AVPPPPSSV |
| 235 | KLQEELNKV |
| 236 | KLMDPGSLPPL |
| 237 | ALIVSLPYL |
| 238 | FLLDGSANV |
| 239 | ALDPSGNQLI |
| 240 | ILIKHLVKV |
| 241 | VLLDTILQL |
| 242 | HLIAEIHTA |
| 243 | SMNGGVFAV |
| 244 | MLAEKLLQA |
| 245 | YMLDIFHEV |
| 246 | ALWLPTDSATV |
| 247 | GLASRILDA |
| 248 | ALSVLRLAL |
| 249 | SYVKVLHHL |

TABLE 3-continued

TAA Peptide sequences

| SEQ ID NO: | Amino Acid Sequence |
|---|---|
| 250 | VYLPKIPSW |
| 251 | NYEDHFPLL |
| 252 | VYIAELEKI |
| 253 | VHFEDTGKTLLF |
| 254 | VLSPFILTL |
| 255 | HLLEGSVGV |

Example 2

γδ T Cell Manufacturing

To isolate γδ T cells, in an aspect, γδ T cells may be isolated from a subject or from a complex sample of a subject. In an aspect, a complex sample may be a peripheral blood sample, a cord blood sample, a tumor, a stem cell precursor, a tumor biopsy, a tissue, a lymph, or from epithelial sites of a subject directly contacting the external milieu or derived from stem precursor cells. γδ T cells may be directly isolated from a complex sample of a subject, for example, by sorting γδ T cells that express one or more cell surface markers with flow cytometry techniques. Wild-type γδ T cells may exhibit numerous antigen recognition, antigen-presentation, co-stimulation, and adhesion molecules that can be associated with a γδ T cells. One or more cell surface markers, such as specific γδ TCRs, antigen recognition, antigen-presentation, ligands, adhesion molecules, or co-stimulatory molecules may be used to isolate wild-type γδ T cells from a complex sample. Various molecules associated with or expressed by γδ T-cells may be used to isolate γδ T cells from a complex sample, e.g., isolation of mixed population of Vδ1+, Vδ2+, Vδ3+ cells or any combination thereof.

For example, peripheral blood mononuclear cells can be collected from a subject, for example, with an apheresis machine, including the Ficoll-Paque™ PLUS (GE Healthcare) system, or another suitable device/system. γδ T-cell(s), or a desired subpopulation of γδ T-cell(s), can be purified from the collected sample with, for example, with flow cytometry techniques. Cord blood cells can also be obtained from cord blood during the birth of a subject.

Positive and/or negative selection of cell surface markers expressed on the collected γδ T cells can be used to directly isolate γδ T cells, or a population of γδ T cells expressing similar cell surface markers from a peripheral blood sample, a cord blood sample, a tumor, a tumor biopsy, a tissue, a lymph, or from an epithelial sample of a subject. For instance, γδ T cells can be isolated from a complex sample based on positive or negative expression of CD2, CD3, CD4, CD8, CD24, CD25, CD44, Kit, TCR α, TCR β, TCR α, TCR δ, NKG2D, CD70, CD27, CD30, CD16, CD337 (NKp30), CD336 (NKp46), OX40, CD46, CCR7, and other suitable cell surface markers.

FIG. 1 shows γδ T cell manufacturing according to an embodiment of the present disclosure. This process may include collecting or obtaining white blood cells or PBMC from leukapheresis products. Leukapheresis may include collecting whole blood from a donor and separating the components using an apheresis machine. An apheresis machine separates out desired blood components and returns the rest to the donor's circulation. For instance, white blood cells, plasma, and platelets can be collected using apheresis equipment, and the red blood cells and neutrophils are returned to the donor's circulation.

Commercially available leukapheresis products may be used in this process. Another way to obtain white blood cells is to obtain them from the buffy coat. To isolate the buffy coat, whole anticoagulated blood is obtained from a donor and centrifuged. After centrifugation, the blood is separated into plasma, red blood cells, and buffy coat. The buffy coat is the layer located between the plasma and red blood cell layers. Leukapheresis collections may result in higher purity and considerably increased mononuclear cell content than that achieved by buffy coat collection. The mononuclear cell content possible with leukapheresis may typically be 20 times higher than that obtained from the buffy coat. In order to enrich for mononuclear cells, the use of a Ficoll gradient may be needed for further separation.

To deplete αβ T cells from PBMC, αβ TCR-expressing cells may be separated from the PBMC by magnetic separation, e.g., using CliniMACS® magnetic beads coated with anti-αβ TCR antibodies, followed by cryopreserving αβ TCR-T cells depleted PBMC. To manufacture "off-the-shelf" T-cell products, cryopreserved αβ TCR-T cells depleted PBMC may be thawed and activated in small/mid-scale, e.g., 24 to 4-6 well plates or T75/T175 flasks, or in large scale, e.g., 50 ml-100 liter bags, in the presence of aminobisphosphonate, e.g., zoledronate, and/or isopentenylpyrophosphate (IPP) and/or cytokines, e.g., interleukin 2 (IL-2), interleukin 15 (IL-15), and/or interleukin 18 (IL-18), and/or other activators, e.g., Toll-like receptor 2 (TLR2) ligand, for 1-10 days, e.g., 2-7 days.

FIG. 1 shows the activated T cells may be engineered by transducing with a viral vector, such as lentiviral vector, expressing exogenous genes of interest, such as ap TCRs against specific cancer antigen and CD8, into isolated γδ T cells. Transduction may be carried out once or multiple times to achieve stable transgene expression in small scale, e.g., 24 to 4-6 well plates, or mid/large scale for ½-5 days, e.g., 1 day.

FIG. 1 further shows expansion of the transduced or engineered γδ T cells may be carried out in the presence of cytokines, e.g., IL-2, IL-15, IL-18, and others, in small/mid-scale, e.g., flasks/G-Rex, or in large scale, e.g., 50 ml-100-liter bags, for 7-35 days, e.g., 7-28 days. The expanded transduced T cell products may then be cryopreserved as "off-the-shelf" T-cell products for infusion into patients.

Example 3

Lentiviral Viral Vectors

The lentiviral vectors used herein contain several elements previously shown to enhance vector function, including a central polypurine tract (cPPT) for improved replication and nuclear import, a promoter from the murine stem cell virus (MSCV) (SEQ ID NO: 1), which has been shown to lessen vector silencing in some cell types, a woodchuck hepatitis virus posttranscriptional responsive element (WPRE) (SEQ ID NO: 9) for improved transcriptional termination, and the backbone was a deleted 3'-LTR self-inactivating (SIN) vector design that may have improved safety, sustained gene expression and anti-silencing properties (Yang et al. *Gene Therapy* (2008) 15, 1411-1423, the content of which is incorporated by reference in its entirety).

In an aspect, vectors, constructs, or sequences described herein comprise mutated forms of WPRE. In another aspect, sequences or vectors described herein comprise mutations in WPRE version 1, e.g., WPREmut1 (SEQ ID NO: 265), or WPRE version 2, e.g., WPREmut2 (SEQ ID NO: 266). In an aspect, WPRE mutants comprise at most one mutation, at most two mutations, at most three mutations, at least four mutations, or at most five mutations. In an aspect, vectors, constructs, or sequences described herein do not comprise WPRE. In another aspect, the disclosure provides for one, two, three, four, five, ten, or 20 substitutions in one of SEQ ID NO: 91-96.

In another aspect, vectors, constructs, or sequences described herein do not include an X protein promoter.

To obtain optimal co-expression levels of TCRαβ and CD8αp in the transduced γδ T cells, lentiviral vectors with various designs were generated. FIG. 2 shows T cells may be transduced with two separate lentiviral vectors (2-in-1) expressing TCRαβ or CD8αp and a single lentiviral vector (4-in-1) co-expressing TCRαβ and CD8αβ. In the 4-in-1 vector, the nucleotides encoding TCRα chain, TCRβ chain, CD8α chain, and CD8β chain may be shuffled in various orders. Various 4-in-1 vectors, thus generated, may be used to transduce γδ T cells, followed by measuring TCR/CD8 co-expression levels of the transduced cells using techniques known in the art, e.g., flow cytometry.

To generate lentiviral vectors co-expressing TCRαβ and CD8αβ, a nucleotide encoding furin-linker (GSG or SGSG (SEQ ID NO: 8))-2A peptide may be positioned between TCRα chain and TCRβ chain, between CD8α chain and CD8p chain, and between a TCR chain and a CD8 chain to enable highly efficient gene expression. The 2A peptide may be selected from P2A (SEQ ID NO: 3), T2A (SEQ ID NO: 4), E2A (SEQ ID NO: 5), or F2A (SEQ ID NO: 6).

Lentiviral viral vectors may also contain post-transcriptional regulatory element (PRE), such as Woodchuck PRE (WPRE) (SEQ ID NO: 9) to enhance the expression of the transgene by increasing both nuclear and cytoplasmic mRNA levels. One or more regulatory elements including mouse RNA transport element (RTE), the constitutive transport element (CTE) of the simian retrovirus type 1 (SRV-1), and the 5' untranslated region of the human heat shock protein 70 (Hsp70 5'UTR) may also be used and/or in combination with WPRE to increase transgene expression.

Lentiviral vectors may be pseudotyped with RD114TR (SEQ ID NO: 97), which is a chimeric glycoprotein containing an extracellular and transmembrane domain of feline endogenous virus (RD114) fused to cytoplasmic tail (TR) of murine leukemia virus. Other viral envelop proteins, such as VSV-G env, MLV 4070A env, RD114 env, chimeric envelope protein RD114pro, baculovirus GP64 env, or GALV env, or derivatives thereof, may also be used.

Figure 3:
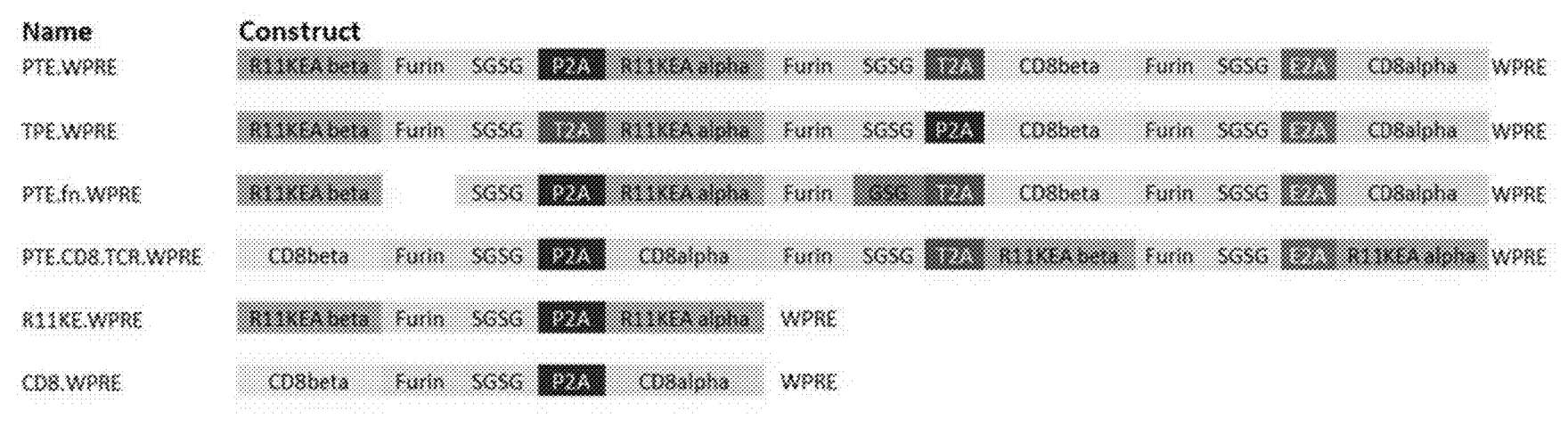

FIG. 3 shows four different 4-in-1 vectors, i.e., PTE WPRE (SEQ ID NO: 91), TPE WPRE (SEQ ID NO: 92), PTE fn WPRE (SEQ ID NO: 93), and PTE CD8 TCR WPRE (SEQ ID NO: 94), co-expressing TCRαβ (R11KEA) and CD8αβ, and two 2-in-1 vectors, i.e., R11 KE WPRE (SEQ ID NO: 95), expressing TCRαβ (R11KEA) and CD8 WPRE (SEQ ID NO: 96) expressing CD8αβ. TCRαβ (R11KEA) binds to PRAME-004 (SLLQHLIGL) (SEQ ID NO: 147) in a complex with an MHC molecule. Linker sequences (GSG or SGSG (SEQ ID NO: 8)) are shown.

Example 4

Co-Expression of TCR and CD8

γδ T cells obtained from Donor 1 and Donor 2 were manufactured by the process shown in FIG. 1. On Day 3 or Day 6 post-activation with zoledronate, IL2, and IL15, γδ T cells were transduced with lentivirus, pseudotyped with RD114TR, e.g., PTE WPRE (SEQ ID NO: 91), TPE WPRE (SEQ ID NO: 92), PTE fn WPRE (SEQ ID NO: 93), and PTE CD8 TCR WPRE (SEQ ID NO: 94), followed by measuring co-expression levels of R11 KEA and CD8 using flow cytometry. Transduction efficiency was assessed using antibodies specific to TCR (Vβ8) and CD8 (CD8α) via flow cytometry.

Figure 4:
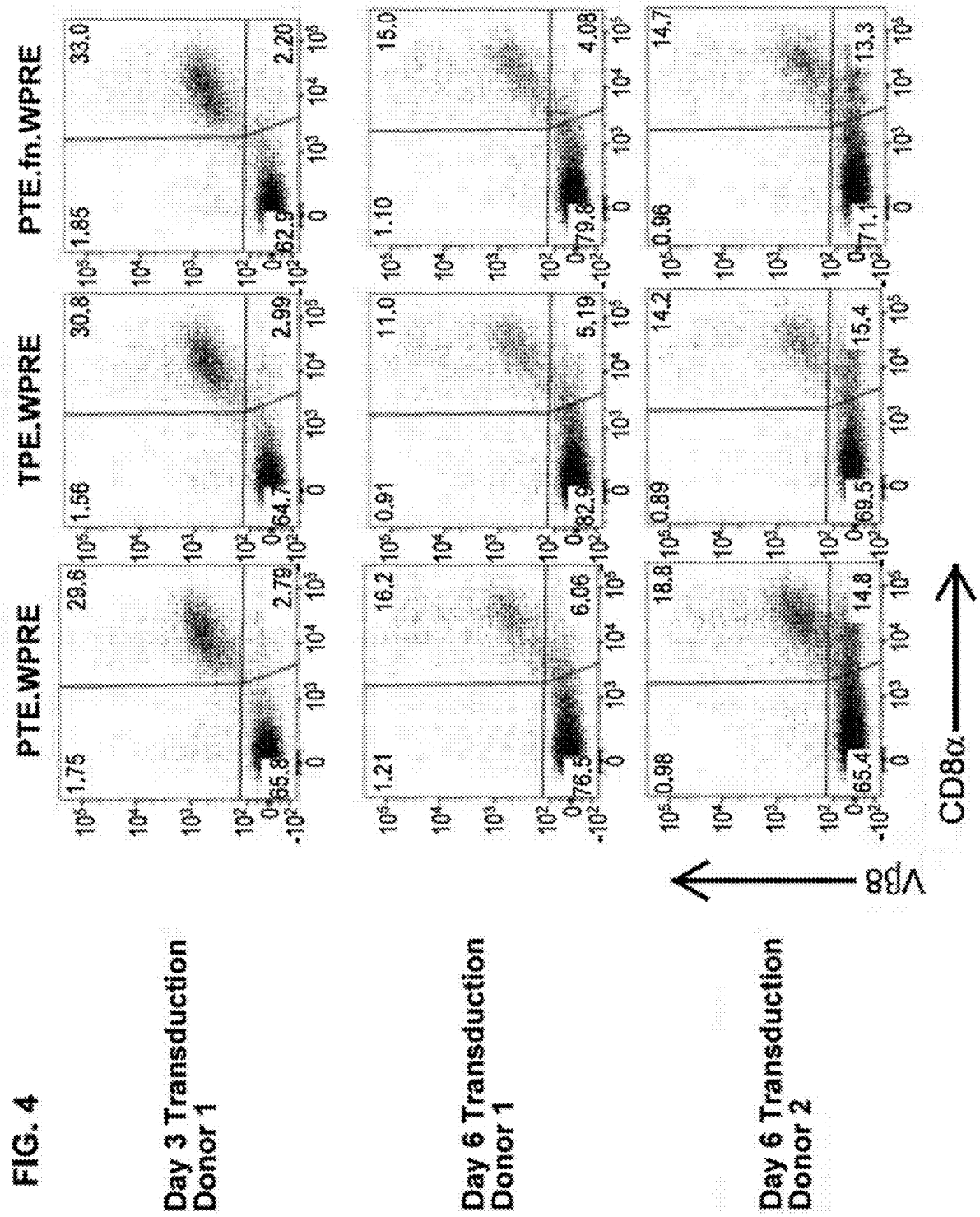
FIG. 4 shows lentiviruses pseudotyped with RD114TR used for transducing γδ T cells on Day 3 or Day 6 post activation with zoledronate, IL-2, and IL-15. Transduction efficiency was assessed using antibodies specific to TCR (Vβ8) and CD8 (CD8α) via flow cytometry.
Figure 4:
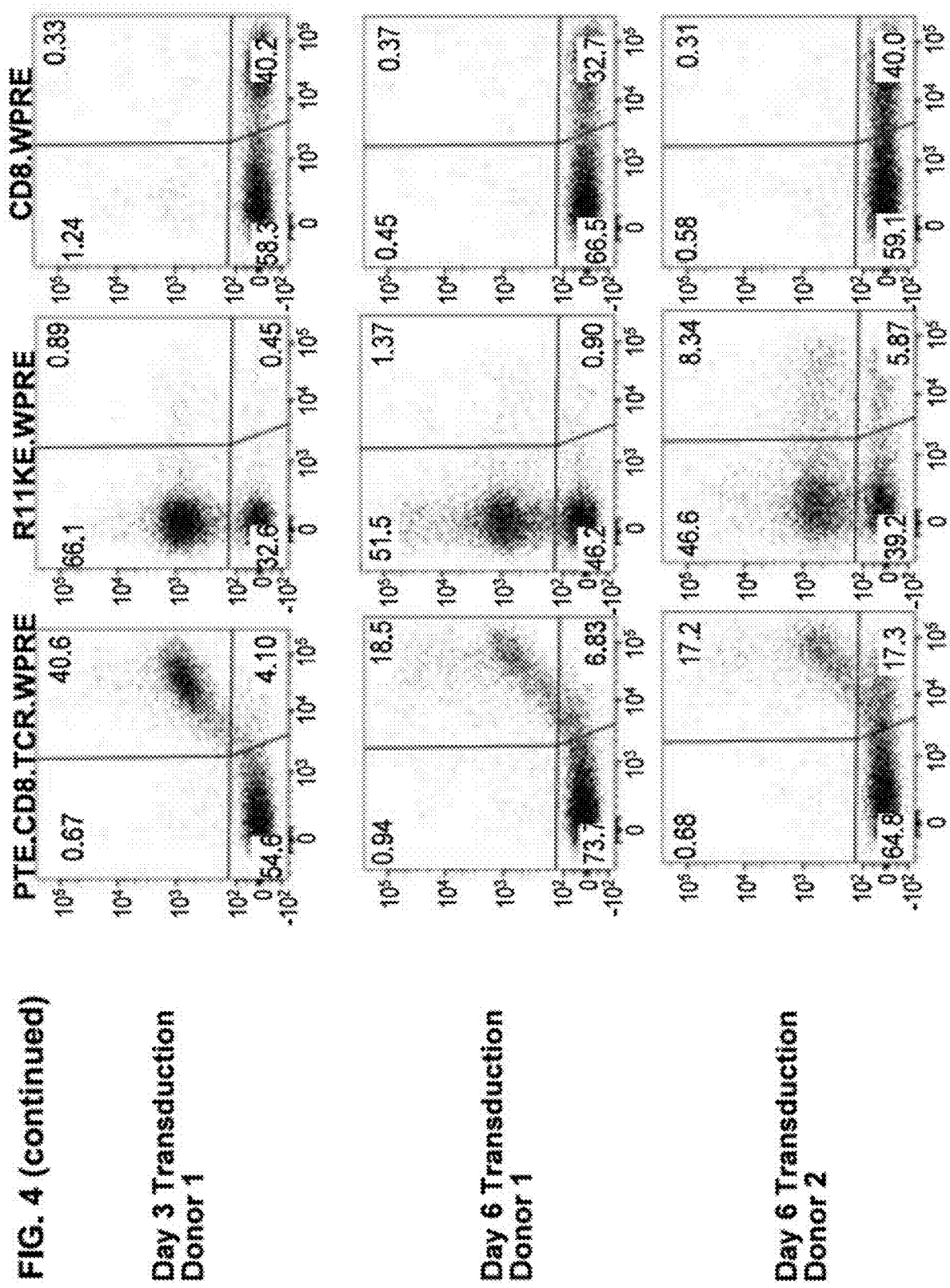

FIG. 4 shows, in γδ T cells from Donor 1, co-expression levels of R11 KEA and CD8 resulted from transduction with PTE CD8 TCR WPRE, i.e., 40.5% (Day 3) and 18.5% (Day 6), are higher than that from transduction with PTE WPRE (29.6% (Day 3), 16.2% (Day 6)), TPE WPRE (30.8% (Day 3), 11.0% (Day 6)), and PTE fn WPRE (33.0% (Day 3), 15.0% (Day 6)). In γδ T cells from Donor 2, co-expression levels of R11 KEA and CD8 on Day 6 post-activation resulted from transduction with PTE WPRE, i.e., 18.8%, is higher than that from transduction with TPE WPRE (14.2%), PTE fn WPRE (14.7%), and PTE CD8 TCR WPRE (17.2%). As controls, background levels of R11 KEA and CD8 were detected in γδ T cells transduced separately with 2-in-1 vectors, i.e., TCRαβ (R11KEA) or CD8 WPRE.

Example 5

Effects on transgene expression and functionality of 4-in-1 viral vectors, e.g., lentiviral vectors, containing sequences encoding CD8αβ chains and sequences encoding TCRαβ chains located at different positions in the vectors.

WO 2019/204662 describes CD4+ cells that express an exogenous CD8αβ co-receptor and one or more exogenous engineered antigen receptors, e.g., TCRs. Table 4 shows a comparison between the 4-in-1 constructs described in WO 2019/204662 and that of according to aspects of the present disclosure.

TABLE 4

| | WO 2019/204662 | Aspects described herein |
|---|---|---|
| Orientation of transgene (from 5' end to 3' end direction) | TCRβ-TCRα-CD8α-CD8β | CD8β-CD8α-TCRβ-TCRα |
| Sources of CD8αβ sequences | GenBank | codon optimized (for enhancing expression) |
| 2A linkers | 2A | 2A + Furin linker (for promoting efficient cleavage of residual 2A sequences for gene of interest) |
| Cell Type | CD4+ cells and CD8+ cells | γδ T cells (low (0-20%) CD8 expression and no CD4 expression) |
| Virus and Pseudotype | retrovirus and RD114 | lentivirus and RD114TR and VSV-G |

The open reading frame (ORF) of the nucleic acid molecules of the present disclosure may be at least partially codon-optimized. Codon-optimization is based on the finding that the translation efficiency may be determined by a different frequency in the occurrence of transfer RNAs (tRNAs) in cells. Thus, the open reading frames of nucleic acid molecules of the present disclosure may be modified compared to the corresponding wild type coding region such that at least one codon of the wild type sequence that codes for a tRNA, which is relatively rare in the cell, may be exchanged for a codon, which codes for a tRNA, which is comparably frequent in the cell and may carry the same amino acid as the relatively rare tRNA. By this modification, the open reading frame of nucleic acid molecules of the present disclosure may be modified such that codons, for which frequently occurring tRNAs are available may replace codons, which correspond to rare tRNAs. In other words, according to the present disclosure, by such a modification all codons of the wild type open reading frame, which code for a rare tRNA, may be exchanged for a codon, which codes for a tRNA, which is more frequent in the cell and which carries the same amino acid as the rare tRNA. Which tRNAs occur relatively frequently in the cell and which, in contrast, occur relatively rarely is known to a person skilled in the art; e.g., Akashi, Curr. Opin. Genet. Dev. 2001, 11(6): 660-666, the contents of which are incorporated by reference in their entireties. In some embodiments, open reading frames of nucleic acid molecules of the present disclosure may be codon-optimized, preferably with respect to the system, in which the nucleic acid molecules of the present disclosure are to be expressed, preferably with respect to the system, in which the nucleic acid molecules of the present disclosure are to be translated. Preferably, the codon usage of open reading frames of the nucleic acid molecules of the present disclosure may be codon-optimized according to mammalian codon usage, more preferably, according to human codon usage. Preferably, the open reading frame may be codon-optimized and G/C-content modified.

To determine which transgene orientation provide better transgene expression and functionality, three 4-in-1 viral vectors each containing sequences encoding TCRαβ chains located upstream from sequences encoding CD8αp chains, e.g., PTE.WPRE (SEQ ID NO: 91), TPE.WPRE (SEQ ID NO: 92), and PTE.fn.WPRE (SEQ ID NO: 93), and a 4-in-1 viral vector containing sequences encoding CD8αp chains located upstream from sequences encoding TCRαβ chains, e.g., PTE.CD8.TCR.WPRE (SEQ ID NO: 94), were transduced into γδ T cells, followed by fluorescence-activated cell sorting (FACS) analysis using fluorescently-tagged anti-CD8 antibodies and fluorescently-tagged anti-TCR VP8 (Vb8) antibodies to detect the expression of CD8 and TCR, respectively, on the cell surface.

Figure 10:
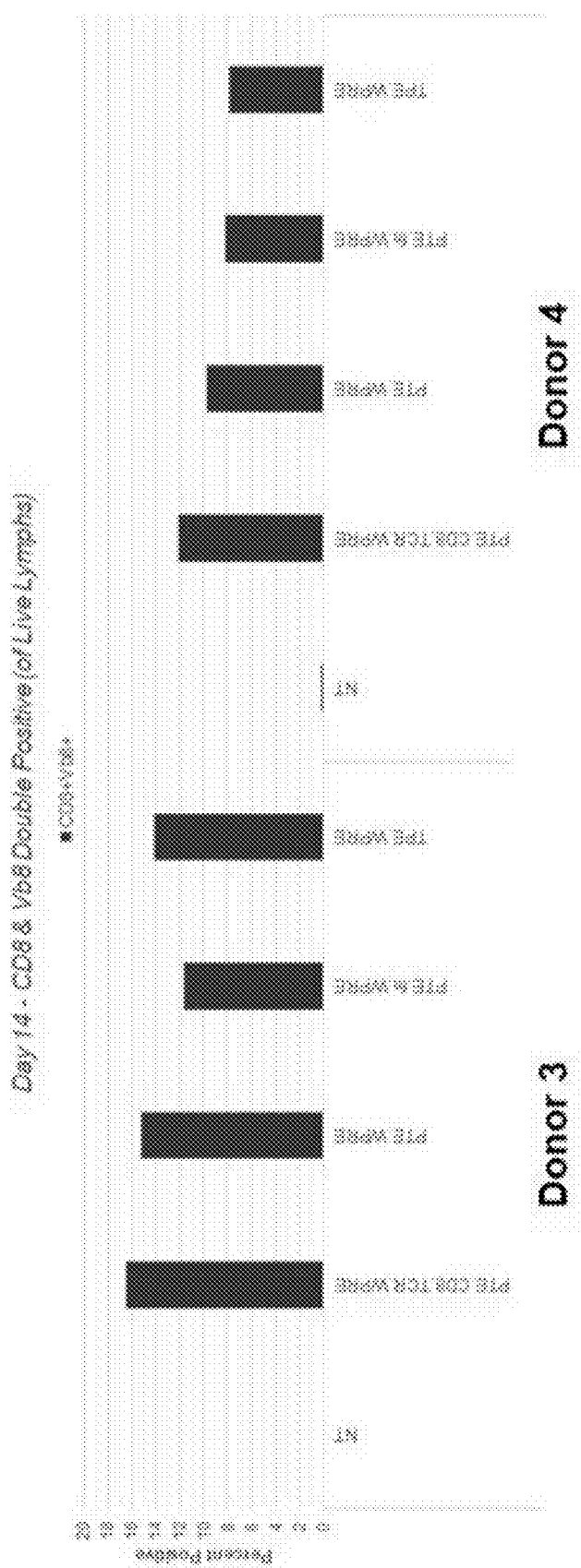
FIG. 10 shows % CD8+TCR+γδ T cells transduced with viral vector containing PTE.CD8.TCR.WPRE, PTE.WPRE, PTE.Fn.WPRE, or TPE.WPRE. Non-transduced (NT) cells serve as control.
Figure 11:
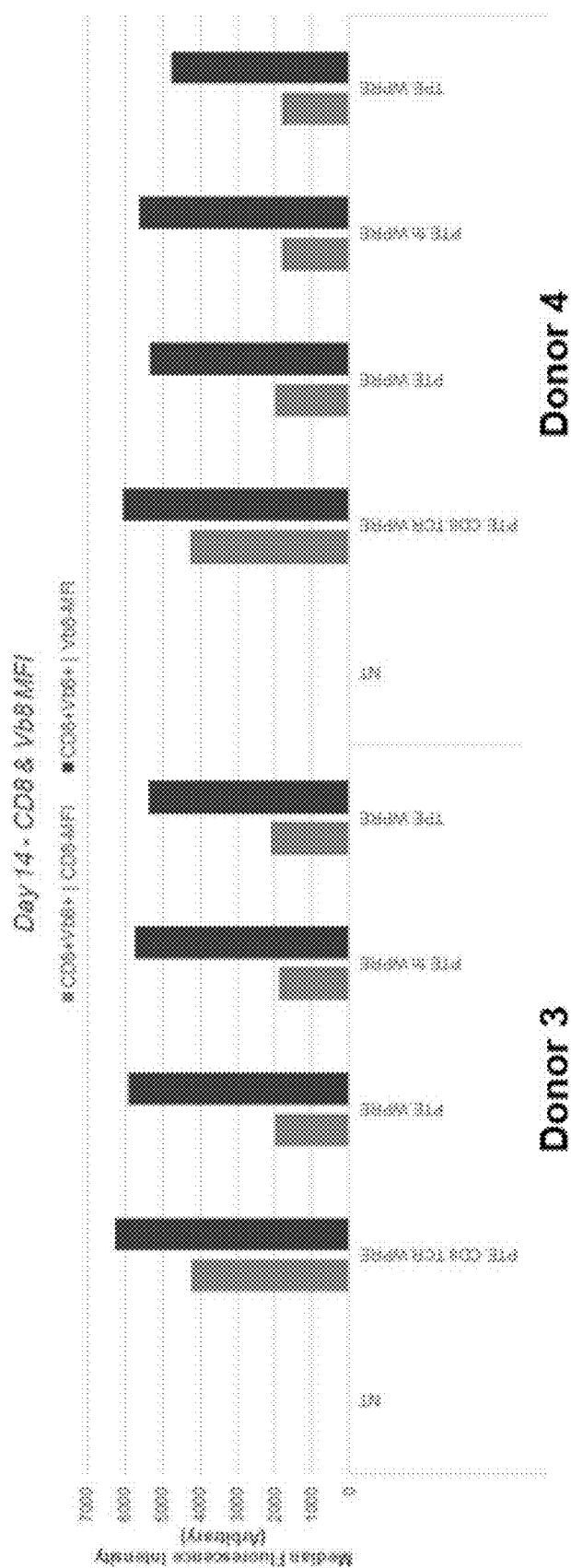
FIG. 11 shows median fluorescence intensity (MFI) of CD8 and TCR in γδ T cells transduced with viral vector containing PTE.CD8.TCR.WPRE, PTE.WPRE, PTE.Fn.WPRE, or TPE.WPRE. Non-transduced (NT) cells serve as control.

FIGS. 10 and 11 show that γδ T cells obtained from Donor 3 and Donor 4 transduced with the 4-in-1 viral vector containing PTE.CD8.TCR.WPRE results in the highest expression of both CD8 and TCR on the cell surface at Day 14 of manufacturing as compared with that transduced with 4-in-1 viral vector containing PTE.WPRE, TPE.WPRE, or PTE.fn.WPRE, based on the % of CD8+Vb8+ double-positive cells (FIG. 10) and the MFI of CD8 or the MFI of Vb8 (FIG. 11).

Figure 13:
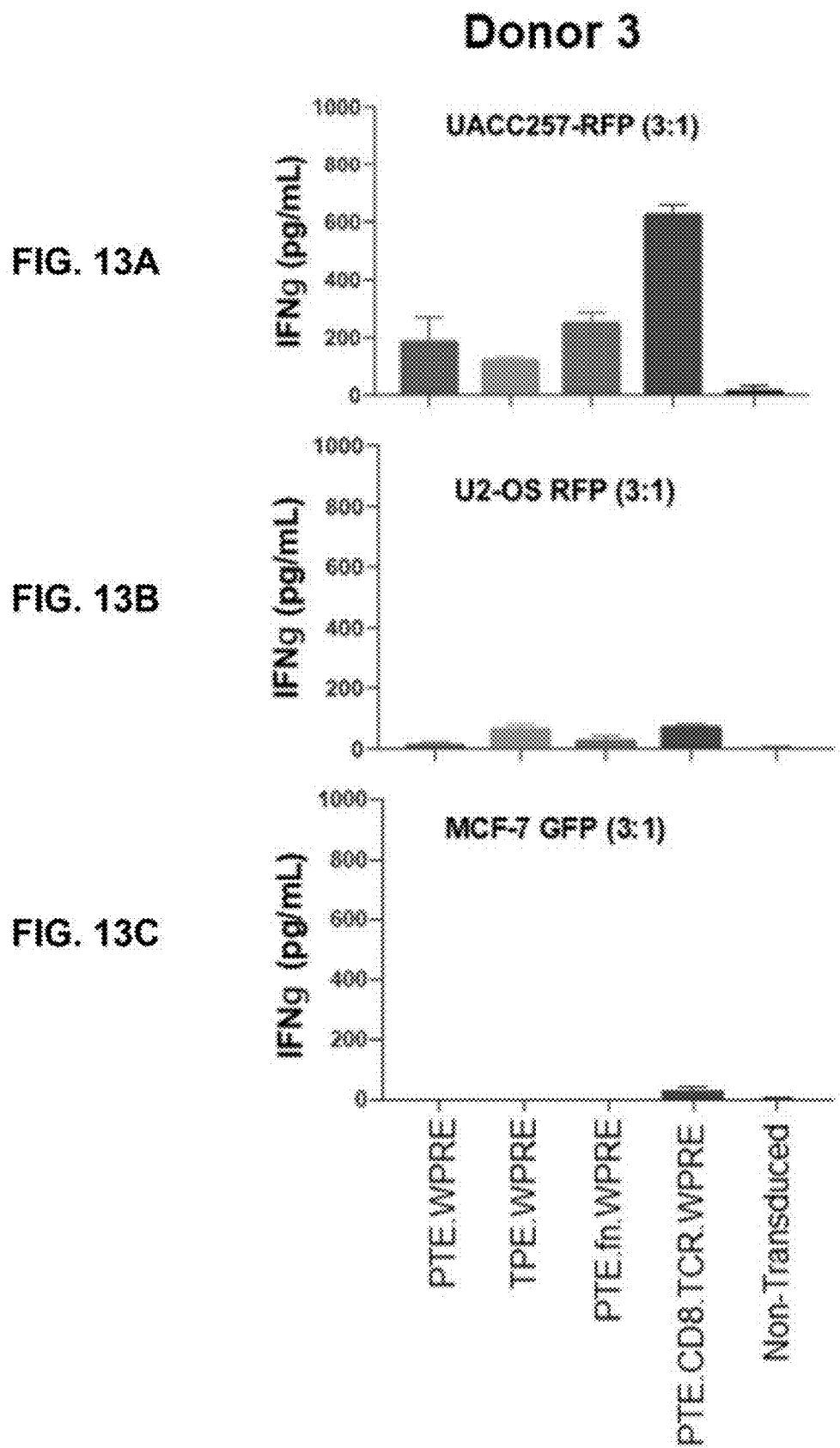
FIGS. 13A-13C show amount of interferon (IFN)-γ secretion by γδ T cells obtained from Donor 3 transduced with viral vector containing PTE.CD8.TCR.WPRE, PTE.WPRE, PTE.Fn.WPRE, or TPE.WPRE in a high antigen expressing tumor cell line, e.g., UACC257 (FIG. 13A), in a low antigen expressing tumor cell line, e.g., U2OS (FIG. 13B), or in antigen-negative tumor cell line, e.g., MCF-7 (FIG. 13C). Non-transduced cells serve as control.

The high expression of both CD8 and TCR on the cell surface of γδ T cells transduced with 4-in-1 viral vector containing PTE.CD8.TCR.WPRE correlates well with their in vitro killing activity. For example, FIG. 12 shows γδ T cells obtained from Donor 3 transduced with 4-in-1 viral vector containing PTE.CD8.TCR.WPRE exhibits the best killing activity against both the high target peptide presenting cell line UACC257 (top panel) and the low target peptide presenting cell line U2OS (bottom panel) as compared with that transduced with 4-in-1 viral vector containing PTE.WPRE, TPE.WPRE, or PTE.fn.WPRE, FIGS. 13A-13C show amount of IFN-γ secretion by the corresponding γδ T cells transduced with 4-in-1 viral vector containing PTE.CD8.TCR.WPRE, PTE.WPRE, TPE.WPRE, or PTE.fn.WPRE in the presence of target cells, e.g., UACC257 (FIG. 13A), U2OS (FIG. 13B), and target-negative cell line MCF-7 (FIG. 13C).

Figure 15:
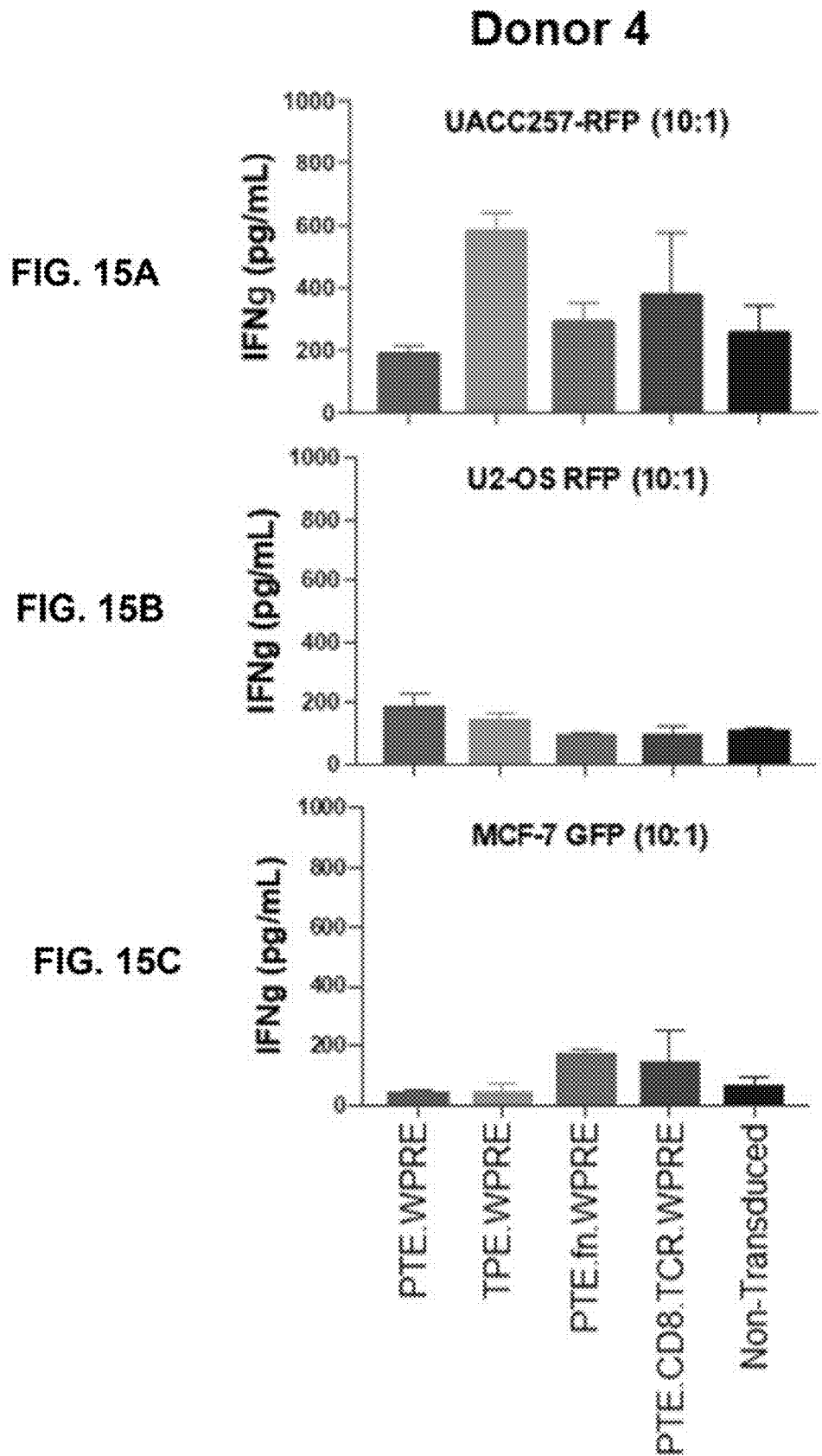
FIGS. 15A-15C show amount of IFN-γ secretion by γδ T cells obtained from Donor 4 transduced with viral vector containing PTE.CD8.TCR.WPRE, PTE.WPRE, PTE.Fn.WPRE, or TPE.WPRE in a high antigen expressing tumor cell line, e.g., UACC257 (FIG. 15A), in a low antigen expressing tumor cell line, e.g., U2OS (FIG. 15B), or in antigen-negative tumor cell line, e.g., MCF-7 (FIG. 15C). Non-transduced cells serve as control.

FIG. 14 shows γδ T cells obtained from Donor 4 transduced with 4-in-1 viral vector containing PTE.CD8.TCR.WPRE also exhibits the best killing activity against both UACC257 (top panel) and U2OS (bottom panel) as compared with that transduced with 4-in-1 viral vector containing PTE.WPRE, TPE.WPRE, or PTE.fn.WPRE, FIGS. 15A-15C show amount of IFN-γ secretion by the corresponding γδ T cells transduced with 4-in-1 viral vector containing PTE.CD8.TCR.WPRE, PTE.WPRE, TPE.WPRE, or PTE.fn.WPRE in the presence of target cells, e.g., UACC257 (FIG. 15A), U2OS (FIG. 15B), and MCF-7 (FIG. 15C).

Figure 16:
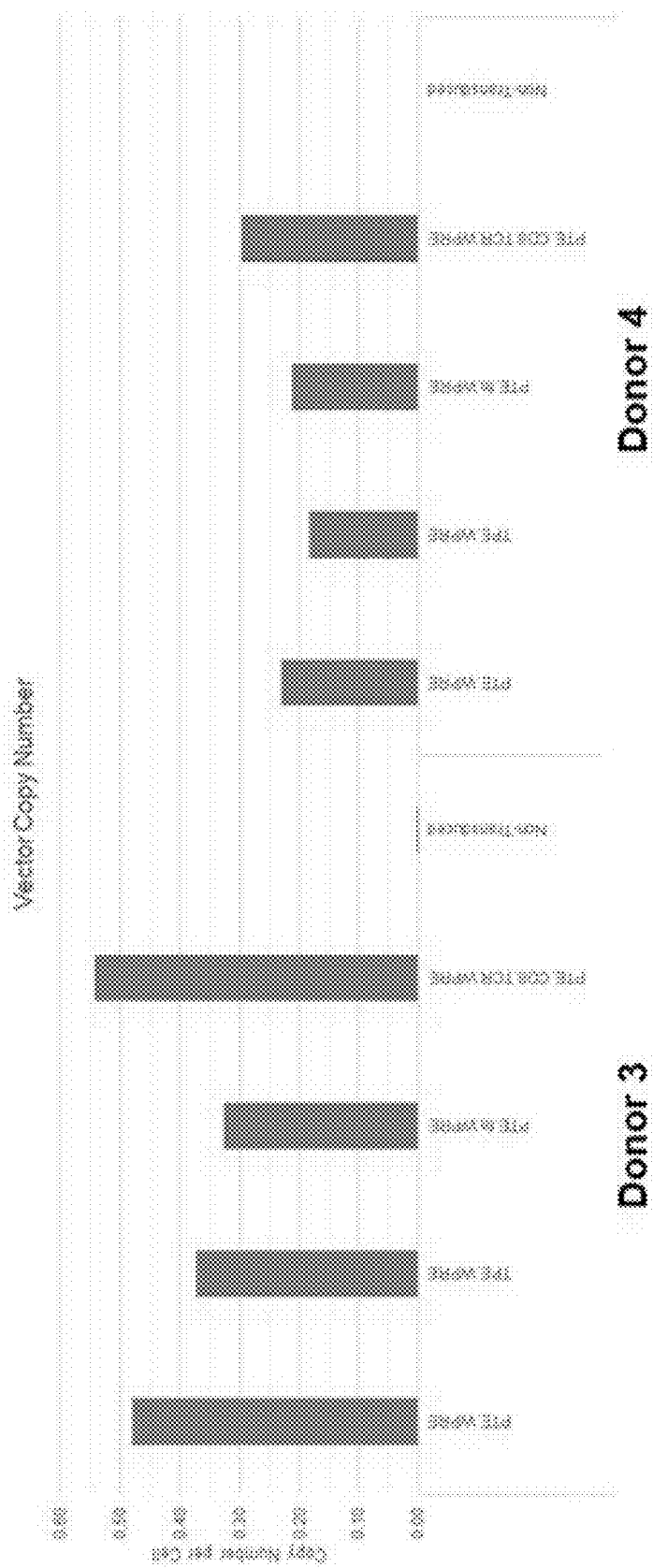
FIG. 16 shows copy number of viral vector in γδ T cells transduced with viral vector containing PTE.CD8.TCR.WPRE, PTE.WPRE, PTE.Fn.WPRE, or TPE.WPRE. Non-transduced cells serve as control.

FIG. 16 shows γδ T cells obtained from Donor 3 and Donor 4 transduced with 4-in-1 viral vector containing PTE.CD8.TCR.WPRE results in fewer than 0.6 copy of integrated vector per cell similar to that transduced with PTE.WPRE, TPE.WPRE, and PTE.fn.WPRE. This low copy number of integrated vector per cell is within the limit of safety requirement, i.e., fewer than 5 copy number of integrated vector per cell.

Figure 17A:
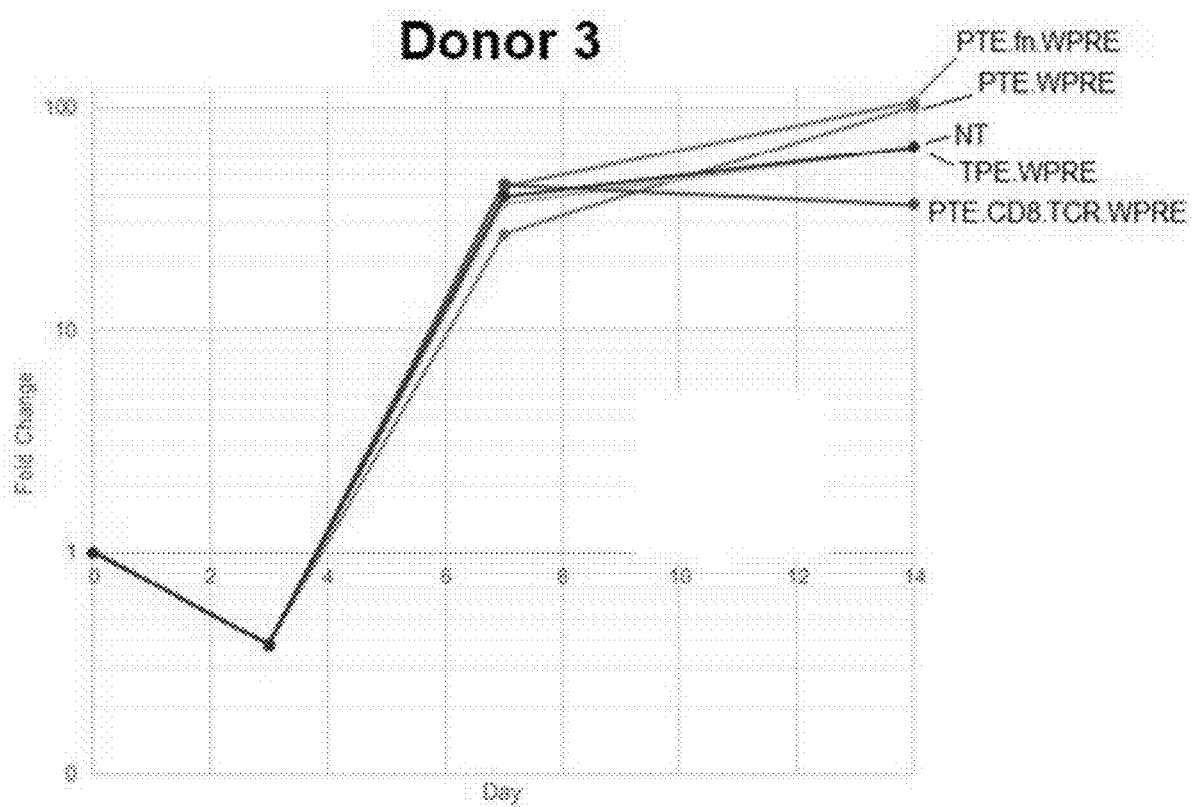
FIGS. 17A and 17B show fold expansion of γδ T cells obtained from Donor 3 (FIG. 17A) or Donor 4 (FIG. 17B) transduced with viral vector containing PTE.CD8.TCR.WPRE, PTE.WPRE, PTE.Fn.WPRE, or TPE.WPRE. Non-transduced (NT) cells serve as control.
Figure 17B:
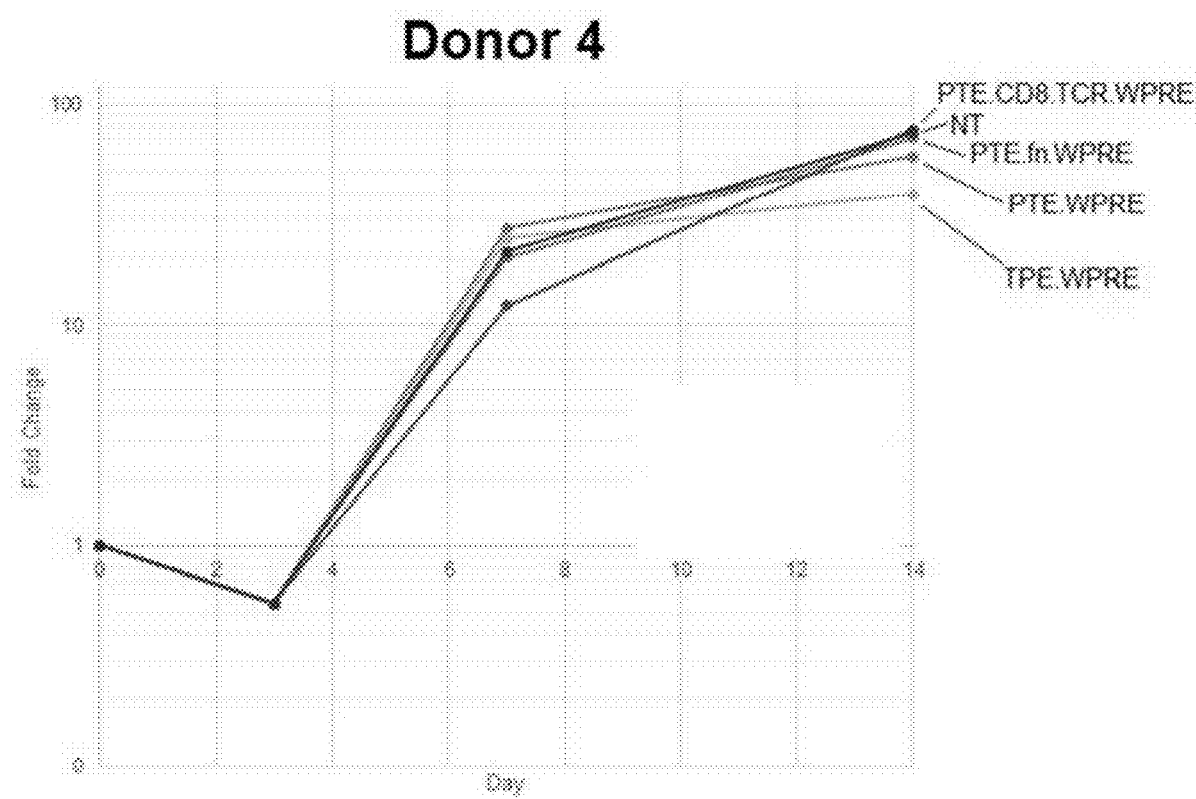

FIGS. 17A and 17B show γδ T cells obtained from Donor 3 and Donor 4, respectively, transduced with 4-in-1 viral vector containing PTE.CD8.TCR.WPRE achieve comparable levels of cell expansion at Day 14 of manufacturing to that transduced with 4-in-1 viral vector containing PTE.WPRE, TPE.WPRE, or PTE.fn.WPRE.

Figure 18A:
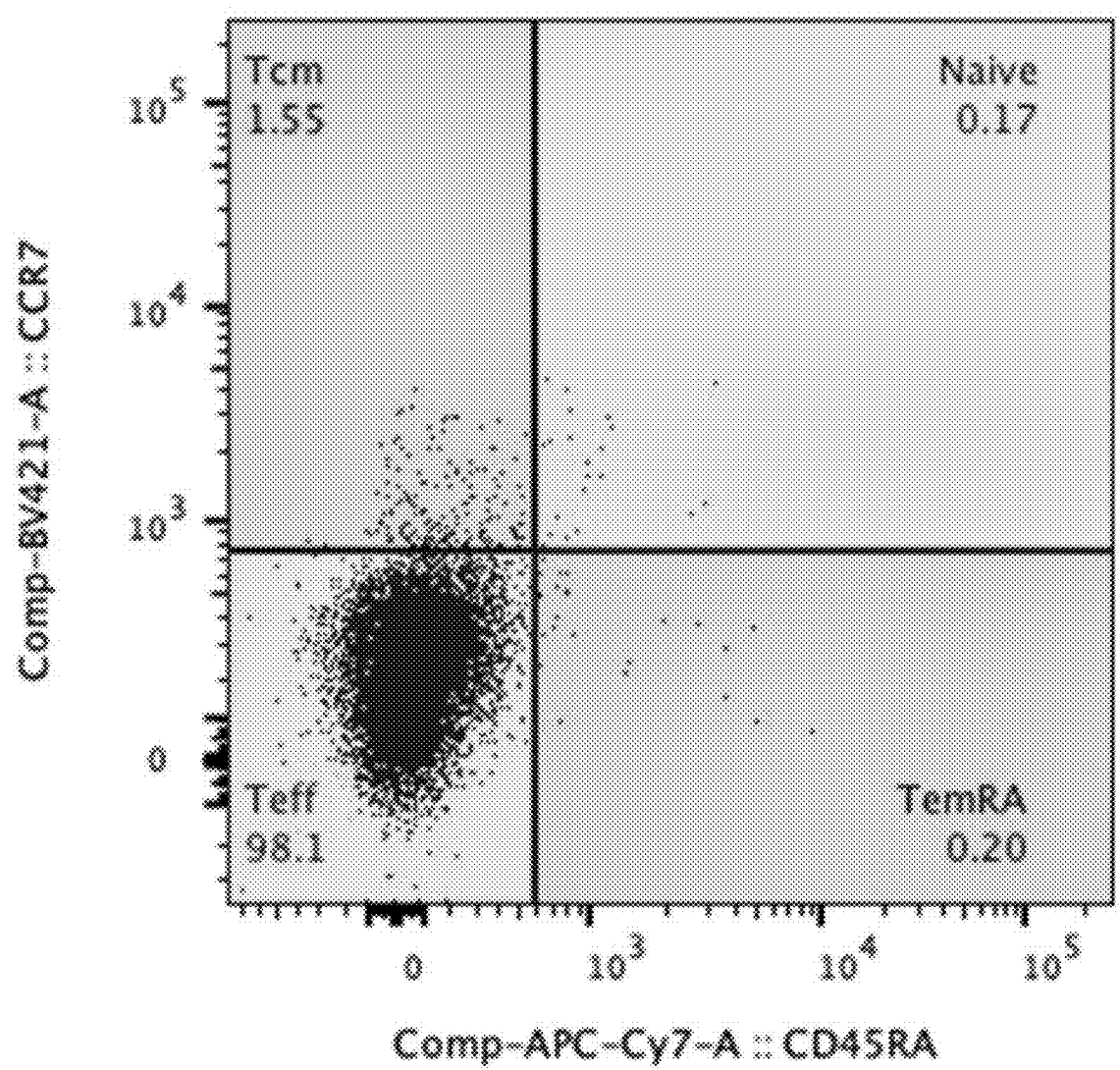
FIG. 18A shows memory phenotypes of γδ T cells determined by flow cytometry in accordance with some embodiments of the present disclosure.

To determine memory cell phenotypes of the transduced γδ T cells, cells were stained by allophycocyanin (APC)-Cy7-tagged anti-CD45RA antibodies and BV421-tagged anti-CCR7 antibodies, followed by FACS analysis to determine the % of Tcm, Naïve T cells, TemRA, and Teff present in the transduced γδ T cells. FIG. 18A shows an example of such an analysis.

Figure 18B:
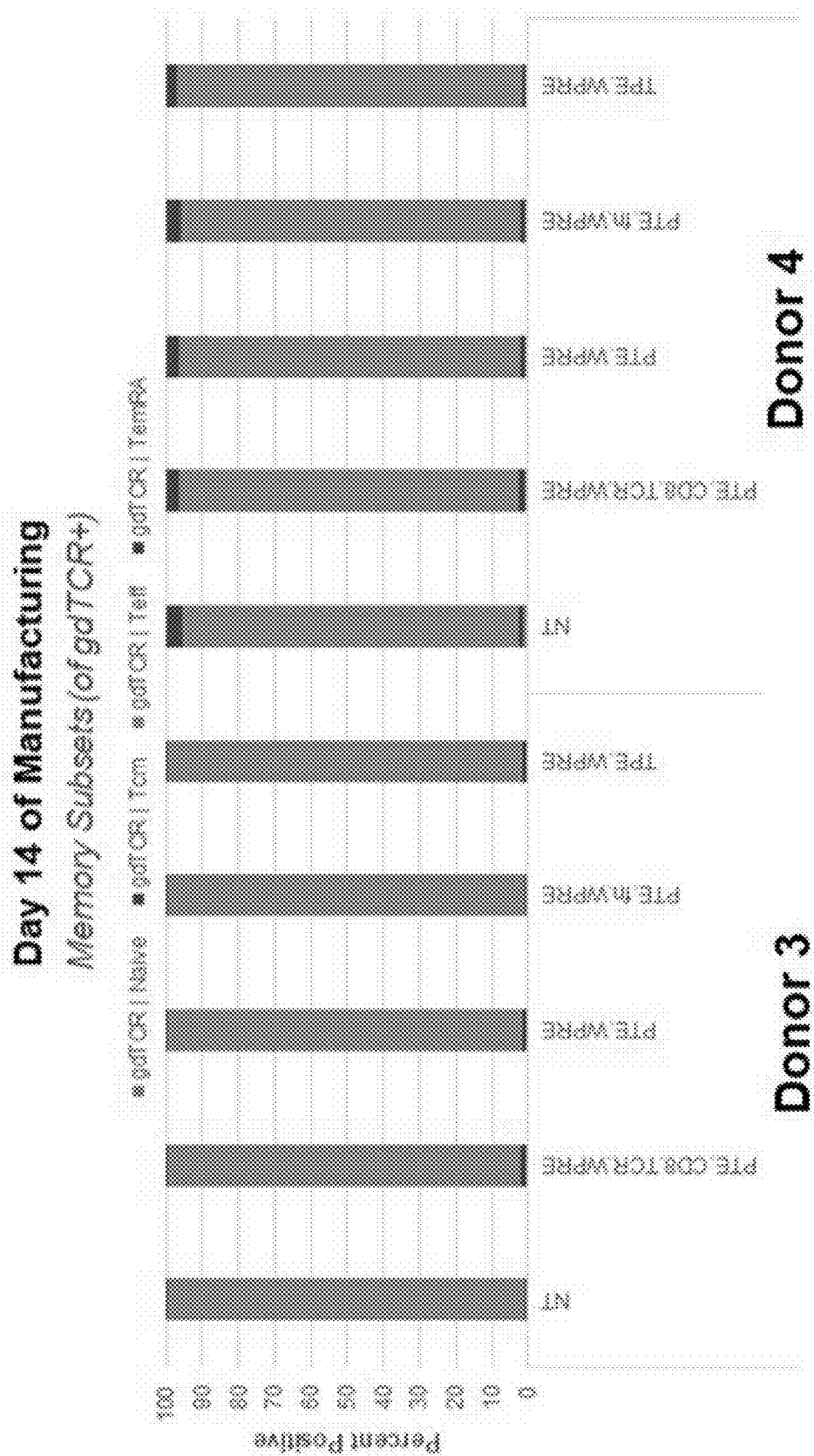
FIG. 18B shows memory phenotypes of γδ T cells transduced with viral vector containing PTE.CD8.TCR.WPRE, PTE.WPRE, PTE.Fn.WPRE, or TPE.WPRE. Non-transduced (NT) cells serve as control.

FIG. 18B shows γδ T cells obtained from Donor 3 and Donor 4 transduced with 4-in-1 viral vector containing PTE.CD8.TCR.WPRE achieve comparable levels of memory T cell phenotypes at Day 14 of manufacturing to that transduced with 4-in-1 viral vector containing PTE.WPRE, TPE.WPRE, or PTE.fn.WPRE.

Example 6

Figure 19:
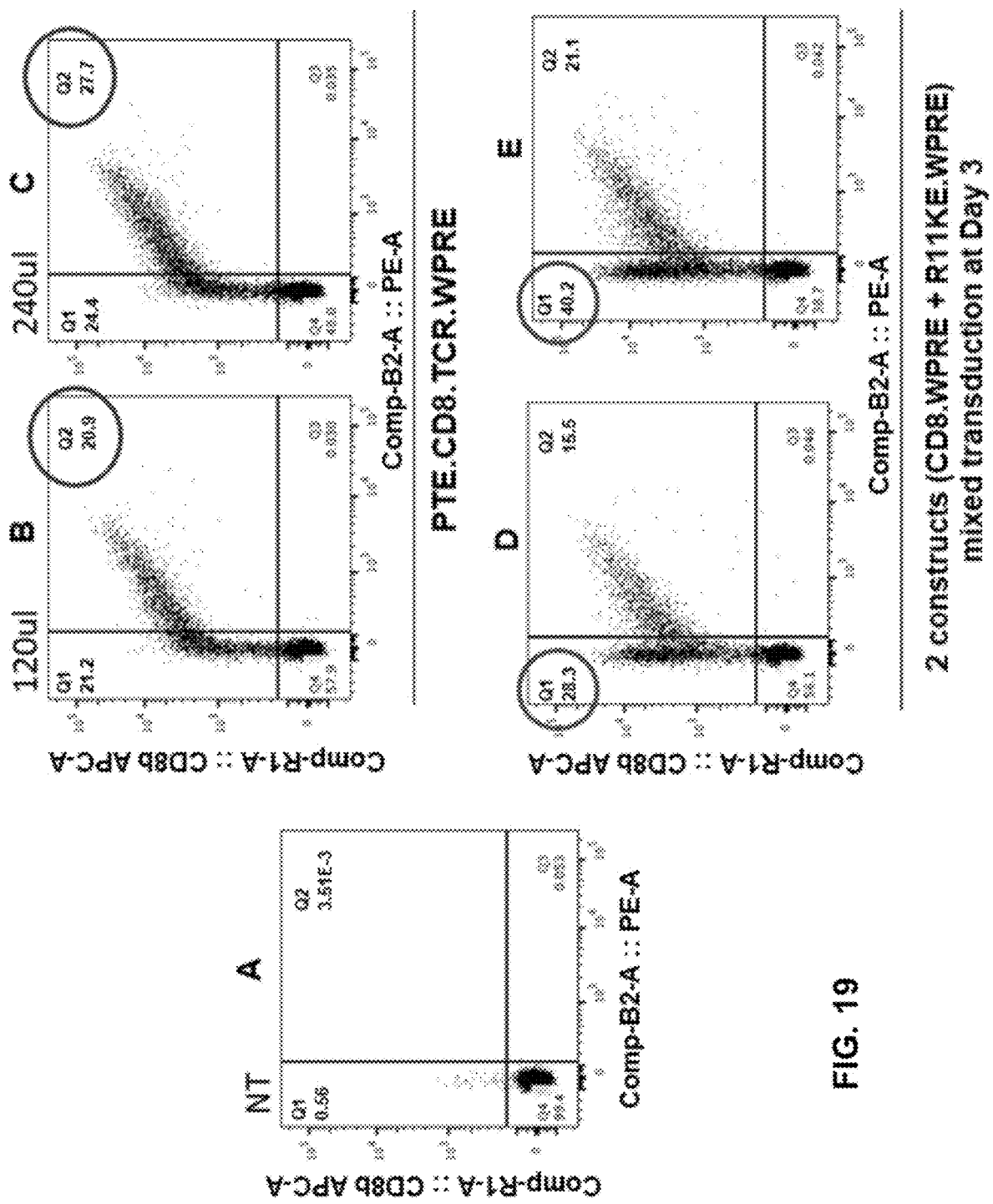
FIG. 19 shows comparison of transduction efficiency between γδ T cells transduced with a single lentiviral vector (LV) containing PTE.CD8.TCR.WPRE (panel B (120 μl) and panel C (240 μl)) or transduced with two separate lentiviral vectors: one containing R11 KE.WPRE and the other containing CD8,WPRE (panels D and E), with increasing amount of viral vectors, e.g., 120 μl of each R11 KE.WPRE and CD8,WPRE (panel D) and 240 μl of each R11 KE.WPRE and CD8,WPRE (panel E). Non-transduced (NT) cells serve as control.

Effects on transgene expression in cells transduced with one 4-in-1 viral vector versus transduced with two 2-in-1 viral vectors FIG. 19 show more CD8+TCR+γδ T cells resulted from transduction with 4-in-1 lentiviral vector containing PTE.CD8.TCR.WPRE (120 μl) (panel B, 20.9%) than that from transduction with a mixture of a 2-in-1 lentiviral vector containing CD8.WPRE (120 μl) and a 2-in-1 lentiviral vector containing R11 KE.WPRE (120 μl) (panel D, 15.5%). On the other hand, more CD8+TCR– γδ T cells resulted from transduction with a mixture of a 2-in-1 lentiviral vector containing CD8.WPRE (120 μl) and a 2-in-1 lentiviral vector containing R11 KE.WPRE (120 μl) (panel D, 28.3%) than that transduced with 4-in-1 lentiviral viral vector containing PTE.CD8.TCR.WPRE (panel B, 21.2%). Similarly, more CD8+TCR+γδ T cells resulted from transduction with 4-in-1 lentiviral vector containing PTE.CD8.TCR.WPRE (240 μl) (panel C, 27.7%) than that transduced with a mixture of a 2-in-1 lentiviral vector containing CD8.WPRE (240 μl) and a 2-in-1 lentiviral vector containing R11 KE.WPRE (240 μl) (panel E, 21.1%). On the other hand, more CD8+TCR– γδ T cells resulted from transduction with a mixture of a 2-in-1 lentiviral vector containing CD8.WPRE (240 μl) and a 2-in-1 lentiviral vector containing R11 KE.WPRE (240 μl) (panel E, 40.2%) than that transduced with 4-in-1 lentiviral vector containing PTE.CD8.TCR.WPRE (panel C, 24.4%). Non-transduced (NT) γδ T cells serves as control (panel A). The 2-color staining was performed using APC-tagged anti-CD8β antibodies and phycoerythrin (PE)-tagged target peptide/MHC complex tetramer. These results suggest that transduction with 4-in-1 lentiviral vector containing sequences encoding CD8αβ and TCRαβ, e.g., PTE.CD8.TCR.WPRE, may result in higher number of CD8+TCR+ T cells than that transduced with a mixture of a 2-in-1 lentiviral vector containing sequences encoding CD8αβ, e.g., CD8.WPRE, and a 2-in-1 lentiviral vector containing sequences encoding TCRαβ, e.g., R11 KE.WPRE. On the other hand, transduction with a mixture of a 2-in-1 lentiviral vector containing sequences encoding CD8αβ, e.g., CD8.WPRE, and a 2-in-1 lentiviral vector containing sequences encoding TCRαβ, e.g., R11 KE.WPRE, may result in higher number of CD8+TCR– T cells than that transduced with 4-in-1 lentiviral vector containing sequences encoding CD8αβ and TCRαβ, e.g., PTE.CD8.TCR.WPRE.

Figure 20:
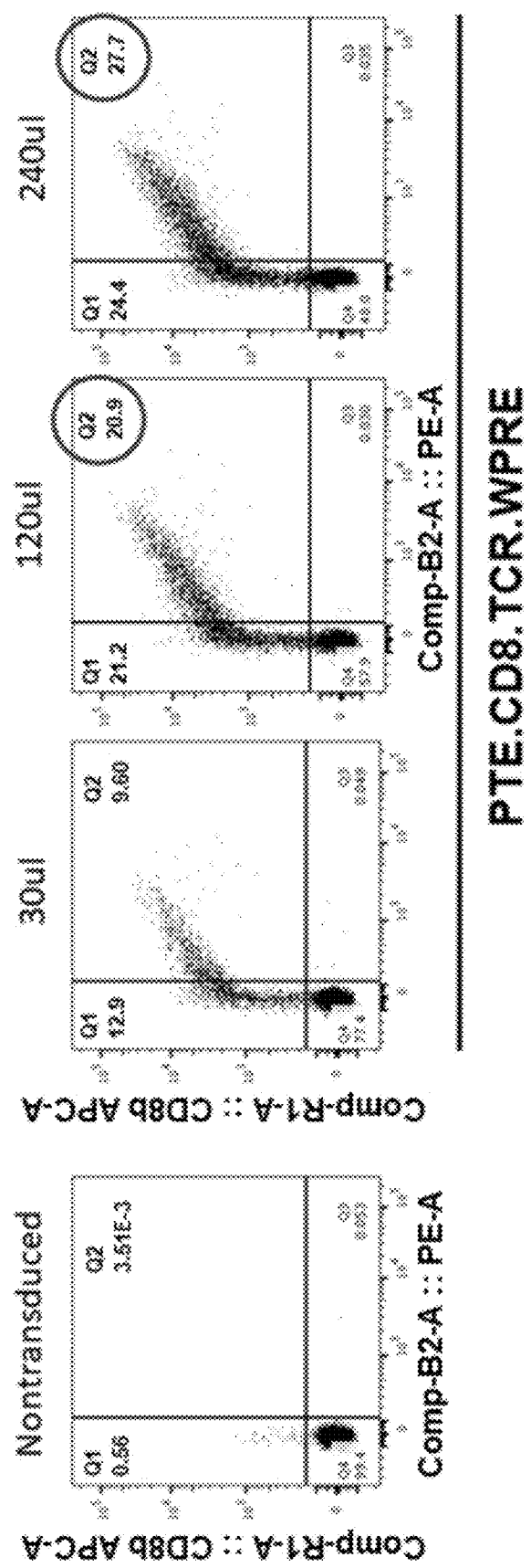
FIG. 20 shows enhanced transduction efficiency in γδ T cells transduced with increasing amount of viral vector containing PTE.CD8.TCR.WPRE, e.g., 30 μl, 120 μl, and 240 μl. Non-transduced cells serve as control.

FIG. 20 shows that increasing amount of 4-in-1 viral vector containing PTE.CD8.TCR.WPRE, e.g., 30 μl, 120 μl, and 240 μl, for transduction enhances transduction efficiency, e.g., the % of CD8+TCR+γδ T cells increases, e.g., 9.6% at 30 μl, 20.9% at 120 μl, and 27.7% at 240 μl. Non-transduced γδ T cells serves as control. The 2-color staining was performed using APC-tagged anti-CD8β antibodies and PE-tagged target peptide/MHC complex tetramer.

Example 7

Expression of 4-In-1 Constructs in αβ T Cells

Figure 37:
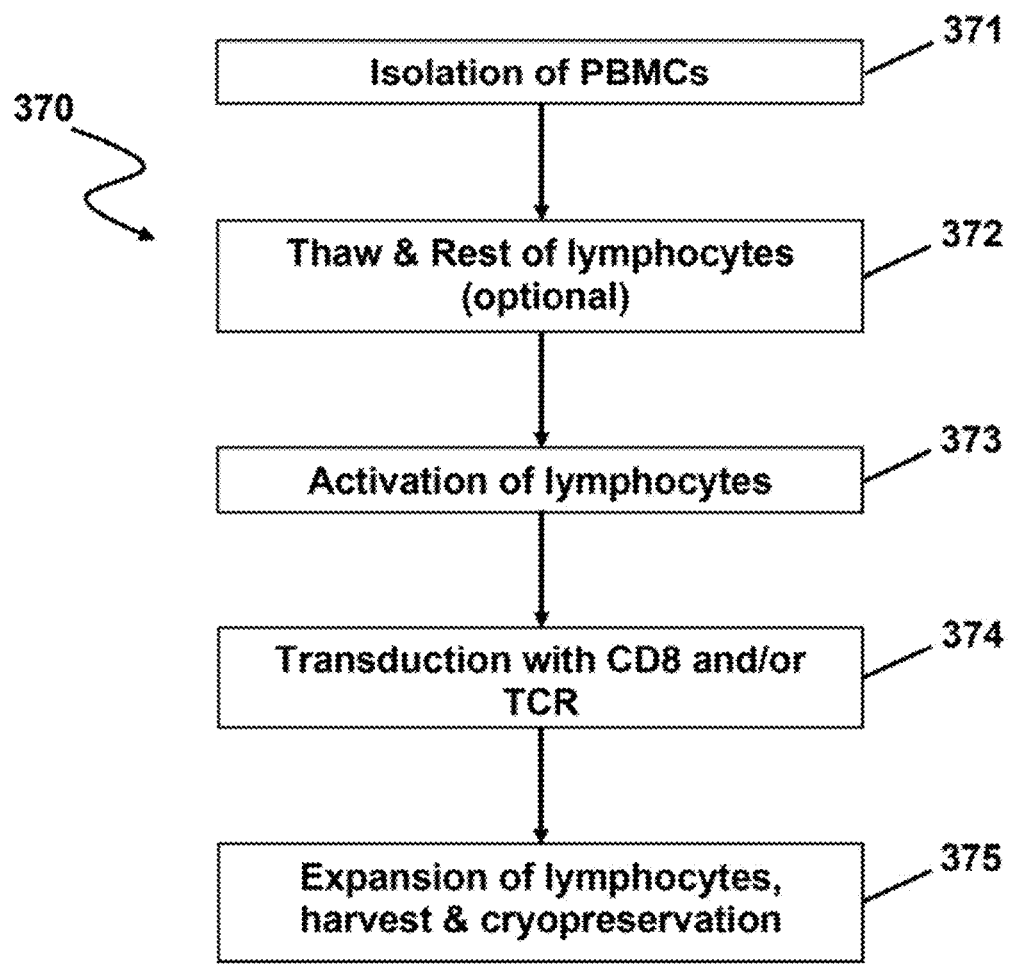
FIG. 37 shows T cell manufacturing process in accordance with one embodiment of the present disclosure.

Engineered lymphocytes including engineered αβ T cells expressing recombinant proteins, e.g., CD8αβ and/or TCRαβ, can be manufactured according to the methods disclosed in US 2019/0247433, the content of which is hereby incorporated by reference in its entirety. For example, FIG. 37 shows a T cell manufacturing process 370, which may include isolation of PBMC (371), in which PBMC may be used fresh or stored frozen till ready for use, or may be leukapheresis products, e.g., leukopaks, or may be used as starting materials for T cell manufacturing and selection of lymphocyte populations (e.g., αβ TCR+ T cells, CD8+, CD4+, or both); thaw and rest lymphocytes overnight, e.g., about 16 hours or about 4-6 hours, (372), which may allow apoptotic cells to die off and restore T cell functionality (this step may not be necessary, if fresh materials are used); activation of lymphocytes (373), which may use anti-CD3 and anti-CD28 antibodies (soluble or surface bound, e.g., magnetic or biodegradable beads, antibodies immobilized on culture vessels); transduction with viral vectors containing sequences encoding recombinant proteins, e.g., CD8αβ and/or TCRαβ polypeptides (374), in which the viral vectors may be lentiviral vectors or retroviral vectors, or transfection may be performed by non-viral methods; and expansion of lymphocytes, harvest, and cryopreservation (375), which may be carried out in the presence of cytokine(s), e.g., IL-7 and IL-15, serum (ABS or FBS), and/or cryopreservation media.

Exogenous CD8 Expression

Figure 21:
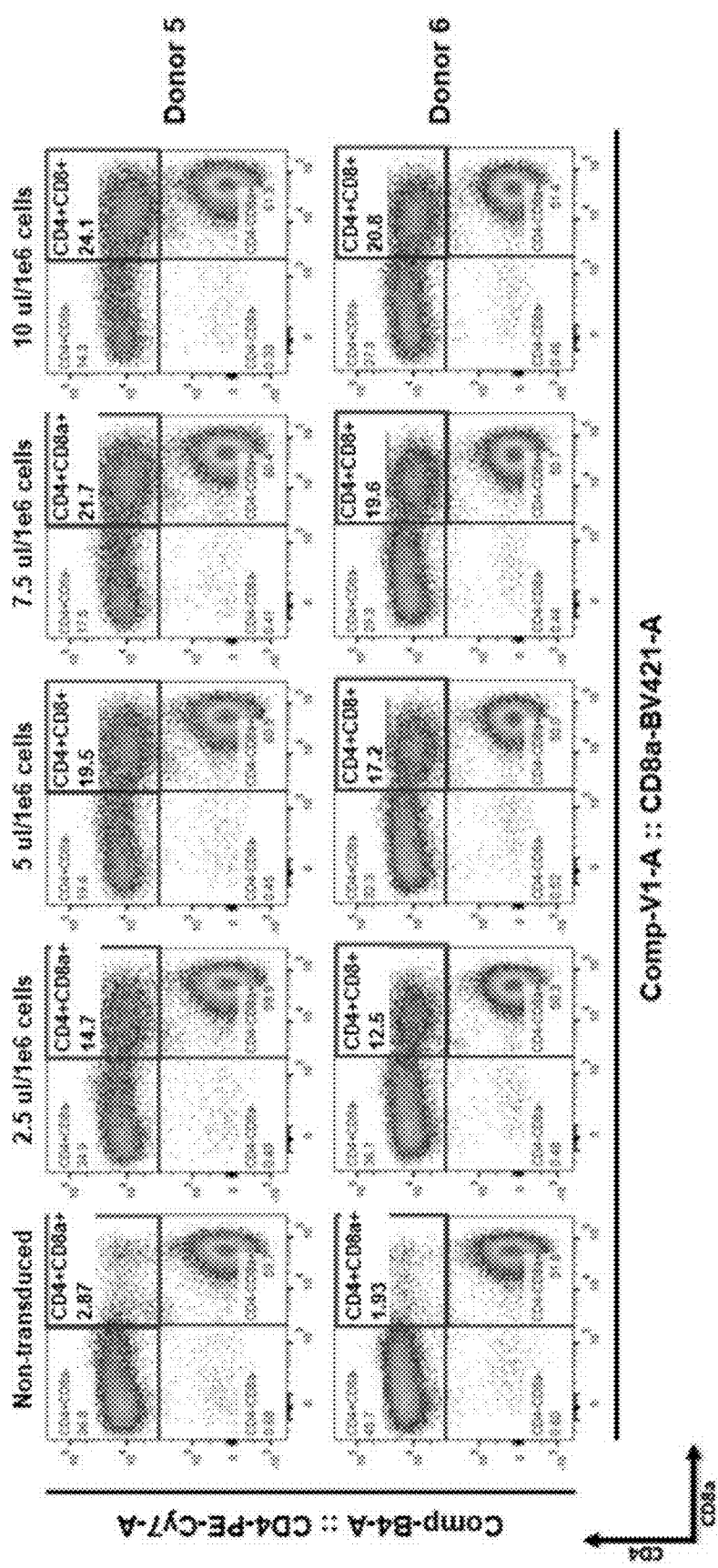
FIG. 21 shows enforced CD8 expression in CD4+ T cells obtained from Donor 5 and Donor 6 using various dilutions of lentiviral vector (LV) expressing 4-in-1 construct of the present disclosure, e.g., LV-PTE.CD8.TCR.WPRE.

To determine the exogenous CD8 expression in ap T cells transduced with viral vectors containing 4-in-1 constructs with sequences encoding CD8 and TCR, T cells obtained from Donor 5 and Donor 6 were transduced with increasing amount of LV-PTE.CD8.TCR.WPRE, followed by FACS gated on Lymphocytes<Singlets<Live cells<CD3+ population to detect % CD8α+ cells in CD4+ cells. FIG. 21 shows % CD8α+CD4+ cells from Donor 5 increases from 2.87% (non-transduced) to 14.7% (2.5 µl/1×10$^6$ cells), 19.5% (5 µl/1×10$^6$ cells), 21.7% (7.5 µl/1×10$^6$ cells), and 24.1% (10 µl/1×10$^6$ cells); and % CD8α+CD4+ cells from Donor 6 increases from 1.93% (non-transduced) to 12.5% (2.5 µl/1×10$^6$ cells), 17.2% (5 µl/1×10$^6$ cells), 19.6% (7.5 µl/1×10$^6$ cells), and 20.8% (10 µl/1×10$^6$ cells).

Exogenous TCR Expression

Figure 22:
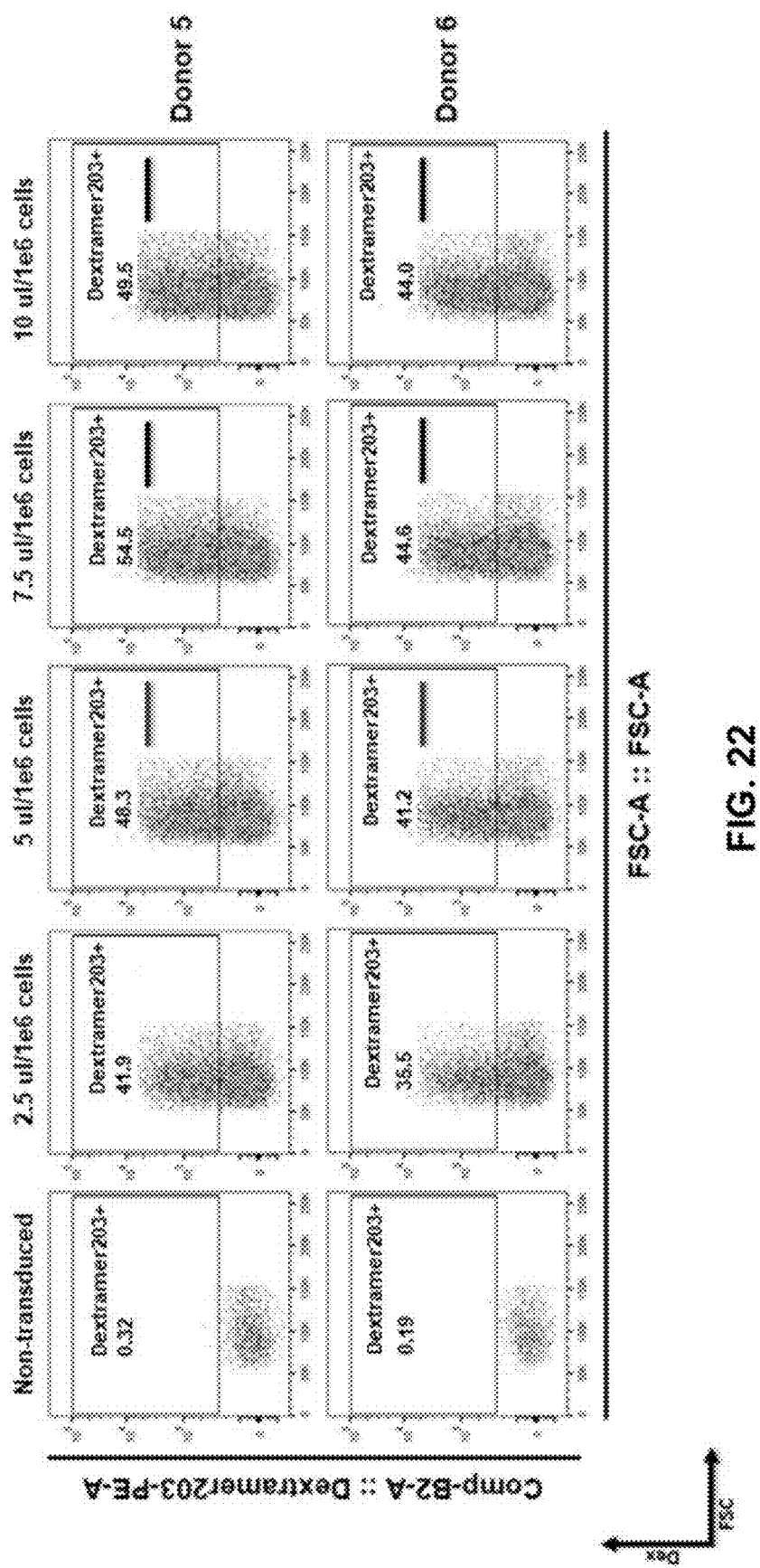
FIG. 22 shows detection of TCR expression in CD4+ T cells using various dilutions of LV expressing 4-in-1 construct of the present disclosure, e.g., LV-PTE.CD8.TCR.WPRE.

To determine the exogenous TCR expression in ap T cells transduced with viral vectors containing 4-in-1 constructs with sequences encoding CD8 and TCR, T cells obtained from Donor 5 and Donor 6 were transduced with increasing amount of LV-PTE.CD8.TCR.WPRE, followed by FACS gated on Lymphocytes<Singlets<Live cells<CD3+<CD4+CD8+ population to detect % target peptide/MHC complex Dextramer203+(i.e., TCR+) cells in CD4+CD8+ cell population. FIG. 22 shows % Dextramer203+ cells from Donor 5 increases from 0.32% (non-transduced) to 41.9% (2.5 µl/1×10$^6$ cells), 48.3% (5 µl/1×10$^6$ cells), 54.5% (7.5 µl/1×10$^6$ cells), and 49.5% (10 µl/1×10$^6$ cells); and % Dextramer203+ cells from Donor 6 increases from 0.19% (non-transduced) to 35.5% (2.5 µl/1×10$^6$ cells), 41.2% (5 µl/1×10$^6$ cells), 44.6% (7.5 µl/1×10$^6$ cells), and 44.0% (10 µl/1×10$^6$ cells).

Figure 23:
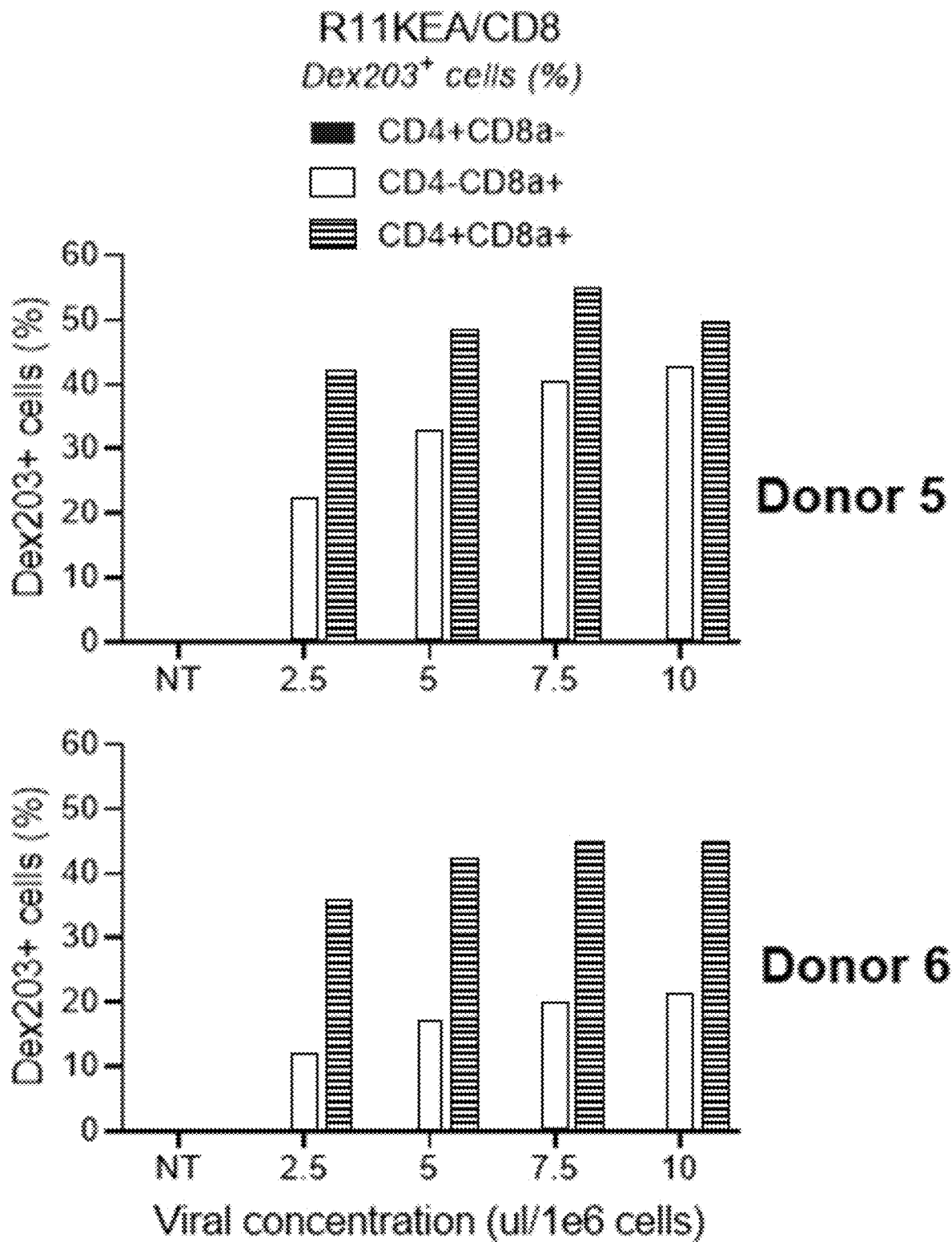
FIG. 23 shows % target peptide/MHC complex Dextramer203 (Dex203)+ in CD4+ and/or CD8+ T cells obtained from Donor 5 (top panel) and Donor 6 (bottom panel) transduced with 4-in-1 construct of the present disclosure, e.g., LV-PTE.CD8.TCR.WPRE.
Figure 24:
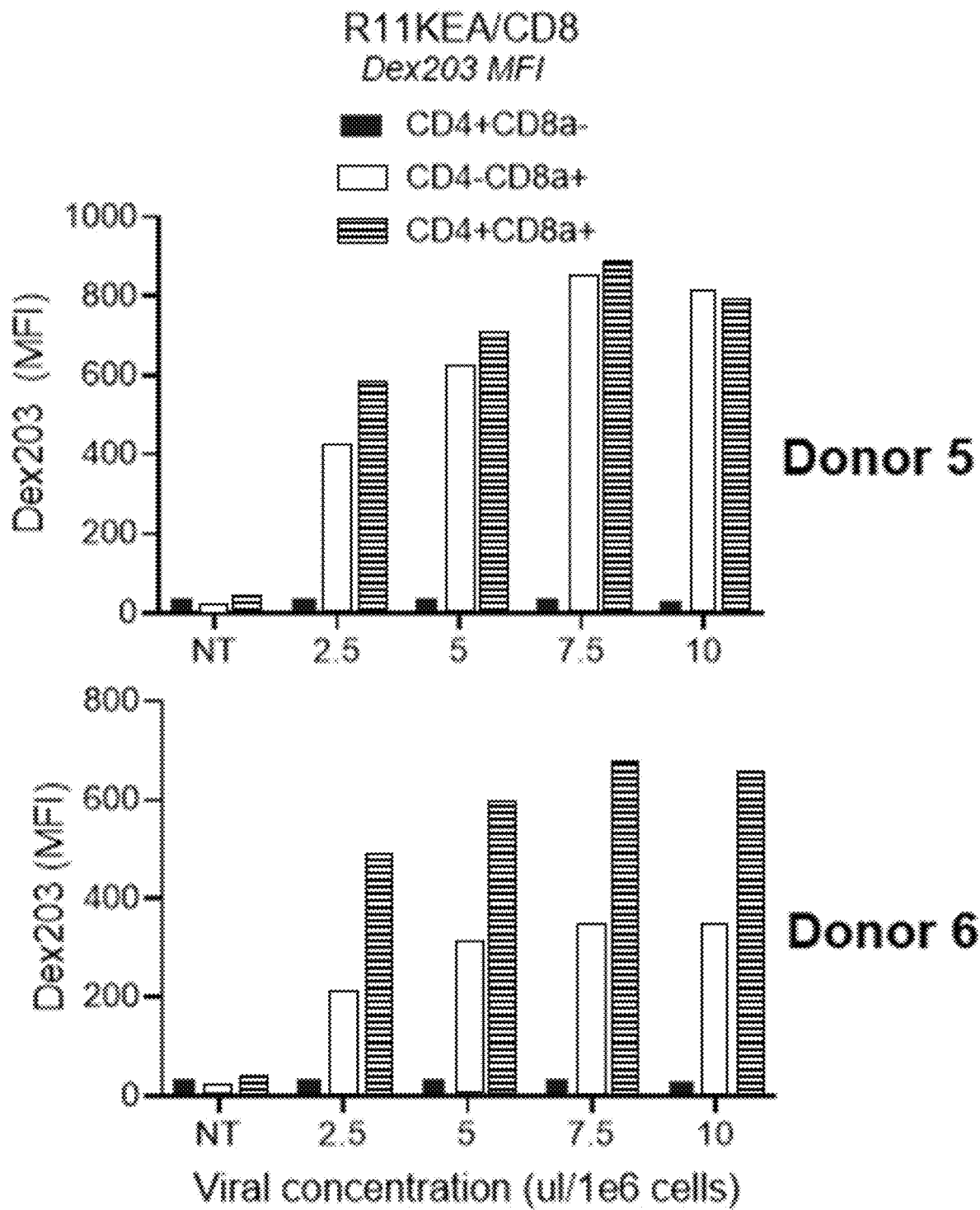
FIG. 24 shows Dex203 MFI in CD4+ and/or CD8+ T cells obtained from Donor 5 (top panel) and Donor 6 (bottom panel) transduced with 4-in-1 construct of the present disclosure, e.g., LV-PTE.CD8.TCR.WPRE.

To detect TCR expression in various ap T cell populations, ap T cells transduced with LV-PTE.CD8.TCR.WPRE were analyzed by FACS gated on Lymphocytes<Singlets<Live cells<CD3+<CD4+/−CD8+/−. FIG. 23 shows % Dextramer203 (Dex203)+(i.e., TCR+) cells obtained from Donor 5 (top panel) and Donor 6 (bottom panel) are generally higher in CD4+CD8α+ cell population than that in CD4−CD8α+ cell population. In contrast, % Dex203+(i.e., TCR+) cells is minimum in CD4+CD8α− cell population. Similarly, FIG. 24 shows % Dextramer203 (Dex203) MFI obtained from Donor 5 (top panel) and Donor 6 (bottom panel) are generally higher in CD4+CD8α+ cell population than that in CD4−CD8α+ cell population. In contrast, % Dex203 MFI is minimum in CD4+CD8α− cell population. These results suggest that exogenous TCR and CD8 encoded by LV-PTE.CD8.TCR.WPRE can be co-expressed in both CD4+ T cells and CD4− T cells.

Example 8

Figure 25:
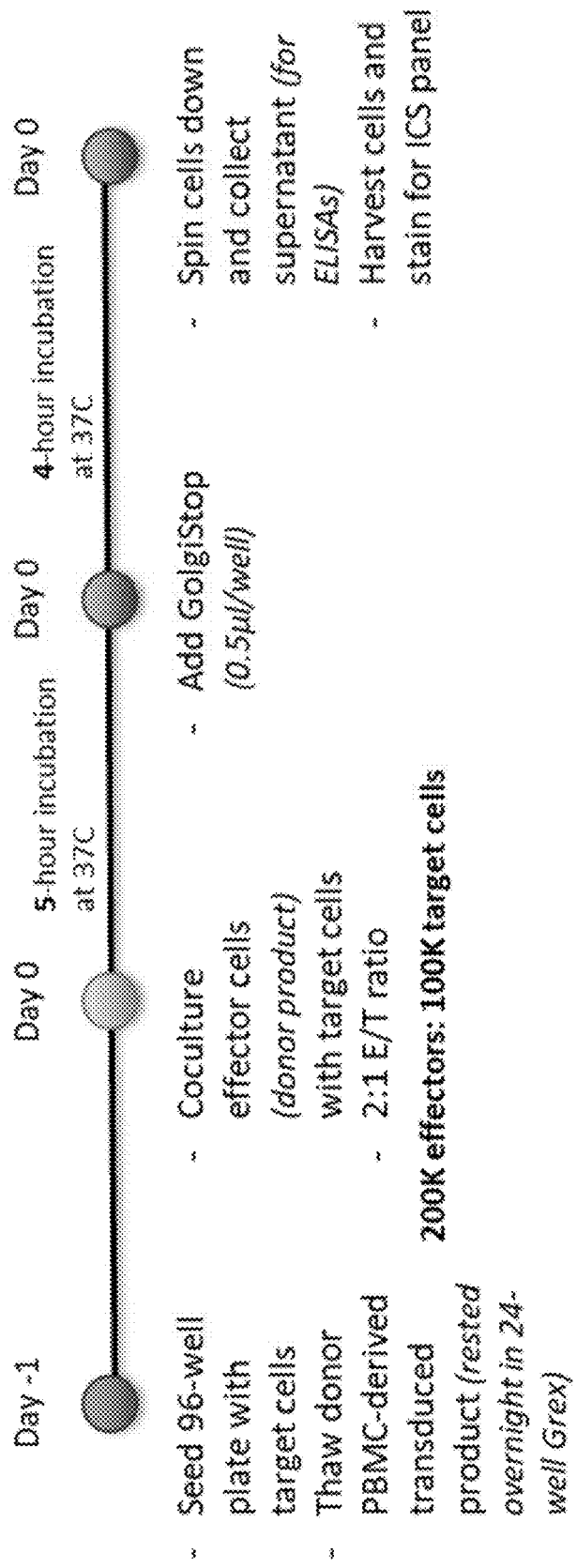
FIG. 25 shows an experimental design for testing functionality of T cells transduced with 4-in-1 construct or TCR-only construct in accordance with one embodiment of the present disclosure.

Functional Analysis of αβ T Cells Expressing 4-In-1 Construct or TCR Only Construct FIG. 25 shows an experimental design for testing functionality of ap T cells transduced with lentiviral vector (LV) containing 4-in-1 construct, e.g., PTE.CD8.TCR.WPRE (LV-CD8.TCR), or TCR-only construct, e.g., R11 KE.WPRE (LV-TCR). Briefly, on Day −1, target cells, e.g., high antigen expressing UACC257+RFP cell line (positive control) and antigen-negative MCF7+GFP cell line (negative control), were seeded in 96-well plates. Donor cell products, e.g., PBMC (obtained from Donors 5, 6, 7, and 8) transduced with LV-CD8.TCR (5 µl/1×10$^6$ cells) or LV-TCR (2.5 µl/1×10$^6$ cells), were thawed and rested overnight in 24-well G-Rex® gas permeable rapid expansion device. On Day 0, donor cell products (effector cells) were co-cultured with target cells, e.g., UACC257+RFP and MCF7+GFP, at an effector cells to target cells (E/T) ratio of 2:1, e.g., 200,000 effector cells:100,000 target cells. After 5-hour incubation at 37° C., protein transport inhibitor, e.g., GolgiStop™ (BD Biosciences), was added to each well at 0.5 µl/well, followed by 4-hour of incubation at 37° C. Cells were then centrifuged to collect supernatants for ELISA to detect IFN-γ expression and to harvest cells for staining using intracellular cytokine staining (ICS) panel, e.g., CD3, CD4, CD8, IFN-γ, Granzyme B, and live/dead.

CD4-CD8+ T Cell Population

Figure 26:
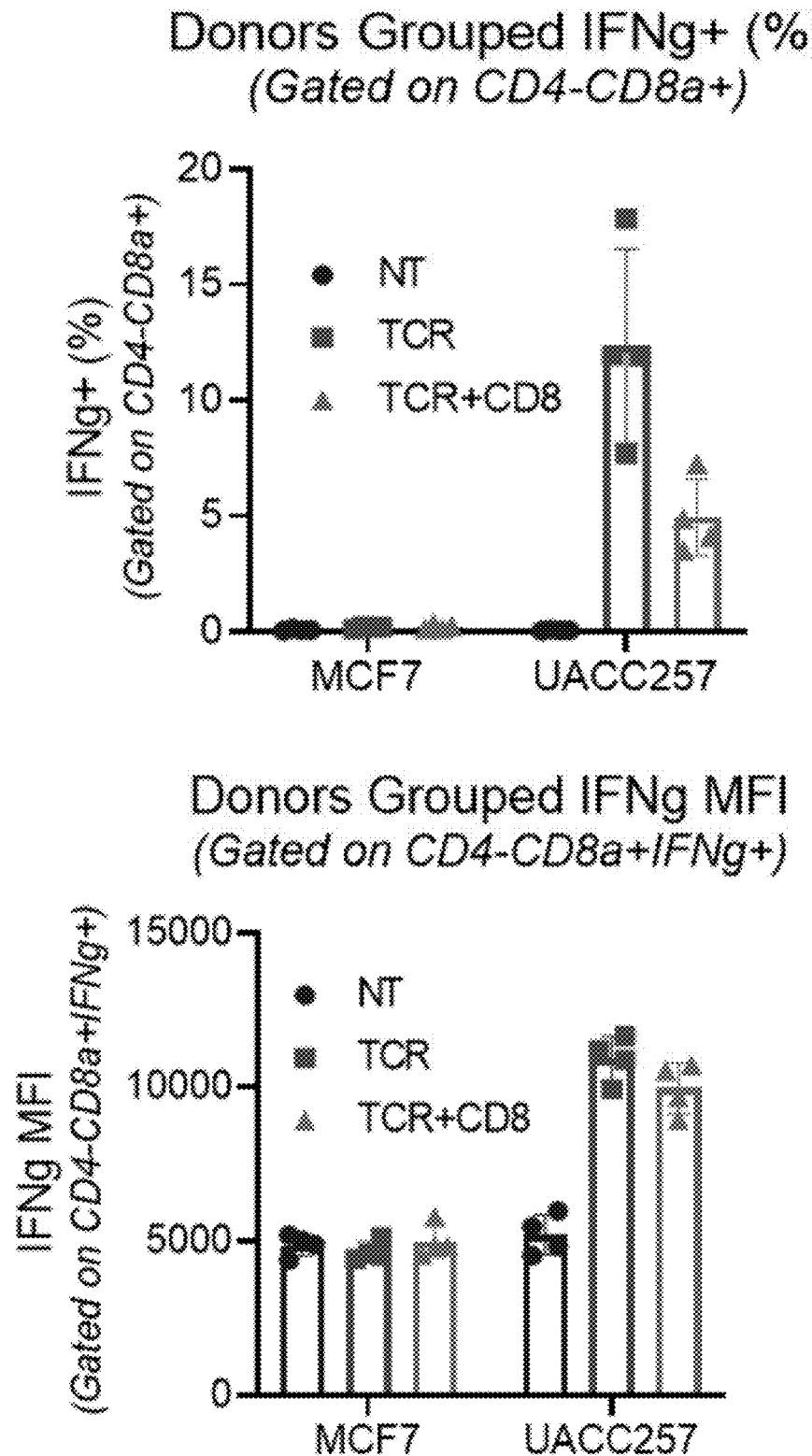
FIG. 26 shows increased % IFN-γ-positive cells (top panel) and increased IFN-γ MFI (bottom panel) in CD4-CD8α+ T cells obtained from grouped donors transduced with a lentiviral vector containing R11 KE.WPRE (LV-TCR) (TCR) or a lentiviral vector containing PTE.CD8.TCR.WPRE (LV-CD8.TCR) (TCR+CD8) followed by co-culturing with high-target expressing UACC257 cells as compared with that co-culturing with non-target expressing MCF7. Non-transduced (NT) cells serve as control. (Effector to target cell ratio=2:1 and Donors grouped N=4).

FIG. 26 shows that co-culturing CD4-CD8α+ T cells obtained from grouped donors transduced with LV-TCR (TCR) or LV-CD8.TCR (TCR+CD8) with high-target expressing UACC257 cells resulted in higher % IFN-γ-positive cells (top panel) and higher IFN-γ MFI (bottom panel) than that without transduction (NT). In contrast, no significant difference in % IFN-γ-positive cells and IFN-γ MFI between transduced and non-transduced cells was observed when co-culturing CD4-CD8α+ T cells transduced with LV-TCR (TCR) or LV-CD8.TCR (TCR+CD8) with antigen-negative MCF7. FACS was gated on CD4-CD8α+ IFN-γ+ T cells. Non-transduced (NT) cells serve as control. (Effector to target cell ratio=2:1 and Donors grouped N=4). These results suggest that CD4-CD8α+ T cells transduced with LV-TCR or LV-CD8.TCR are functionally active, e.g., by expressing IFN-γ, when contacting high antigen expressing target cells, e.g., UACC257 cells, and the transduced cells have little effect on antigen-negative cells, e.g., MCF7 cells.

Figure 27:
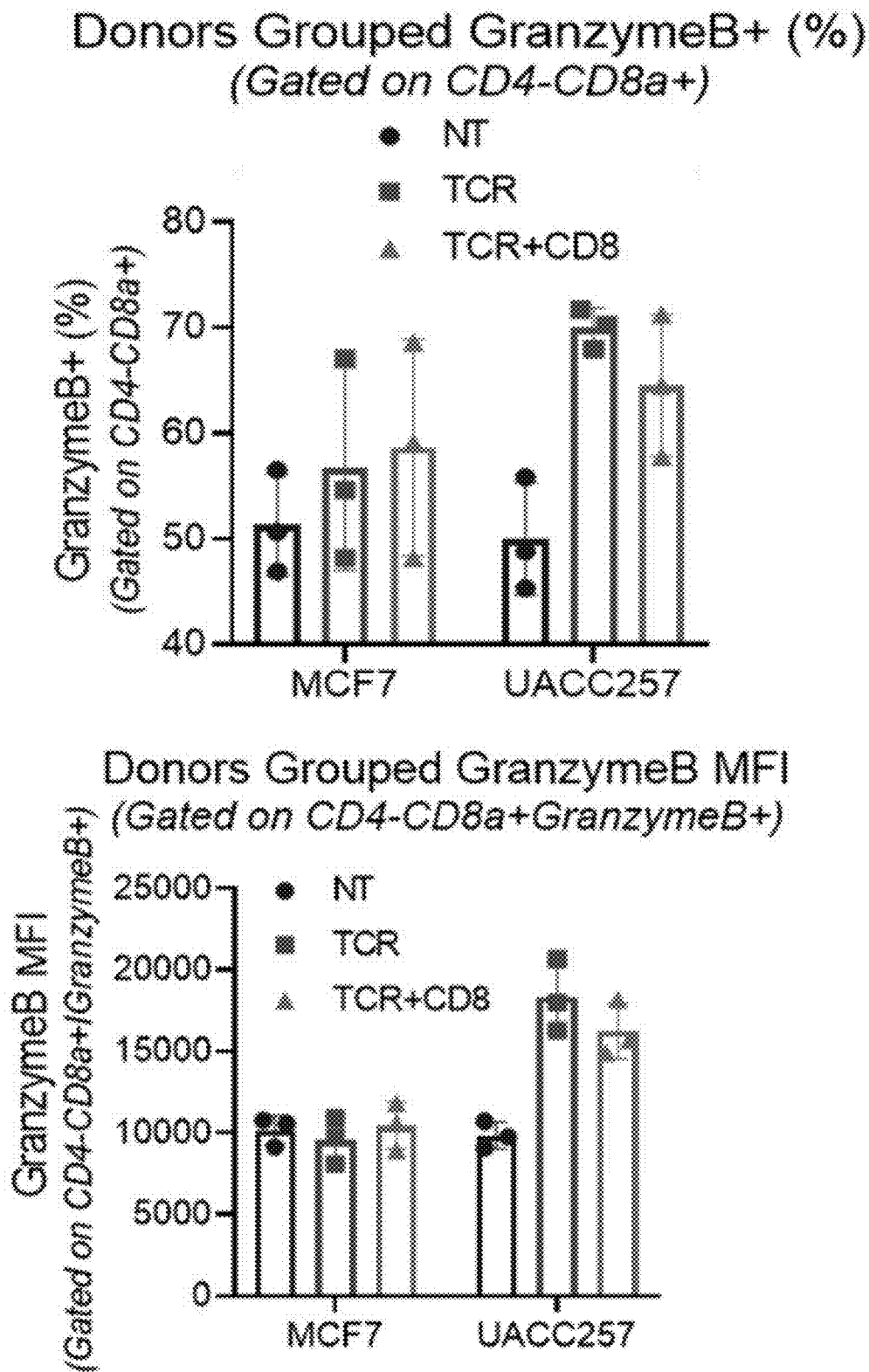
FIG. 27 shows increased % Granzyme B-positive cells (top panel) and increased Granzyme B MFI (bottom panel) in CD4-CD8α+ T cells obtained from grouped donors transduced with LV-TCR (TCR) or LV-CD8.TCR (TCR+CD8) followed by co-culturing with high-target expressing UACC257 cells as compared with that co-culturing with non-target expressing MCF7. Non-transduced (NT) cells serve as control. (Effector to target cell ratio=2:1 and Donors grouped N=3).

FIG. 27 shows that co-culturing CD4-CD8α+ T cells obtained from grouped donors transduced with LV-TCR (TCR) or LV-CD8.TCR (TCR+CD8) with high-target expressing UACC257 cells resulted in higher % Granzyme B-positive cells (top panel) and higher Granzyme B MFI (bottom panel) than that without transduction (NT). In contrast, no significant difference in % Granzyme B-positive cells and Granzyme B MFI between transduced and non-transduced cells was observed when co-culturing CD4-CD8α+ T cells transduced with LV-TCR (TCR) or LV-CD8.TCR (TCR+CD8) with antigen-negative MCF7. FACS was gated on CD4-CD8α+Granzyme B+ T cells. Non-transduced (NT) cells serve as control. (Effector to target cell ratio=2:1 and Donors grouped N=3). These results suggest that CD4-CD8α+ T cells transduced with LV-TCR or LV-CD8.TCR are functionally active, e.g., by expressing Granzyme B, when contacting high antigen expressing target cells, e.g., UACC257 cells, and the transduced cells may have little effect on antigen-negative cells, e.g., MCF7 cells.

CD4+CD8+ T Cell Population

Figure 28:
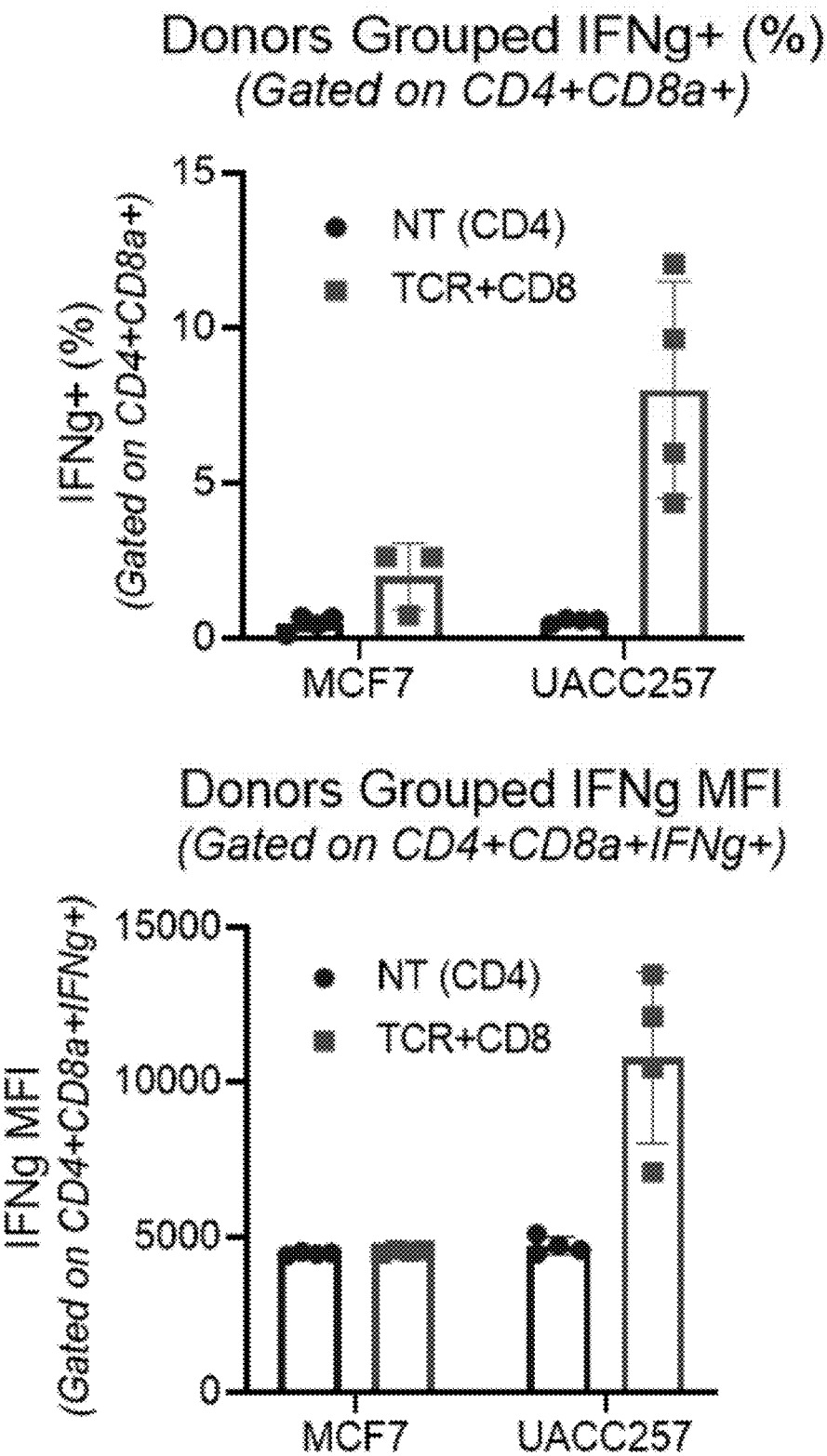
FIG. 28 shows increased % IFN-γ-positive cells (top panel) and increased IFN-γ MFI (bottom panel) in CD4+CD8α+ T cells obtained from grouped donors transduced with LV-CD8.TCR (TCR+CD8) or without transduction (NT) followed by co-culturing with high-target expressing UACC257 cells as compared with that co-culturing with non-target expressing MCF7. (Effector to target cell ratio=2:1 and Donors grouped N=4).

FIG. 28 shows that co-culturing CD4+CD8α+ T cells obtained from grouped donors transduced with LV-CD8.TCR (TCR+CD8) with high-target expressing UACC257 cells resulted in higher % IFN-γ-positive cells (top panel) and higher IFN-γ MFI (bottom panel) than that without transduction (NT). In contrast, no significant difference in % IFN-γ-positive cells and IFN-γ MFI between transduced and non-transduced cells was observed when co-culturing CD4+CD8α+ T cells transduced with LV-CD8.TCR (TCR+CD8) with antigen-negative MCF7. FACS was gated on CD4+CD8α-IFN-γ+ for the NT cells and CD4+CD8α+IFN-γ+ for the LV-CD8.TCR-transduced cells. Non-transduced (NT) cells serve as control. (Effector to target cell ratio=2:1 and Donors grouped N=4). These results suggest that CD4+CD8α+ T cells transduced with LV-CD8.TCR are functionally active, e.g., by expressing IFN-γ, when contacting high antigen expressing target cells, e.g., UACC257 cells, and the transduced cells may have little effect on antigen-negative cells, e.g., MCF7 cells.

Figure 29:
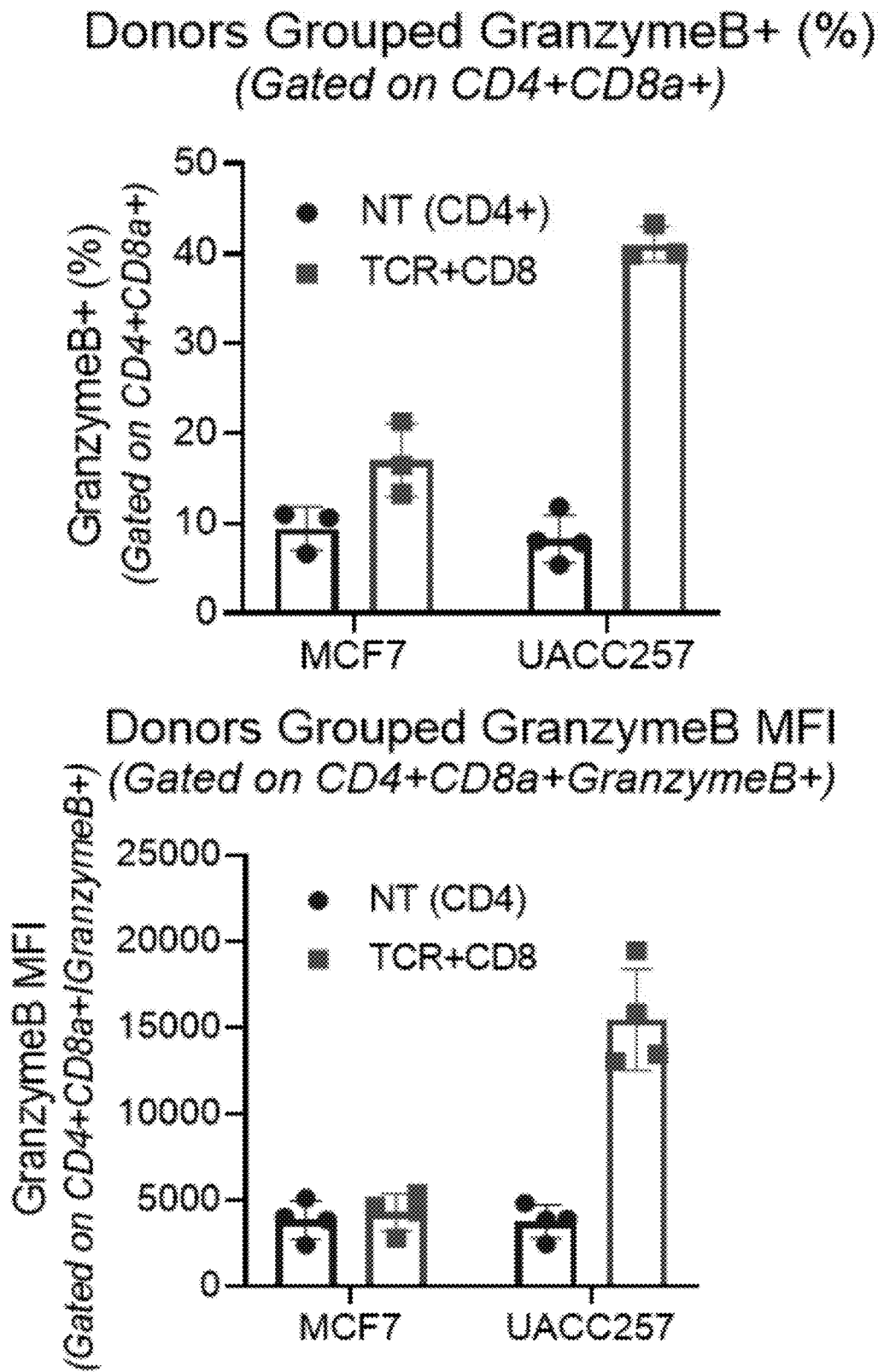
FIG. 29 shows increased % Granzyme B-positive cells (top panel) and increased Granzyme B MFI (bottom panel) in CD4+CD8α+ T cells obtained from grouped donors transduced with LV-CD8.TCR (TCR+CD8) or without transduction (NT) followed by co-culturing with high-target expressing UACC257 cells as compared with that co-culturing with non-target expressing MCF7. (Effector to target cell ratio=2:1 and Donors grouped N=4).

FIG. 29 shows that co-culturing CD4+CD8α+ T cells obtained from grouped donors transduced with LV-CD8.TCR (TCR+CD8) with high-target expressing UACC257 cells resulted in higher % Granzyme B-positive cells (top panel) and higher Granzyme B MFI (bottom panel) than that without transduction (NT). In contrast, no significant difference in % Granzyme B-positive cells and Granzyme B MFI between transduced and non-transduced cells was observed when co-culturing CD4+CD8α+ T cells transduced with LV-CD8.TCR (TCR+CD8) with antigen-negative MCF7. FACS was gated on CD4+CD8α-Granzyme B+ for the NT cells and CD4+CD8α+Granzyme B+ for the LV-CD8.TCR-transduced T cells. Non-transduced (NT) cells serve as control. (Effector to target cell ratio=2:1 and Donors grouped N=3). These results suggest that CD4+CD8α+ T cells transduced with LV-CD8.TCR are functionally active, e.g., by expressing Granzyme B, when contacting high antigen expressing target cells, e.g., UACC257 cells, and the transduced cells may have little effect on antigen-negative cells, e.g., MCF7 cells.

CD3+ T cells

FIG. 30 shows that co-culturing CD3+ T cells obtained from grouped donors transduced with LV-TCR (TCR) or LV-CD8.TCR (TCR+CD8) with high-target expressing UACC257 cells resulted in higher % IFN-γ-positive cells (top panel) and higher IFN-γ MFI (bottom panel) than that without transduction (NT). In contrast, no significant difference in % IFN-γ-positive cells and IFN-γ MFI between transduced and non-transduced cells was observed when co-culturing CD4-CD8α+ T cells transduced with LV-TCR (TCR) or LV-CD8.TCR (TCR+CD8) with antigen-negative MCF7. FACS was gated on CD3+ T cells. Non-transduced (NT) cells serve as control. (Effector to target cell ratio=2:1 and Donors grouped N=4). These results suggest that CD3+ T cells transduced with LV-TCR or LV-CD8.TCR are functionally active, e.g., by expressing IFN-γ, when contacting high antigen expressing target cells, e.g., UACC257 cells, and the transduced cells may have little effect on antigen-negative cells, e.g., MCF7 cells.

FIG. 31 shows that co-culturing CD3+ T cells obtained from grouped donors transduced with LV-TCR (TCR) or LV-CD8.TCR (TCR+CD8) with high-target expressing UACC257 cells resulted in higher % Granzyme B-positive cells (top panel) and higher Granzyme B MFI (bottom panel) than that without transduction (NT). In contrast, no significant difference in % Granzyme B-positive cells and Granzyme B MFI between transduced and non-transduced cells was observed when co-culturing CD3+ T cells transduced with LV-TCR (TCR) or LV-CD8.TCR (TCR+CD8) with antigen-negative MCF7. FACS was gated on CD3+ T cells. Non-transduced (NT) cells serve as control. (Effector to target cell ratio=2:1 and Donors grouped N=3). These results suggest that CD3+ T cells transduced with LV-TCR or LV-CD8.TCR are functionally active, e.g., by expressing Granzyme B, when contacting high antigen expressing target cells, e.g., UACC257 cells, and the transduced cells may have little effect on antigen-negative cells, e.g., MCF7 cells.

Figure 32:
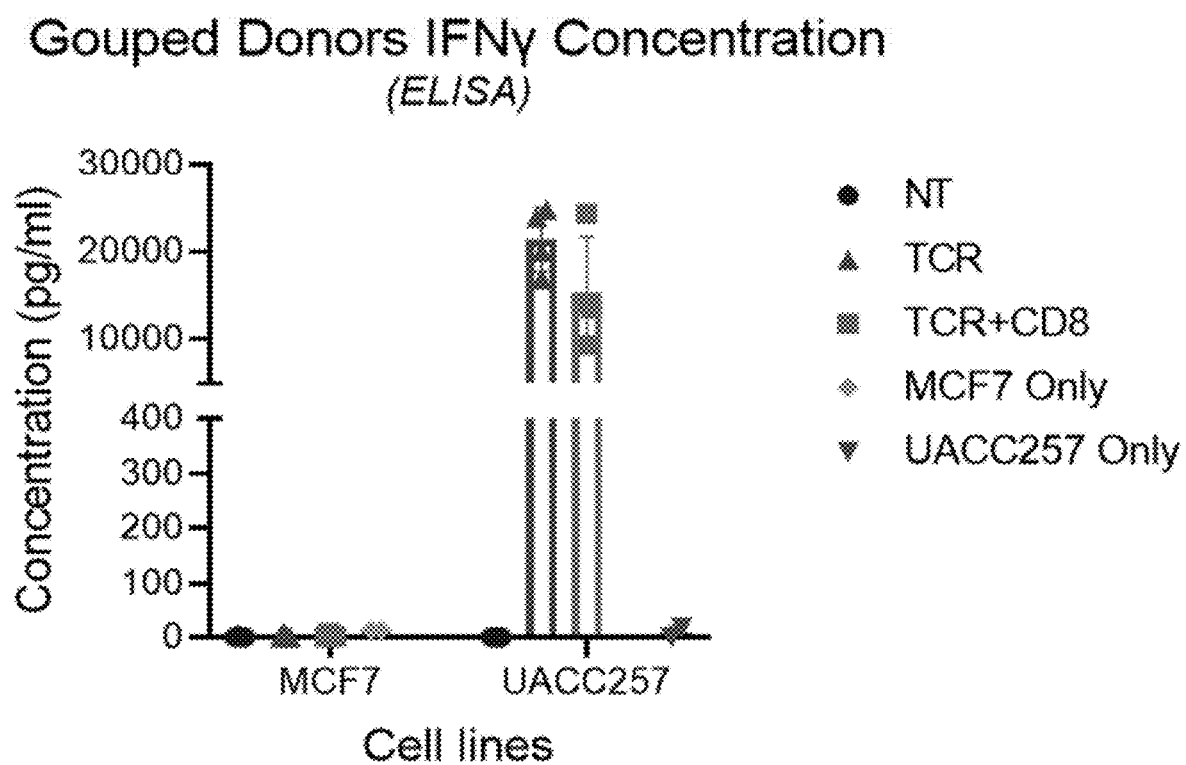
FIG. 32 shows increased IFN-γ secretion in CD3+ T cells obtained from grouped donors transduced with LV-TCR (TCR) or LV-CD8.TCR (TCR+CD8) followed by co-culturing with high-target expressing UACC257 cells as compared with that co-culturing with non-target expressing MCF7. Non-transduced (NT) cells, UACC257 cells, and MCF7 cells serve as control. (Effector to target cell ratio=2:1 and Donors grouped N=4).

FIG. 32 shows that co-culturing CD3+ T cells obtained from group donors transduced with LV-TCR (TCR) or LV-CD8.TCR (TCR+CD8) with high-target expressing UACC257 cells resulted in higher levels of IFN-γ secretion than that without transduction (NT), MCF7 cells only, and UACC257 cells only. In contrast, no significant difference in the levels of IFN-γ secretion between transduced and non-transduced cells was observed when co-culturing CD4-CD8α+ T cells transduced with LV-TCR (TCR) or LV-CD8.TCR (TCR+CD8) with antigen-negative MCF7. (Effector to target cell ratio=2:1 and Donors grouped N=4). These results suggest that CD3+ T cells transduced with LV-TCR or LV-CD8.TCR are functionally active, e.g., by secreting IFN-γ, when contacting high antigen expressing target cells, e.g., UACC257 cells, and the transduced cells may have little effect on antigen-negative cells, e.g., MCF7 cells.

Figure 33:
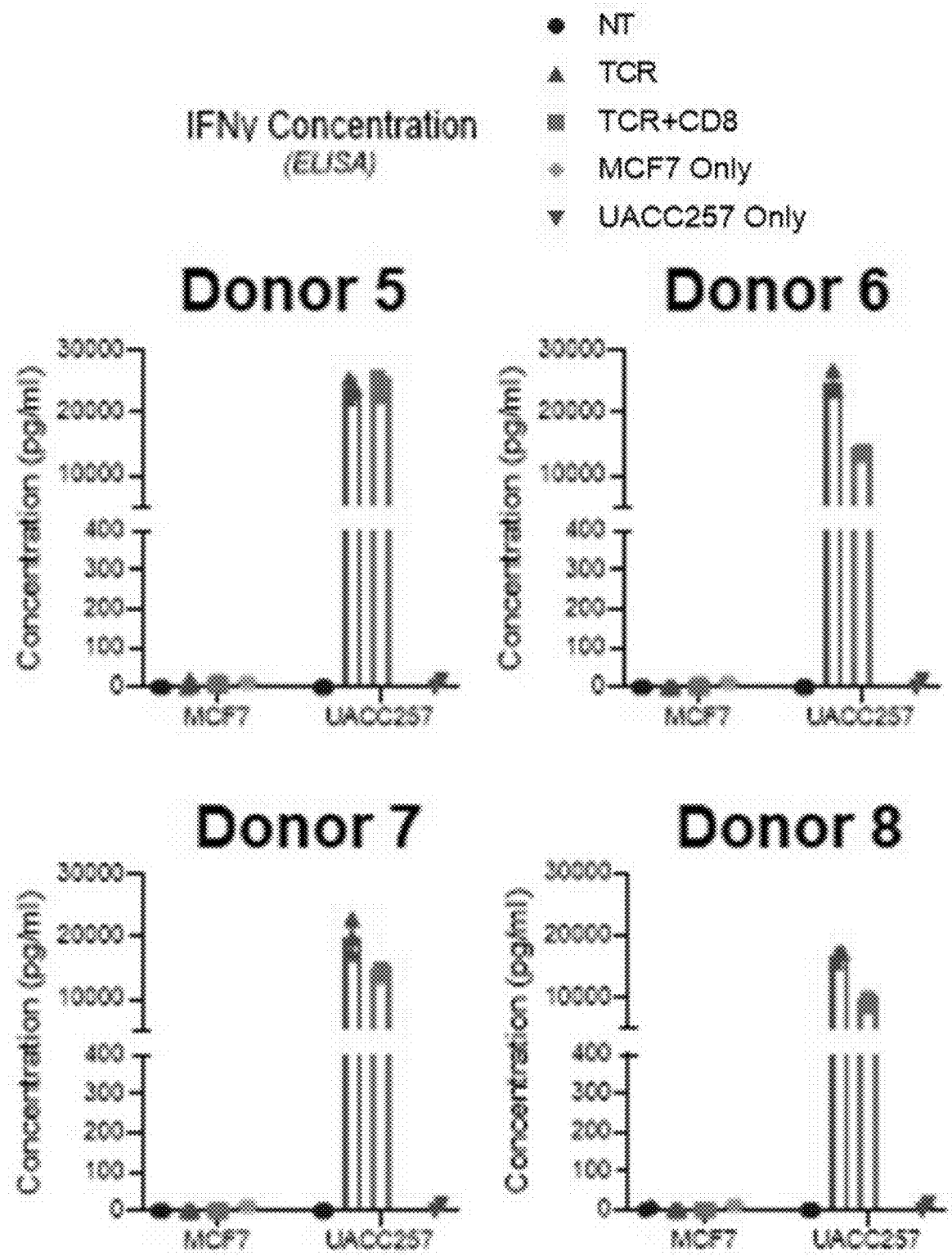
FIG. 33 shows increased IFN-γ secretion in CD3+ T cells obtained from individual Donors 5, 6, 7, and 8 transduced with LV-TCR (TCR) or LV-CD8.TCR (TCR+CD8) followed by co-culturing with high-target expressing UACC257 cells as compared with that co-culturing with non-target expressing MCF7. Non-transduced (NT) cells, UACC257 cells only, and MCF7 cells only serve as control. (Effector to target cell ratio=2:1).

FIG. 33 shows that co-culturing CD3+ T cells obtained from individual Donors 5, 6, 7, and 8 transduced with LV-TCR (TCR) or LV-CD8.TCR (TCR+CD8) with high-target expressing UACC257 cells resulted in higher levels of IFN-γ secretion than that without transduction (NT), MCF7 cells only, and UACC257 cells only. In contrast, no significant difference in the levels of IFN-γ secretion between transduced and non-transduced cells was observed when co-culturing CD4-CD8α+ T cells transduced with LV-TCR (TCR) or LV-CD8.TCR (TCR+CD8) with antigen-negative MCF7. (Effector to target cell ratio=2:1). These results suggest that CD3+ T cells obtained from individual donors transduced with LV-TCR or LV-CD8.TCR are functionally active, e.g., by secreting IFN-γ, when contacting high antigen expressing target cells, e.g., UACC257 cells, and the transduced cells may have little effect on antigen-negative cells, e.g., MCF7 cells.

Example 9

Effect of Statins on the Expression of T Cell Activation Markers

To determine the effect of statins on the expression of T cell activation markers, T cells were treated with statins, e.g., atorvastatin, pravastatin, or rosuvastatin, followed by FACS analysis to measure the expression of T cell activation markers, e.g., CD25, CD69, and hLDLR.

CD4+ T Cell Population

Figure 34:
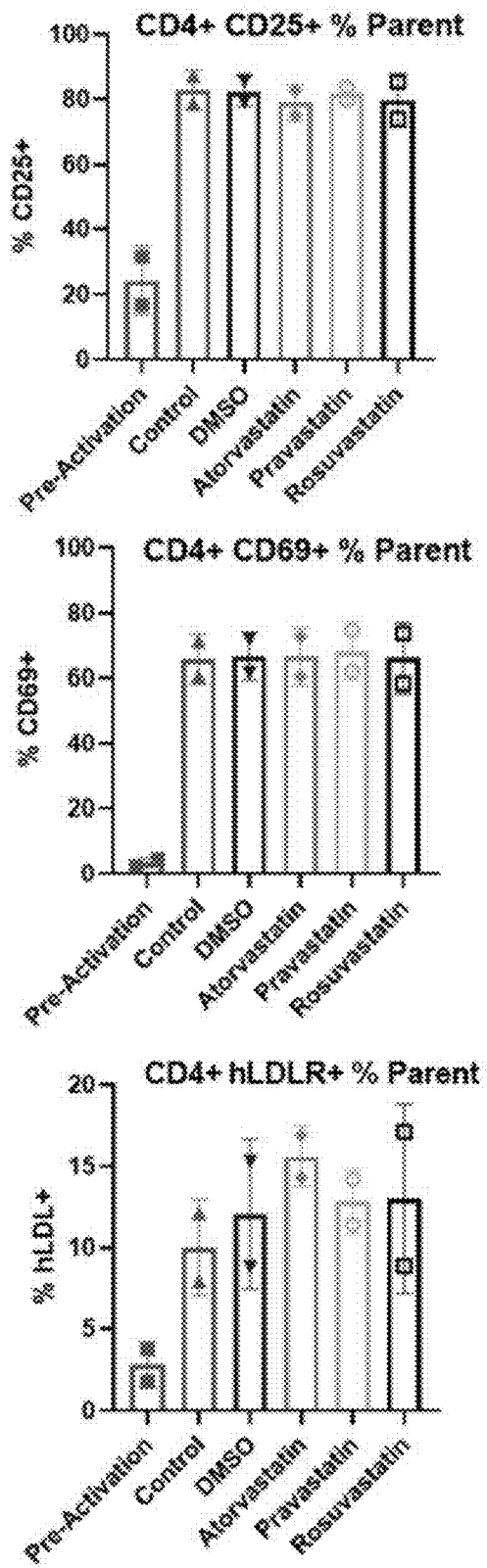
FIG. 34 shows % CD25+ cells (top panel), % CD69+ cells (middle panel), and % human low-density lipoprotein receptor (hLDLR)+ cells (bottom panel) in CD3+CD4+ T cells treated with atorvastatin, pravastatin, or rosuvastatin. Pre-activated cells, cells activated without statin or DMSO (control), and DMSO serve as controls.

FIG. 34 shows % CD25+ cells (top panel), % CD69+ cells (middle panel), and % hLDLR+ cells (bottom panel) in CD3+CD4+ T cells treated with atorvastatin, pravastatin, or rosuvastatin. Pre-activated cells, cells activated without statin or DMSO (control), and DMSO serve as controls. These results show that, while atorvastatin, pravastatin, and rosuvastatin have little effect on the % CD4+CD25+ cells and the % CD4+CD69+ cells, statins, e.g., atorvastatin, may increase the % CD4+hLDLR+ cells. FACS was gated on Lymphocytes>Singlets>Live/Dead>CD3+>CD4+.

CD8+ T Cell Population

Figure 35:
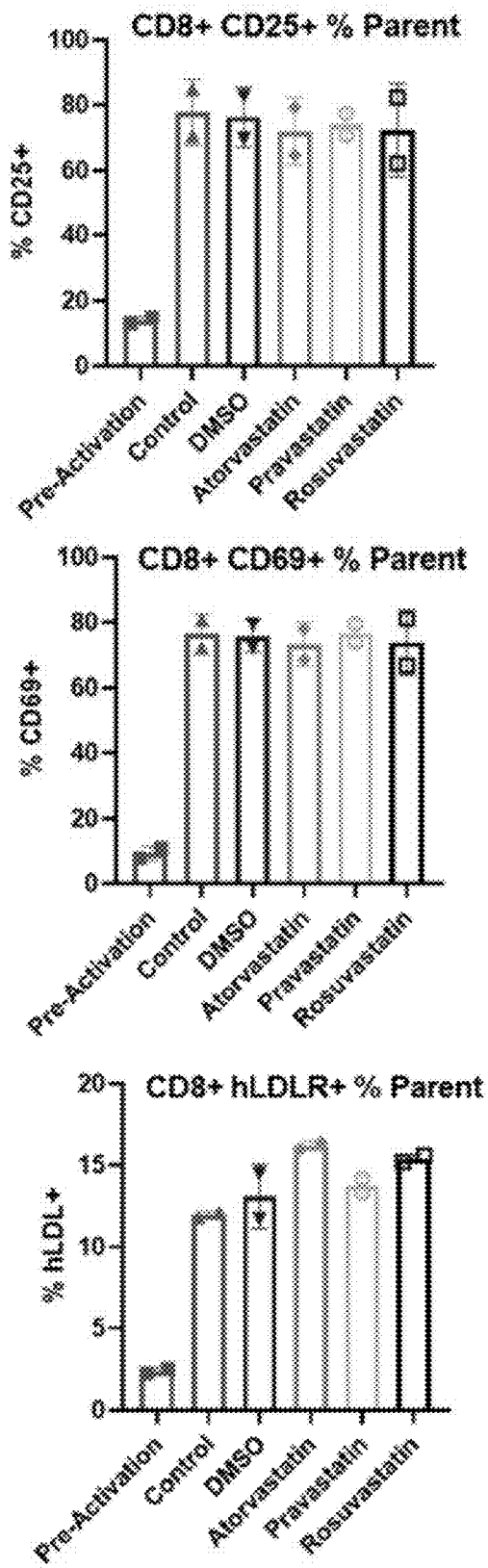
FIG. 35 shows % CD25+ cells (top panel), % CD69+ cells (middle panel), and % hLDLR+ cells (bottom panel) in CD3+CD8+ T cells treated with atorvastatin, pravastatin, or rosuvastatin. Pre-activated cells, cells activated without statin or DMSO (control), and DMSO serve as controls.

FIG. 35 shows % CD25+ cells (top panel), % CD69+ cells (middle panel), and % hLDLR+ cells (bottom panel) in CD3+CD8+ T cells treated with atorvastatin, pravastatin, or rosuvastatin. Pre-activated cells, cells activated without statin or DMSO (control), and DMSO serve as controls. These results show that, while atorvastatin, pravastatin, and rosuvastatin have little effect on the % CD8+CD25+ cells and the % CD8+CD69+ cells, statins, e.g., atorvastatin, may increase the % CD8+hLDLR+ cells. FACS was gated on Lymphocytes>Singlets>Live/Dead>CD3+>CD8+.

Example 10

Effect of WPRE on Lentiviral Titers

Figure 36:
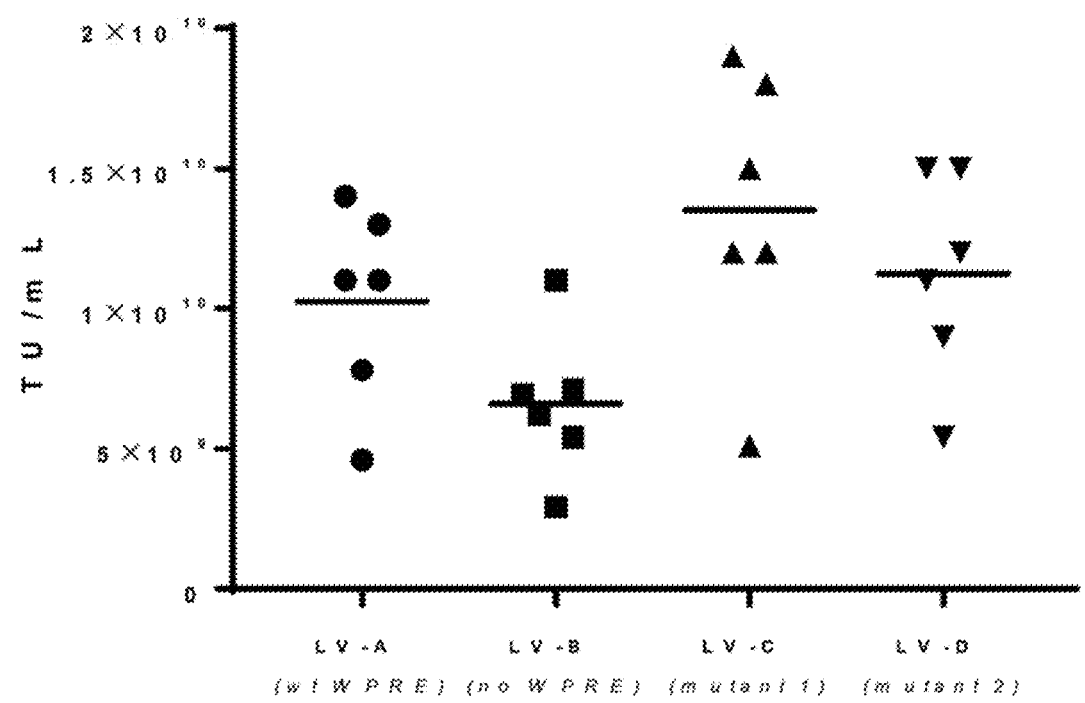
FIG. 36 shows titers of lentiviral vectors in accordance with one embodiment of the present disclosure.

To determine the effect of WPRE on lentiviral titers, lentiviral vectors (LV) containing wild type (wt) WPRE (SEQ ID NO: 9) (LV-A), no WPRE (LV-B), WPREmut1 (SEQ ID NO: 265) (LV-C), or WPREmut2 (SEQ ID NO: 266) (LV-D) were generated. HEK293T cells were transfected with LV-A, LV-B, LV-C, or LV-D followed by titer determination using methods known in the art. FIG. 36 shows the titers of these lentiviral vectors are in the order of LV-C>LV-D≥LV-A>LV-B. These results suggest that WPREmut1 and WPREmut2 may be useful to improving lentiviral vector production.

Advantages of the present disclosure may include generation of viral vectors that co-express multiple transgenes, e.g., 4 polypeptides, in a single vector, and generation of γδ T cells that co-express TCRαβ and CD8αβ as safe and target-specific "off-the-shelf" T cell products for adoptive cellular therapy.

All references cited in this specification are herein incorporated by reference as though each reference was specifically and individually indicated to be incorporated by reference. The citation of any reference is for its disclosure prior to the filing date and should not be construed as an admission that the present disclosure is not entitled to antedate such reference by virtue of prior invention.

What is claimed is:

1. A vector comprising a nucleotide sequence S1 encoding a CD8α polypeptide, a nucleotide sequence S2 encoding a CD80 polypeptide, a nucleotide sequence S3 encoding a T cell receptor (TCR)α polypeptide, and a nucleotide sequence S4 encoding a TCRβ polypeptide, wherein the nucleotide sequences are arranged in tandem in a 5' to 3' orientation of S2-S1-S4-S3.

2. The vector of claim 1, wherein the CD8α polypeptide comprises the amino acid sequence of SEQ ID NO: 11 and the CD8β polypeptide comprises the amino acid sequence of SEQ ID NO: 12.

3. The vector of claim 2, further comprising a nucleotide sequence S5 encoding a 2A peptide and a nucleotide sequence S6 encoding a linker peptide, wherein S5 and S6 are positioned between S1 and S2, S1 and S4, and/or S3 and S4.

4. The vector of claim 3, wherein the 2A peptide is selected from P2A (SEQ ID NO: 3), T2A (SEQ ID NO: 4), E2A (SEQ ID NO: 5), or F2A (SEQ ID NO: 6).

5. The vector of claim 3, wherein the linker peptide is GSG or SGSG (SEQ ID NO: 8).

6. The vector of claim 3, further comprising a nucleotide sequence S7 encoding a furin peptide (SEQ ID NO: 2), wherein S7 is positioned between S1 and S2, S1 and S4, and/or S3 and S4.

7. The vector of claim 1, further comprising a nucleotide sequence S5 encoding a 2A peptide and a nucleotide sequence S6 encoding a linker peptide, wherein S5 and S6 are positioned between S1 and S2, S1 and S4, and/or S3 and S4.

8. The vector of claim 7, wherein the 2A peptide is selected from P2A (SEQ ID NO: 3), T2A (SEQ ID NO: 4), E2A (SEQ ID NO: 5), or F2A (SEQ ID NO: 6).

9. The vector of claim 7, wherein the linker peptide is GSG or SGSG (SEQ ID NO: 8).

10. The vector of claim 1, further comprising a nucleotide sequence S7 encoding a furin peptide (SEQ ID NO: 2), wherein S7 is positioned between S1 and S2, S1 and S4, and/or S3 and S4.

11. A method of preparing T cells for immunotherapy comprising
isolating T cells from a blood sample of a human subject,
activating the isolated T cells,
transducing the activated T cells with the vector of claim 1, and
expanding the transduced T cells.

12. The method of claim 11, wherein the T cells are isolated from a leukapheresis human sample.

13. The method of claim 11, wherein the T cells are activated in the presence of an aminobisphosphonate and wherein the aminobisphosphonate is optionally selected from pamidronic acid, alendronic acid, zoledronic acid, risedronic acid, ibandronic acid, incadronic acid, a salt of any of the foregoing and/or a hydrate thereof.

14. The method of claim 13, wherein the activating is further in the presence of human recombinant interleukin 2 (IL-2) and human recombinant interleukin 15 (IL-15).

15. The method of claim 11, wherein the expanding is in the presence of IL-2 and IL-15.

16. The method of claim 11, wherein the T cells are γδ T cells.

* * * * *

UNITED STATES PATENT AND TRADEMARK OFFICE
CERTIFICATE OF CORRECTION

PATENT NO. : 11,975,025 B2
APPLICATION NO. : 16/884804
DATED : May 7, 2024
INVENTOR(S) : Melinda Mata et al.

Page 1 of 1

It is certified that error appears in the above-identified patent and that said Letters Patent is hereby corrected as shown below:

In the Claims

In Column 309 (Line 21):
In Claim 1, Line 3 should be:...CD8β polypeptide, a nucleotide sequence S3 encoding a T...

Signed and Sealed this
Twentieth Day of May, 2025

Coke Morgan Stewart
*Acting Director of the United States Patent and Trademark Office*

SEQUENCE LISTING

<160> NUMBER OF SEQ ID NOS: 266

<210> SEQ ID NO 1
<211> LENGTH: 367
<212> TYPE: DNA
<213> ORGANISM: Artificial Sequence
<220> FEATURE:
<223> OTHER INFORMATION: murine stem cell virus promoter

<400> SEQUENCE: 1
tgaaagaccc cacctgtagg tttggcaagc tagcttaagt aacgccattt tgcaaggcat      60
ggaaaataca taactgagaa tagagaagtt cagatcaagg ttaggaacag agagacagca     120
gaatatgggc caaacaggat atctgtggta agcagttcct gccccggctc agggccaaga     180
acagatggtc cccagatgcg gtcccgccct cagcagtttc tagagaacca tcagatgttt     240
ccagggtgcc ccaaggacct gaaaatgacc ctgtgcctta tttgaactaa ccaatcagtt     300
cgcttctcgc ttctgttcgc gcgcttctgc tccccgagct caataaaaga gcccacaacc     360
cctcact                                                              367

<210> SEQ ID NO 2
<211> LENGTH: 4
<212> TYPE: PRT
<213> ORGANISM: Artificial Sequence
<220> FEATURE:
<223> OTHER INFORMATION: Furin

<400> SEQUENCE: 2

Arg Ala Lys Arg
1

<210> SEQ ID NO 3
<211> LENGTH: 19
<212> TYPE: PRT
<213> ORGANISM: Artificial Sequence
<220> FEATURE:
<223> OTHER INFORMATION: P2A peptide

<400> SEQUENCE: 3

Ala Thr Asn Phe Ser Leu Leu Lys Gln Ala Gly Asp Val Glu Glu Asn
1               5                   10                  15

Pro Gly Pro

<210> SEQ ID NO 4
<211> LENGTH: 18
<212> TYPE: PRT
<213> ORGANISM: Artificial Sequence
<220> FEATURE:
<223> OTHER INFORMATION: T2A peptide

<400> SEQUENCE: 4

Glu Gly Arg Gly Ser Leu Leu Thr Cys Gly Asp Val Glu Glu Asn Pro
1               5                   10                  15

Gly Pro

<210> SEQ ID NO 5
<211> LENGTH: 20
<212> TYPE: PRT
<213> ORGANISM: Artificial Sequence
<220> FEATURE:
<223> OTHER INFORMATION: E2A peptide

<400> SEQUENCE: 5

Gln Cys Thr Asn Tyr Ala Leu Leu Lys Leu Ala Gly Asp Val Glu Ser
1               5                   10                  15

Asn Pro Gly Pro
            20

<210> SEQ ID NO 6
<211> LENGTH: 22
<212> TYPE: PRT
<213> ORGANISM: Artificial Sequence
<220> FEATURE:
<223> OTHER INFORMATION: F2A peptide

<400> SEQUENCE: 6

Val Lys Gln Thr Leu Asn Phe Asp Leu Leu Lys Leu Ala Gly Asp Val
1               5                   10                  15

Glu Ser Asn Pro Gly Pro
            20

<210> SEQ ID NO 7
<211> LENGTH: 4
<212> TYPE: PRT
<213> ORGANISM: Artificial Sequence
<220> FEATURE:
<223> OTHER INFORMATION: Furin consensus sequence
<220> FEATURE:
<221> NAME/KEY: misc_feature
<222> LOCATION: (2)..(3)
<223> OTHER INFORMATION: Xaa can be any naturally occurring amino acid

<400> SEQUENCE: 7

Arg Xaa Xaa Arg
1

<210> SEQ ID NO 8
<211> LENGTH: 4
<212> TYPE: PRT
<213> ORGANISM: Artificial Sequence
<220> FEATURE:
<223> OTHER INFORMATION: Linker peptide

<400> SEQUENCE: 8

Ser Gly Ser Gly
1

<210> SEQ ID NO 9
<211> LENGTH: 607
<212> TYPE: DNA
<213> ORGANISM: Artificial Sequence
<220> FEATURE:
<223> OTHER INFORMATION: WPRE

<400> SEQUENCE: 9

```
cagtctgacg tacgcgtaat caacctctgg attacaaaat ttgtgaaaga ttgactggta    60
ttcttaacta tgttgctcct tttacgctat gtggatacgc tgctttaatg cctttgtatc   120
atgctattgc ttcccgtatg gctttcattt tctcctcctt gtataaatcc tggttgctgt   180
ctctttatga ggagttgtgg cccgttgtca ggcaacgtgg cgtggtgtgc actgtgtttg   240
ctgacgcaac ccccactggt tggggcattg ccaccacctg tcagctcctt ccgggactt    300
tcgctttccc cctccctatt gccacggcgg aactcatcgc cgcctgcctt gcccgctgct   360
ggacaggggc tcggctgttg ggcactgaca attccgtggt gttgtcgggg aagctgacgt   420
cctttccatg gctgctcgcc tgtgttgcca cctggattct gcgcgggacg tccttctgct   480
acgtcccttc ggccctcaat ccagcggacc ttccttcccg cggcctgctg ccggctctgc   540
ggcctcttcc gcgtcttcgc cttcgccctc agacgagtcg gatctccctt tgggccgcct   600
ccccgcc                                                             607
```

<210> SEQ ID NO 10
<211> LENGTH: 21
<212> TYPE: DNA
<213> ORGANISM: Artificial Sequence
<220> FEATURE:
<223> OTHER INFORMATION: X protein promoter

<400> SEQUENCE: 10

```
ggggaagctg acgtcctttc c                                              21
```

<210> SEQ ID NO 11
<211> LENGTH: 235
<212> TYPE: PRT
<213> ORGANISM: Homo sapiens

<400> SEQUENCE: 11

```
Met Ala Leu Pro Val Thr Ala Leu Leu Leu Pro Leu Ala Leu Leu Leu
1               5                   10                  15

His Ala Ala Arg Pro Ser Gln Phe Arg Val Ser Pro Leu Asp Arg Thr
                20                  25                  30

Trp Asn Leu Gly Glu Thr Val Glu Leu Lys Cys Gln Val Leu Leu Ser
            35                  40                  45

Asn Pro Thr Ser Gly Cys Ser Trp Leu Phe Gln Pro Arg Gly Ala Ala
        50                  55                  60

Ala Ser Pro Thr Phe Leu Leu Tyr Leu Ser Gln Asn Lys Pro Lys Ala
65                  70                  75                  80

Ala Glu Gly Leu Asp Thr Gln Arg Phe Ser Gly Lys Arg Leu Gly Asp
                85                  90                  95

Thr Phe Val Leu Thr Leu Ser Asp Phe Arg Arg Glu Asn Glu Gly Tyr
                100                 105                 110

Tyr Phe Cys Ser Ala Leu Ser Asn Ser Ile Met Tyr Phe Ser His Phe
            115                 120                 125

Val Pro Val Phe Leu Pro Ala Lys Pro Thr Thr Thr Pro Ala Pro Arg
        130                 135                 140

Pro Pro Thr Pro Ala Pro Thr Ile Ala Ser Gln Pro Leu Ser Leu Arg
```

```
                    145                 150                 155                 160

Pro Glu Ala Cys Arg Pro Ala Ala Gly Gly Ala Val His Thr Arg Gly
                165                 170                 175

Leu Asp Phe Ala Cys Asp Ile Tyr Ile Trp Ala Pro Leu Ala Gly Thr
                180                 185                 190

Cys Gly Val Leu Leu Ser Leu Val Ile Thr Leu Tyr Cys Asn His
                195                 200                 205

Arg Asn Arg Arg Val Cys Lys Cys Pro Arg Pro Val Val Lys Ser
210                 215                 220

Gly Asp Lys Pro Ser Leu Ser Ala Arg Tyr Val
225                 230                 235

<210> SEQ ID NO 12
<211> LENGTH: 243
<212> TYPE: PRT
<213> ORGANISM: Homo sapiens

<400> SEQUENCE: 12

Met Arg Pro Arg Leu Trp Leu Leu Leu Ala Ala Gln Leu Thr Val Leu
1               5                   10                  15

His Gly Asn Ser Val Leu Gln Gln Thr Pro Ala Tyr Ile Lys Val Gln
                20                  25                  30

Thr Asn Lys Met Val Met Leu Ser Cys Glu Ala Lys Ile Ser Leu Ser
            35                  40                  45

Asn Met Arg Ile Tyr Trp Leu Arg Gln Arg Gln Ala Pro Ser Ser Asp
        50                  55                  60

Ser His His Glu Phe Leu Ala Leu Trp Asp Ser Ala Lys Gly Thr Ile
65                  70                  75                  80

His Gly Glu Glu Val Glu Gln Glu Lys Ile Ala Val Phe Arg Asp Ala
                85                  90                  95

Ser Arg Phe Ile Leu Asn Leu Thr Ser Val Lys Pro Glu Asp Ser Gly
                100                 105                 110

Ile Tyr Phe Cys Met Ile Val Gly Ser Pro Glu Leu Thr Phe Gly Lys
            115                 120                 125

Gly Thr Gln Leu Ser Val Val Asp Phe Leu Pro Thr Thr Ala Gln Pro
        130                 135                 140

Thr Lys Lys Ser Thr Leu Lys Lys Arg Val Cys Arg Leu Pro Arg Pro
145                 150                 155                 160

Glu Thr Gln Lys Gly Pro Leu Cys Ser Pro Ile Thr Leu Gly Leu Leu
                165                 170                 175

Val Ala Gly Val Leu Val Leu Leu Val Ser Leu Gly Val Ala Ile His
                180                 185                 190

Leu Cys Cys Arg Arg Arg Arg Ala Arg Leu Arg Phe Met Lys Gln Pro
            195                 200                 205

Gln Gly Glu Gly Ile Ser Gly Thr Phe Val Pro Gln Cys Leu His Gly
        210                 215                 220

Tyr Tyr Ser Asn Thr Thr Thr Ser Gln Lys Leu Leu Asn Pro Trp Ile
225                 230                 235                 240

Leu Lys Thr

<210> SEQ ID NO 13
<211> LENGTH: 273
<212> TYPE: PRT
<213> ORGANISM: Artificial Sequence
<220> FEATURE:
<223> OTHER INFORMATION: R11KEA alpha chain
```

<400> SEQUENCE: 13

```
Met Glu Lys Asn Pro Leu Ala Ala Pro Leu Leu Ile Leu Trp Phe His
1               5                   10                  15

Leu Asp Cys Val Ser Ser Ile Leu Asn Val Glu Gln Ser Pro Gln Ser
            20                  25                  30

Leu His Val Gln Glu Gly Asp Ser Thr Asn Phe Thr Cys Ser Phe Pro
        35                  40                  45

Ser Ser Asn Phe Tyr Ala Leu His Trp Tyr Arg Lys Glu Thr Ala Lys
    50                  55                  60

Ser Pro Glu Ala Leu Phe Val Met Thr Leu Asn Gly Asp Glu Lys Lys
65                  70                  75                  80

Lys Gly Arg Ile Ser Ala Thr Leu Asn Thr Lys Glu Gly Tyr Ser Tyr
                85                  90                  95

Leu Tyr Ile Lys Gly Ser Gln Pro Glu Asp Ser Ala Thr Tyr Leu Cys
            100                 105                 110

Ala Leu Tyr Asn Asn Asn Asp Met Arg Phe Gly Ala Gly Thr Arg Leu
        115                 120                 125

Thr Val Lys Pro Asn Ile Gln Asn Pro Asp Pro Ala Val Tyr Gln Leu
    130                 135                 140

Arg Asp Ser Lys Ser Ser Asp Lys Ser Val Cys Leu Phe Thr Asp Phe
145                 150                 155                 160

Asp Ser Gln Thr Asn Val Ser Gln Ser Lys Asp Ser Asp Val Tyr Ile
                165                 170                 175

Thr Asp Lys Thr Val Leu Asp Met Arg Ser Met Asp Phe Lys Ser Asn
            180                 185                 190

Ser Ala Val Ala Trp Ser Asn Lys Ser Asp Phe Ala Cys Ala Asn Ala
        195                 200                 205

Phe Asn Asn Ser Ile Ile Pro Glu Asp Thr Phe Phe Pro Ser Pro Glu
    210                 215                 220

Ser Ser Cys Asp Val Lys Leu Val Glu Lys Ser Phe Glu Thr Asp Thr
225                 230                 235                 240

Asn Leu Asn Phe Gln Asn Leu Ser Val Ile Gly Phe Arg Ile Leu Leu
                245                 250                 255

Leu Lys Val Ala Gly Phe Asn Leu Leu Met Thr Leu Arg Leu Trp Ser
            260                 265                 270

Ser
```

<210> SEQ ID NO 14
<211> LENGTH: 311
<212> TYPE: PRT
<213> ORGANISM: Artificial Sequence
<220> FEATURE:
<223> OTHER INFORMATION: R11KE beta chain

<400> SEQUENCE: 14

```
Met Asp Ser Trp Thr Phe Cys Cys Val Ser Leu Cys Ile Leu Val Ala
1               5                   10                  15

Lys His Thr Asp Ala Gly Val Ile Gln Ser Pro Arg His Glu Val Thr
            20                  25                  30

Glu Met Gly Gln Glu Val Thr Leu Arg Cys Lys Pro Ile Ser Gly His
        35                  40                  45

Asn Ser Leu Phe Trp Tyr Arg Glu Thr Met Met Arg Gly Leu Glu Leu
    50                  55                  60

Leu Ile Tyr Phe Asn Asn Asn Val Pro Ile Asp Asp Ser Gly Met Pro
```

```
            65                  70                  75                  80
Glu Asp Arg Phe Ser Ala Lys Met Pro Asn Ala Ser Phe Ser Thr Leu
                85                  90                  95

Lys Ile Gln Pro Ser Glu Pro Arg Asp Ser Ala Val Tyr Phe Cys Ala
            100                 105                 110

Ser Ser Pro Gly Ser Thr Asp Thr Gln Tyr Phe Gly Pro Gly Thr Arg
            115                 120                 125

Leu Thr Val Leu Glu Asp Leu Lys Asn Val Phe Pro Pro Glu Val Ala
        130                 135                 140

Val Phe Glu Pro Ser Glu Ala Glu Ile Ser His Thr Gln Lys Ala Thr
145                 150                 155                 160

Leu Val Cys Leu Ala Thr Gly Phe Tyr Pro Asp His Val Glu Leu Ser
                165                 170                 175

Trp Trp Val Asn Gly Lys Glu Val His Ser Gly Val Ser Thr Asp Pro
                180                 185                 190

Gln Pro Leu Lys Glu Gln Pro Ala Leu Asn Asp Ser Arg Tyr Cys Leu
            195                 200                 205

Ser Ser Arg Leu Arg Val Ser Ala Thr Phe Trp Gln Asn Pro Arg Asn
        210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Glu Ser Tyr Gln Gln
                260                 265                 270

Gly Val Leu Ser Ala Thr Ile Leu Tyr Glu Ile Leu Leu Gly Lys Ala
            275                 280                 285

Thr Leu Tyr Ala Val Leu Val Ser Ala Leu Val Leu Met Ala Met Val
        290                 295                 300

Lys Arg Lys Asp Ser Arg Gly
305                 310

<210> SEQ ID NO 15
<211> LENGTH: 274
<212> TYPE: PRT
<213> ORGANISM: Homo sapiens

<400> SEQUENCE: 15

Met Glu Lys Met Leu Glu Cys Ala Phe Ile Val Leu Trp Leu Gln Leu
1               5                   10                  15

Gly Trp Leu Ser Gly Glu Asp Gln Val Thr Gln Ser Pro Glu Ala Leu
            20                  25                  30

Arg Leu Gln Glu Gly Glu Ser Ser Ser Leu Asn Cys Ser Tyr Thr Val
        35                  40                  45

Ser Gly Leu Arg Gly Leu Phe Trp Tyr Arg Gln Asp Pro Gly Lys Gly
    50                  55                  60

Pro Glu Phe Leu Phe Thr Leu Tyr Ser Ala Gly Glu Glu Lys Glu Lys
65                  70                  75                  80

Glu Arg Leu Lys Ala Thr Leu Thr Lys Lys Glu Ser Phe Leu His Ile
                85                  90                  95

Thr Ala Pro Lys Pro Glu Asp Ser Ala Thr Tyr Leu Cys Ala Val Gln
            100                 105                 110

Gly Glu Asn Ser Gly Tyr Ser Thr Leu Thr Phe Gly Lys Gly Thr Met
        115                 120                 125
```

```
Leu Leu Val Ser Pro Asp Ile Gln Asn Pro Asp Pro Ala Val Tyr Gln
    130                 135                 140
Leu Arg Asp Ser Lys Ser Asp Lys Ser Val Cys Leu Phe Thr Asp
145                 150                 155                 160
Phe Asp Ser Gln Thr Asn Val Ser Gln Ser Lys Asp Ser Asp Val Tyr
                165                 170                 175
Ile Thr Asp Lys Thr Val Leu Asp Met Arg Ser Met Asp Phe Lys Ser
                180                 185                 190
Asn Ser Ala Val Ala Trp Ser Asn Lys Ser Asp Phe Ala Cys Ala Asn
                195                 200                 205
Ala Phe Asn Asn Ser Ile Ile Pro Glu Asp Thr Phe Phe Pro Ser Pro
    210                 215                 220
Glu Ser Ser Cys Asp Val Lys Leu Val Glu Lys Ser Phe Glu Thr Asp
225                 230                 235                 240
Thr Asn Leu Asn Phe Gln Asn Leu Ser Val Ile Gly Phe Arg Ile Leu
                245                 250                 255
Leu Leu Lys Val Ala Gly Phe Asn Leu Leu Met Thr Leu Arg Leu Trp
                260                 265                 270
Ser Ser

<210> SEQ ID NO 16
<211> LENGTH: 314
<212> TYPE: PRT
<213> ORGANISM: Homo sapiens

<400> SEQUENCE: 16

Met Gly Pro Gln Leu Leu Gly Tyr Val Val Leu Cys Leu Leu Gly Ala
1               5                   10                  15
Gly Pro Leu Glu Ala Gln Val Thr Gln Asn Pro Arg Tyr Leu Ile Thr
                20                  25                  30
Val Thr Gly Lys Lys Leu Thr Val Thr Cys Ser Gln Asn Met Asn His
            35                  40                  45
Glu Tyr Met Ser Trp Tyr Arg Gln Asp Pro Gly Leu Gly Leu Arg Gln
        50                  55                  60
Ile Tyr Tyr Ser Met Asn Val Glu Val Thr Asp Lys Gly Asp Val Pro
65                  70                  75                  80
Glu Gly Tyr Lys Val Ser Arg Lys Glu Lys Arg Asn Phe Pro Leu Ile
                85                  90                  95
Leu Glu Ser Pro Ser Pro Asn Gln Thr Ser Leu Tyr Phe Cys Ala Ser
                100                 105                 110
Ser Leu Gly Pro Gly Leu Ala Ala Tyr Asn Glu Gln Phe Gly Pro
            115                 120                 125
Gly Thr Arg Leu Thr Val Leu Glu Asp Leu Lys Asn Val Phe Pro Pro
    130                 135                 140
Glu Val Ala Val Phe Glu Pro Ser Glu Ala Glu Ile Ser His Thr Gln
145                 150                 155                 160
Lys Ala Thr Leu Val Cys Leu Ala Thr Gly Phe Tyr Pro Asp His Val
                165                 170                 175
Glu Leu Ser Trp Trp Val Asn Gly Lys Glu Val His Ser Gly Val Ser
                180                 185                 190
Thr Asp Pro Gln Pro Leu Lys Glu Gln Pro Ala Leu Asn Asp Ser Arg
            195                 200                 205
Tyr Cys Leu Ser Ser Arg Leu Arg Val Ser Ala Thr Phe Trp Gln Asn
    210                 215                 220
```

Pro Arg Asn His Phe Arg Cys Gln Val Gln Phe Tyr Gly Leu Ser Glu
225                 230                 235                 240

Asn Asp Glu Trp Thr Gln Asp Arg Ala Lys Pro Val Thr Gln Ile Val
            245                 250                 255

Ser Ala Glu Ala Trp Gly Arg Ala Asp Cys Gly Phe Thr Ser Glu Ser
        260                 265                 270

Tyr Gln Gln Gly Val Leu Ser Ala Thr Ile Leu Tyr Glu Ile Leu Leu
    275                 280                 285

Gly Lys Ala Thr Leu Tyr Ala Val Leu Val Ser Ala Leu Val Leu Met
290                 295                 300

Ala Met Val Lys Arg Lys Asp Ser Arg Gly
305                 310

<210> SEQ ID NO 17
<211> LENGTH: 272
<212> TYPE: PRT
<213> ORGANISM: Homo sapiens

<400> SEQUENCE: 17

Met Lys Thr Phe Ala Gly Phe Ser Phe Leu Phe Leu Trp Leu Gln Leu
1               5                   10                  15

Asp Cys Met Ser Arg Gly Glu Asp Val Glu Gln Ser Leu Phe Leu Ser
            20                  25                  30

Val Arg Glu Gly Asp Ser Ser Val Ile Asn Cys Thr Tyr Thr Asp Ser
        35                  40                  45

Ser Ser Thr Tyr Leu Tyr Trp Tyr Lys Gln Glu Pro Gly Ala Gly Leu
    50                  55                  60

Gln Leu Leu Thr Tyr Ile Phe Ser Asn Met Asp Met Lys Gln Asp Gln
65                  70                  75                  80

Arg Leu Thr Val Leu Leu Asn Lys Lys Asp Lys His Leu Ser Leu Arg
                85                  90                  95

Ile Ala Asp Thr Gln Thr Gly Asp Ser Ala Ile Tyr Phe Cys Ala Glu
            100                 105                 110

Tyr Ser Ser Ala Ser Lys Ile Ile Phe Gly Ser Gly Thr Arg Leu Ser
        115                 120                 125

Ile Arg Pro Asn Ile Gln Asn Pro Asp Pro Ala Val Tyr Gln Leu Arg
    130                 135                 140

Asp Ser Lys Ser Ser Asp Lys Ser Val Cys Leu Phe Thr Asp Phe Asp
145                 150                 155                 160

Ser Gln Thr Asn Val Ser Gln Ser Lys Asp Ser Asp Val Tyr Ile Thr
                165                 170                 175

Asp Lys Thr Val Leu Asp Met Arg Ser Met Asp Phe Lys Ser Asn Ser
            180                 185                 190

Ala Val Ala Trp Ser Asn Lys Ser Asp Phe Ala Cys Ala Asn Ala Phe
        195                 200                 205

Asn Asn Ser Ile Ile Pro Glu Asp Thr Phe Phe Pro Ser Pro Glu Ser
    210                 215                 220

Ser Cys Asp Val Lys Leu Val Glu Lys Ser Phe Glu Thr Asp Thr Asn
225                 230                 235                 240

Leu Asn Phe Gln Asn Leu Ser Val Ile Gly Phe Arg Ile Leu Leu Leu
                245                 250                 255

Lys Val Ala Gly Phe Asn Leu Leu Met Thr Leu Arg Leu Trp Ser Ser
            260                 265                 270

<210> SEQ ID NO 18

```
<211> LENGTH: 310
<212> TYPE: PRT
<213> ORGANISM: Homo sapiens

<400> SEQUENCE: 18

Met Gly Ser Trp Thr Leu Cys Cys Val Ser Leu Cys Ile Leu Val Ala
1               5                   10                  15

Lys His Thr Asp Ala Gly Val Ile Gln Ser Pro Arg His Glu Val Thr
            20                  25                  30

Glu Met Gly Gln Glu Val Thr Leu Arg Cys Lys Pro Ile Ser Gly His
        35                  40                  45

Asp Tyr Leu Phe Trp Tyr Arg Gln Thr Met Met Arg Gly Leu Glu Leu
    50                  55                  60

Leu Ile Tyr Phe Asn Asn Asn Val Pro Ile Asp Asp Ser Gly Met Pro
65                  70                  75                  80

Glu Asp Arg Phe Ser Ala Lys Met Pro Asn Ala Ser Phe Ser Thr Leu
                85                  90                  95

Lys Ile Gln Pro Ser Glu Pro Arg Asp Ser Ala Val Tyr Phe Cys Ala
            100                 105                 110

Ser Arg Ala Asn Thr Gly Glu Leu Phe Phe Gly Glu Gly Ser Arg Leu
        115                 120                 125

Thr Val Leu Glu Asp Leu Lys Asn Val Phe Pro Pro Glu Val Ala Val
    130                 135                 140

Phe Glu Pro Ser Glu Ala Glu Ile Ser His Thr Gln Lys Ala Thr Leu
145                 150                 155                 160

Val Cys Leu Ala Thr Gly Phe Tyr Pro Asp His Val Glu Leu Ser Trp
                165                 170                 175

Trp Val Asn Gly Lys Glu Val His Ser Gly Val Ser Thr Asp Pro Gln
            180                 185                 190

Pro Leu Lys Glu Gln Pro Ala Leu Asn Asp Ser Arg Tyr Cys Leu Ser
        195                 200                 205

Ser Arg Leu Arg Val Ser Ala Thr Phe Trp Gln Asn Pro Arg Asn His
    210                 215                 220

Phe Arg Cys Gln Val Gln Phe Tyr Gly Leu Ser Glu Asn Asp Glu Trp
225                 230                 235                 240

Thr Gln Asp Arg Ala Lys Pro Val Thr Gln Ile Val Ser Ala Glu Ala
                245                 250                 255

Trp Gly Arg Ala Asp Cys Gly Phe Thr Ser Glu Ser Tyr Gln Gln Gly
            260                 265                 270

Val Leu Ser Ala Thr Ile Leu Tyr Glu Ile Leu Leu Gly Lys Ala Thr
        275                 280                 285

Leu Tyr Ala Val Leu Val Ser Ala Leu Val Leu Met Ala Met Val Lys
    290                 295                 300

Arg Lys Asp Ser Arg Gly
305                 310

<210> SEQ ID NO 19
<211> LENGTH: 277
<212> TYPE: PRT
<213> ORGANISM: Homo sapiens

<400> SEQUENCE: 19

Met Leu Thr Ala Ser Leu Leu Arg Ala Val Ile Ala Ser Ile Cys Val
1               5                   10                  15

Val Ser Ser Met Ala Gln Lys Val Thr Gln Ala Gln Thr Glu Ile Ser
            20                  25                  30
```

```
Val Val Glu Lys Glu Asp Val Thr Leu Asp Cys Val Tyr Glu Thr Arg
         35                  40                  45

Asp Thr Thr Tyr Tyr Leu Phe Trp Tyr Lys Gln Pro Pro Ser Gly Glu
 50                  55                  60

Leu Val Phe Leu Ile Arg Arg Asn Ser Phe Asp Glu Gln Asn Glu Ile
 65                  70                  75                  80

Ser Gly Arg Tyr Ser Trp Asn Phe Gln Lys Ser Thr Ser Ser Phe Asn
                 85                  90                  95

Phe Thr Ile Thr Ala Ser Gln Val Val Asp Ser Ala Val Tyr Phe Cys
                100                 105                 110

Ala Leu Ser Glu Gly Asn Ser Gly Asn Thr Pro Leu Val Phe Gly Lys
                115                 120                 125

Gly Thr Arg Leu Ser Val Ile Ala Asn Ile Gln Asn Pro Asp Pro Ala
        130                 135                 140

Val Tyr Gln Leu Arg Asp Ser Lys Ser Ser Asp Lys Ser Val Cys Leu
145                 150                 155                 160

Phe Thr Asp Phe Asp Ser Gln Thr Asn Val Ser Gln Ser Lys Asp Ser
                165                 170                 175

Asp Val Tyr Ile Thr Asp Lys Thr Val Leu Asp Met Arg Ser Met Asp
                180                 185                 190

Phe Lys Ser Asn Ser Ala Val Ala Trp Ser Asn Lys Ser Asp Phe Ala
                195                 200                 205

Cys Ala Asn Ala Phe Asn Asn Ser Ile Ile Pro Glu Asp Thr Phe Phe
        210                 215                 220

Pro Ser Pro Glu Ser Ser Cys Asp Val Lys Leu Val Glu Lys Ser Phe
225                 230                 235                 240

Glu Thr Asp Thr Asn Leu Asn Phe Gln Asn Leu Ser Val Ile Gly Phe
                245                 250                 255

Arg Ile Leu Leu Leu Lys Val Ala Gly Phe Asn Leu Leu Met Thr Leu
                260                 265                 270

Arg Leu Trp Ser Ser
        275

<210> SEQ ID NO 20
<211> LENGTH: 313
<212> TYPE: PRT
<213> ORGANISM: Homo sapiens

<400> SEQUENCE: 20

Met Gly Ile Arg Leu Leu Cys Arg Val Ala Phe Cys Phe Leu Ala Val
 1               5                  10                  15

Gly Leu Val Asp Val Lys Val Thr Gln Ser Ser Arg Tyr Leu Val Lys
                 20                  25                  30

Arg Thr Gly Glu Lys Val Phe Leu Glu Cys Val Gln Asp Met Asp His
         35                  40                  45

Glu Asn Met Phe Trp Tyr Arg Gln Asp Pro Gly Leu Gly Leu Arg Leu
 50                  55                  60

Ile Tyr Phe Ser Tyr Asp Val Lys Met Lys Glu Lys Gly Asp Ile Pro
 65                  70                  75                  80

Glu Gly Tyr Ser Val Ser Arg Glu Lys Lys Glu Arg Phe Ser Leu Ile
                 85                  90                  95

Leu Glu Ser Ala Ser Thr Asn Gln Thr Ser Met Tyr Leu Cys Ala Ser
                100                 105                 110

Ser Leu Ser Ser Gly Ser His Gln Glu Thr Gln Tyr Phe Gly Pro Gly
```

```
            115                 120                 125
Thr Arg Leu Leu Val Leu Glu Asp Leu Lys Asn Val Phe Pro Pro Glu
130                 135                 140

Val Ala Val Phe Glu Pro Ser Glu Ala Glu Ile Ser His Thr Gln Lys
145                 150                 155                 160

Ala Thr Leu Val Cys Leu Ala Thr Gly Phe Tyr Pro Asp His Val Glu
                165                 170                 175

Leu Ser Trp Trp Val Asn Gly Lys Glu Val His Ser Gly Val Ser Thr
            180                 185                 190

Asp Pro Gln Pro Leu Lys Glu Gln Pro Ala Leu Asn Asp Ser Arg Tyr
        195                 200                 205

Cys Leu Ser Ser Arg Leu Arg Val Ser Ala Thr Phe Trp Gln Asn Pro
210                 215                 220

Arg Asn His Phe Arg Cys Gln Val Gln Phe Tyr Gly Leu Ser Glu Asn
225                 230                 235                 240

Asp Glu Trp Thr Gln Asp Arg Ala Lys Pro Val Thr Gln Ile Val Ser
                245                 250                 255

Ala Glu Ala Trp Gly Arg Ala Asp Cys Gly Phe Thr Ser Glu Ser Tyr
            260                 265                 270

Gln Gln Gly Val Leu Ser Ala Thr Ile Leu Tyr Glu Ile Leu Leu Gly
        275                 280                 285

Lys Ala Thr Leu Tyr Ala Val Leu Val Ser Ala Leu Val Leu Met Ala
290                 295                 300

Met Val Lys Arg Lys Asp Ser Arg Gly
305                 310

<210> SEQ ID NO 21
<211> LENGTH: 271
<212> TYPE: PRT
<213> ORGANISM: Homo sapiens

<400> SEQUENCE: 21

Met Lys Thr Phe Ala Gly Phe Ser Phe Leu Phe Leu Trp Leu Gln Leu
1               5                   10                  15

Asp Cys Met Ser Arg Gly Glu Asp Val Glu Gln Ser Leu Phe Leu Ser
                20                  25                  30

Val Arg Glu Gly Asp Ser Ser Val Ile Asn Cys Thr Tyr Thr Asp Ser
            35                  40                  45

Ser Ser Thr Tyr Leu Tyr Trp Tyr Lys Gln Glu Pro Gly Ala Gly Leu
        50                  55                  60

Gln Leu Leu Thr Tyr Ile Phe Ser Asn Met Asp Met Lys Gln Asp Gln
65                  70                  75                  80

Arg Leu Thr Val Leu Leu Asn Lys Lys Asp Lys His Leu Ser Leu Arg
                85                  90                  95

Ile Ala Asp Thr Gln Thr Gly Asp Ser Ala Ile Tyr Phe Cys Ala Glu
            100                 105                 110

Ser Lys Glu Thr Arg Leu Met Phe Gly Asp Gly Thr Gln Leu Val Val
        115                 120                 125

Lys Pro Asn Ile Gln Asn Pro Asp Pro Ala Val Tyr Gln Leu Arg Asp
130                 135                 140

Ser Lys Ser Ser Asp Lys Ser Val Cys Leu Phe Thr Asp Phe Asp Ser
                145                 150                 155                 160

Gln Thr Asn Val Ser Gln Ser Lys Asp Ser Asp Val Tyr Ile Thr Asp
            165                 170                 175
```

```
Lys Thr Val Leu Asp Met Arg Ser Met Asp Phe Lys Ser Asn Ser Ala
                180                 185                 190

Val Ala Trp Ser Asn Lys Ser Asp Phe Ala Cys Ala Asn Ala Phe Asn
            195                 200                 205

Asn Ser Ile Ile Pro Glu Asp Thr Phe Phe Pro Ser Pro Glu Ser Ser
        210                 215                 220

Cys Asp Val Lys Leu Val Glu Lys Ser Phe Glu Thr Asp Thr Asn Leu
225                 230                 235                 240

Asn Phe Gln Asn Leu Ser Val Ile Gly Phe Arg Ile Leu Leu Leu Lys
                245                 250                 255

Val Ala Gly Phe Asn Leu Leu Met Thr Leu Arg Leu Trp Ser Ser
            260                 265                 270

<210> SEQ ID NO 22
<211> LENGTH: 317
<212> TYPE: PRT
<213> ORGANISM: Homo sapiens

<400> SEQUENCE: 22

Met Leu Leu Leu Leu Leu Leu Gly Pro Gly Ile Ser Leu Leu Leu
1               5                   10                  15

Pro Gly Ser Leu Ala Gly Ser Gly Leu Gly Ala Trp Ser Gln His Pro
                20                  25                  30

Ser Val Trp Ile Cys Lys Ser Gly Thr Ser Val Lys Ile Glu Cys Arg
            35                  40                  45

Ser Leu Asp Phe Gln Ala Thr Thr Met Phe Trp Tyr Arg Gln Phe Pro
        50                  55                  60

Lys Gln Ser Leu Met Leu Met Ala Thr Ser Asn Glu Gly Ser Lys Ala
65                  70                  75                  80

Thr Tyr Glu Gln Gly Val Glu Lys Asp Lys Phe Leu Ile Asn His Ala
                85                  90                  95

Ser Leu Thr Leu Ser Thr Leu Thr Val Thr Ser Ala His Pro Glu Asp
            100                 105                 110

Ser Ser Phe Tyr Ile Cys Ser Ala Arg Ala Gly Gly His Glu Gln Phe
        115                 120                 125

Phe Gly Pro Gly Thr Arg Leu Thr Val Leu Glu Asp Leu Lys Asn Val
130                 135                 140

Phe Pro Pro Glu Val Ala Val Phe Glu Pro Ser Glu Ala Glu Ile Ser
145                 150                 155                 160

His Thr Gln Lys Ala Thr Leu Val Cys Leu Ala Thr Gly Phe Tyr Pro
                165                 170                 175

Asp His Val Glu Leu Ser Trp Val Trp Asn Gly Lys Glu Val His Ser
            180                 185                 190

Gly Val Ser Thr Asp Pro Gln Pro Leu Lys Glu Gln Pro Ala Leu Asn
        195                 200                 205

Asp Ser Arg Tyr Cys Leu Ser Ser Arg Leu Arg Val Ser Ala Thr Phe
210                 215                 220

Trp Gln Asn Pro Arg Asn His Phe Arg Cys Gln Val Gln Phe Tyr Gly
225                 230                 235                 240

Leu Ser Glu Asn Asp Glu Trp Thr Gln Asp Arg Ala Lys Pro Val Thr
                245                 250                 255

Gln Ile Val Ser Ala Glu Ala Trp Gly Arg Ala Asp Cys Gly Phe Thr
            260                 265                 270

Ser Glu Ser Tyr Gln Gln Gly Val Leu Ser Ala Thr Ile Leu Tyr Glu
        275                 280                 285
```

Ile Leu Leu Gly Lys Ala Thr Leu Tyr Ala Val Leu Val Ser Ala Leu
            290                 295                 300

Val Leu Met Ala Met Val Lys Arg Lys Asp Ser Arg Gly
305                 310                 315

<210> SEQ ID NO 23
<211> LENGTH: 271
<212> TYPE: PRT
<213> ORGANISM: Homo sapiens

<400> SEQUENCE: 23

Met Lys Ser Leu Arg Val Leu Leu Val Ile Leu Trp Leu Gln Leu Ser
1               5                   10                  15

Trp Val Trp Ser Gln Gln Lys Glu Val Glu Gln Asn Ser Gly Pro Leu
            20                  25                  30

Ser Val Pro Glu Gly Ala Ile Ala Ser Leu Asn Cys Thr Tyr Ser Asp
        35                  40                  45

Arg Gly Ser Gln Ser Phe Phe Trp Tyr Arg Gln Tyr Ser Gly Lys Ser
    50                  55                  60

Pro Glu Leu Ile Met Phe Ile Tyr Ser Asn Gly Asp Lys Glu Asp Gly
65                  70                  75                  80

Arg Phe Thr Ala Gln Leu Asn Lys Ala Ser Gln Tyr Val Ser Leu Leu
                85                  90                  95

Ile Arg Asp Ser Gln Pro Ser Asp Ser Ala Thr Tyr Leu Cys Ala Val
            100                 105                 110

Asn Phe His Asp Lys Ile Ile Phe Gly Lys Gly Thr Arg Leu His Ile
        115                 120                 125

Leu Pro Asn Ile Gln Asn Pro Asp Pro Ala Val Tyr Gln Leu Arg Asp
    130                 135                 140

Ser Lys Ser Ser Asp Lys Ser Val Cys Leu Phe Thr Asp Phe Asp Ser
145                 150                 155                 160

Gln Thr Asn Val Ser Gln Ser Lys Asp Ser Asp Val Tyr Ile Thr Asp
                165                 170                 175

Lys Thr Val Leu Asp Met Arg Ser Met Asp Phe Lys Ser Asn Ser Ala
            180                 185                 190

Val Ala Trp Ser Asn Lys Ser Asp Phe Ala Cys Ala Asn Ala Phe Asn
        195                 200                 205

Asn Ser Ile Ile Pro Glu Asp Thr Phe Phe Pro Ser Pro Glu Ser Ser
    210                 215                 220

Cys Asp Val Lys Leu Val Glu Lys Ser Phe Glu Thr Asp Thr Asn Leu
225                 230                 235                 240

Asn Phe Gln Asn Leu Ser Val Ile Gly Phe Arg Ile Leu Leu Leu Lys
                245                 250                 255

Val Ala Gly Phe Asn Leu Leu Met Thr Leu Arg Leu Trp Ser Ser
            260                 265                 270

<210> SEQ ID NO 24
<211> LENGTH: 308
<212> TYPE: PRT
<213> ORGANISM: Homo sapiens

<400> SEQUENCE: 24

Met Gly Phe Arg Leu Leu Cys Cys Val Ala Phe Cys Leu Leu Gly Ala
1               5                   10                  15

Gly Pro Val Asp Ser Gly Val Thr Gln Thr Pro Lys His Leu Ile Thr
            20                  25                  30

-continued

```
Ala Thr Gly Gln Arg Val Thr Leu Arg Cys Ser Pro Arg Ser Gly Asp
            35                  40                  45

Leu Ser Val Tyr Trp Tyr Gln Gln Ser Leu Asp Gln Gly Leu Gln Phe
 50                  55                  60

Leu Ile His Tyr Tyr Asn Gly Glu Glu Arg Ala Lys Gly Asn Ile Leu
 65                  70                  75                  80

Glu Arg Phe Ser Ala Gln Gln Phe Pro Asp Leu His Ser Glu Leu Asn
                85                  90                  95

Leu Ser Ser Leu Glu Leu Gly Asp Ser Ala Leu Tyr Phe Cys Ala Ser
                100                 105                 110

Ser Val Ala Ser Ala Tyr Gly Tyr Thr Phe Gly Ser Gly Thr Arg Leu
            115                 120                 125

Thr Val Val Glu Asp Leu Asn Lys Val Phe Pro Pro Glu Val Ala Val
130                 135                 140

Phe Glu Pro Ser Glu Ala Glu Ile Ser His Thr Gln Lys Ala Thr Leu
145                 150                 155                 160

Val Cys Leu Ala Thr Gly Phe Phe Pro Asp His Val Glu Leu Ser Trp
                165                 170                 175

Trp Val Asn Gly Lys Glu Val His Ser Gly Val Ser Thr Asp Pro Gln
                180                 185                 190

Pro Leu Lys Glu Gln Pro Ala Leu Asn Asp Ser Arg Tyr Cys Leu Ser
            195                 200                 205

Ser Arg Leu Arg Val Ser Ala Thr Phe Trp Gln Asn Pro Arg Asn His
210                 215                 220

Phe Arg Cys Gln Val Gln Phe Tyr Gly Leu Ser Glu Asn Asp Glu Trp
225                 230                 235                 240

Thr Gln Asp Arg Ala Lys Pro Val Thr Gln Ile Val Ser Ala Glu Ala
                245                 250                 255

Trp Gly Arg Ala Asp Cys Gly Phe Thr Ser Val Ser Tyr Gln Gln Gly
                260                 265                 270

Val Leu Ser Ala Thr Ile Leu Tyr Glu Ile Leu Leu Gly Lys Ala Thr
            275                 280                 285

Leu Tyr Ala Val Leu Val Ser Ala Leu Val Leu Met Ala Met Val Lys
        290                 295                 300

Arg Lys Asp Phe
305

<210> SEQ ID NO 25
<211> LENGTH: 274
<212> TYPE: PRT
<213> ORGANISM: Homo sapiens

<400> SEQUENCE: 25

Met Lys Ser Leu Arg Val Leu Val Ile Leu Trp Leu Gln Leu Ser
1               5                   10                  15

Trp Val Trp Ser Gln Gln Lys Glu Val Glu Gln Asn Ser Gly Pro Leu
                20                  25                  30

Ser Val Pro Glu Gly Ala Ile Ala Ser Leu Asn Cys Thr Tyr Ser Asp
            35                  40                  45

Arg Gly Ser Gln Ser Phe Phe Trp Tyr Arg Gln Tyr Ser Gly Lys Ser
        50                  55                  60

Pro Glu Leu Ile Met Phe Ile Tyr Ser Asn Gly Asp Lys Glu Asp Gly
65                  70                  75                  80

Arg Phe Thr Ala Gln Leu Asn Lys Ala Ser Gln Tyr Val Ser Leu Leu
```

-continued

```
                85                  90                  95
Ile Arg Asp Ser Gln Pro Ser Asp Ser Ala Thr Tyr Leu Cys Ala Ala
            100                 105                 110

Tyr Ser Gly Ala Gly Ser Tyr Gln Leu Thr Phe Gly Lys Gly Thr Lys
            115                 120                 125

Leu Ser Val Ile Pro Asn Ile Gln Asn Pro Asp Pro Ala Val Tyr Gln
130                 135                 140

Leu Arg Asp Ser Lys Ser Ser Asp Lys Ser Val Cys Leu Phe Thr Asp
145                 150                 155                 160

Phe Asp Ser Gln Thr Asn Val Ser Gln Ser Lys Asp Ser Asp Val Tyr
                165                 170                 175

Ile Thr Asp Lys Thr Val Leu Asp Met Arg Ser Met Asp Phe Lys Ser
            180                 185                 190

Asn Ser Ala Val Ala Trp Ser Asn Lys Ser Asp Phe Ala Cys Ala Asn
        195                 200                 205

Ala Phe Asn Asn Ser Ile Ile Pro Glu Asp Thr Phe Phe Pro Ser Pro
210                 215                 220

Glu Ser Ser Cys Asp Val Lys Leu Val Glu Lys Ser Phe Glu Thr Asp
225                 230                 235                 240

Thr Asn Leu Asn Phe Gln Asn Leu Ser Val Ile Gly Phe Arg Ile Leu
                245                 250                 255

Leu Leu Lys Val Ala Gly Phe Asn Leu Leu Met Thr Leu Arg Leu Trp
            260                 265                 270

Ser Ser
```

<210> SEQ ID NO 26
<211> LENGTH: 308
<212> TYPE: PRT
<213> ORGANISM: Homo sapiens

<400> SEQUENCE: 26

```
Met Gly Phe Arg Leu Leu Cys Cys Val Ala Phe Cys Leu Leu Gly Ala
1               5                   10                  15

Gly Pro Val Asp Ser Gly Val Thr Gln Thr Pro Lys His Leu Ile Thr
            20                  25                  30

Ala Thr Gly Gln Arg Val Thr Leu Arg Cys Ser Pro Arg Ser Gly Asp
        35                  40                  45

Leu Ser Val Tyr Trp Tyr Gln Gln Ser Leu Asp Gln Gly Leu Gln Phe
    50                  55                  60

Leu Ile Gln Tyr Tyr Asn Gly Glu Glu Arg Ala Lys Gly Asn Ile Leu
65                  70                  75                  80

Glu Arg Phe Ser Ala Gln Gln Phe Pro Asp Leu His Ser Glu Leu Asn
                85                  90                  95

Leu Ser Ser Leu Glu Leu Gly Asp Ser Ala Leu Tyr Phe Cys Ala Ser
            100                 105                 110

Ser Val Glu Ser Ser Tyr Gly Tyr Thr Phe Gly Ser Gly Thr Arg Leu
        115                 120                 125

Thr Val Val Glu Asp Leu Asn Lys Val Phe Pro Pro Glu Val Ala Val
130                 135                 140

Phe Glu Pro Ser Glu Ala Glu Ile Ser His Thr Gln Lys Ala Thr Leu
145                 150                 155                 160

Val Cys Leu Ala Thr Gly Phe Phe Pro Asp His Val Glu Leu Ser Trp
                165                 170                 175

Trp Val Asn Gly Lys Glu Val His Ser Gly Val Ser Thr Asp Pro Gln
```

```
                    180                 185                 190
Pro Leu Lys Glu Gln Pro Ala Leu Asn Asp Ser Arg Tyr Cys Leu Ser
            195                 200                 205

Ser Arg Leu Arg Val Ser Ala Thr Phe Trp Gln Asn Pro Arg Asn His
        210                 215                 220

Phe Arg Cys Gln Val Gln Phe Tyr Gly Leu Ser Glu Asn Asp Glu Trp
225                 230                 235                 240

Thr Gln Asp Arg Ala Lys Pro Val Thr Gln Ile Val Ser Ala Glu Ala
                245                 250                 255

Trp Gly Arg Ala Asp Cys Gly Phe Thr Ser Val Ser Tyr Gln Gln Gly
            260                 265                 270

Val Leu Ser Ala Thr Ile Leu Tyr Glu Ile Leu Leu Gly Lys Ala Thr
        275                 280                 285

Leu Tyr Ala Val Leu Val Ser Ala Leu Val Leu Met Ala Met Val Lys
    290                 295                 300

Arg Lys Asp Phe
305

<210> SEQ ID NO 27
<211> LENGTH: 271
<212> TYPE: PRT
<213> ORGANISM: Homo sapiens

<400> SEQUENCE: 27

Met Lys Ser Leu Arg Val Leu Leu Val Ile Leu Trp Leu Gln Leu Ser
1               5                   10                  15

Trp Val Trp Ser Gln Gln Lys Glu Val Glu Gln Asn Ser Gly Pro Leu
            20                  25                  30

Ser Val Pro Glu Gly Ala Ile Ala Ser Leu Asn Cys Thr Tyr Ser Asp
        35                  40                  45

Arg Gly Ser Gln Ser Phe Phe Trp Tyr Arg Gln Tyr Ser Gly Lys Ser
    50                  55                  60

Pro Glu Leu Ile Met Phe Ile Tyr Ser Asn Gly Asp Lys Glu Asp Gly
65                  70                  75                  80

Arg Phe Thr Ala Gln Leu Asn Lys Ala Ser Gln Tyr Val Ser Leu Leu
                85                  90                  95

Ile Arg Asp Ser Gln Pro Ser Asp Ser Ala Thr Tyr Leu Cys Ala Val
            100                 105                 110

Lys Ala Gly Asn Gln Phe Tyr Phe Gly Thr Gly Thr Ser Leu Thr Val
        115                 120                 125

Ile Pro Asn Ile Gln Asn Pro Asp Pro Ala Val Tyr Gln Leu Arg Asp
    130                 135                 140

Ser Lys Ser Ser Asp Lys Ser Val Cys Leu Phe Thr Asp Phe Asp Ser
145                 150                 155                 160

Gln Thr Asn Val Ser Gln Ser Lys Asp Ser Asp Val Tyr Ile Thr Asp
                165                 170                 175

Lys Thr Val Leu Asp Met Arg Ser Met Asp Phe Lys Ser Asn Ser Ala
            180                 185                 190

Val Ala Trp Ser Asn Lys Ser Asp Phe Ala Cys Ala Asn Ala Phe Asn
        195                 200                 205

Asn Ser Ile Ile Pro Glu Asp Thr Phe Phe Pro Ser Pro Glu Ser Ser
    210                 215                 220

Cys Asp Val Lys Leu Val Glu Lys Ser Phe Glu Thr Asp Thr Asn Leu
225                 230                 235                 240
```

-continued

Asn Phe Gln Asn Leu Ser Val Ile Gly Phe Arg Ile Leu Leu Lys
                245                 250                 255

Val Ala Gly Phe Asn Leu Leu Met Thr Leu Arg Leu Trp Ser Ser
            260                 265                 270

<210> SEQ ID NO 28
<211> LENGTH: 314
<212> TYPE: PRT
<213> ORGANISM: Homo sapiens

<400> SEQUENCE: 28

Met Gly Thr Arg Leu Leu Cys Trp Val Val Leu Gly Phe Leu Gly Thr
1               5                   10                  15

Asp His Thr Gly Ala Gly Val Ser Gln Ser Pro Arg Tyr Lys Val Ala
            20                  25                  30

Lys Arg Gly Gln Asp Val Ala Leu Arg Cys Asp Pro Ile Ser Gly His
        35                  40                  45

Val Ser Leu Phe Trp Tyr Gln Gln Ala Leu Gly Gln Gly Pro Glu Phe
    50                  55                  60

Leu Thr Tyr Phe Gln Asn Glu Ala Gln Leu Asp Lys Ser Gly Leu Pro
65                  70                  75                  80

Ser Asp Arg Phe Phe Ala Glu Arg Pro Glu Gly Ser Val Ser Thr Leu
                85                  90                  95

Lys Ile Gln Arg Thr Gln Gln Glu Asp Ser Ala Val Tyr Leu Cys Ala
            100                 105                 110

Ser Ser Leu Leu Thr Ser Gly Gly Asp Asn Glu Gln Phe Phe Gly Pro
        115                 120                 125

Gly Thr Arg Leu Thr Val Leu Glu Asp Leu Lys Asn Val Phe Pro Pro
    130                 135                 140

Glu Val Ala Val Phe Glu Pro Ser Glu Ala Glu Ile Ser His Thr Gln
145                 150                 155                 160

Lys Ala Thr Leu Val Cys Leu Ala Thr Gly Phe Tyr Pro Asp His Val
                165                 170                 175

Glu Leu Ser Trp Trp Val Asn Gly Lys Glu Val His Ser Gly Val Ser
            180                 185                 190

Thr Asp Pro Gln Pro Leu Lys Glu Gln Pro Ala Leu Asn Asp Ser Arg
        195                 200                 205

Tyr Cys Leu Ser Ser Arg Leu Arg Val Ser Ala Thr Phe Trp Gln Asn
    210                 215                 220

Pro Arg Asn His Phe Arg Cys Gln Val Gln Phe Tyr Gly Leu Ser Glu
225                 230                 235                 240

Asn Asp Glu Trp Thr Gln Asp Arg Ala Lys Pro Val Thr Gln Ile Val
                245                 250                 255

Ser Ala Glu Ala Trp Gly Arg Ala Asp Cys Gly Phe Thr Ser Glu Ser
            260                 265                 270

Tyr Gln Gln Gly Val Leu Ser Ala Thr Ile Leu Tyr Glu Ile Leu Leu
        275                 280                 285

Gly Lys Ala Thr Leu Tyr Ala Val Leu Val Ser Ala Leu Val Leu Met
    290                 295                 300

Ala Met Val Lys Arg Lys Asp Ser Arg Gly
305                 310

<210> SEQ ID NO 29
<211> LENGTH: 270
<212> TYPE: PRT
<213> ORGANISM: Homo sapiens

<400> SEQUENCE: 29

```
Met Glu Thr Leu Leu Gly Val Ser Leu Val Ile Leu Trp Leu Gln Leu
1               5                   10                  15

Ala Arg Val Asn Ser Gln Gln Gly Glu Glu Asp Pro Gln Ala Leu Ser
            20                  25                  30

Ile Gln Glu Gly Glu Asn Ala Thr Met Asn Cys Ser Tyr Lys Thr Ser
        35                  40                  45

Ile Asn Asn Leu Gln Trp Tyr Arg Gln Asn Ser Gly Arg Gly Leu Val
    50                  55                  60

His Leu Ile Leu Ile Arg Ser Asn Glu Arg Glu Lys His Ser Gly Arg
65                  70                  75                  80

Leu Arg Val Thr Leu Asp Thr Ser Lys Lys Ser Ser Ser Leu Leu Ile
                85                  90                  95

Thr Ala Ser Arg Ala Ala Asp Thr Ala Ser Tyr Phe Cys Ala Thr Val
            100                 105                 110

Ser Asn Tyr Gln Leu Ile Trp Gly Ala Gly Thr Lys Leu Ile Ile Lys
        115                 120                 125

Pro Asp Ile Gln Asn Pro Asp Pro Ala Val Tyr Gln Leu Arg Asp Ser
    130                 135                 140

Lys Ser Ser Asp Lys Ser Val Cys Leu Phe Thr Asp Phe Asp Ser Gln
145                 150                 155                 160

Thr Asn Val Ser Gln Ser Lys Asp Ser Asp Val Tyr Ile Thr Asp Lys
                165                 170                 175

Thr Val Leu Asp Met Arg Ser Met Asp Phe Lys Ser Asn Ser Ala Val
            180                 185                 190

Ala Trp Ser Asn Lys Ser Asp Phe Ala Cys Ala Asn Ala Phe Asn Asn
        195                 200                 205

Ser Ile Ile Pro Glu Asp Thr Phe Phe Pro Ser Pro Glu Ser Ser Cys
    210                 215                 220

Asp Val Lys Leu Val Glu Lys Ser Phe Glu Thr Asp Thr Asn Leu Asn
225                 230                 235                 240

Phe Gln Asn Leu Ser Val Ile Gly Phe Arg Ile Leu Leu Leu Lys Val
                245                 250                 255

Ala Gly Phe Asn Leu Leu Met Thr Leu Arg Leu Trp Ser Ser
            260                 265                 270
```

<210> SEQ ID NO 30
<211> LENGTH: 314
<212> TYPE: PRT
<213> ORGANISM: Homo sapiens

<400> SEQUENCE: 30

```
Met Gly Pro Gln Leu Leu Gly Tyr Val Val Leu Cys Leu Leu Gly Ala
1               5                   10                  15

Gly Pro Leu Glu Ala Gln Val Thr Gln Asn Pro Arg Tyr Leu Ile Thr
            20                  25                  30

Val Thr Gly Lys Lys Leu Thr Val Thr Cys Ser Gln Asn Met Asn His
        35                  40                  45

Glu Tyr Met Ser Trp Tyr Arg Gln Asp Pro Gly Leu Gly Leu Arg Gln
    50                  55                  60

Ile Tyr Tyr Ser Met Asn Val Glu Val Thr Asp Lys Gly Asp Val Pro
65                  70                  75                  80

Glu Gly Tyr Lys Val Ser Arg Lys Glu Lys Arg Asn Phe Pro Leu Ile
                85                  90                  95
```

```
Leu Glu Ser Pro Ser Pro Asn Gln Thr Ser Leu Tyr Phe Cys Ala Ser
                100                 105                 110

Ser Ser Thr Ser Gly Gly Leu Ser Gly Glu Thr Gln Tyr Phe Gly Pro
            115                 120                 125

Gly Thr Arg Leu Leu Val Leu Glu Asp Leu Lys Asn Val Phe Pro Pro
        130                 135                 140

Glu Val Ala Val Phe Glu Pro Ser Glu Ala Glu Ile Ser His Thr Gln
145                 150                 155                 160

Lys Ala Thr Leu Val Cys Leu Ala Thr Gly Phe Tyr Pro Asp His Val
                165                 170                 175

Glu Leu Ser Trp Trp Val Asn Gly Lys Glu Val His Ser Gly Val Ser
            180                 185                 190

Thr Asp Pro Gln Pro Leu Lys Glu Gln Pro Ala Leu Asn Asp Ser Arg
        195                 200                 205

Tyr Cys Leu Ser Ser Arg Leu Arg Val Ser Ala Thr Phe Trp Gln Asn
210                 215                 220

Pro Arg Asn His Phe Arg Cys Gln Val Gln Phe Tyr Gly Leu Ser Glu
225                 230                 235                 240

Asn Asp Glu Trp Thr Gln Asp Arg Ala Lys Pro Val Thr Gln Ile Val
            245                 250                 255

Ser Ala Glu Ala Trp Gly Arg Ala Asp Cys Gly Phe Thr Ser Glu Ser
        260                 265                 270

Tyr Gln Gln Gly Val Leu Ser Ala Thr Ile Leu Tyr Glu Ile Leu Leu
    275                 280                 285

Gly Lys Ala Thr Leu Tyr Ala Val Leu Val Ser Ala Leu Val Leu Met
290                 295                 300

Ala Met Val Lys Arg Lys Asp Ser Arg Gly
305                 310

<210> SEQ ID NO 31
<211> LENGTH: 272
<212> TYPE: PRT
<213> ORGANISM: Homo sapiens

<400> SEQUENCE: 31

Met Lys Lys His Leu Thr Thr Phe Leu Val Ile Leu Trp Leu Tyr Phe
1               5                   10                  15

Tyr Arg Gly Asn Gly Lys Asn Gln Val Glu Gln Ser Pro Gln Ser Leu
            20                  25                  30

Ile Ile Leu Glu Gly Lys Asn Cys Thr Leu Gln Cys Asn Tyr Thr Val
        35                  40                  45

Ser Pro Phe Ser Asn Leu Arg Trp Tyr Lys Gln Asp Thr Gly Arg Gly
    50                  55                  60

Pro Val Ser Leu Thr Ile Met Thr Phe Ser Glu Asn Thr Lys Ser Asn
65                  70                  75                  80

Gly Arg Tyr Thr Ala Thr Leu Asp Ala Asp Thr Lys Gln Ser Ser Leu
                85                  90                  95

His Ile Thr Ala Ser Gln Leu Ser Asp Ser Ala Ser Tyr Ile Cys Val
            100                 105                 110

Val Ser Ala Tyr Gly Lys Leu Gln Phe Gly Ala Gly Thr Gln Val Val
        115                 120                 125

Val Thr Pro Asp Ile Gln Asn Pro Asp Pro Ala Val Tyr Gln Leu Arg
    130                 135                 140

Asp Ser Lys Ser Ser Asp Lys Ser Val Cys Leu Phe Thr Asp Phe Asp
```

```
                145                 150                 155                 160
            Ser Gln Thr Asn Val Ser Gln Ser Lys Asp Ser Asp Val Tyr Ile Thr
                                165                 170                 175

Asp Lys Thr Val Leu Asp Met Arg Ser Met Asp Phe Lys Ser Asn Ser
                            180                 185                 190

Ala Val Ala Trp Ser Asn Lys Ser Asp Phe Ala Cys Ala Asn Ala Phe
                        195                 200                 205

Asn Asn Ser Ile Ile Pro Glu Asp Thr Phe Phe Pro Ser Pro Glu Ser
                    210                 215                 220

Ser Cys Asp Val Lys Leu Val Glu Lys Ser Phe Glu Thr Asp Thr Asn
            225                 230                 235                 240

Leu Asn Phe Gln Asn Leu Ser Val Ile Gly Phe Arg Ile Leu Leu Leu
                                245                 250                 255

Lys Val Ala Gly Phe Asn Leu Leu Met Thr Leu Arg Leu Trp Ser Ser
                            260                 265                 270

<210> SEQ ID NO 32
<211> LENGTH: 312
<212> TYPE: PRT
<213> ORGANISM: Homo sapiens

<400> SEQUENCE: 32

Met Asp Ser Trp Thr Phe Cys Cys Val Ser Leu Cys Ile Leu Val Ala
            1               5                   10                  15

Lys His Thr Asp Ala Gly Val Ile Gln Ser Pro Arg His Glu Val Thr
                            20                  25                  30

Glu Met Gly Gln Glu Val Thr Leu Arg Cys Lys Pro Ile Ser Gly His
                        35                  40                  45

Asn Ser Leu Phe Trp Tyr Arg Gln Thr Met Met Arg Gly Leu Glu Leu
                    50                  55                  60

Leu Ile Tyr Phe Asn Asn Asn Val Pro Ile Asp Asp Ser Gly Met Pro
            65                  70                  75                  80

Glu Asp Arg Phe Ser Ala Lys Met Pro Asn Ala Ser Phe Ser Thr Leu
                                85                  90                  95

Lys Ile Gln Pro Ser Glu Pro Arg Asp Ser Ala Val Tyr Phe Cys Ala
                            100                 105                 110

Ser Ser Leu Gly Ser Pro Asp Gly Asn Gln Pro Gln His Phe Gly Asp
                        115                 120                 125

Gly Thr Arg Leu Ser Ile Leu Glu Asp Leu Asn Lys Val Phe Pro Pro
                    130                 135                 140

Glu Val Ala Val Phe Glu Pro Ser Glu Ala Glu Ile Ser His Thr Gln
            145                 150                 155                 160

Lys Ala Thr Leu Val Cys Leu Ala Thr Gly Phe Phe Pro Asp His Val
                                165                 170                 175

Glu Leu Ser Trp Trp Val Asn Gly Lys Glu Val His Ser Gly Val Ser
                            180                 185                 190

Thr Asp Pro Gln Pro Leu Lys Glu Gln Pro Ala Leu Asn Asp Ser Arg
                        195                 200                 205

Tyr Cys Leu Ser Ser Arg Leu Arg Val Ser Ala Thr Phe Trp Gln Asn
                    210                 215                 220

Pro Arg Asn His Phe Arg Cys Gln Val Gln Phe Tyr Gly Leu Ser Glu
            225                 230                 235                 240

Asn Asp Glu Trp Thr Gln Asp Arg Ala Lys Pro Val Thr Gln Ile Val
                                245                 250                 255
```

Ser Ala Glu Ala Trp Gly Arg Ala Asp Cys Gly Phe Thr Ser Val Ser
    260                 265                 270

Tyr Gln Gln Gly Val Leu Ser Ala Thr Ile Leu Tyr Glu Ile Leu Leu
        275                 280                 285

Gly Lys Ala Thr Leu Tyr Ala Val Leu Val Ser Ala Leu Val Leu Met
    290                 295                 300

Ala Met Val Lys Arg Lys Asp Phe
305                 310

<210> SEQ ID NO 33
<211> LENGTH: 279
<212> TYPE: PRT
<213> ORGANISM: Homo sapiens

<400> SEQUENCE: 33

Met Ala Cys Pro Gly Phe Leu Trp Ala Leu Val Ile Ser Thr Cys Leu
1               5                   10                  15

Glu Phe Ser Met Ala Gln Thr Val Thr Gln Ser Gln Pro Glu Met Ser
            20                  25                  30

Val Gln Glu Ala Glu Thr Val Thr Leu Ser Cys Thr Tyr Asp Thr Ser
        35                  40                  45

Glu Ser Asp Tyr Tyr Leu Phe Trp Tyr Lys Gln Pro Pro Ser Arg Gln
    50                  55                  60

Met Ile Leu Val Ile Arg Gln Glu Ala Tyr Lys Gln Gln Asn Ala Thr
65                  70                  75                  80

Glu Asn Arg Phe Ser Val Asn Phe Gln Lys Ala Ala Lys Ser Phe Ser
                85                  90                  95

Leu Lys Ile Ser Asp Ser Gln Leu Gly Asp Ala Ala Met Tyr Phe Cys
            100                 105                 110

Ala Tyr Asn Ser Tyr Ala Gly Gly Thr Ser Tyr Gly Lys Leu Thr Phe
        115                 120                 125

Gly Gln Gly Thr Ile Leu Thr Val His Pro Asn Ile Gln Asn Pro Asp
    130                 135                 140

Pro Ala Val Tyr Gln Leu Arg Asp Ser Lys Ser Ser Asp Lys Ser Val
145                 150                 155                 160

Cys Leu Phe Thr Asp Phe Asp Ser Gln Thr Asn Val Ser Gln Ser Lys
                165                 170                 175

Asp Ser Asp Val Tyr Ile Thr Asp Lys Thr Val Leu Asp Met Arg Ser
            180                 185                 190

Met Asp Phe Lys Ser Asn Ser Ala Val Ala Trp Ser Asn Lys Ser Asp
        195                 200                 205

Phe Ala Cys Ala Asn Ala Phe Asn Asn Ser Ile Ile Pro Glu Asp Thr
    210                 215                 220

Phe Phe Pro Ser Pro Glu Ser Ser Cys Asp Val Lys Leu Val Glu Lys
225                 230                 235                 240

Ser Phe Glu Thr Asp Thr Asn Leu Asn Phe Gln Asn Leu Ser Val Ile
                245                 250                 255

Gly Phe Arg Ile Leu Leu Leu Lys Val Ala Gly Phe Asn Leu Leu Met
            260                 265                 270

Thr Leu Arg Leu Trp Ser Ser
        275

<210> SEQ ID NO 34
<211> LENGTH: 310
<212> TYPE: PRT
<213> ORGANISM: Homo sapiens

<400> SEQUENCE: 34

```
Met Gly Pro Gly Leu Leu Cys Trp Val Leu Leu Cys Leu Leu Gly Ala
1               5                   10                  15

Gly Pro Val Asp Ala Gly Val Thr Gln Ser Pro Thr His Leu Ile Lys
            20                  25                  30

Thr Arg Gly Gln Gln Val Thr Leu Arg Cys Ser Pro Ile Ser Gly His
        35                  40                  45

Lys Ser Val Ser Trp Tyr Gln Val Leu Gly Gly Pro Gln Phe
50                  55                  60

Ile Phe Gln Tyr Tyr Glu Lys Glu Arg Gly Arg Gly Asn Phe Pro
65                  70                  75                  80

Asp Arg Phe Ser Ala Arg Gln Phe Pro Asn Tyr Ser Ser Glu Leu Asn
                85                  90                  95

Val Asn Ala Leu Leu Leu Gly Asp Ser Ala Leu Tyr Leu Cys Ala Ser
                100                 105                 110

Ser Leu Asp Gly Thr Ser Glu Gln Tyr Phe Gly Pro Gly Thr Arg Leu
            115                 120                 125

Thr Val Thr Glu Asp Leu Lys Asn Val Phe Pro Pro Glu Val Ala Val
130                 135                 140

Phe Glu Pro Ser Glu Ala Glu Ile Ser His Thr Gln Lys Ala Thr Leu
145                 150                 155                 160

Val Cys Leu Ala Thr Gly Phe Tyr Pro Asp His Val Glu Leu Ser Trp
                165                 170                 175

Trp Val Asn Gly Lys Glu Val His Ser Gly Val Ser Thr Asp Pro Gln
            180                 185                 190

Pro Leu Lys Glu Gln Pro Ala Leu Asn Asp Ser Arg Tyr Cys Leu Ser
        195                 200                 205

Ser Arg Leu Arg Val Ser Ala Thr Phe Trp Gln Asn Pro Arg Asn His
    210                 215                 220

Phe Arg Cys Gln Val Gln Phe Tyr Gly Leu Ser Glu Asn Asp Glu Trp
225                 230                 235                 240

Thr Gln Asp Arg Ala Lys Pro Val Thr Gln Ile Val Ser Ala Glu Ala
                245                 250                 255

Trp Gly Arg Ala Asp Cys Gly Phe Thr Ser Glu Ser Tyr Gln Gln Gly
            260                 265                 270

Val Leu Ser Ala Thr Ile Leu Tyr Glu Ile Leu Leu Gly Lys Ala Thr
        275                 280                 285

Leu Tyr Ala Val Leu Val Ser Ala Leu Val Leu Met Ala Met Val Lys
    290                 295                 300

Arg Lys Asp Ser Arg Gly
305                 310
```

<210> SEQ ID NO 35
<211> LENGTH: 271
<212> TYPE: PRT
<213> ORGANISM: Homo sapiens

<400> SEQUENCE: 35

```
Met Glu Thr Leu Leu Gly Val Ser Leu Val Ile Leu Trp Leu Gln Leu
1               5                   10                  15

Ala Arg Val Asn Ser Gln Gln Gly Glu Glu Asp Pro Gln Ala Leu Ser
            20                  25                  30

Ile Gln Glu Gly Glu Asn Ala Thr Met Asn Cys Ser Tyr Lys Thr Ser
        35                  40                  45
```

Ile Asn Asn Leu Gln Trp Tyr Arg Gln Asn Ser Gly Arg Gly Leu Val
 50                  55                  60

His Leu Ile Leu Ile Arg Ser Asn Glu Arg Glu Lys His Ser Gly Arg
 65                  70                  75                  80

Leu Arg Val Thr Leu Asp Thr Ser Lys Lys Ser Ser Ser Leu Leu Ile
                 85                  90                  95

Thr Ala Ser Arg Ala Ala Asp Thr Ala Ser Tyr Phe Cys Leu Ile Gly
                100                 105                 110

Ala Ser Gly Ser Arg Leu Thr Phe Gly Glu Gly Thr Gln Leu Thr Val
                115                 120                 125

Asn Pro Asp Ile Gln Asn Pro Asp Pro Ala Val Tyr Gln Leu Arg Asp
            130                 135                 140

Ser Lys Ser Ser Asp Lys Ser Val Cys Leu Phe Thr Asp Phe Asp Ser
145                 150                 155                 160

Gln Thr Asn Val Ser Gln Ser Lys Asp Ser Asp Val Tyr Ile Thr Asp
                165                 170                 175

Lys Thr Val Leu Asp Met Arg Ser Met Asp Phe Lys Ser Asn Ser Ala
                180                 185                 190

Val Ala Trp Ser Asn Lys Ser Asp Phe Ala Cys Ala Asn Ala Phe Asn
            195                 200                 205

Asn Ser Ile Ile Pro Glu Asp Thr Phe Phe Pro Ser Pro Glu Ser Ser
210                 215                 220

Cys Asp Val Lys Leu Val Glu Lys Ser Phe Glu Thr Asp Thr Asn Leu
225                 230                 235                 240

Asn Phe Gln Asn Leu Ser Val Ile Gly Phe Arg Ile Leu Leu Leu Lys
                245                 250                 255

Val Ala Gly Phe Asn Leu Leu Met Thr Leu Arg Leu Trp Ser Ser
            260                 265                 270

<210> SEQ ID NO 36
<211> LENGTH: 310
<212> TYPE: PRT
<213> ORGANISM: Homo sapiens

<400> SEQUENCE: 36

Met Gly Ser Trp Thr Leu Cys Cys Val Ser Leu Cys Ile Leu Val Ala
 1                   5                  10                  15

Lys His Thr Asp Ala Gly Val Ile Gln Ser Pro Arg His Glu Val Thr
                 20                  25                  30

Glu Met Gly Gln Glu Val Thr Leu Arg Cys Lys Pro Ile Ser Gly His
             35                  40                  45

Asp Tyr Leu Phe Trp Tyr Arg Gln Thr Met Met Arg Gly Leu Glu Leu
 50                  55                  60

Leu Ile Tyr Phe Asn Asn Asn Val Pro Ile Asp Asp Ser Gly Met Pro
 65                  70                  75                  80

Glu Asp Arg Phe Ser Ala Lys Met Pro Asn Ala Ser Phe Ser Thr Leu
                 85                  90                  95

Lys Ile Gln Pro Ser Glu Pro Arg Asp Ser Ala Val Tyr Phe Cys Ala
                100                 105                 110

Ser Ser Tyr Phe Gly Trp Asn Glu Lys Leu Phe Phe Gly Ser Gly Thr
            115                 120                 125

Gln Leu Ser Val Leu Glu Asp Leu Asn Lys Val Phe Pro Pro Glu Val
            130                 135                 140

Ala Val Phe Glu Pro Ser Glu Ala Glu Ile Ser His Thr Gln Lys Ala

```
                 145                 150                 155                 160
            Thr Leu Val Cys Leu Ala Thr Gly Phe Phe Pro Asp His Val Glu Leu
                             165                 170                 175

Ser Trp Trp Val Asn Gly Lys Glu Val His Ser Gly Val Ser Thr Asp
                             180                 185                 190

Pro Gln Pro Leu Lys Glu Gln Pro Ala Leu Asn Asp Ser Arg Tyr Cys
                             195                 200                 205

Leu Ser Ser Arg Leu Arg Val Ser Ala Thr Phe Trp Gln Asn Pro Arg
                210                 215                 220

Asn His Phe Arg Cys Gln Val Gln Phe Tyr Gly Leu Ser Glu Asn Asp
            225                 230                 235                 240

Glu Trp Thr Gln Asp Arg Ala Lys Pro Val Thr Gln Ile Val Ser Ala
                             245                 250                 255

Glu Ala Trp Gly Arg Ala Asp Cys Gly Phe Thr Ser Val Ser Tyr Gln
                             260                 265                 270

Gln Gly Val Leu Ser Ala Thr Ile Leu Tyr Glu Ile Leu Leu Gly Lys
                             275                 280                 285

Ala Thr Leu Tyr Ala Val Leu Val Ser Ala Leu Val Leu Met Ala Met
                290                 295                 300

Val Lys Arg Lys Asp Phe
            305                 310

<210> SEQ ID NO 37
<211> LENGTH: 276
<212> TYPE: PRT
<213> ORGANISM: Homo sapiens

<400> SEQUENCE: 37

Met Met Lys Ser Leu Arg Val Leu Leu Val Ile Leu Trp Leu Gln Leu
            1               5                   10                  15

Ser Trp Val Trp Ser Gln Gln Lys Glu Val Glu Gln Asp Pro Gly Pro
                             20                  25                  30

Leu Ser Val Pro Glu Gly Ala Ile Val Ser Leu Asn Cys Thr Tyr Ser
                             35                  40                  45

Asn Ser Ala Phe Gln Tyr Phe Met Trp Tyr Arg Gln Tyr Ser Arg Lys
                50                  55                  60

Gly Pro Glu Leu Leu Met Tyr Thr Tyr Ser Ser Gly Asn Lys Glu Asp
            65                  70                  75                  80

Gly Arg Phe Thr Ala Gln Val Asp Lys Ser Ser Lys Tyr Ile Ser Leu
                             85                  90                  95

Phe Ile Arg Asp Ser Gln Pro Ser Asp Ser Ala Thr Tyr Leu Cys Ala
                             100                 105                 110

Met Ser Asp Val Ser Gly Gly Tyr Asn Lys Leu Ile Phe Gly Ala Gly
                             115                 120                 125

Thr Arg Leu Ala Val His Pro Tyr Ile Gln Asn Pro Asp Pro Ala Val
                130                 135                 140

Tyr Gln Leu Arg Asp Ser Lys Ser Ser Asp Lys Ser Val Cys Leu Phe
            145                 150                 155                 160

Thr Asp Phe Asp Ser Gln Thr Asn Val Ser Gln Ser Lys Asp Ser Asp
                             165                 170                 175

Val Tyr Ile Thr Asp Lys Thr Val Leu Asp Met Arg Ser Met Asp Phe
                             180                 185                 190

Lys Ser Asn Ser Ala Val Ala Trp Ser Asn Lys Ser Asp Phe Ala Cys
                             195                 200                 205
```

```
Ala Asn Ala Phe Asn Asn Ser Ile Ile Pro Glu Asp Thr Phe Phe Pro
    210                 215                 220

Ser Pro Glu Ser Ser Cys Asp Val Lys Leu Val Glu Lys Ser Phe Glu
225                 230                 235                 240

Thr Asp Thr Asn Leu Asn Phe Gln Asn Leu Ser Val Ile Gly Phe Arg
                245                 250                 255

Ile Leu Leu Leu Lys Val Ala Gly Phe Asn Leu Leu Met Thr Leu Arg
                260                 265                 270

Leu Trp Ser Ser
            275

<210> SEQ ID NO 38
<211> LENGTH: 311
<212> TYPE: PRT
<213> ORGANISM: Homo sapiens

<400> SEQUENCE: 38

Met Gly Pro Gln Leu Leu Gly Tyr Val Val Leu Cys Leu Leu Gly Ala
1               5                   10                  15

Gly Pro Leu Glu Ala Gln Val Thr Gln Asn Pro Arg Tyr Leu Ile Thr
            20                  25                  30

Val Thr Gly Lys Lys Leu Thr Val Thr Cys Ser Gln Asn Met Asn His
                35                  40                  45

Glu Tyr Met Ser Trp Tyr Arg Gln Asp Pro Gly Leu Gly Leu Arg Gln
50                  55                  60

Ile Tyr Tyr Ser Met Asn Val Glu Val Thr Asp Lys Gly Asp Val Pro
65                  70                  75                  80

Glu Gly Tyr Lys Val Ser Arg Lys Glu Lys Arg Asn Phe Pro Leu Ile
                85                  90                  95

Leu Glu Ser Pro Ser Pro Asn Gln Thr Ser Leu Tyr Phe Cys Ala Ser
            100                 105                 110

Thr Thr Pro Asp Gly Thr Asp Glu Gln Phe Phe Gly Pro Gly Thr Arg
        115                 120                 125

Leu Thr Val Leu Glu Asp Leu Lys Asn Val Phe Pro Pro Glu Val Ala
    130                 135                 140

Val Phe Glu Pro Ser Glu Ala Glu Ile Ser His Thr Gln Lys Ala Thr
145                 150                 155                 160

Leu Val Cys Leu Ala Thr Gly Phe Tyr Pro Asp His Val Glu Leu Ser
                165                 170                 175

Trp Trp Val Asn Gly Lys Glu Val His Ser Gly Val Ser Thr Asp Pro
            180                 185                 190

Gln Pro Leu Lys Glu Gln Pro Ala Leu Asn Asp Ser Arg Tyr Cys Leu
        195                 200                 205

Ser Ser Arg Leu Arg Val Ser Ala Thr Phe Trp Gln Asn Pro Arg Asn
    210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Glu Ser Tyr Gln Gln
            260                 265                 270

Gly Val Leu Ser Ala Thr Ile Leu Tyr Glu Ile Leu Leu Gly Lys Ala
        275                 280                 285

Thr Leu Tyr Ala Val Leu Val Ser Ala Leu Val Leu Met Ala Met Val
    290                 295                 300
```

```
Lys Arg Lys Asp Ser Arg Gly
305                 310

<210> SEQ ID NO 39
<211> LENGTH: 274
<212> TYPE: PRT
<213> ORGANISM: Homo sapiens

<400> SEQUENCE: 39

Met Ala Ser Ala Pro Ile Ser Met Leu Ala Met Leu Phe Thr Leu Ser
1               5                   10                  15

Gly Leu Arg Ala Gln Ser Val Ala Gln Pro Glu Asp Gln Val Asn Val
                20                  25                  30

Ala Glu Gly Asn Pro Leu Thr Val Lys Cys Thr Tyr Ser Val Ser Gly
            35                  40                  45

Asn Pro Tyr Leu Phe Trp Tyr Val Gln Tyr Pro Asn Arg Gly Leu Gln
        50                  55                  60

Phe Leu Leu Lys Tyr Ile Thr Gly Asp Asn Leu Val Lys Gly Ser Tyr
65                  70                  75                  80

Gly Phe Glu Ala Glu Phe Asn Lys Ser Gln Thr Ser Phe His Leu Lys
                85                  90                  95

Lys Pro Ser Ala Leu Val Ser Asp Ser Ala Leu Tyr Phe Cys Ala Val
            100                 105                 110

Arg Asp Met Asn Arg Asp Asp Lys Ile Ile Phe Gly Lys Gly Thr Arg
        115                 120                 125

Leu His Ile Leu Pro Asn Ile Gln Asn Pro Asp Pro Ala Val Tyr Gln
    130                 135                 140

Leu Arg Asp Ser Lys Ser Ser Asp Lys Ser Val Cys Leu Phe Thr Asp
145                 150                 155                 160

Phe Asp Ser Gln Thr Asn Val Ser Gln Ser Lys Asp Ser Asp Val Tyr
                165                 170                 175

Ile Thr Asp Lys Thr Val Leu Asp Met Arg Ser Met Asp Phe Lys Ser
            180                 185                 190

Asn Ser Ala Val Ala Trp Ser Asn Lys Ser Asp Phe Ala Cys Ala Asn
        195                 200                 205

Ala Phe Asn Asn Ser Ile Ile Pro Glu Asp Thr Phe Phe Pro Ser Pro
    210                 215                 220

Glu Ser Ser Cys Asp Val Lys Leu Val Glu Lys Ser Phe Glu Thr Asp
225                 230                 235                 240

Thr Asn Leu Asn Phe Gln Asn Leu Ser Val Ile Gly Phe Arg Ile Leu
                245                 250                 255

Leu Leu Lys Val Ala Gly Phe Asn Leu Leu Met Thr Leu Arg Leu Trp
            260                 265                 270

Ser Ser

<210> SEQ ID NO 40
<211> LENGTH: 310
<212> TYPE: PRT
<213> ORGANISM: Homo sapiens

<400> SEQUENCE: 40

Met Ser Asn Gln Val Leu Cys Cys Val Val Leu Cys Phe Leu Gly Ala
1               5                   10                  15

Asn Thr Val Asp Gly Gly Ile Thr Gln Ser Pro Lys Tyr Leu Phe Arg
                20                  25                  30
```

Lys Glu Gly Gln Asn Val Thr Leu Ser Cys Glu Gln Asn Leu Asn His
            35                  40                  45

Asp Ala Met Tyr Trp Tyr Arg Gln Asp Pro Gly Gln Gly Leu Arg Leu
 50                  55                  60

Ile Tyr Tyr Ser Gln Ile Val Asn Asp Phe Gln Lys Gly Asp Ile Ala
 65                  70                  75                  80

Glu Gly Tyr Ser Val Ser Arg Glu Lys Lys Glu Ser Phe Pro Leu Thr
                 85                  90                  95

Val Thr Ser Ala Gln Lys Asn Pro Thr Ala Phe Tyr Leu Cys Ala Ser
            100                 105                 110

Ser Arg Ala Glu Gly Gly Glu Gln Tyr Phe Gly Pro Gly Thr Arg Leu
            115                 120                 125

Thr Val Thr Glu Asp Leu Lys Asn Val Phe Pro Pro Glu Val Ala Val
130                 135                 140

Phe Glu Pro Ser Glu Ala Glu Ile Ser His Thr Gln Lys Ala Thr Leu
145                 150                 155                 160

Val Cys Leu Ala Thr Gly Phe Tyr Pro Asp His Val Glu Leu Ser Trp
                165                 170                 175

Trp Val Asn Gly Lys Glu Val His Ser Gly Val Ser Thr Asp Pro Gln
            180                 185                 190

Pro Leu Lys Glu Gln Pro Ala Leu Asn Asp Ser Arg Tyr Cys Leu Ser
            195                 200                 205

Ser Arg Leu Arg Val Ser Ala Thr Phe Trp Gln Asn Pro Arg Asn His
210                 215                 220

Phe Arg Cys Gln Val Gln Phe Tyr Gly Leu Ser Glu Asn Asp Glu Trp
225                 230                 235                 240

Thr Gln Asp Arg Ala Lys Pro Val Thr Gln Ile Val Ser Ala Glu Ala
                245                 250                 255

Trp Gly Arg Ala Asp Cys Gly Phe Thr Ser Glu Ser Tyr Gln Gln Gly
            260                 265                 270

Val Leu Ser Ala Thr Ile Leu Tyr Glu Ile Leu Leu Gly Lys Ala Thr
            275                 280                 285

Leu Tyr Ala Val Leu Val Ser Ala Leu Val Leu Met Ala Met Val Lys
290                 295                 300

Arg Lys Asp Ser Arg Gly
305                 310

<210> SEQ ID NO 41
<211> LENGTH: 273
<212> TYPE: PRT
<213> ORGANISM: Homo sapiens

<400> SEQUENCE: 41

Met Thr Ser Ile Arg Ala Val Phe Ile Phe Leu Trp Leu Gln Leu Asp
 1               5                  10                  15

Leu Val Asn Gly Glu Asn Val Glu Gln His Pro Ser Thr Leu Ser Val
            20                  25                  30

Gln Glu Gly Asp Ser Ala Val Ile Lys Cys Thr Tyr Ser Asp Ser Ala
            35                  40                  45

Ser Asn Tyr Phe Pro Trp Tyr Lys Gln Glu Leu Gly Lys Arg Pro Gln
 50                  55                  60

Leu Ile Ile Asp Ile Arg Ser Asn Val Gly Glu Lys Lys Asp Gln Arg
 65                  70                  75                  80

Ile Ala Val Thr Leu Asn Lys Thr Ala Lys His Phe Ser Leu His Ile
                 85                  90                  95

```
Thr Glu Thr Gln Pro Glu Asp Ser Ala Val Tyr Phe Cys Ala Ala Ser
            100                 105                 110

Pro Thr Gly Gly Tyr Asn Lys Leu Ile Phe Gly Ala Gly Thr Arg Leu
            115                 120                 125

Ala Val His Pro Tyr Ile Gln Asn Pro Asp Pro Ala Val Tyr Gln Leu
        130                 135                 140

Arg Asp Ser Lys Ser Ser Asp Lys Ser Val Cys Leu Phe Thr Asp Phe
145                 150                 155                 160

Asp Ser Gln Thr Asn Val Ser Gln Ser Lys Asp Ser Asp Val Tyr Ile
                165                 170                 175

Thr Asp Lys Thr Val Leu Asp Met Arg Ser Met Asp Phe Lys Ser Asn
            180                 185                 190

Ser Ala Val Ala Trp Ser Asn Lys Ser Asp Phe Ala Cys Ala Asn Ala
        195                 200                 205

Phe Asn Asn Ser Ile Ile Pro Glu Asp Thr Phe Phe Pro Ser Pro Glu
210                 215                 220

Ser Ser Cys Asp Val Lys Leu Val Glu Lys Ser Phe Glu Thr Asp Thr
225                 230                 235                 240

Asn Leu Asn Phe Gln Asn Leu Ser Val Ile Gly Phe Arg Ile Leu Leu
                245                 250                 255

Leu Lys Val Ala Gly Phe Asn Leu Leu Met Thr Leu Arg Leu Trp Ser
            260                 265                 270

Ser

<210> SEQ ID NO 42
<211> LENGTH: 311
<212> TYPE: PRT
<213> ORGANISM: Homo sapiens

<400> SEQUENCE: 42

Met Ser Ile Gly Leu Leu Cys Cys Ala Ala Leu Ser Leu Leu Trp Ala
1               5                   10                  15

Gly Pro Val Asn Ala Gly Val Thr Gln Thr Pro Lys Phe Gln Val Leu
            20                  25                  30

Lys Thr Gly Gln Ser Met Thr Leu Gln Cys Ala Gln Asp Met Asn His
        35                  40                  45

Glu Tyr Met Ser Trp Tyr Arg Gln Asp Pro Gly Met Gly Leu Arg Leu
    50                  55                  60

Ile His Tyr Ser Val Gly Ala Gly Ile Thr Asp Gln Gly Glu Val Pro
65                  70                  75                  80

Asn Gly Tyr Asn Val Ser Arg Ser Thr Thr Glu Asp Phe Pro Leu Arg
                85                  90                  95

Leu Leu Ser Ala Ala Pro Ser Gln Thr Ser Val Tyr Phe Cys Ala Ser
            100                 105                 110

Ser Leu Gly Gly Ala Ser Gln Glu Gln Tyr Phe Gly Pro Gly Thr Arg
        115                 120                 125

Leu Thr Val Thr Glu Asp Leu Lys Asn Val Phe Pro Pro Glu Val Ala
    130                 135                 140

Val Phe Glu Pro Ser Glu Ala Glu Ile Ser His Thr Gln Lys Ala Thr
145                 150                 155                 160

Leu Val Cys Leu Ala Thr Gly Phe Tyr Pro Asp His Val Glu Leu Ser
                165                 170                 175

Trp Trp Val Asn Gly Lys Glu Val His Ser Gly Val Ser Thr Asp Pro
            180                 185                 190
```

```
Gln Pro Leu Lys Glu Gln Pro Ala Leu Asn Asp Ser Arg Tyr Cys Leu
            195                 200                 205

Ser Ser Arg Leu Arg Val Ser Ala Thr Phe Trp Gln Asn Pro Arg Asn
210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
            245                 250                 255

Ala Trp Gly Arg Ala Asp Cys Gly Phe Thr Ser Glu Ser Tyr Gln Gln
            260                 265                 270

Gly Val Leu Ser Ala Thr Ile Leu Tyr Glu Ile Leu Leu Gly Lys Ala
            275                 280                 285

Thr Leu Tyr Ala Val Leu Val Ser Ala Leu Val Leu Met Ala Met Val
            290                 295                 300

Lys Arg Lys Asp Ser Arg Gly
305                 310

<210> SEQ ID NO 43
<211> LENGTH: 266
<212> TYPE: PRT
<213> ORGANISM: Homo sapiens

<400> SEQUENCE: 43

Met Lys Leu Val Thr Ser Ile Thr Val Leu Leu Ser Leu Gly Ile Met
1               5                   10                  15

Gly Asp Ala Lys Thr Thr Gln Pro Asn Ser Met Glu Ser Asn Glu Glu
            20                  25                  30

Glu Pro Val His Leu Pro Cys Asn His Ser Thr Ile Ser Gly Thr Asp
            35                  40                  45

Tyr Ile His Trp Tyr Arg Gln Leu Pro Ser Gln Gly Pro Glu Tyr Val
        50                  55                  60

Ile His Gly Leu Thr Ser Asn Val Asn Asn Arg Met Ala Ser Leu Ala
65                  70                  75                  80

Ile Ala Glu Asp Arg Lys Ser Ser Thr Leu Ile Leu His Arg Ala Thr
            85                  90                  95

Leu Arg Asp Ala Ala Val Tyr Tyr Cys Ile Leu Phe Asn Phe Asn Lys
            100                 105                 110

Phe Tyr Phe Gly Ser Gly Thr Lys Leu Asn Val Lys Pro Asn Ile Gln
            115                 120                 125

Asn Pro Asp Pro Ala Val Tyr Gln Leu Arg Asp Ser Lys Ser Ser Asp
130                 135                 140

Lys Ser Val Cys Leu Phe Thr Asp Phe Asp Ser Gln Thr Asn Val Ser
145                 150                 155                 160

Gln Ser Lys Asp Ser Asp Val Tyr Ile Thr Asp Lys Thr Val Leu Asp
            165                 170                 175

Met Arg Ser Met Asp Phe Lys Ser Asn Ser Ala Val Ala Trp Ser Asn
            180                 185                 190

Lys Ser Asp Phe Ala Cys Ala Asn Ala Phe Asn Asn Ser Ile Ile Pro
            195                 200                 205

Glu Asp Thr Phe Phe Pro Ser Pro Glu Ser Ser Cys Asp Val Lys Leu
            210                 215                 220

Val Glu Lys Ser Phe Glu Thr Asp Thr Asn Leu Asn Phe Gln Asn Leu
225                 230                 235                 240

Ser Val Ile Gly Phe Arg Ile Leu Leu Leu Lys Val Ala Gly Phe Asn
```

```
                        245                 250                 255

Leu Leu Met Thr Leu Arg Leu Trp Ser Ser
            260                 265

<210> SEQ ID NO 44
<211> LENGTH: 309
<212> TYPE: PRT
<213> ORGANISM: Homo sapiens

<400> SEQUENCE: 44

Met Gly Pro Gly Leu Leu His Trp Met Ala Leu Cys Leu Leu Gly Thr
1               5                   10                  15

Gly His Gly Asp Ala Met Val Ile Gln Asn Pro Arg Tyr Gln Val Thr
            20                  25                  30

Gln Phe Gly Lys Pro Val Thr Leu Ser Cys Ser Gln Thr Leu Asn His
        35                  40                  45

Asn Val Met Tyr Trp Tyr Gln Gln Lys Ser Ser Gln Ala Pro Lys Leu
    50                  55                  60

Leu Phe His Tyr Tyr Asp Lys Asp Phe Asn Asn Glu Ala Asp Thr Pro
65                  70                  75                  80

Asp Asn Phe Gln Ser Arg Arg Pro Asn Thr Ser Phe Cys Phe Leu Asp
                85                  90                  95

Ile Arg Ser Pro Gly Leu Gly Asp Ala Ala Met Tyr Leu Cys Ala Thr
            100                 105                 110

Ser Ser Gly Glu Thr Asn Glu Lys Leu Phe Phe Gly Ser Gly Thr Gln
        115                 120                 125

Leu Ser Val Leu Glu Asp Leu Asn Lys Val Phe Pro Pro Glu Val Ala
130                 135                 140

Val Phe Glu Pro Ser Glu Ala Glu Ile Ser His Thr Gln Lys Ala Thr
145                 150                 155                 160

Leu Val Cys Leu Ala Thr Gly Phe Phe Pro Asp His Val Glu Leu Ser
                165                 170                 175

Trp Trp Val Asn Gly Lys Glu Val His Ser Gly Val Ser Thr Asp Pro
            180                 185                 190

Gln Pro Leu Lys Glu Gln Pro Ala Leu Asn Asp Ser Arg Tyr Cys Leu
        195                 200                 205

Ser Ser Arg Leu Arg Val Ser Ala Thr Phe Trp Gln Asn Pro Arg Asn
210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Val Ser Tyr Gln Gln
            260                 265                 270

Gly Val Leu Ser Ala Thr Ile Leu Tyr Glu Ile Leu Leu Gly Lys Ala
        275                 280                 285

Thr Leu Tyr Ala Val Leu Val Ser Ala Leu Val Leu Met Ala Met Val
290                 295                 300

Lys Arg Lys Asp Phe
305

<210> SEQ ID NO 45
<211> LENGTH: 277
<212> TYPE: PRT
<213> ORGANISM: Homo sapiens
```

<400> SEQUENCE: 45

Met Thr Arg Val Ser Leu Leu Trp Ala Val Val Ser Thr Cys Leu
1               5                   10                  15

Glu Ser Gly Met Ala Gln Thr Val Thr Gln Ser Gln Pro Glu Met Ser
            20                  25                  30

Val Gln Glu Ala Glu Thr Val Thr Leu Ser Cys Thr Tyr Asp Thr Ser
        35                  40                  45

Glu Ser Asn Tyr Tyr Leu Phe Trp Tyr Lys Gln Pro Pro Ser Arg Gln
    50                  55                  60

Met Ile Leu Val Ile Arg Gln Glu Ala Tyr Lys Gln Gln Asn Ala Thr
65                  70                  75                  80

Glu Asn Arg Phe Ser Val Asn Phe Gln Lys Ala Ala Lys Ser Phe Ser
                85                  90                  95

Leu Lys Ile Ser Asp Ser Gln Leu Gly Asp Thr Ala Met Tyr Phe Cys
            100                 105                 110

Ala Phe Gly Tyr Ser Gly Gly Gly Ala Asp Gly Leu Thr Phe Gly Lys
        115                 120                 125

Gly Thr His Leu Ile Ile Gln Pro Tyr Ile Gln Asn Pro Asp Pro Ala
    130                 135                 140

Val Tyr Gln Leu Arg Asp Ser Lys Ser Ser Asp Lys Ser Val Cys Leu
145                 150                 155                 160

Phe Thr Asp Phe Asp Ser Gln Thr Asn Val Ser Gln Ser Lys Asp Ser
                165                 170                 175

Asp Val Tyr Ile Thr Asp Lys Thr Val Leu Asp Met Arg Ser Met Asp
            180                 185                 190

Phe Lys Ser Asn Ser Ala Val Ala Trp Ser Asn Lys Ser Asp Phe Ala
        195                 200                 205

Cys Ala Asn Ala Phe Asn Asn Ser Ile Ile Pro Glu Asp Thr Phe Phe
    210                 215                 220

Pro Ser Pro Glu Ser Ser Cys Asp Val Lys Leu Val Glu Lys Ser Phe
225                 230                 235                 240

Glu Thr Asp Thr Asn Leu Asn Phe Gln Asn Leu Ser Val Ile Gly Phe
                245                 250                 255

Arg Ile Leu Leu Leu Lys Val Ala Gly Phe Asn Leu Leu Met Thr Leu
            260                 265                 270

Arg Leu Trp Ser Ser
        275

<210> SEQ ID NO 46
<211> LENGTH: 311
<212> TYPE: PRT
<213> ORGANISM: Homo sapiens

<400> SEQUENCE: 46

Met Gly Pro Gly Leu Leu Cys Trp Ala Leu Leu Cys Leu Leu Gly Ala
1               5                   10                  15

Gly Leu Val Asp Ala Gly Val Thr Gln Ser Pro Thr His Leu Ile Lys
            20                  25                  30

Thr Arg Gly Gln Gln Val Thr Leu Arg Cys Ser Pro Lys Ser Gly His
        35                  40                  45

Asp Thr Val Ser Trp Tyr Gln Gln Ala Leu Gly Gln Gly Pro Gln Phe
    50                  55                  60

Ile Phe Gln Tyr Tyr Glu Glu Glu Glu Arg Gln Arg Gly Asn Phe Pro
65                  70                  75                  80

```
Asp Arg Phe Ser Gly His Gln Phe Pro Asn Tyr Ser Glu Leu Asn
            85                  90                  95

Val Asn Ala Leu Leu Leu Gly Asp Ser Ala Leu Tyr Leu Cys Ala Ser
            100                 105                 110

Ser Asn Glu Gly Gln Gly Trp Glu Ala Glu Ala Phe Phe Gly Gln Gly
            115                 120                 125

Thr Arg Leu Thr Val Val Glu Asp Leu Asn Lys Val Phe Pro Pro Glu
            130                 135                 140

Val Ala Val Phe Glu Pro Ser Glu Ala Glu Ile Ser His Thr Gln Lys
145                 150                 155                 160

Ala Thr Leu Val Cys Leu Ala Thr Gly Phe Phe Pro Asp His Val Glu
                165                 170                 175

Leu Ser Trp Trp Val Asn Gly Lys Glu Val His Ser Gly Val Ser Thr
                180                 185                 190

Asp Pro Gln Pro Leu Lys Glu Gln Pro Ala Leu Asn Asp Ser Arg Tyr
            195                 200                 205

Cys Leu Ser Ser Arg Leu Arg Val Ser Ala Thr Phe Trp Gln Asn Pro
    210                 215                 220

Arg Asn His Phe Arg Cys Gln Val Gln Phe Tyr Gly Leu Ser Glu Asn
225                 230                 235                 240

Asp Glu Trp Thr Gln Asp Arg Ala Lys Pro Val Thr Gln Ile Val Ser
                245                 250                 255

Ala Glu Ala Trp Gly Arg Ala Asp Cys Gly Phe Thr Ser Val Ser Tyr
                260                 265                 270

Gln Gln Gly Val Leu Ser Ala Thr Ile Leu Tyr Glu Ile Leu Leu Gly
            275                 280                 285

Lys Ala Thr Leu Tyr Ala Val Leu Val Ser Ala Leu Val Leu Met Ala
            290                 295                 300

Met Val Lys Arg Lys Asp Phe
305                 310

<210> SEQ ID NO 47
<211> LENGTH: 268
<212> TYPE: PRT
<213> ORGANISM: Homo sapiens

<400> SEQUENCE: 47

Met Lys Arg Ile Leu Gly Ala Leu Leu Gly Leu Leu Ser Ala Gln Val
1               5                   10                  15

Cys Cys Val Arg Gly Ile Gln Val Glu Gln Ser Pro Pro Asp Leu Ile
            20                  25                  30

Leu Gln Glu Gly Ala Asn Ser Thr Leu Arg Cys Asn Phe Ser Asp Ser
            35                  40                  45

Val Asn Asn Leu Gln Trp Phe His Gln Asn Pro Trp Gly Gln Leu Ile
        50                  55                  60

Asn Leu Phe Tyr Ile Pro Ser Gly Thr Lys Gln Asn Gly Arg Leu Ser
65                  70                  75                  80

Ala Thr Thr Val Ala Thr Glu Arg Tyr Ser Leu Leu Tyr Ile Ser Ser
                85                  90                  95

Ser Gln Thr Thr Asp Ser Gly Val Tyr Phe Cys Ala Val His Asn Phe
            100                 105                 110

Asn Lys Phe Tyr Phe Gly Ser Gly Thr Lys Leu Asn Val Lys Pro Asn
            115                 120                 125

Ile Gln Asn Pro Asp Pro Ala Val Tyr Gln Leu Arg Asp Ser Lys Ser
            130                 135                 140
```

Ser Asp Lys Ser Val Cys Leu Phe Thr Asp Phe Asp Ser Gln Thr Asn
145                 150                 155                 160

Val Ser Gln Ser Lys Asp Ser Asp Val Tyr Ile Thr Asp Lys Thr Val
                165                 170                 175

Leu Asp Met Arg Ser Met Asp Phe Lys Ser Asn Ser Ala Val Ala Trp
            180                 185                 190

Ser Asn Lys Ser Asp Phe Ala Cys Ala Asn Ala Phe Asn Asn Ser Ile
        195                 200                 205

Ile Pro Glu Asp Thr Phe Phe Pro Ser Pro Glu Ser Ser Cys Asp Val
    210                 215                 220

Lys Leu Val Glu Lys Ser Phe Glu Thr Asp Thr Asn Leu Asn Phe Gln
225                 230                 235                 240

Asn Leu Ser Val Ile Gly Phe Arg Ile Leu Leu Leu Lys Val Ala Gly
                245                 250                 255

Phe Asn Leu Leu Met Thr Leu Arg Leu Trp Ser Ser
            260                 265

<210> SEQ ID NO 48
<211> LENGTH: 322
<212> TYPE: PRT
<213> ORGANISM: Homo sapiens

<400> SEQUENCE: 48

Met Leu Ser Pro Asp Leu Pro Asp Ser Ala Trp Asn Thr Arg Leu Leu
1               5                   10                  15

Cys His Val Met Leu Cys Leu Leu Gly Ala Val Ser Val Ala Ala Gly
            20                  25                  30

Val Ile Gln Ser Pro Arg His Leu Ile Lys Glu Lys Arg Glu Thr Ala
            35                  40                  45

Thr Leu Lys Cys Tyr Pro Ile Pro Arg His Asp Thr Val Tyr Trp Tyr
        50                  55                  60

Gln Gln Gly Pro Gly Gln Asp Pro Gln Phe Leu Ile Ser Phe Tyr Glu
65                  70                  75                  80

Lys Met Gln Ser Asp Lys Gly Ser Ile Pro Asp Arg Phe Ser Ala Gln
                85                  90                  95

Gln Phe Ser Asp Tyr His Ser Glu Leu Asn Met Ser Ser Leu Glu Leu
            100                 105                 110

Gly Asp Ser Ala Leu Tyr Phe Cys Ala Ser Ser Leu Leu Gly Gln Gly
        115                 120                 125

Tyr Asn Glu Gln Phe Phe Gly Pro Gly Thr Arg Leu Thr Val Leu Glu
130                 135                 140

Asp Leu Lys Asn Val Phe Pro Pro Glu Val Ala Val Phe Glu Pro Ser
145                 150                 155                 160

Glu Ala Glu Ile Ser His Thr Gln Lys Ala Thr Leu Val Cys Leu Ala
                165                 170                 175

Thr Gly Phe Tyr Pro Asp His Val Glu Leu Ser Trp Trp Val Asn Gly
            180                 185                 190

Lys Glu Val His Ser Gly Val Ser Thr Asp Pro Gln Pro Leu Lys Glu
        195                 200                 205

Gln Pro Ala Leu Asn Asp Ser Arg Tyr Cys Leu Ser Ser Arg Leu Arg
    210                 215                 220

Val Ser Ala Thr Phe Trp Gln Asn Pro Arg Asn His Phe Arg Cys Gln
225                 230                 235                 240

Val Gln Phe Tyr Gly Leu Ser Glu Asn Asp Glu Trp Thr Gln Asp Arg

```
                        245                 250                 255
Ala Lys Pro Val Thr Gln Ile Val Ser Ala Glu Ala Trp Gly Arg Ala
                260                 265                 270
Asp Cys Gly Phe Thr Ser Glu Ser Tyr Gln Gln Gly Val Leu Ser Ala
            275                 280                 285
Thr Ile Leu Tyr Glu Ile Leu Leu Gly Lys Ala Thr Leu Tyr Ala Val
        290                 295                 300
Leu Val Ser Ala Leu Val Leu Met Ala Met Val Lys Arg Lys Asp Ser
305                 310                 315                 320
Arg Gly

<210> SEQ ID NO 49
<211> LENGTH: 276
<212> TYPE: PRT
<213> ORGANISM: Homo sapiens

<400> SEQUENCE: 49

Met Leu Thr Ala Ser Leu Leu Arg Ala Val Ile Ala Ser Ile Cys Val
1               5                   10                  15
Val Ser Ser Met Ala Gln Lys Val Thr Gln Ala Gln Thr Glu Ile Ser
            20                  25                  30
Val Val Glu Lys Glu Asp Val Thr Leu Asp Cys Val Tyr Glu Thr Arg
        35                  40                  45
Asp Thr Thr Tyr Tyr Leu Phe Trp Tyr Lys Gln Pro Pro Ser Gly Glu
    50                  55                  60
Leu Val Phe Leu Ile Arg Arg Asn Ser Phe Asp Glu Gln Asn Glu Ile
65                  70                  75                  80
Ser Gly Arg Tyr Ser Trp Asn Phe Gln Lys Ser Thr Ser Ser Phe Asn
                85                  90                  95
Phe Thr Ile Thr Ala Ser Gln Val Val Asp Ser Ala Val Tyr Phe Cys
            100                 105                 110
Ala Leu Ser Asn Asn Asn Ala Gly Asn Met Leu Thr Phe Gly Gly Gly
        115                 120                 125
Thr Arg Leu Met Val Lys Pro His Ile Gln Asn Pro Asp Pro Ala Val
    130                 135                 140
Tyr Gln Leu Arg Asp Ser Lys Ser Ser Asp Lys Ser Val Cys Leu Phe
145                 150                 155                 160
Thr Asp Phe Asp Ser Gln Thr Asn Val Ser Gln Ser Lys Asp Ser Asp
                165                 170                 175
Val Tyr Ile Thr Asp Lys Thr Val Leu Asp Met Arg Ser Met Asp Phe
            180                 185                 190
Lys Ser Asn Ser Ala Val Ala Trp Ser Asn Lys Ser Asp Phe Ala Cys
        195                 200                 205
Ala Asn Ala Phe Asn Asn Ser Ile Ile Pro Glu Asp Thr Phe Phe Pro
    210                 215                 220
Ser Pro Glu Ser Ser Cys Asp Val Lys Leu Val Glu Lys Ser Phe Glu
225                 230                 235                 240
Thr Asp Thr Asn Leu Asn Phe Gln Asn Leu Ser Val Ile Gly Phe Arg
                245                 250                 255
Ile Leu Leu Leu Lys Val Ala Gly Phe Asn Leu Leu Met Thr Leu Arg
            260                 265                 270
Leu Trp Ser Ser
        275
```

```
<210> SEQ ID NO 50
<211> LENGTH: 323
<212> TYPE: PRT
<213> ORGANISM: Homo sapiens

<400> SEQUENCE: 50

Met Leu Ser Pro Asp Leu Pro Asp Ser Ala Trp Asn Thr Arg Leu Leu
1               5                   10                  15

Cys His Val Met Leu Cys Leu Leu Gly Ala Val Ser Val Ala Ala Gly
            20                  25                  30

Val Ile Gln Ser Pro Arg His Leu Ile Lys Glu Lys Arg Glu Thr Ala
        35                  40                  45

Thr Leu Lys Cys Tyr Pro Ile Pro Arg His Asp Thr Val Tyr Trp Tyr
    50                  55                  60

Gln Gln Gly Pro Gly Gln Asp Pro Gln Phe Leu Ile Ser Phe Tyr Glu
65                  70                  75                  80

Lys Met Gln Ser Asp Lys Gly Ser Ile Pro Asp Arg Phe Ser Ala Gln
                85                  90                  95

Gln Phe Ser Asp Tyr His Ser Glu Leu Asn Met Ser Ser Leu Glu Leu
            100                 105                 110

Gly Asp Ser Ala Leu Tyr Phe Cys Ala Ser Ser Pro Thr Gly Thr Ser
        115                 120                 125

Gly Tyr Asn Glu Gln Phe Phe Gly Pro Gly Thr Arg Leu Thr Val Leu
    130                 135                 140

Glu Asp Leu Lys Asn Val Phe Pro Pro Glu Val Ala Val Phe Glu Pro
145                 150                 155                 160

Ser Glu Ala Glu Ile Ser His Thr Gln Lys Ala Thr Leu Val Cys Leu
                165                 170                 175

Ala Thr Gly Phe Tyr Pro Asp His Val Glu Leu Ser Trp Trp Val Asn
            180                 185                 190

Gly Lys Glu Val His Ser Gly Val Ser Thr Asp Pro Gln Pro Leu Lys
        195                 200                 205

Glu Gln Pro Ala Leu Asn Asp Ser Arg Tyr Cys Leu Ser Ser Arg Leu
    210                 215                 220

Arg Val Ser Ala Thr Phe Trp Gln Asn Pro Arg Asn His Phe Arg Cys
225                 230                 235                 240

Gln Val Gln Phe Tyr Gly Leu Ser Glu Asn Asp Glu Trp Thr Gln Asp
                245                 250                 255

Arg Ala Lys Pro Val Thr Gln Ile Val Ser Ala Glu Ala Trp Gly Arg
            260                 265                 270

Ala Asp Cys Gly Phe Thr Ser Glu Ser Tyr Gln Gln Gly Val Leu Ser
        275                 280                 285

Ala Thr Ile Leu Tyr Glu Ile Leu Leu Gly Lys Ala Thr Leu Tyr Ala
    290                 295                 300

Val Leu Val Ser Ala Leu Val Leu Met Ala Met Val Lys Arg Lys Asp
305                 310                 315                 320

Ser Arg Gly

<210> SEQ ID NO 51
<211> LENGTH: 273
<212> TYPE: PRT
<213> ORGANISM: Homo sapiens

<400> SEQUENCE: 51

Met Glu Lys Asn Pro Leu Ala Ala Pro Leu Leu Ile Leu Trp Phe His
1               5                   10                  15
```

-continued

```
Leu Asp Cys Val Ser Ser Ile Leu Asn Val Glu Gln Ser Pro Gln Ser
                 20                  25                  30
Leu His Val Gln Glu Gly Asp Ser Thr Asn Phe Thr Cys Ser Phe Pro
             35                  40                  45
Ser Ser Asn Phe Tyr Ala Leu His Trp Tyr Arg Trp Glu Thr Ala Lys
 50                  55                  60
Ser Pro Glu Ala Leu Phe Val Met Thr Leu Asn Gly Asp Glu Lys Lys
 65                  70                  75                  80
Lys Gly Arg Ile Ser Ala Thr Leu Asn Thr Lys Glu Gly Tyr Ser Tyr
                 85                  90                  95
Leu Tyr Ile Lys Gly Ser Gln Pro Glu Asp Ser Ala Thr Tyr Leu Cys
            100                 105                 110
Ala Leu Asn Arg Asp Asp Lys Ile Ile Phe Gly Lys Gly Thr Arg Leu
        115                 120                 125
His Ile Leu Pro Asn Ile Gln Asn Pro Asp Pro Ala Val Tyr Gln Leu
130                 135                 140
Arg Asp Ser Lys Ser Ser Asp Lys Ser Val Cys Leu Phe Thr Asp Phe
145                 150                 155                 160
Asp Ser Gln Thr Asn Val Ser Gln Ser Lys Asp Ser Asp Val Tyr Ile
                165                 170                 175
Thr Asp Lys Thr Val Leu Asp Met Arg Ser Met Asp Phe Lys Ser Asn
            180                 185                 190
Ser Ala Val Ala Trp Ser Asn Lys Ser Asp Phe Ala Cys Ala Asn Ala
        195                 200                 205
Phe Asn Asn Ser Ile Ile Pro Glu Asp Thr Phe Phe Pro Ser Pro Glu
210                 215                 220
Ser Ser Cys Asp Val Lys Leu Val Glu Lys Ser Phe Glu Thr Asp Thr
225                 230                 235                 240
Asn Leu Asn Phe Gln Asn Leu Ser Val Ile Gly Phe Arg Ile Leu Leu
                245                 250                 255
Leu Lys Val Ala Gly Phe Asn Leu Leu Met Thr Leu Arg Leu Trp Ser
            260                 265                 270
Ser

<210> SEQ ID NO 52
<211> LENGTH: 311
<212> TYPE: PRT
<213> ORGANISM: Homo sapiens

<400> SEQUENCE: 52

Met Gly Ile Arg Leu Leu Cys Arg Val Ala Phe Cys Phe Leu Ala Val
1               5                  10                  15
Gly Leu Val Asp Val Lys Val Thr Gln Ser Ser Arg Tyr Leu Val Lys
                 20                  25                  30
Arg Thr Gly Glu Lys Val Phe Leu Glu Cys Val Gln Asp Met Asp His
             35                  40                  45
Glu Asn Met Phe Trp Tyr Arg Gln Asp Pro Gly Leu Gly Leu Arg Leu
 50                  55                  60
Ile Tyr Phe Ser Tyr Asp Val Lys Met Lys Glu Lys Gly Asp Ile Pro
 65                  70                  75                  80
Glu Gly Tyr Ser Val Ser Arg Glu Lys Lys Glu Arg Phe Ser Leu Ile
                 85                  90                  95
Leu Glu Ser Ala Ser Thr Asn Gln Thr Ser Met Tyr Leu Cys Ala Ser
            100                 105                 110
```

-continued

```
Arg Leu Pro Ser Arg Thr Tyr Glu Gln Tyr Phe Gly Pro Gly Thr Arg
            115                 120                 125
Leu Thr Val Thr Glu Asp Leu Lys Asn Val Phe Pro Pro Glu Val Ala
        130                 135                 140
Val Phe Glu Pro Ser Glu Ala Glu Ile Ser His Thr Gln Lys Ala Thr
145                 150                 155                 160
Leu Val Cys Leu Ala Thr Gly Phe Tyr Pro Asp His Val Glu Leu Ser
                165                 170                 175
Trp Trp Val Asn Gly Lys Glu Val His Ser Gly Val Ser Thr Asp Pro
            180                 185                 190
Gln Pro Leu Lys Glu Gln Pro Ala Leu Asn Asp Ser Arg Tyr Cys Leu
        195                 200                 205
Ser Ser Arg Leu Arg Val Ser Ala Thr Phe Trp Gln Asn Pro Arg Asn
210                 215                 220
His Phe Arg Cys Gln Val Gln Phe Tyr Gly Leu Ser Glu Asn Asp Glu
225                 230                 235                 240
Trp Thr Gln Asp Arg Ala Lys Pro Val Thr Gln Ile Val Ser Ala Glu
                245                 250                 255
Ala Trp Gly Arg Ala Asp Cys Gly Phe Thr Ser Glu Ser Tyr Gln Gln
            260                 265                 270
Gly Val Leu Ser Ala Thr Ile Leu Tyr Glu Ile Leu Leu Gly Lys Ala
        275                 280                 285
Thr Leu Tyr Ala Val Leu Val Ser Ala Leu Val Leu Met Ala Met Val
        290                 295                 300
Lys Arg Lys Asp Ser Arg Gly
305                 310

<210> SEQ ID NO 53
<211> LENGTH: 270
<212> TYPE: PRT
<213> ORGANISM: Homo sapiens

<400> SEQUENCE: 53

Met Glu Thr Leu Leu Gly Leu Leu Ile Leu Trp Leu Gln Leu Gln Trp
1               5                   10                  15
Val Ser Ser Lys Gln Glu Val Thr Gln Ile Pro Ala Ala Leu Ser Val
            20                  25                  30
Pro Glu Gly Glu Asn Leu Val Leu Asn Cys Ser Phe Thr Asp Ser Ala
        35                  40                  45
Ile Tyr Asn Leu Gln Trp Phe Arg Gln Asp Pro Gly Lys Gly Leu Thr
    50                  55                  60
Ser Leu Leu Leu Ile Gln Ser Ser Gln Arg Glu Gln Thr Ser Gly Arg
65                  70                  75                  80
Leu Asn Ala Ser Leu Asp Lys Ser Ser Gly Arg Ser Thr Leu Tyr Ile
                85                  90                  95
Ala Ala Ser Gln Pro Gly Asp Ser Ala Thr Tyr Leu Cys Ala Val Asn
            100                 105                 110
Ser Asp Tyr Lys Leu Ser Phe Gly Ala Gly Thr Thr Val Thr Val Arg
        115                 120                 125
Ala Asn Ile Gln Asn Pro Asp Pro Ala Val Tyr Gln Leu Arg Asp Ser
    130                 135                 140
Lys Ser Ser Asp Lys Ser Val Cys Leu Phe Thr Asp Phe Asp Ser Gln
145                 150                 155                 160
Thr Asn Val Ser Gln Ser Lys Asp Ser Asp Val Tyr Ile Thr Asp Lys
```

```
                      165                 170                 175
Thr Val Leu Asp Met Arg Ser Met Asp Phe Lys Ser Asn Ser Ala Val
                180                 185                 190

Ala Trp Ser Asn Lys Ser Asp Phe Ala Cys Ala Asn Ala Phe Asn Asn
            195                 200                 205

Ser Ile Ile Pro Glu Asp Thr Phe Phe Pro Ser Pro Glu Ser Ser Cys
        210                 215                 220

Asp Val Lys Leu Val Glu Lys Ser Phe Glu Thr Asp Thr Asn Leu Asn
225                 230                 235                 240

Phe Gln Asn Leu Ser Val Ile Gly Phe Arg Ile Leu Leu Leu Lys Val
                245                 250                 255

Ala Gly Phe Asn Leu Leu Met Thr Leu Arg Leu Trp Ser Ser
                260                 265                 270

<210> SEQ ID NO 54
<211> LENGTH: 321
<212> TYPE: PRT
<213> ORGANISM: Homo sapiens

<400> SEQUENCE: 54

Met Leu Ser Pro Asp Leu Pro Asp Ser Ala Trp Asn Thr Arg Leu Leu
1               5                   10                  15

Cys His Val Met Leu Cys Leu Leu Gly Ala Val Ser Val Ala Ala Gly
                20                  25                  30

Val Ile Gln Ser Pro Arg His Leu Ile Lys Glu Lys Arg Glu Thr Ala
            35                  40                  45

Thr Leu Lys Cys Tyr Pro Ile Pro Arg His Asp Thr Val Tyr Trp Tyr
        50                  55                  60

Gln Gln Gly Pro Gly Gln Asp Pro Gln Phe Leu Ile Ser Phe Tyr Glu
65                  70                  75                  80

Lys Met Gln Ser Asp Lys Gly Ser Ile Pro Asp Arg Phe Ser Ala Gln
                85                  90                  95

Gln Phe Ser Asp Tyr His Ser Glu Leu Asn Met Ser Ser Leu Glu Leu
                100                 105                 110

Gly Asp Ser Ala Leu Tyr Phe Cys Ala Ser Ser Leu Gly Leu Gly Thr
            115                 120                 125

Gly Asp Tyr Gly Tyr Thr Phe Gly Ser Gly Thr Arg Leu Thr Val Val
        130                 135                 140

Glu Asp Leu Asn Lys Val Phe Pro Pro Glu Val Ala Val Phe Glu Pro
145                 150                 155                 160

Ser Glu Ala Glu Ile Ser His Thr Gln Lys Ala Thr Leu Val Cys Leu
                165                 170                 175

Ala Thr Gly Phe Phe Pro Asp His Val Glu Leu Ser Trp Trp Val Asn
                180                 185                 190

Gly Lys Glu Val His Ser Gly Val Ser Thr Asp Pro Gln Pro Leu Lys
            195                 200                 205

Glu Gln Pro Ala Leu Asn Asp Ser Arg Tyr Cys Leu Ser Ser Arg Leu
        210                 215                 220

Arg Val Ser Ala Thr Phe Trp Gln Asn Pro Arg Asn His Phe Arg Cys
225                 230                 235                 240

Gln Val Gln Phe Tyr Gly Leu Ser Glu Asn Asp Glu Trp Thr Gln Asp
                245                 250                 255

Arg Ala Lys Pro Val Thr Gln Ile Val Ser Ala Glu Ala Trp Gly Arg
                260                 265                 270
```

```
Ala Asp Cys Gly Phe Thr Ser Val Ser Tyr Gln Gln Gly Val Leu Ser
            275                 280                 285

Ala Thr Ile Leu Tyr Glu Ile Leu Leu Gly Lys Ala Thr Leu Tyr Ala
    290                 295                 300

Val Leu Val Ser Ala Leu Val Leu Met Ala Met Val Lys Arg Lys Asp
305                 310                 315                 320

Phe

<210> SEQ ID NO 55
<211> LENGTH: 273
<212> TYPE: PRT
<213> ORGANISM: Homo sapiens

<400> SEQUENCE: 55

Met Glu Lys Asn Pro Leu Ala Ala Pro Leu Leu Ile Leu Trp Phe His
1               5                   10                  15

Leu Asp Cys Val Ser Ser Ile Leu Asn Val Glu Gln Ser Pro Gln Ser
            20                  25                  30

Leu His Val Gln Glu Gly Asp Ser Thr Asn Phe Thr Cys Ser Phe Pro
        35                  40                  45

Ser Ser Asn Phe Tyr Ala Leu His Trp Tyr Arg Trp Glu Thr Ala Lys
    50                  55                  60

Ser Pro Glu Ala Leu Phe Val Met Thr Leu Asn Gly Asp Glu Lys Lys
65                  70                  75                  80

Lys Gly Arg Ile Ser Ala Thr Leu Asn Thr Lys Glu Gly Tyr Ser Tyr
                85                  90                  95

Leu Tyr Ile Lys Gly Ser Gln Pro Glu Asp Ser Ala Thr Tyr Leu Cys
            100                 105                 110

Ala Leu Tyr Asn Asn Asn Asp Met Arg Phe Gly Ala Gly Thr Arg Leu
        115                 120                 125

Thr Val Lys Pro Asn Ile Gln Asn Pro Asp Pro Ala Val Tyr Gln Leu
130                 135                 140

Arg Asp Ser Lys Ser Ser Asp Lys Ser Val Cys Leu Phe Thr Asp Phe
145                 150                 155                 160

Asp Ser Gln Thr Asn Val Ser Gln Ser Lys Asp Ser Asp Val Tyr Ile
                165                 170                 175

Thr Asp Lys Thr Val Leu Asp Met Arg Ser Met Asp Phe Lys Ser Asn
            180                 185                 190

Ser Ala Val Ala Trp Ser Asn Lys Ser Asp Phe Ala Cys Ala Asn Ala
        195                 200                 205

Phe Asn Asn Ser Ile Ile Pro Glu Asp Thr Phe Phe Pro Ser Pro Glu
    210                 215                 220

Ser Ser Cys Asp Val Lys Leu Val Glu Lys Ser Phe Glu Thr Asp Thr
225                 230                 235                 240

Asn Leu Asn Phe Gln Asn Leu Ser Val Ile Gly Phe Arg Ile Leu Leu
                245                 250                 255

Leu Lys Val Ala Gly Phe Asn Leu Leu Met Thr Leu Arg Leu Trp Ser
            260                 265                 270

Ser

<210> SEQ ID NO 56
<211> LENGTH: 311
<212> TYPE: PRT
<213> ORGANISM: Homo sapiens

<400> SEQUENCE: 56
```

Met Asp Ser Trp Thr Phe Cys Cys Val Ser Leu Cys Ile Leu Val Ala
1               5                   10                  15

Lys His Thr Asp Ala Gly Val Ile Gln Ser Pro Arg His Glu Val Thr
            20                  25                  30

Glu Met Gly Gln Glu Val Thr Leu Arg Cys Lys Pro Ile Ser Gly His
        35                  40                  45

Asn Ser Leu Phe Trp Tyr Arg Gln Thr Met Met Arg Gly Leu Glu Leu
    50                  55                  60

Leu Ile Tyr Phe Asn Asn Asn Val Pro Ile Asp Asp Ser Gly Met Pro
65                  70                  75                  80

Glu Asp Arg Phe Ser Ala Lys Met Pro Asn Ala Ser Phe Ser Thr Leu
                85                  90                  95

Lys Ile Gln Pro Ser Glu Pro Arg Asp Ser Ala Val Tyr Phe Cys Ala
            100                 105                 110

Ser Ser Pro Gly Ser Thr Asp Thr Gln Tyr Phe Gly Pro Gly Thr Arg
        115                 120                 125

Leu Thr Val Leu Glu Asp Leu Lys Asn Val Phe Pro Pro Glu Val Ala
    130                 135                 140

Val Phe Glu Pro Ser Glu Ala Glu Ile Ser His Thr Gln Lys Ala Thr
145                 150                 155                 160

Leu Val Cys Leu Ala Thr Gly Phe Tyr Pro Asp His Val Glu Leu Ser
                165                 170                 175

Trp Trp Val Asn Gly Lys Glu Val His Ser Gly Val Ser Thr Asp Pro
            180                 185                 190

Gln Pro Leu Lys Glu Gln Pro Ala Leu Asn Asp Ser Arg Tyr Cys Leu
        195                 200                 205

Ser Ser Arg Leu Arg Val Ser Ala Thr Phe Trp Gln Asn Pro Arg Asn
210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Glu Ser Tyr Gln Gln
            260                 265                 270

Gly Val Leu Ser Ala Thr Leu Leu Tyr Glu Ile Leu Leu Gly Lys Ala
        275                 280                 285

Thr Leu Tyr Ala Val Leu Val Ser Ala Leu Val Leu Met Ala Met Val
    290                 295                 300

Lys Arg Lys Asp Ser Arg Gly
305                 310

<210> SEQ ID NO 57
<211> LENGTH: 275
<212> TYPE: PRT
<213> ORGANISM: Homo sapiens

<400> SEQUENCE: 57

Met Lys Ser Leu Arg Val Leu Leu Val Ile Leu Trp Leu Gln Leu Ser
1               5                   10                  15

Trp Val Trp Ser Gln Gln Lys Glu Val Glu Gln Asn Ser Gly Pro Leu
            20                  25                  30

Ser Val Pro Glu Gly Ala Ile Ala Ser Leu Asn Cys Thr Tyr Ser Asp
        35                  40                  45

Arg Gly Ser Gln Ser Phe Phe Trp Tyr Arg Gln Tyr Ser Gly Lys Ser

```
             50                  55                  60
Pro Glu Leu Ile Met Phe Ile Tyr Ser Asn Gly Asp Lys Glu Asp Gly
 65                  70                  75                  80

Arg Phe Thr Ala Gln Leu Asn Lys Ala Ser Gln Tyr Val Ser Leu Leu
                     85                  90                  95

Ile Arg Asp Ser Gln Pro Ser Asp Ser Ala Thr Tyr Leu Cys Ala Ala
                100                 105                 110

Val Ile Ser Asn Phe Gly Asn Glu Lys Leu Thr Phe Gly Thr Gly Thr
            115                 120                 125

Arg Leu Thr Ile Ile Pro Asn Ile Gln Asn Pro Asp Pro Ala Val Tyr
        130                 135                 140

Gln Leu Arg Asp Ser Lys Ser Ser Asp Lys Ser Val Cys Leu Phe Thr
145                 150                 155                 160

Asp Phe Asp Ser Gln Thr Asn Val Ser Gln Ser Lys Asp Ser Asp Val
                165                 170                 175

Tyr Ile Thr Asp Lys Thr Val Leu Asp Met Arg Ser Met Asp Phe Lys
                180                 185                 190

Ser Asn Ser Ala Val Ala Trp Ser Asn Lys Ser Asp Phe Ala Cys Ala
                195                 200                 205

Asn Ala Phe Asn Asn Ser Ile Ile Pro Glu Asp Thr Phe Phe Pro Ser
            210                 215                 220

Pro Glu Ser Ser Cys Asp Val Lys Leu Val Glu Lys Ser Phe Glu Thr
225                 230                 235                 240

Asp Thr Asn Leu Asn Phe Gln Asn Leu Ser Val Ile Gly Phe Arg Ile
                245                 250                 255

Leu Leu Leu Lys Val Ala Gly Phe Asn Leu Leu Met Thr Leu Arg Leu
                260                 265                 270

Trp Ser Ser
        275

<210> SEQ ID NO 58
<211> LENGTH: 311
<212> TYPE: PRT
<213> ORGANISM: Homo sapiens

<400> SEQUENCE: 58

Met Gly Ser Arg Leu Leu Cys Trp Val Leu Leu Cys Leu Leu Gly Ala
  1               5                  10                  15

Gly Pro Val Lys Ala Gly Val Thr Gln Thr Pro Arg Tyr Leu Ile Lys
                 20                  25                  30

Thr Arg Gly Gln Gln Val Thr Leu Ser Cys Ser Pro Ile Ser Gly His
             35                  40                  45

Arg Ser Val Ser Trp Tyr Gln Gln Thr Pro Gly Gln Gly Leu Gln Phe
         50                  55                  60

Leu Phe Glu Tyr Phe Ser Glu Thr Gln Arg Asn Lys Gly Asn Phe Pro
 65                  70                  75                  80

Gly Arg Phe Ser Gly Arg Gln Phe Ser Asn Ser Arg Ser Glu Met Asn
                 85                  90                  95

Val Ser Thr Leu Glu Leu Gly Asp Ser Ala Leu Tyr Leu Cys Ala Ser
                100                 105                 110

Ser Pro Trp Asp Ser Pro Asn Glu Gln Tyr Phe Gly Pro Gly Thr Arg
            115                 120                 125

Leu Thr Val Thr Glu Asp Leu Lys Asn Val Phe Pro Pro Glu Val Ala
        130                 135                 140
```

```
Val Phe Glu Pro Ser Glu Ala Glu Ile Ser His Thr Gln Lys Ala Thr
145                 150                 155                 160

Leu Val Cys Leu Ala Thr Gly Phe Tyr Pro Asp His Val Glu Leu Ser
                165                 170                 175

Trp Trp Val Asn Gly Lys Glu Val His Ser Gly Val Ser Thr Asp Pro
            180                 185                 190

Gln Pro Leu Lys Glu Gln Pro Ala Leu Asn Asp Ser Arg Tyr Cys Leu
        195                 200                 205

Ser Ser Arg Leu Arg Val Ser Ala Thr Phe Trp Gln Asn Pro Arg Asn
210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Glu Ser Tyr Gln Gln
                260                 265                 270

Gly Val Leu Ser Ala Thr Ile Leu Tyr Glu Ile Leu Leu Gly Lys Ala
            275                 280                 285

Thr Leu Tyr Ala Val Leu Val Ser Ala Leu Val Leu Met Ala Met Val
290                 295                 300

Lys Arg Lys Asp Ser Arg Gly
305                 310

<210> SEQ ID NO 59
<211> LENGTH: 274
<212> TYPE: PRT
<213> ORGANISM: Homo sapiens

<400> SEQUENCE: 59

Met Met Lys Ser Leu Arg Val Leu Leu Val Ile Leu Trp Leu Gln Leu
1               5                   10                  15

Ser Trp Val Trp Ser Gln Gln Lys Glu Val Glu Gln Asp Pro Gly Pro
            20                  25                  30

Leu Ser Val Pro Glu Gly Ala Ile Val Ser Leu Asn Cys Thr Tyr Ser
        35                  40                  45

Asn Ser Ala Phe Gln Tyr Phe Met Trp Tyr Arg Gln Tyr Ser Arg Lys
50                  55                  60

Gly Pro Glu Leu Leu Met Tyr Thr Tyr Ser Ser Gly Asn Lys Glu Asp
65                  70                  75                  80

Gly Arg Phe Thr Ala Gln Val Asp Lys Ser Ser Lys Tyr Ile Ser Leu
                85                  90                  95

Phe Ile Arg Asp Ser Gln Pro Ser Asp Ser Ala Thr Tyr Leu Cys Ala
            100                 105                 110

Met Ser Glu Ala Ala Gly Asn Lys Leu Thr Phe Gly Gly Gly Thr Arg
        115                 120                 125

Val Leu Val Lys Pro Asn Ile Gln Asn Pro Asp Pro Ala Val Tyr Gln
130                 135                 140

Leu Arg Asp Ser Lys Ser Ser Asp Lys Ser Val Cys Leu Phe Thr Asp
145                 150                 155                 160

Phe Asp Ser Gln Thr Asn Val Ser Gln Ser Lys Asp Ser Asp Val Tyr
                165                 170                 175

Ile Thr Asp Lys Thr Val Leu Asp Met Arg Ser Met Asp Phe Lys Ser
            180                 185                 190

Asn Ser Ala Val Ala Trp Ser Asn Lys Ser Asp Phe Ala Cys Ala Asn
        195                 200                 205
```

```
Ala Phe Asn Asn Ser Ile Ile Pro Glu Asp Thr Phe Phe Pro Ser Pro
    210                 215                 220

Glu Ser Ser Cys Asp Val Lys Leu Val Glu Lys Ser Phe Glu Thr Asp
225                 230                 235                 240

Thr Asn Leu Asn Phe Gln Asn Leu Ser Val Ile Gly Phe Arg Ile Leu
            245                 250                 255

Leu Leu Lys Val Ala Gly Phe Asn Leu Leu Met Thr Leu Arg Leu Trp
        260                 265                 270

Ser Ser
```

<210> SEQ ID NO 60
<211> LENGTH: 309
<212> TYPE: PRT
<213> ORGANISM: Homo sapiens

<400> SEQUENCE: 60

```
Met Gly Thr Arg Leu Leu Cys Trp Ala Ala Leu Cys Leu Leu Gly Ala
1               5                   10                  15

Glu Leu Thr Glu Ala Gly Val Ala Gln Ser Pro Arg Tyr Lys Ile Ile
            20                  25                  30

Glu Lys Arg Gln Ser Val Ala Phe Trp Cys Asn Pro Ile Ser Gly His
        35                  40                  45

Ala Thr Leu Tyr Trp Tyr Gln Gln Ile Leu Gly Gln Gly Pro Lys Leu
    50                  55                  60

Leu Ile Gln Phe Gln Asn Asn Gly Val Val Asp Asp Ser Gln Leu Pro
65                  70                  75                  80

Lys Asp Arg Phe Ser Ala Glu Arg Leu Lys Gly Val Asp Ser Thr Leu
                85                  90                  95

Lys Ile Gln Pro Ala Lys Leu Glu Asp Ser Ala Val Tyr Leu Cys Ala
            100                 105                 110

Ser Ser Tyr Thr Asn Gln Gly Glu Ala Phe Phe Gly Gln Gly Thr Arg
        115                 120                 125

Leu Thr Val Val Glu Asp Leu Asn Lys Val Phe Pro Pro Glu Val Ala
    130                 135                 140

Val Phe Glu Pro Ser Glu Ala Glu Ile Ser His Thr Gln Lys Ala Thr
145                 150                 155                 160

Leu Val Cys Leu Ala Thr Gly Phe Phe Pro Asp His Val Glu Leu Ser
                165                 170                 175

Trp Trp Val Asn Gly Lys Glu Val His Ser Gly Val Ser Thr Asp Pro
            180                 185                 190

Gln Pro Leu Lys Glu Gln Pro Ala Leu Asn Asp Ser Arg Tyr Cys Leu
        195                 200                 205

Ser Ser Arg Leu Arg Val Ser Ala Thr Phe Trp Gln Asn Pro Arg Asn
    210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Val Ser Tyr Gln Gln
            260                 265                 270

Gly Val Leu Ser Ala Thr Ile Leu Tyr Glu Ile Leu Leu Gly Lys Ala
        275                 280                 285

Thr Leu Tyr Ala Val Leu Val Ser Ala Leu Val Leu Met Ala Met Val
    290                 295                 300
```

```
Lys Arg Lys Asp Phe
305

<210> SEQ ID NO 61
<211> LENGTH: 273
<212> TYPE: PRT
<213> ORGANISM: Homo sapiens

<400> SEQUENCE: 61

Met Lys Ser Leu Arg Val Leu Leu Val Ile Leu Trp Leu Gln Leu Ser
1               5                   10                  15

Trp Val Trp Ser Gln Gln Lys Glu Val Glu Gln Asn Ser Gly Pro Leu
            20                  25                  30

Ser Val Pro Glu Gly Ala Ile Ala Ser Leu Asn Cys Thr Tyr Ser Asp
        35                  40                  45

Arg Gly Ser Gln Ser Phe Phe Trp Tyr Arg Gln Tyr Ser Gly Lys Ser
    50                  55                  60

Pro Glu Leu Ile Met Ser Ile Tyr Ser Asn Gly Asp Lys Glu Asp Gly
65                  70                  75                  80

Arg Phe Thr Ala Gln Leu Asn Lys Ala Ser Gln Tyr Val Ser Leu Leu
                85                  90                  95

Ile Arg Asp Ser Gln Pro Ser Asp Ser Ala Thr Tyr Leu Cys Ala Val
            100                 105                 110

Leu Asn Gln Ala Gly Thr Ala Leu Ile Phe Gly Lys Gly Thr Thr Leu
        115                 120                 125

Ser Val Ser Ser Asn Ile Gln Asn Pro Asp Pro Ala Val Tyr Gln Leu
    130                 135                 140

Arg Asp Ser Lys Ser Ser Asp Lys Ser Val Cys Leu Phe Thr Asp Phe
145                 150                 155                 160

Asp Ser Gln Thr Asn Val Ser Gln Ser Lys Asp Ser Asp Val Tyr Ile
                165                 170                 175

Thr Asp Lys Thr Val Leu Asp Met Arg Ser Met Asp Phe Lys Ser Asn
            180                 185                 190

Ser Ala Val Ala Trp Ser Asn Lys Ser Asp Phe Ala Cys Ala Asn Ala
        195                 200                 205

Phe Asn Asn Ser Ile Ile Pro Glu Asp Thr Phe Phe Pro Ser Pro Glu
    210                 215                 220

Ser Ser Cys Asp Val Lys Leu Val Glu Lys Ser Phe Glu Thr Asp Thr
225                 230                 235                 240

Asn Leu Asn Phe Gln Asn Leu Ser Val Ile Gly Phe Arg Ile Leu Leu
                245                 250                 255

Leu Lys Val Ala Gly Phe Asn Leu Leu Met Thr Leu Arg Leu Trp Ser
            260                 265                 270

Ser

<210> SEQ ID NO 62
<211> LENGTH: 314
<212> TYPE: PRT
<213> ORGANISM: Homo sapiens

<400> SEQUENCE: 62

Met Gly Phe Arg Leu Leu Cys Cys Val Ala Phe Cys Leu Leu Gly Ala
1               5                   10                  15

Gly Pro Val Asp Ser Gly Val Thr Gln Thr Pro Lys His Leu Ile Thr
            20                  25                  30
```

```
Ala Thr Gly Gln Arg Val Thr Leu Arg Cys Ser Pro Arg Ser Gly Asp
            35                  40                  45

Leu Ser Val Tyr Trp Tyr Gln Ser Leu Asp Gln Gly Leu Gln Phe
 50                  55                  60

Leu Ile Gln Tyr Tyr Asn Gly Glu Glu Arg Ala Lys Gly Asn Ile Leu
 65                  70                  75                  80

Glu Arg Phe Ser Ala Gln Gln Phe Pro Asp Leu His Ser Glu Leu Asn
                85                  90                  95

Leu Ser Ser Leu Glu Leu Gly Asp Ser Ala Leu Tyr Phe Cys Ala Ser
            100                 105                 110

Ser Ala Glu Thr Gly Pro Trp Leu Gly Asn Glu Gln Phe Phe Gly Pro
            115                 120                 125

Gly Thr Arg Leu Thr Val Leu Glu Asp Leu Lys Asn Val Phe Pro Pro
130                 135                 140

Glu Val Ala Val Phe Glu Pro Ser Glu Ala Glu Ile Ser His Thr Gln
145                 150                 155                 160

Lys Ala Thr Leu Val Cys Leu Ala Thr Gly Phe Tyr Pro Asp His Val
                165                 170                 175

Glu Leu Ser Trp Trp Val Asn Gly Lys Glu Val His Ser Gly Val Ser
            180                 185                 190

Thr Asp Pro Gln Pro Leu Lys Glu Gln Pro Ala Leu Asn Asp Ser Arg
            195                 200                 205

Tyr Cys Leu Ser Ser Arg Leu Arg Val Ser Ala Thr Phe Trp Gln Asn
210                 215                 220

Pro Arg Asn His Phe Arg Cys Gln Val Gln Phe Tyr Gly Leu Ser Glu
225                 230                 235                 240

Asn Asp Glu Trp Thr Gln Asp Arg Ala Lys Pro Val Thr Gln Ile Val
                245                 250                 255

Ser Ala Glu Ala Trp Gly Arg Ala Asp Cys Gly Phe Thr Ser Glu Ser
            260                 265                 270

Tyr Gln Gln Gly Val Leu Ser Ala Thr Ile Leu Tyr Glu Ile Leu Leu
            275                 280                 285

Gly Lys Ala Thr Leu Tyr Ala Val Leu Val Ser Ala Leu Val Leu Met
290                 295                 300

Ala Met Val Lys Arg Lys Asp Ser Arg Gly
305                 310

<210> SEQ ID NO 63
<211> LENGTH: 277
<212> TYPE: PRT
<213> ORGANISM: Homo sapiens

<400> SEQUENCE: 63

Met Ala Cys Pro Gly Phe Leu Trp Ala Leu Val Ile Ser Thr Cys Leu
1               5                   10                  15

Glu Phe Ser Met Ala Gln Thr Val Thr Gln Ser Gln Pro Glu Met Ser
            20                  25                  30

Val Gln Glu Ala Glu Thr Val Thr Leu Ser Cys Thr Tyr Asp Thr Ser
            35                  40                  45

Glu Ser Asp Tyr Tyr Leu Phe Trp Tyr Lys Gln Pro Pro Ser Arg Gln
        50                  55                  60

Met Ile Leu Val Ile Arg Gln Glu Ala Tyr Lys Gln Gln Asn Ala Thr
65                  70                  75                  80

Glu Asn Arg Phe Ser Val Asn Phe Gln Lys Ala Ala Lys Ser Phe Ser
                85                  90                  95
```

```
Leu Lys Ile Ser Asp Ser Gln Leu Gly Asp Ala Ala Met Tyr Phe Cys
            100                 105                 110

Ala Tyr Arg Trp Ala Gln Gly Ser Glu Lys Leu Val Phe Gly Lys
        115                 120                 125

Gly Thr Lys Leu Thr Val Asn Pro Tyr Ile Gln Lys Pro Asp Pro Ala
130                 135                 140

Val Tyr Gln Leu Arg Asp Ser Lys Ser Ser Asp Lys Ser Val Cys Leu
145                 150                 155                 160

Phe Thr Asp Phe Asp Ser Gln Thr Asn Val Ser Gln Ser Lys Asp Ser
                165                 170                 175

Asp Val Tyr Ile Thr Asp Lys Thr Val Leu Asp Met Arg Ser Met Asp
            180                 185                 190

Phe Lys Ser Asn Ser Ala Val Ala Trp Ser Asn Lys Ser Asp Phe Ala
        195                 200                 205

Cys Ala Asn Ala Phe Asn Asn Ser Ile Ile Pro Glu Asp Thr Phe Phe
210                 215                 220

Pro Ser Pro Glu Ser Ser Cys Asp Val Lys Leu Val Glu Lys Ser Phe
225                 230                 235                 240

Glu Thr Asp Thr Asn Leu Asn Phe Gln Asn Leu Ser Val Ile Gly Phe
                245                 250                 255

Arg Ile Leu Leu Leu Lys Val Ala Gly Phe Asn Leu Leu Met Thr Leu
            260                 265                 270

Arg Leu Trp Ser Ser
        275

<210> SEQ ID NO 64
<211> LENGTH: 313
<212> TYPE: PRT
<213> ORGANISM: Homo sapiens

<400> SEQUENCE: 64

Met Thr Ile Arg Leu Leu Cys Tyr Met Gly Phe Tyr Phe Leu Gly Ala
1               5                   10                  15

Gly Leu Met Glu Ala Asp Ile Tyr Gln Thr Pro Arg Tyr Leu Val Ile
            20                  25                  30

Gly Thr Gly Lys Lys Ile Thr Leu Glu Cys Ser Gln Thr Met Gly His
        35                  40                  45

Asp Lys Met Tyr Trp Tyr Gln Gln Asp Pro Gly Met Glu Leu His Leu
    50                  55                  60

Ile His Tyr Ser Tyr Gly Val Asn Ser Thr Glu Lys Gly Asp Leu Ser
65                  70                  75                  80

Ser Glu Ser Thr Val Ser Arg Ile Arg Thr Glu His Phe Pro Leu Thr
                85                  90                  95

Leu Glu Ser Ala Arg Pro Ser His Thr Ser Gln Tyr Leu Cys Ala Thr
            100                 105                 110

Glu Leu Trp Ser Ser Gly Gly Thr Gly Glu Leu Phe Phe Gly Glu Gly
        115                 120                 125

Ser Arg Leu Thr Val Leu Glu Asp Leu Lys Asn Val Phe Pro Pro Glu
130                 135                 140

Val Ala Val Phe Glu Pro Ser Glu Ala Glu Ile Ser His Thr Gln Lys
145                 150                 155                 160

Ala Thr Leu Val Cys Leu Ala Thr Gly Phe Tyr Pro Asp His Val Glu
                165                 170                 175

Leu Ser Trp Trp Val Asn Gly Lys Glu Val His Ser Gly Val Ser Thr
```

```
                180             185             190
Asp Pro Gln Pro Leu Lys Glu Gln Pro Ala Leu Asn Asp Ser Arg Tyr
            195                 200                 205

Cys Leu Ser Ser Arg Leu Arg Val Ser Ala Thr Phe Trp Gln Asn Pro
    210                 215                 220

Arg Asn His Phe Arg Cys Gln Val Gln Phe Tyr Gly Leu Ser Glu Asn
225                 230                 235                 240

Asp Glu Trp Thr Gln Asp Arg Ala Lys Pro Val Thr Gln Ile Val Ser
                245                 250                 255

Ala Glu Ala Trp Gly Arg Ala Asp Cys Gly Phe Thr Ser Glu Ser Tyr
                260                 265                 270

Gln Gln Gly Val Leu Ser Ala Thr Ile Leu Tyr Glu Ile Leu Leu Gly
            275                 280                 285

Lys Ala Thr Leu Tyr Ala Val Leu Val Ser Ala Leu Val Leu Met Ala
            290                 295                 300

Met Val Lys Arg Lys Asp Ser Arg Gly
305                 310
```

<210> SEQ ID NO 65
<211> LENGTH: 206
<212> TYPE: PRT
<213> ORGANISM: Homo sapiens

<400> SEQUENCE: 65

```
Ile Met Ser Ile Tyr Ser Asn Gly Asp Lys Glu Asp Gly Arg Phe Thr
1               5                   10                  15

Ala Gln Leu Asn Lys Ala Ser Gln Tyr Val Ser Leu Leu Ile Arg Asp
            20                  25                  30

Ser Gln Pro Ser Asp Ser Ala Thr Tyr Leu Cys Ala Val Gly Pro Ser
        35                  40                  45

Gly Thr Tyr Lys Tyr Ile Phe Gly Thr Gly Thr Arg Leu Lys Val Leu
    50                  55                  60

Ala Asn Ile Gln Asn Pro Asp Pro Ala Val Tyr Gln Leu Arg Asp Ser
65                  70                  75                  80

Lys Ser Ser Asp Lys Ser Val Cys Leu Phe Thr Asp Phe Asp Ser Gln
                85                  90                  95

Thr Asn Val Ser Gln Ser Lys Asp Ser Asp Val Tyr Ile Thr Asp Lys
            100                 105                 110

Thr Val Leu Asp Met Arg Ser Met Asp Phe Lys Ser Asn Ser Ala Val
        115                 120                 125

Ala Trp Ser Asn Lys Ser Asp Phe Ala Cys Ala Asn Ala Phe Asn Asn
    130                 135                 140

Ser Ile Ile Pro Glu Asp Thr Phe Phe Pro Ser Pro Glu Ser Ser Cys
145                 150                 155                 160

Asp Val Lys Leu Val Glu Lys Ser Phe Glu Thr Asp Thr Asn Leu Asn
                165                 170                 175

Phe Gln Asn Leu Ser Val Ile Gly Phe Arg Ile Leu Leu Leu Lys Val
            180                 185                 190

Ala Gly Phe Asn Leu Leu Met Thr Leu Arg Leu Trp Ser Ser
        195                 200                 205
```

<210> SEQ ID NO 66
<211> LENGTH: 311
<212> TYPE: PRT
<213> ORGANISM: Homo sapiens

<400> SEQUENCE: 66

Met Gly Pro Gln Leu Leu Gly Tyr Val Leu Cys Leu Leu Gly Ala
1               5                   10                  15

Gly Pro Leu Glu Ala Gln Val Thr Gln Asn Pro Arg Tyr Leu Ile Thr
            20                  25                  30

Val Thr Gly Lys Lys Leu Thr Val Thr Cys Ser Gln Asn Met Asn His
        35                  40                  45

Glu Tyr Met Ser Trp Tyr Arg Gln Asp Pro Gly Leu Gly Leu Arg Gln
    50                  55                  60

Ile Tyr Tyr Ser Met Asn Val Glu Val Thr Asp Lys Gly Asp Val Pro
65              70                  75                  80

Glu Gly Tyr Lys Val Ser Arg Lys Glu Lys Arg Asn Phe Pro Leu Ile
                85                  90                  95

Leu Glu Ser Pro Ser Pro Asn Gln Thr Ser Leu Tyr Phe Cys Ala Ser
            100                 105                 110

Ser Pro Gly Gly Ser Gly Asn Glu Gln Phe Phe Gly Pro Gly Thr Arg
        115                 120                 125

Leu Thr Val Leu Glu Asp Leu Lys Asn Val Phe Pro Pro Glu Val Ala
    130                 135                 140

Val Phe Glu Pro Ser Glu Ala Glu Ile Ser His Thr Gln Lys Ala Thr
145                 150                 155                 160

Leu Val Cys Leu Ala Thr Gly Phe Tyr Pro Asp His Val Glu Leu Ser
                165                 170                 175

Trp Trp Val Asn Gly Lys Glu Val His Ser Gly Val Ser Thr Asp Pro
            180                 185                 190

Gln Pro Leu Lys Glu Gln Pro Ala Leu Asn Asp Ser Arg Tyr Cys Leu
        195                 200                 205

Ser Ser Arg Leu Arg Val Ser Ala Thr Phe Trp Gln Asn Pro Arg Asn
    210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Glu Ser Tyr Gln Gln
            260                 265                 270

Gly Val Leu Ser Ala Thr Ile Leu Tyr Glu Ile Leu Leu Gly Lys Ala
        275                 280                 285

Thr Leu Tyr Ala Val Leu Val Ser Ala Leu Val Leu Met Ala Met Val
    290                 295                 300

Lys Arg Lys Asp Ser Arg Gly
305                 310

<210> SEQ ID NO 67
<211> LENGTH: 274
<212> TYPE: PRT
<213> ORGANISM: Homo sapiens

<400> SEQUENCE: 67

Met Lys Ser Leu Arg Val Leu Leu Val Ile Leu Trp Leu Gln Leu Ser
1               5                   10                  15

Trp Val Trp Ser Gln Gln Lys Glu Val Glu Gln Asn Ser Gly Pro Leu
            20                  25                  30

Ser Val Pro Glu Gly Ala Ile Ala Ser Leu Asn Cys Thr Tyr Ser Asp
        35                  40                  45

```
Arg Gly Ser Gln Ser Phe Phe Trp Tyr Arg Gln Tyr Ser Gly Lys Ser
    50                  55                  60

Pro Glu Leu Ile Met Phe Ile Tyr Ser Asn Gly Asp Lys Glu Asp Gly
65                  70                  75                  80

Arg Phe Thr Ala Gln Leu Asn Lys Ala Ser Gln Tyr Val Ser Leu Leu
                85                  90                  95

Ile Arg Asp Ser Gln Pro Ser Asp Ser Ala Thr Tyr Leu Cys Ala Val
            100                 105                 110

Val Ser Gly Gly Gly Ala Asp Gly Leu Thr Phe Gly Lys Gly Thr His
            115                 120                 125

Leu Ile Ile Gln Pro Tyr Ile Gln Lys Pro Asp Pro Ala Val Tyr Gln
130                 135                 140

Leu Arg Asp Ser Lys Ser Ser Asp Lys Ser Val Cys Leu Phe Thr Asp
145                 150                 155                 160

Phe Asp Ser Gln Thr Asn Val Ser Gln Ser Lys Asp Ser Asp Val Tyr
                165                 170                 175

Ile Thr Asp Lys Thr Val Leu Asp Met Arg Ser Met Asp Phe Lys Ser
            180                 185                 190

Asn Ser Ala Val Ala Trp Ser Asn Lys Ser Asp Phe Ala Cys Ala Asn
            195                 200                 205

Ala Phe Asn Asn Ser Ile Ile Pro Glu Asp Thr Phe Phe Pro Ser Pro
    210                 215                 220

Glu Ser Ser Cys Asp Val Lys Leu Val Glu Lys Ser Phe Glu Thr Asp
225                 230                 235                 240

Thr Asn Leu Asn Phe Gln Asn Leu Ser Val Ile Gly Phe Arg Ile Leu
                245                 250                 255

Leu Leu Lys Val Ala Gly Phe Asn Leu Leu Met Thr Leu Arg Leu Trp
            260                 265                 270

Ser Ser

<210> SEQ ID NO 68
<211> LENGTH: 319
<212> TYPE: PRT
<213> ORGANISM: Homo sapiens

<400> SEQUENCE: 68

Met Leu Ser Pro Asp Leu Pro Asp Ser Ala Trp Asn Thr Arg Leu Leu
1               5                   10                  15

Cys His Val Met Leu Cys Leu Leu Gly Ala Val Ser Val Ala Ala Gly
                20                  25                  30

Val Ile Gln Ser Pro Arg His Leu Ile Lys Glu Lys Arg Glu Thr Ala
            35                  40                  45

Thr Leu Lys Cys Tyr Pro Ile Pro Arg His Asp Thr Val Tyr Trp Tyr
    50                  55                  60

Gln Gln Gly Pro Gly Gln Asp Pro Gln Phe Leu Ile Ser Phe Tyr Glu
65                  70                  75                  80

Lys Met Gln Ser Asp Lys Gly Ser Ile Pro Asp Arg Phe Ser Ala Gln
                85                  90                  95

Gln Phe Ser Asp Tyr His Ser Glu Leu Asn Met Ser Ser Leu Glu Leu
            100                 105                 110

Gly Asp Ser Ala Leu Tyr Phe Cys Ala Ser Ser Leu Gly Arg Gly Gly
            115                 120                 125

Gln Pro Gln His Phe Gly Asp Gly Thr Arg Leu Ser Ile Leu Glu Asp
        130                 135                 140
```

Leu Asn Lys Val Phe Pro Pro Glu Val Ala Val Phe Glu Pro Ser Glu
145                 150                 155                 160

Ala Glu Ile Ser His Thr Gln Lys Ala Thr Leu Val Cys Leu Ala Thr
                165                 170                 175

Gly Phe Phe Pro Asp His Val Glu Leu Ser Trp Trp Val Asn Gly Lys
                180                 185                 190

Glu Val His Ser Gly Val Ser Thr Asp Pro Gln Pro Leu Lys Glu Gln
                195                 200                 205

Pro Ala Leu Asn Asp Ser Arg Tyr Cys Leu Ser Ser Arg Leu Arg Val
210                 215                 220

Ser Ala Thr Phe Trp Gln Asn Pro Arg Asn His Phe Arg Cys Gln Val
225                 230                 235                 240

Gln Phe Tyr Gly Leu Ser Glu Asn Asp Glu Trp Thr Gln Asp Arg Ala
                245                 250                 255

Lys Pro Val Thr Gln Ile Val Ser Ala Glu Ala Trp Gly Arg Ala Asp
                260                 265                 270

Cys Gly Phe Thr Ser Val Ser Tyr Gln Gln Gly Val Leu Ser Ala Thr
                275                 280                 285

Ile Leu Tyr Glu Ile Leu Leu Gly Lys Ala Thr Leu Tyr Ala Val Leu
                290                 295                 300

Val Ser Ala Leu Val Leu Met Ala Met Val Lys Arg Lys Asp Phe
305                 310                 315

<210> SEQ ID NO 69
<211> LENGTH: 273
<212> TYPE: PRT
<213> ORGANISM: Artificial Sequence
<220> FEATURE:
<223> OTHER INFORMATION: R11P3D3KE alpha chain

<400> SEQUENCE: 69

Met Glu Lys Asn Pro Leu Ala Ala Pro Leu Leu Ile Leu Trp Phe His
1               5                   10                  15

Leu Asp Cys Val Ser Ser Ile Leu Asn Val Glu Gln Ser Pro Gln Ser
                20                  25                  30

Leu His Val Gln Glu Gly Asp Ser Thr Asn Phe Thr Cys Ser Phe Pro
            35                  40                  45

Ser Ser Asn Phe Tyr Ala Leu His Trp Tyr Arg Lys Glu Thr Ala Lys
            50                  55                  60

Ser Pro Glu Ala Leu Phe Val Met Thr Leu Asn Gly Asp Glu Lys Lys
65                  70                  75                  80

Lys Gly Arg Ile Ser Ala Thr Leu Asn Thr Lys Glu Gly Tyr Ser Tyr
                85                  90                  95

Leu Tyr Ile Lys Gly Ser Gln Pro Glu Asp Ser Ala Thr Tyr Leu Cys
                100                 105                 110

Ala Leu Tyr Asn Asn Asn Asp Met Arg Phe Gly Ala Gly Thr Arg Leu
            115                 120                 125

Thr Val Lys Pro Asn Ile Gln Asn Pro Asp Pro Ala Val Tyr Gln Leu
            130                 135                 140

Arg Asp Ser Lys Ser Ser Asp Lys Ser Val Cys Leu Phe Thr Asp Phe
145                 150                 155                 160

Asp Ser Gln Thr Asn Val Ser Gln Ser Lys Asp Ser Asp Val Tyr Ile
                165                 170                 175

Thr Asp Lys Thr Val Leu Asp Met Arg Ser Met Asp Phe Lys Ser Asn
                180                 185                 190

```
Ser Ala Val Ala Trp Ser Asn Lys Ser Asp Phe Ala Cys Ala Asn Ala
            195                 200                 205

Phe Asn Asn Ser Ile Ile Pro Glu Asp Thr Phe Phe Pro Ser Pro Glu
            210                 215                 220

Ser Ser Cys Asp Val Lys Leu Val Glu Lys Ser Phe Glu Thr Asp Thr
225                 230                 235                 240

Asn Leu Asn Phe Gln Asn Leu Ser Val Ile Gly Phe Arg Ile Leu Leu
            245                 250                 255

Leu Lys Val Ala Gly Phe Asn Leu Leu Met Thr Leu Arg Leu Trp Ser
            260                 265                 270

Ser

<210> SEQ ID NO 70
<211> LENGTH: 243
<212> TYPE: PRT
<213> ORGANISM: Artificial Sequence
<220> FEATURE:
<223> OTHER INFORMATION: R11P3D3KE beta chain

<400> SEQUENCE: 70

Asn Asn Asn Val Pro Ile Asp Asp Ser Gly Met Pro Glu Asp Arg Phe
1               5                   10                  15

Ser Ala Lys Met Pro Asn Ala Ser Phe Ser Thr Leu Lys Ile Gln Pro
            20                  25                  30

Ser Glu Pro Arg Asp Ser Ala Val Tyr Phe Cys Ala Ser Ser Pro Gly
            35                  40                  45

Ser Thr Asp Thr Gln Tyr Phe Gly Pro Gly Thr Arg Leu Thr Val Leu
50                  55                  60

Glu Asp Leu Lys Asn Val Phe Pro Pro Glu Val Ala Val Phe Glu Pro
65                  70                  75                  80

Ser Glu Ala Glu Ile Ser His Thr Gln Lys Ala Thr Leu Val Cys Leu
            85                  90                  95

Ala Thr Gly Phe Tyr Pro Asp His Val Glu Leu Ser Trp Trp Val Asn
            100                 105                 110

Gly Lys Glu Val His Ser Gly Val Ser Thr Asp Pro Gln Pro Leu Lys
            115                 120                 125

Glu Gln Pro Ala Leu Asn Asp Ser Arg Tyr Cys Leu Ser Ser Arg Leu
            130                 135                 140

Arg Val Ser Ala Thr Phe Trp Gln Asn Pro Arg Asn His Phe Arg Cys
145                 150                 155                 160

Gln Val Gln Phe Tyr Gly Leu Ser Glu Asn Asp Glu Trp Thr Gln Asp
            165                 170                 175

Arg Ala Lys Pro Val Thr Gln Ile Val Ser Ala Glu Ala Trp Gly Arg
            180                 185                 190

Ala Asp Cys Gly Phe Thr Ser Glu Ser Tyr Gln Gln Gly Val Leu Ser
            195                 200                 205

Ala Thr Leu Leu Tyr Glu Ile Leu Leu Gly Lys Ala Thr Leu Tyr Ala
            210                 215                 220

Val Leu Val Ser Ala Leu Val Leu Met Ala Met Val Lys Arg Lys Asp
225                 230                 235                 240

Ser Arg Gly

<210> SEQ ID NO 71
<211> LENGTH: 223
<212> TYPE: PRT
<213> ORGANISM: Homo sapiens
```

```
<400> SEQUENCE: 71

Thr Tyr Leu Tyr Trp Tyr Lys Gln Glu Pro Gly Ala Gly Leu Gln Leu
  1               5                  10                  15

Leu Thr Tyr Ile Phe Ser Asn Met Asp Met Lys Gln Asp Gln Arg Leu
                 20                  25                  30

Thr Val Leu Leu Asn Lys Lys Asp Lys His Leu Ser Leu Arg Ile Ala
             35                  40                  45

Asp Thr Gln Thr Gly Asp Ser Ala Ile Tyr Phe Cys Ala Glu Ile Asp
     50                  55                  60

Asn Gln Gly Gly Lys Leu Ile Phe Gly Gln Gly Thr Glu Leu Ser Val
 65                  70                  75                  80

Lys Pro Asn Ile Gln Asn Pro Asp Pro Ala Val Tyr Gln Leu Arg Asp
                 85                  90                  95

Ser Lys Ser Ser Asp Lys Ser Val Cys Leu Phe Thr Asp Phe Asp Ser
                100                 105                 110

Gln Thr Asn Val Ser Gln Ser Lys Asp Ser Asp Val Tyr Ile Thr Asp
            115                 120                 125

Lys Thr Val Leu Asp Met Arg Ser Met Asp Phe Lys Ser Asn Ser Ala
130                 135                 140

Val Ala Trp Ser Asn Lys Ser Asp Phe Ala Cys Ala Asn Ala Phe Asn
145                 150                 155                 160

Asn Ser Ile Ile Pro Glu Asp Thr Phe Phe Pro Ser Pro Glu Ser Ser
                165                 170                 175

Cys Asp Val Lys Leu Val Glu Lys Ser Phe Glu Thr Asp Thr Asn Leu
                180                 185                 190

Asn Phe Gln Asn Leu Ser Val Ile Gly Phe Arg Ile Leu Leu Leu Lys
            195                 200                 205

Val Ala Gly Phe Asn Leu Leu Met Thr Leu Arg Leu Trp Ser Ser
        210                 215                 220

<210> SEQ ID NO 72
<211> LENGTH: 307
<212> TYPE: PRT
<213> ORGANISM: Homo sapiens

<400> SEQUENCE: 72

Met Gly Pro Gly Leu Leu Cys Trp Ala Leu Leu Cys Leu Leu Gly Ala
  1               5                  10                  15

Gly Leu Val Asp Ala Gly Val Thr Gln Ser Pro Thr His Leu Ile Lys
                 20                  25                  30

Thr Arg Gly Gln Gln Val Thr Leu Arg Cys Ser Pro Lys Ser Gly His
             35                  40                  45

Asp Thr Val Ser Trp Tyr Gln Ala Leu Gly Gly Pro Gln Phe
     50                  55                  60

Ile Phe Gln Tyr Tyr Glu Glu Glu Arg Gln Arg Gly Asn Phe Pro
 65                  70                  75                  80

Asp Arg Phe Ser Gly His Gln Phe Pro Asn Tyr Ser Ser Glu Leu Asn
                 85                  90                  95

Val Asn Ala Leu Leu Leu Gly Asp Ser Ala Leu Tyr Leu Cys Ala Ser
                100                 105                 110

Ser Gln Leu Asn Thr Glu Ala Phe Phe Gly Gln Gly Thr Arg Leu Thr
            115                 120                 125

Val Val Glu Asp Leu Asn Lys Val Phe Pro Pro Glu Val Ala Val Phe
130                 135                 140
```

```
Glu Pro Ser Glu Ala Glu Ile Ser His Thr Gln Lys Ala Thr Leu Val
145                 150                 155                 160

Cys Leu Ala Thr Gly Phe Phe Pro Asp His Val Glu Leu Ser Trp Trp
            165                 170                 175

Val Asn Gly Lys Glu Val His Ser Gly Val Ser Thr Asp Pro Gln Pro
        180                 185                 190

Leu Lys Glu Gln Pro Ala Leu Asn Asp Ser Arg Tyr Cys Leu Ser Ser
    195                 200                 205

Arg Leu Arg Val Ser Ala Thr Phe Trp Gln Asn Pro Arg Asn His Phe
210                 215                 220

Arg Cys Gln Val Gln Phe Tyr Gly Leu Ser Glu Asn Asp Glu Trp Thr
225                 230                 235                 240

Gln Asp Arg Ala Lys Pro Val Thr Gln Ile Val Ser Ala Glu Ala Trp
                245                 250                 255

Gly Arg Ala Asp Cys Gly Phe Thr Ser Val Ser Tyr Gln Gln Gly Val
                260                 265                 270

Leu Ser Ala Thr Ile Leu Tyr Glu Ile Leu Leu Gly Lys Ala Thr Leu
            275                 280                 285

Tyr Ala Val Leu Val Ser Ala Leu Val Leu Met Ala Met Val Lys Arg
        290                 295                 300

Lys Asp Phe
305

<210> SEQ ID NO 73
<211> LENGTH: 270
<212> TYPE: PRT
<213> ORGANISM: Homo sapiens

<400> SEQUENCE: 73

Met Lys Ser Leu Arg Val Leu Leu Val Ile Leu Trp Leu Gln Leu Ser
1               5                   10                  15

Trp Val Trp Ser Gln Gln Lys Glu Val Glu Gln Asn Ser Gly Pro Leu
            20                  25                  30

Ser Val Pro Glu Gly Ala Ile Ala Ser Leu Asn Cys Thr Tyr Ser Asp
        35                  40                  45

Arg Gly Ser Gln Ser Phe Phe Trp Tyr Arg Gln Tyr Ser Gly Lys Ser
    50                  55                  60

Pro Glu Leu Ile Met Phe Ile Tyr Ser Asn Gly Asp Lys Glu Asp Gly
65                  70                  75                  80

Arg Phe Thr Ala Gln Leu Asn Lys Ala Ser Gln Tyr Val Ser Leu Leu
                85                  90                  95

Ile Arg Asp Ser Gln Pro Ser Asp Ser Ala Thr Tyr Leu Cys Ala Val
            100                 105                 110

Asn Asn Ala Arg Leu Met Phe Gly Asp Gly Thr Gln Leu Val Val Lys
        115                 120                 125

Pro Asn Ile Gln Asn Pro Asp Pro Ala Val Tyr Gln Leu Arg Asp Ser
    130                 135                 140

Lys Ser Ser Asp Lys Ser Val Cys Leu Phe Thr Asp Phe Asp Ser Gln
145                 150                 155                 160

Thr Asn Val Ser Gln Ser Lys Asp Ser Asp Val Tyr Ile Thr Asp Lys
                165                 170                 175

Thr Val Leu Asp Met Arg Ser Met Asp Phe Lys Ser Asn Ser Ala Val
            180                 185                 190

Ala Trp Ser Asn Lys Ser Asp Phe Ala Cys Ala Asn Ala Phe Asn Asn
```

```
            195                 200                 205
Ser Ile Ile Pro Glu Asp Thr Phe Phe Pro Ser Pro Glu Ser Ser Cys
    210                 215                 220

Asp Val Lys Leu Val Glu Lys Ser Phe Glu Thr Asp Thr Asn Leu Asn
225                 230                 235                 240

Phe Gln Asn Leu Ser Val Ile Gly Phe Arg Ile Leu Leu Leu Lys Val
                245                 250                 255

Ala Gly Phe Asn Leu Leu Met Thr Leu Arg Leu Trp Ser Ser
            260                 265                 270

<210> SEQ ID NO 74
<211> LENGTH: 311
<212> TYPE: PRT
<213> ORGANISM: Homo sapiens

<400> SEQUENCE: 74

Met Asp Thr Trp Leu Val Cys Trp Ala Ile Phe Ser Leu Leu Lys Ala
1               5                   10                  15

Gly Leu Thr Glu Pro Glu Val Thr Gln Thr Pro Ser His Gln Val Thr
                20                  25                  30

Gln Met Gly Gln Glu Val Ile Leu Arg Cys Val Pro Ile Ser Asn His
            35                  40                  45

Leu Tyr Phe Tyr Trp Tyr Arg Gln Ile Leu Gly Gln Lys Val Glu Phe
        50                  55                  60

Leu Val Ser Phe Tyr Asn Asn Glu Ile Ser Glu Lys Ser Glu Ile Phe
65                  70                  75                  80

Asp Asp Gln Phe Ser Val Glu Arg Pro Asp Gly Ser Asn Phe Thr Leu
                85                  90                  95

Lys Ile Arg Ser Thr Lys Leu Glu Asp Ser Ala Met Tyr Phe Cys Ala
            100                 105                 110

Ser Ser Gly Gln Gly Ala Asn Glu Gln Tyr Phe Gly Pro Gly Thr Arg
        115                 120                 125

Leu Thr Val Thr Glu Asp Leu Lys Asn Val Phe Pro Pro Glu Val Ala
    130                 135                 140

Val Phe Glu Pro Ser Glu Ala Glu Ile Ser His Thr Gln Lys Ala Thr
145                 150                 155                 160

Leu Val Cys Leu Ala Thr Gly Phe Tyr Pro Asp His Val Glu Leu Ser
                165                 170                 175

Trp Trp Val Asn Gly Lys Glu Val His Ser Gly Val Ser Thr Asp Pro
            180                 185                 190

Gln Pro Leu Lys Glu Gln Pro Ala Leu Asn Asp Ser Arg Tyr Cys Leu
        195                 200                 205

Ser Ser Arg Leu Arg Val Ser Ala Thr Phe Trp Gln Asn Pro Arg Asn
    210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Glu Ser Tyr Gln Gln
            260                 265                 270

Gly Val Leu Ser Ala Thr Ile Leu Tyr Glu Ile Leu Leu Gly Lys Ala
        275                 280                 285

Thr Leu Tyr Ala Val Leu Val Ser Ala Leu Val Leu Met Ala Met Val
    290                 295                 300
```

Lys Arg Lys Asp Ser Arg Gly
305                 310

<210> SEQ ID NO 75
<211> LENGTH: 272
<212> TYPE: PRT
<213> ORGANISM: Homo sapiens

<400> SEQUENCE: 75

Met Ala Cys Pro Gly Phe Leu Trp Ala Leu Val Ile Ser Thr Cys Leu
1               5                   10                  15

Glu Phe Ser Met Ala Gln Thr Val Thr Gln Ser Gln Pro Glu Met Ser
            20                  25                  30

Val Gln Glu Ala Glu Thr Val Thr Leu Ser Cys Thr Tyr Asp Thr Ser
        35                  40                  45

Glu Ser Asp Tyr Tyr Leu Phe Trp Tyr Lys Gln Pro Pro Ser Arg Gln
    50                  55                  60

Met Ile Leu Val Ile Arg Gln Glu Ala Tyr Lys Gln Gln Asn Ala Thr
65                  70                  75                  80

Glu Asn Arg Phe Ser Val Asn Phe Gln Lys Ala Ala Lys Ser Phe Ser
                85                  90                  95

Leu Lys Ile Ser Asp Ser Gln Leu Gly Asp Ala Ala Met Tyr Phe Cys
            100                 105                 110

Ala Tyr Leu Asn Tyr Gln Leu Ile Trp Gly Ala Gly Thr Lys Leu Ile
        115                 120                 125

Ile Lys Pro Asp Ile Gln Asn Pro Asp Pro Ala Val Tyr Gln Leu Arg
    130                 135                 140

Asp Ser Lys Ser Ser Asp Lys Ser Val Cys Leu Phe Thr Asp Phe Asp
145                 150                 155                 160

Ser Gln Thr Asn Val Ser Gln Ser Lys Asp Ser Asp Val Tyr Ile Thr
                165                 170                 175

Asp Lys Thr Val Leu Asp Met Arg Ser Met Asp Phe Lys Ser Asn Ser
            180                 185                 190

Ala Val Ala Trp Ser Asn Lys Ser Asp Phe Ala Cys Ala Asn Ala Phe
        195                 200                 205

Asn Asn Ser Ile Ile Pro Glu Asp Thr Phe Phe Pro Ser Pro Glu Ser
    210                 215                 220

Ser Cys Asp Val Lys Leu Val Glu Lys Ser Phe Glu Thr Asp Thr Asn
225                 230                 235                 240

Leu Asn Phe Gln Asn Leu Ser Val Ile Gly Phe Arg Ile Leu Leu Leu
                245                 250                 255

Lys Val Ala Gly Phe Asn Leu Leu Met Thr Leu Arg Leu Trp Ser Ser
            260                 265                 270

<210> SEQ ID NO 76
<211> LENGTH: 311
<212> TYPE: PRT
<213> ORGANISM: Homo sapiens

<400> SEQUENCE: 76

Met Asp Thr Trp Leu Val Cys Trp Ala Ile Phe Ser Leu Leu Lys Ala
1               5                   10                  15

Gly Leu Thr Glu Pro Glu Val Thr Gln Thr Pro Ser His Gln Val Thr
            20                  25                  30

Gln Met Gly Gln Glu Val Ile Leu Arg Cys Val Pro Ile Ser Asn His
        35                  40                  45

-continued

```
Leu Tyr Phe Tyr Trp Tyr Arg Gln Ile Leu Gly Gln Lys Val Glu Phe
 50                  55                  60

Leu Val Ser Phe Tyr Asn Asn Glu Ile Ser Glu Lys Ser Glu Ile Phe
 65                  70                  75                  80

Asp Asp Gln Phe Ser Val Glu Arg Pro Asp Gly Ser Asn Phe Thr Leu
                 85                  90                  95

Lys Ile Arg Ser Thr Lys Leu Glu Asp Ser Ala Met Tyr Phe Cys Ala
                100                 105                 110

Ser Ser Glu Met Thr Ala Val Gly Gln Tyr Phe Gly Pro Gly Thr Arg
            115                 120                 125

Leu Thr Val Thr Glu Asp Leu Lys Asn Val Phe Pro Pro Glu Val Ala
130                 135                 140

Val Phe Glu Pro Ser Glu Ala Glu Ile Ser His Thr Gln Lys Ala Thr
145                 150                 155                 160

Leu Val Cys Leu Ala Thr Gly Phe Tyr Pro Asp His Val Glu Leu Ser
                165                 170                 175

Trp Trp Val Asn Gly Lys Glu Val His Ser Gly Val Ser Thr Asp Pro
            180                 185                 190

Gln Pro Leu Lys Glu Gln Pro Ala Leu Asn Asp Ser Arg Tyr Cys Leu
        195                 200                 205

Ser Ser Arg Leu Arg Val Ser Ala Thr Phe Trp Gln Asn Pro Arg Asn
210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Glu Ser Tyr Gln Gln
            260                 265                 270

Gly Val Leu Ser Ala Thr Ile Leu Tyr Glu Ile Leu Leu Gly Lys Ala
        275                 280                 285

Thr Leu Tyr Ala Val Leu Val Ser Ala Leu Val Leu Met Ala Met Val
    290                 295                 300

Lys Arg Lys Asp Ser Arg Gly
305                 310

<210> SEQ ID NO 77
<211> LENGTH: 271
<212> TYPE: PRT
<213> ORGANISM: Homo sapiens

<400> SEQUENCE: 77

Met Lys Ser Leu Arg Val Leu Leu Val Ile Leu Trp Leu Gln Leu Ser
  1               5                  10                  15

Trp Val Trp Ser Gln Gln Lys Glu Val Glu Gln Asn Ser Gly Pro Leu
                 20                  25                  30

Ser Val Pro Glu Gly Ala Ile Ala Ser Leu Asn Cys Thr Tyr Ser Asp
             35                  40                  45

Arg Gly Ser Gln Ser Phe Phe Trp Tyr Arg Gln Tyr Ser Gly Lys Ser
 50                  55                  60

Pro Glu Leu Ile Met Phe Ile Tyr Ser Asn Gly Asp Lys Glu Asp Gly
 65                  70                  75                  80

Arg Phe Thr Ala Gln Leu Asn Lys Ala Ser Gln Tyr Val Ser Leu Leu
                 85                  90                  95

Ile Arg Asp Ser Gln Pro Ser Asp Ser Ala Thr Tyr Leu Cys Ala Ala
                100                 105                 110
```

```
Phe Ser Gly Tyr Ala Leu Asn Phe Gly Lys Gly Thr Ser Leu Leu Val
            115                 120                 125

Thr Pro His Ile Gln Asn Pro Asp Pro Ala Val Tyr Gln Leu Arg Asp
        130                 135                 140

Ser Lys Ser Ser Asp Lys Ser Val Cys Leu Phe Thr Asp Phe Asp Ser
145                 150                 155                 160

Gln Thr Asn Val Ser Gln Ser Lys Asp Ser Asp Val Tyr Ile Thr Asp
                165                 170                 175

Lys Thr Val Leu Asp Met Arg Ser Met Asp Phe Lys Ser Asn Ser Ala
            180                 185                 190

Val Ala Trp Ser Asn Lys Ser Asp Phe Ala Cys Ala Asn Ala Phe Asn
        195                 200                 205

Asn Ser Ile Ile Pro Glu Asp Thr Phe Phe Pro Ser Pro Glu Ser Ser
    210                 215                 220

Cys Asp Val Lys Leu Val Glu Lys Ser Phe Glu Thr Asp Thr Asn Leu
225                 230                 235                 240

Asn Phe Gln Asn Leu Ser Val Ile Gly Phe Arg Ile Leu Leu Leu Lys
                245                 250                 255

Val Ala Gly Phe Asn Leu Leu Met Thr Leu Arg Leu Trp Ser Ser
            260                 265                 270

<210> SEQ ID NO 78
<211> LENGTH: 310
<212> TYPE: PRT
<213> ORGANISM: Homo sapiens

<400> SEQUENCE: 78

Met Asp Thr Trp Leu Val Cys Trp Ala Ile Phe Ser Leu Leu Lys Ala
1               5                   10                  15

Gly Leu Thr Glu Pro Glu Val Thr Gln Thr Pro Ser His Gln Val Thr
            20                  25                  30

Gln Met Gly Gln Glu Val Ile Leu Arg Cys Val Pro Ile Ser Asn His
        35                  40                  45

Leu Tyr Phe Tyr Trp Tyr Arg Gln Ile Leu Gly Gln Lys Val Glu Phe
    50                  55                  60

Leu Val Ser Phe Tyr Asn Asn Glu Ile Ser Glu Lys Ser Glu Ile Phe
65                  70                  75                  80

Asp Asp Gln Phe Ser Val Glu Arg Pro Asp Gly Ser Asn Phe Thr Leu
                85                  90                  95

Lys Ile Arg Ser Thr Lys Leu Glu Asp Ser Ala Met Tyr Phe Cys Ala
            100                 105                 110

Ser Ser Gln Tyr Thr Gly Glu Leu Phe Phe Gly Glu Gly Ser Arg Leu
        115                 120                 125

Thr Val Leu Glu Asp Leu Lys Asn Val Phe Pro Pro Glu Val Ala Val
    130                 135                 140

Phe Glu Pro Ser Glu Ala Glu Ile Ser His Thr Gln Lys Ala Thr Leu
145                 150                 155                 160

Val Cys Leu Ala Thr Gly Phe Tyr Pro Asp His Val Glu Leu Ser Trp
                165                 170                 175

Trp Val Asn Gly Lys Glu Val His Ser Gly Val Ser Thr Asp Pro Gln
            180                 185                 190

Pro Leu Lys Glu Gln Pro Ala Leu Asn Asp Ser Arg Tyr Cys Leu Ser
        195                 200                 205

Ser Arg Leu Arg Val Ser Ala Thr Phe Trp Gln Asn Pro Arg Asn His
```

```
              210                 215                 220
Phe Arg Cys Gln Val Gln Phe Tyr Gly Leu Ser Glu Asn Asp Glu Trp
225                 230                 235                 240

Thr Gln Asp Arg Ala Lys Pro Val Thr Gln Ile Val Ser Ala Glu Ala
                245                 250                 255

Trp Gly Arg Ala Asp Cys Gly Phe Thr Ser Glu Ser Tyr Gln Gln Gly
                260                 265                 270

Val Leu Ser Ala Thr Ile Leu Tyr Glu Ile Leu Gly Lys Ala Thr
                275                 280                 285

Leu Tyr Ala Val Leu Val Ser Ala Leu Val Leu Met Ala Met Val Lys
                290                 295                 300

Arg Lys Asp Ser Arg Gly
305                 310

<210> SEQ ID NO 79
<211> LENGTH: 270
<212> TYPE: PRT
<213> ORGANISM: Homo sapiens

<400> SEQUENCE: 79

Met Lys Ser Leu Arg Val Leu Leu Val Ile Leu Trp Leu Gln Leu Ser
1               5                   10                  15

Trp Val Trp Ser Gln Gln Lys Glu Val Glu Gln Asn Ser Gly Pro Leu
                20                  25                  30

Ser Val Pro Glu Gly Ala Ile Ala Ser Leu Asn Cys Thr Tyr Ser Asp
                35                  40                  45

Arg Gly Ser Gln Ser Phe Phe Trp Tyr Arg Gln Tyr Ser Gly Lys Ser
            50                  55                  60

Pro Glu Leu Ile Met Phe Ile Tyr Ser Asn Gly Asp Lys Glu Asp Gly
65                  70                  75                  80

Arg Phe Thr Ala Gln Leu Asn Lys Ala Ser Gln Tyr Val Ser Leu Leu
                85                  90                  95

Ile Arg Asp Ser Gln Pro Ser Asp Ser Ala Thr Tyr Leu Cys Ala Val
                100                 105                 110

Asn Gly Gly Asp Met Arg Phe Gly Ala Gly Thr Arg Leu Thr Val Lys
                115                 120                 125

Pro Asn Ile Gln Asn Pro Asp Pro Ala Val Tyr Gln Leu Arg Asp Ser
130                 135                 140

Lys Ser Ser Asp Lys Ser Val Cys Leu Phe Thr Asp Phe Asp Ser Gln
145                 150                 155                 160

Thr Asn Val Ser Gln Ser Lys Asp Ser Asp Val Tyr Ile Thr Asp Lys
                165                 170                 175

Thr Val Leu Asp Met Arg Ser Met Asp Phe Lys Ser Asn Ser Ala Val
                180                 185                 190

Ala Trp Ser Asn Lys Ser Asp Phe Ala Cys Ala Asn Ala Phe Asn Asn
                195                 200                 205

Ser Ile Ile Pro Glu Asp Thr Phe Phe Pro Ser Pro Glu Ser Ser Cys
                210                 215                 220

Asp Val Lys Leu Val Glu Lys Ser Phe Glu Thr Asp Thr Asn Leu Asn
225                 230                 235                 240

Phe Gln Asn Leu Ser Val Ile Gly Phe Arg Ile Leu Leu Leu Lys Val
                245                 250                 255

Ala Gly Phe Asn Leu Leu Met Thr Leu Arg Leu Trp Ser Ser
                260                 265                 270
```

<210> SEQ ID NO 80
<211> LENGTH: 311
<212> TYPE: PRT
<213> ORGANISM: Homo sapiens

<400> SEQUENCE: 80

Met Asp Thr Trp Leu Val Cys Trp Ala Ile Phe Ser Leu Leu Lys Ala
1               5                   10                  15

Gly Leu Thr Glu Pro Glu Val Thr Gln Thr Pro Ser His Gln Val Thr
            20                  25                  30

Gln Met Gly Gln Glu Val Ile Leu Arg Cys Val Pro Ile Ser Asn His
        35                  40                  45

Leu Tyr Phe Tyr Trp Tyr Arg Gln Ile Leu Gly Gln Lys Val Glu Phe
    50                  55                  60

Leu Val Ser Phe Tyr Asn Asn Glu Ile Ser Glu Lys Ser Glu Ile Phe
65                  70                  75                  80

Asp Asp Gln Phe Ser Val Glu Arg Pro Asp Gly Ser Asn Phe Thr Leu
                85                  90                  95

Lys Ile Arg Ser Thr Lys Leu Glu Asp Ser Ala Met Tyr Phe Cys Ala
            100                 105                 110

Ser Ser Gly Gln Gly Ala Leu Glu Gln Tyr Phe Gly Pro Gly Thr Arg
        115                 120                 125

Leu Thr Val Thr Glu Asp Leu Lys Asn Val Phe Pro Pro Glu Val Ala
    130                 135                 140

Val Phe Glu Pro Ser Glu Ala Glu Ile Ser His Thr Gln Lys Ala Thr
145                 150                 155                 160

Leu Val Cys Leu Ala Thr Gly Phe Tyr Pro Asp His Val Glu Leu Ser
                165                 170                 175

Trp Trp Val Asn Gly Lys Glu Val His Ser Gly Val Ser Thr Asp Pro
            180                 185                 190

Gln Pro Leu Lys Glu Gln Pro Ala Leu Asn Asp Ser Arg Tyr Cys Leu
        195                 200                 205

Ser Ser Arg Leu Arg Val Ser Ala Thr Phe Trp Gln Asn Pro Arg Asn
    210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Glu Ser Tyr Gln Gln
            260                 265                 270

Gly Val Leu Ser Ala Thr Ile Leu Tyr Glu Ile Leu Leu Gly Lys Ala
        275                 280                 285

Thr Leu Tyr Ala Val Leu Val Ser Ala Leu Val Leu Met Ala Met Val
    290                 295                 300

Lys Arg Lys Asp Ser Arg Gly
305                 310

<210> SEQ ID NO 81
<211> LENGTH: 281
<212> TYPE: PRT
<213> ORGANISM: Homo sapiens

<400> SEQUENCE: 81

Met Ala Met Leu Leu Gly Ala Ser Val Leu Ile Leu Trp Leu Gln Pro
1               5                   10                  15

-continued

```
Asp Trp Val Asn Ser Gln Gln Lys Asn Asp Gln Gln Val Lys Gln
                20                  25                  30

Asn Ser Pro Ser Leu Ser Val Gln Glu Gly Arg Ile Ser Ile Leu Asn
        35                  40                  45

Cys Asp Tyr Thr Asn Ser Met Phe Asp Tyr Phe Leu Trp Tyr Lys Lys
 50                  55                  60

Tyr Pro Ala Glu Gly Pro Thr Phe Leu Ile Ser Ile Ser Ser Ile Lys
 65                  70                  75                  80

Asp Lys Asn Glu Asp Gly Arg Phe Thr Val Phe Leu Asn Lys Ser Ala
                85                  90                  95

Lys His Leu Ser Leu His Ile Val Pro Ser Gln Pro Gly Asp Ser Ala
                100                 105                 110

Val Tyr Phe Cys Ala Ala Ser Gly Leu Tyr Asn Gln Gly Gly Lys Leu
                115                 120                 125

Ile Phe Gly Gln Gly Thr Glu Leu Ser Val Lys Pro Asn Ile Gln Asn
                130                 135                 140

Pro Asp Pro Ala Val Tyr Gln Leu Arg Asp Ser Lys Ser Ser Asp Lys
145                 150                 155                 160

Ser Val Cys Leu Phe Thr Asp Phe Asp Ser Gln Thr Asn Val Ser Gln
                165                 170                 175

Ser Lys Asp Ser Asp Val Tyr Ile Thr Asp Lys Thr Val Leu Asp Met
                180                 185                 190

Arg Ser Met Asp Phe Lys Ser Asn Ser Ala Val Ala Trp Ser Asn Lys
                195                 200                 205

Ser Asp Phe Ala Cys Ala Asn Ala Phe Asn Asn Ser Ile Ile Pro Glu
                210                 215                 220

Asp Thr Phe Phe Pro Ser Pro Glu Ser Ser Cys Asp Val Lys Leu Val
225                 230                 235                 240

Glu Lys Ser Phe Glu Thr Asp Thr Asn Leu Asn Phe Gln Asn Leu Ser
                245                 250                 255

Val Ile Gly Phe Arg Ile Leu Leu Leu Lys Val Ala Gly Phe Asn Leu
                260                 265                 270

Leu Met Thr Leu Arg Leu Trp Ser Ser
                275                 280

<210> SEQ ID NO 82
<211> LENGTH: 311
<212> TYPE: PRT
<213> ORGANISM: Homo sapiens

<400> SEQUENCE: 82

Met Gly Cys Arg Leu Leu Cys Cys Val Val Phe Cys Leu Leu Gln Ala
1                5                  10                  15

Gly Pro Leu Asp Thr Ala Val Ser Gln Thr Pro Lys Tyr Leu Val Thr
                20                  25                  30

Gln Met Gly Asn Asp Lys Ser Ile Lys Cys Glu Gln Asn Leu Gly His
                35                  40                  45

Asp Thr Met Tyr Trp Tyr Lys Gln Asp Ser Lys Lys Phe Leu Lys Ile
        50                  55                  60

Met Phe Ser Tyr Asn Asn Lys Glu Leu Ile Ile Asn Glu Thr Val Pro
 65                  70                  75                  80

Asn Arg Phe Ser Pro Lys Ser Pro Asp Lys Ala His Leu Asn Leu His
                85                  90                  95

Ile Asn Ser Leu Glu Leu Gly Asp Ser Ala Val Tyr Phe Cys Ala Ser
                100                 105                 110
```

```
Ser Leu Gly Asp Arg Gly Tyr Glu Gln Tyr Phe Gly Pro Gly Thr Arg
        115                 120                 125

Leu Thr Val Thr Glu Asp Leu Lys Asn Val Phe Pro Pro Glu Val Ala
    130                 135                 140

Val Phe Glu Pro Ser Glu Ala Glu Ile Ser His Thr Gln Lys Ala Thr
145                 150                 155                 160

Leu Val Cys Leu Ala Thr Gly Phe Tyr Pro Asp His Val Glu Leu Ser
                165                 170                 175

Trp Trp Val Asn Gly Lys Glu Val His Ser Gly Val Ser Thr Asp Pro
            180                 185                 190

Gln Pro Leu Lys Glu Gln Pro Ala Leu Asn Asp Ser Arg Tyr Cys Leu
        195                 200                 205

Ser Ser Arg Leu Arg Val Ser Ala Thr Phe Trp Gln Asn Pro Arg Asn
    210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Glu Ser Tyr Gln Gln
            260                 265                 270

Gly Val Leu Ser Ala Thr Ile Leu Tyr Glu Ile Leu Leu Gly Lys Ala
        275                 280                 285

Thr Leu Tyr Ala Val Leu Val Ser Ala Leu Val Leu Met Ala Met Val
    290                 295                 300

Lys Arg Lys Asp Ser Arg Gly
305                 310

<210> SEQ ID NO 83
<211> LENGTH: 272
<212> TYPE: PRT
<213> ORGANISM: Homo sapiens

<400> SEQUENCE: 83

Met Lys Thr Phe Ala Gly Phe Ser Phe Leu Phe Leu Trp Leu Gln Leu
1               5                   10                  15

Asp Cys Met Ser Arg Gly Glu Asp Val Glu Gln Ser Leu Phe Leu Ser
                20                  25                  30

Val Arg Glu Gly Asp Ser Ser Val Ile Asn Cys Thr Tyr Thr Asp Ser
            35                  40                  45

Ser Ser Thr Tyr Leu Tyr Trp Tyr Lys Gln Glu Pro Gly Ala Gly Leu
        50                  55                  60

Gln Leu Leu Thr Tyr Ile Phe Ser Asn Met Asp Met Lys Gln Asp Gln
65                  70                  75                  80

Arg Leu Thr Val Leu Leu Asn Lys Lys Asp Lys His Leu Ser Leu Arg
                85                  90                  95

Ile Ala Asp Thr Gln Thr Gly Asp Ser Ala Ile Tyr Phe Cys Ala Glu
            100                 105                 110

Ile Asn Asn Asn Ala Arg Leu Met Phe Gly Asp Gly Thr Gln Leu Val
        115                 120                 125

Val Lys Pro Asn Ile Gln Asn Pro Asp Pro Ala Val Tyr Gln Leu Arg
    130                 135                 140

Asp Ser Lys Ser Ser Asp Lys Ser Val Cys Leu Phe Thr Asp Phe Asp
145                 150                 155                 160

Ser Gln Thr Asn Val Ser Gln Ser Lys Asp Ser Asp Val Tyr Ile Thr
```

```
                165                 170                 175
Asp Lys Thr Val Leu Asp Met Arg Ser Met Asp Phe Lys Ser Asn Ser
            180                 185                 190

Ala Val Ala Trp Ser Asn Lys Ser Asp Phe Ala Cys Ala Asn Ala Phe
            195                 200                 205

Asn Asn Ser Ile Ile Pro Glu Asp Thr Phe Phe Pro Ser Pro Glu Ser
        210                 215                 220

Ser Cys Asp Val Lys Leu Val Glu Lys Ser Phe Glu Thr Asp Thr Asn
225                 230                 235                 240

Leu Asn Phe Gln Asn Leu Ser Val Ile Gly Phe Arg Ile Leu Leu Leu
                245                 250                 255

Lys Val Ala Gly Phe Asn Leu Leu Met Thr Leu Arg Leu Trp Ser Ser
            260                 265                 270

<210> SEQ ID NO 84
<211> LENGTH: 320
<212> TYPE: PRT
<213> ORGANISM: Homo sapiens

<400> SEQUENCE: 84

Met Leu Ser Pro Asp Leu Pro Asp Ser Ala Trp Asn Thr Arg Leu Leu
1               5                   10                  15

Cys His Val Met Leu Cys Leu Leu Gly Ala Val Ser Val Ala Ala Gly
            20                  25                  30

Val Ile Gln Ser Pro Arg His Leu Ile Lys Glu Lys Arg Glu Thr Ala
        35                  40                  45

Thr Leu Lys Cys Tyr Pro Ile Pro Arg His Asp Thr Val Tyr Trp Tyr
    50                  55                  60

Gln Gln Gly Pro Gly Gln Asp Pro Gln Phe Leu Ile Ser Phe Tyr Glu
65                  70                  75                  80

Lys Met Gln Ser Asp Lys Gly Ser Ile Pro Asp Arg Phe Ser Ala Gln
                85                  90                  95

Gln Phe Ser Asp Tyr His Ser Glu Leu Asn Met Ser Ser Leu Glu Leu
            100                 105                 110

Gly Asp Ser Ala Leu Tyr Phe Cys Ala Ser Ser Pro Asp Gln Asn
        115                 120                 125

Thr Gln Tyr Phe Gly Pro Gly Thr Arg Leu Thr Val Leu Glu Asp Leu
    130                 135                 140

Lys Asn Val Phe Pro Pro Glu Val Ala Val Phe Glu Pro Ser Glu Ala
145                 150                 155                 160

Glu Ile Ser His Thr Gln Lys Ala Thr Leu Val Cys Leu Ala Thr Gly
                165                 170                 175

Phe Tyr Pro Asp His Val Glu Leu Ser Trp Trp Val Asn Gly Lys Glu
            180                 185                 190

Val His Ser Gly Val Ser Thr Asp Pro Gln Pro Leu Lys Glu Gln Pro
        195                 200                 205

Ala Leu Asn Asp Ser Arg Tyr Cys Leu Ser Ser Arg Leu Arg Val Ser
    210                 215                 220

Ala Thr Phe Trp Gln Asn Pro Arg Asn His Phe Arg Cys Gln Val Gln
225                 230                 235                 240

Phe Tyr Gly Leu Ser Glu Asn Asp Glu Trp Thr Gln Asp Arg Ala Lys
                245                 250                 255

Pro Val Thr Gln Ile Val Ser Ala Glu Ala Trp Gly Arg Ala Asp Cys
            260                 265                 270
```

Gly Phe Thr Ser Glu Ser Tyr Gln Gln Gly Val Leu Ser Ala Thr Ile
            275                 280                 285

Leu Tyr Glu Ile Leu Leu Gly Lys Ala Thr Leu Tyr Ala Val Leu Val
290                 295                 300

Ser Ala Leu Val Leu Met Ala Met Val Lys Arg Lys Asp Ser Arg Gly
305                 310                 315                 320

<210> SEQ ID NO 85
<211> LENGTH: 273
<212> TYPE: PRT
<213> ORGANISM: Homo sapiens

<400> SEQUENCE: 85

Met Leu Leu Leu Leu Val Pro Val Leu Glu Val Ile Phe Thr Leu Gly
1               5                   10                  15

Gly Thr Arg Ala Gln Ser Val Thr Gln Leu Gly Ser His Val Ser Val
            20                  25                  30

Ser Glu Gly Ala Leu Val Leu Leu Arg Cys Asn Tyr Ser Ser Ser Val
        35                  40                  45

Pro Pro Tyr Leu Phe Trp Tyr Val Gln Tyr Pro Asn Gln Gly Leu Gln
    50                  55                  60

Leu Leu Leu Lys Tyr Thr Thr Gly Ala Thr Leu Val Lys Gly Ile Asn
65                  70                  75                  80

Gly Phe Glu Ala Glu Phe Lys Lys Ser Glu Thr Ser Phe His Leu Thr
                85                  90                  95

Lys Pro Ser Ala His Met Ser Asp Ala Ala Glu Tyr Phe Cys Ala Val
            100                 105                 110

Arg Ile Phe Gly Asn Glu Lys Leu Thr Phe Gly Thr Gly Thr Arg Leu
        115                 120                 125

Thr Ile Ile Pro Asn Ile Gln Asn Pro Asp Pro Ala Val Tyr Gln Leu
    130                 135                 140

Arg Asp Ser Lys Ser Ser Asp Lys Ser Val Cys Leu Phe Thr Asp Phe
145                 150                 155                 160

Asp Ser Gln Thr Asn Val Ser Gln Ser Lys Asp Ser Asp Val Tyr Ile
                165                 170                 175

Thr Asp Lys Thr Val Leu Asp Met Arg Ser Met Asp Phe Lys Ser Asn
            180                 185                 190

Ser Ala Val Ala Trp Ser Asn Lys Ser Asp Phe Ala Cys Ala Asn Ala
        195                 200                 205

Phe Asn Asn Ser Ile Ile Pro Glu Asp Thr Phe Phe Pro Ser Pro Glu
    210                 215                 220

Ser Ser Cys Asp Val Lys Leu Val Glu Lys Ser Phe Glu Thr Asp Thr
225                 230                 235                 240

Asn Leu Asn Phe Gln Asn Leu Ser Val Ile Gly Phe Arg Ile Leu Leu
                245                 250                 255

Leu Lys Val Ala Gly Phe Asn Leu Leu Met Thr Leu Arg Leu Trp Ser
            260                 265                 270

Ser

<210> SEQ ID NO 86
<211> LENGTH: 312
<212> TYPE: PRT
<213> ORGANISM: Homo sapiens

<400> SEQUENCE: 86

Met Gly Ile Arg Leu Leu Cys Arg Val Ala Phe Cys Phe Leu Ala Val

```
                1               5                   10                  15
            Gly Leu Val Asp Val Lys Val Thr Gln Ser Ser Arg Tyr Leu Val Lys
                            20                  25                  30

Arg Thr Gly Glu Lys Val Phe Leu Glu Cys Val Gln Asp Met Asp His
                            35                  40                  45

Glu Asn Met Phe Trp Tyr Arg Gln Asp Pro Gly Leu Gly Leu Arg Leu
                    50                  55                  60

Ile Tyr Phe Ser Tyr Asp Val Lys Met Lys Lys Gly Asp Ile Pro
             65                  70                  75                  80

Glu Gly Tyr Ser Val Ser Arg Glu Lys Lys Glu Arg Phe Ser Leu Ile
                                85                  90                  95

Leu Glu Ser Ala Ser Thr Asn Gln Thr Ser Met Tyr Leu Cys Ala Ser
                            100                 105                 110

Ser Leu Met Gly Glu Leu Thr Gly Glu Leu Phe Phe Gly Glu Gly Ser
                            115                 120                 125

Arg Leu Thr Val Leu Glu Asp Leu Lys Asn Val Phe Pro Pro Glu Val
                    130                 135                 140

Ala Val Phe Glu Pro Ser Glu Ala Glu Ile Ser His Thr Gln Lys Ala
            145                 150                 155                 160

Thr Leu Val Cys Leu Ala Thr Gly Phe Tyr Pro Asp His Val Glu Leu
                            165                 170                 175

Ser Trp Trp Val Asn Gly Lys Glu Val His Ser Gly Val Ser Thr Asp
                            180                 185                 190

Pro Gln Pro Leu Lys Glu Gln Pro Ala Leu Asn Asp Ser Arg Tyr Cys
                    195                 200                 205

Leu Ser Ser Arg Leu Arg Val Ser Ala Thr Phe Trp Gln Asn Pro Arg
            210                 215                 220

Asn His Phe Arg Cys Gln Val Gln Phe Tyr Gly Leu Ser Glu Asn Asp
            225                 230                 235                 240

Glu Trp Thr Gln Asp Arg Ala Lys Pro Val Thr Gln Ile Val Ser Ala
                            245                 250                 255

Glu Ala Trp Gly Arg Ala Asp Cys Gly Phe Thr Ser Glu Ser Tyr Gln
                            260                 265                 270

Gln Gly Val Leu Ser Ala Thr Ile Leu Tyr Glu Ile Leu Leu Gly Lys
                            275                 280                 285

Ala Thr Leu Tyr Ala Val Leu Val Ser Ala Leu Val Leu Met Ala Met
                    290                 295                 300

Val Lys Arg Lys Asp Ser Arg Gly
            305                 310

<210> SEQ ID NO 87
<211> LENGTH: 276
<212> TYPE: PRT
<213> ORGANISM: Homo sapiens

<400> SEQUENCE: 87

Met Met Lys Ser Leu Arg Val Leu Leu Val Ile Leu Trp Leu Gln Leu
            1               5                   10                  15

Ser Trp Val Trp Ser Gln Gln Lys Glu Val Glu Gln Asp Pro Gly Pro
                            20                  25                  30

Leu Ser Val Pro Glu Gly Ala Ile Val Ser Leu Asn Cys Thr Tyr Ser
                            35                  40                  45

Asn Ser Ala Phe Gln Tyr Phe Met Trp Tyr Arg Gln Tyr Ser Arg Lys
                    50                  55                  60
```

Gly Pro Glu Leu Leu Met Tyr Thr Tyr Ser Ser Gly Asn Lys Glu Asp
65                  70                  75                  80

Gly Arg Phe Thr Ala Gln Val Asp Lys Ser Ser Lys Tyr Ile Ser Leu
                85                  90                  95

Phe Ile Arg Asp Ser Gln Pro Ser Asp Ser Ala Thr Tyr Leu Cys Ala
            100                 105                 110

Met Met Gly Asp Thr Gly Thr Ala Ser Lys Leu Thr Phe Gly Thr Gly
            115                 120                 125

Thr Arg Leu Gln Val Thr Leu Asp Ile Gln Asn Pro Asp Pro Ala Val
        130                 135                 140

Tyr Gln Leu Arg Asp Ser Lys Ser Ser Asp Lys Ser Val Cys Leu Phe
145                 150                 155                 160

Thr Asp Phe Asp Ser Gln Thr Asn Val Ser Gln Ser Lys Asp Ser Asp
            165                 170                 175

Val Tyr Ile Thr Asp Lys Thr Val Leu Asp Met Arg Ser Met Asp Phe
            180                 185                 190

Lys Ser Asn Ser Ala Val Ala Trp Ser Asn Lys Ser Asp Phe Ala Cys
        195                 200                 205

Ala Asn Ala Phe Asn Asn Ser Ile Ile Pro Glu Asp Thr Phe Phe Pro
210                 215                 220

Ser Pro Glu Ser Ser Cys Asp Val Lys Leu Val Glu Lys Ser Phe Glu
225                 230                 235                 240

Thr Asp Thr Asn Leu Asn Phe Gln Asn Leu Ser Val Ile Gly Phe Arg
            245                 250                 255

Ile Leu Leu Leu Lys Val Ala Gly Phe Asn Leu Leu Met Thr Leu Arg
        260                 265                 270

Leu Trp Ser Ser
        275

<210> SEQ ID NO 88
<211> LENGTH: 309
<212> TYPE: PRT
<213> ORGANISM: Homo sapiens

<400> SEQUENCE: 88

Met Gly Ile Arg Leu Leu Cys Arg Val Ala Phe Cys Phe Leu Ala Val
1               5                   10                  15

Gly Leu Val Asp Val Lys Val Thr Gln Ser Ser Arg Tyr Leu Val Lys
            20                  25                  30

Arg Thr Gly Glu Lys Val Phe Leu Glu Cys Val Gln Asp Met Asp His
        35                  40                  45

Glu Asn Met Phe Trp Tyr Arg Gln Asp Pro Gly Leu Gly Leu Arg Leu
50                  55                  60

Ile Tyr Phe Ser Tyr Asp Val Lys Met Lys Glu Lys Gly Asp Ile Pro
65                  70                  75                  80

Glu Gly Tyr Ser Val Ser Arg Glu Lys Lys Glu Arg Phe Ser Leu Ile
            85                  90                  95

Leu Glu Ser Ala Ser Thr Asn Gln Thr Ser Met Tyr Leu Cys Ala Ser
            100                 105                 110

Ser Phe Gly Gly Tyr Glu Gln Tyr Phe Gly Pro Gly Thr Arg Leu Thr
        115                 120                 125

Val Thr Glu Asp Leu Lys Asn Val Phe Pro Pro Glu Val Ala Val Phe
        130                 135                 140

Glu Pro Ser Glu Ala Glu Ile Ser His Thr Gln Lys Ala Thr Leu Val
145                 150                 155                 160

```
Cys Leu Ala Thr Gly Phe Tyr Pro Asp His Val Glu Leu Ser Trp Trp
                165                 170                 175

Val Asn Gly Lys Glu Val His Ser Gly Val Ser Thr Asp Pro Gln Pro
            180                 185                 190

Leu Lys Glu Gln Pro Ala Leu Asn Asp Ser Arg Tyr Cys Leu Ser Ser
        195                 200                 205

Arg Leu Arg Val Ser Ala Thr Phe Trp Gln Asn Pro Arg Asn His Phe
    210                 215                 220

Arg Cys Gln Val Gln Phe Tyr Gly Leu Ser Glu Asn Asp Glu Trp Thr
225                 230                 235                 240

Gln Asp Arg Ala Lys Pro Val Thr Gln Ile Val Ser Ala Glu Ala Trp
                245                 250                 255

Gly Arg Ala Asp Cys Gly Phe Thr Ser Glu Ser Tyr Gln Gln Gly Val
            260                 265                 270

Leu Ser Ala Thr Ile Leu Tyr Glu Ile Leu Leu Gly Lys Ala Thr Leu
        275                 280                 285

Tyr Ala Val Leu Val Ser Ala Leu Val Leu Met Ala Met Val Lys Arg
    290                 295                 300

Lys Asp Ser Arg Gly
305

<210> SEQ ID NO 89
<211> LENGTH: 144
<212> TYPE: PRT
<213> ORGANISM: Homo sapiens

<400> SEQUENCE: 89

Val Lys Pro Asn Ile Gln Asn Pro Asp Pro Ala Val Tyr Gln Leu Arg
1               5                   10                  15

Asp Ser Lys Ser Ser Asp Lys Ser Val Cys Leu Phe Thr Asp Phe Asp
            20                  25                  30

Ser Gln Thr Asn Val Ser Gln Ser Lys Asp Ser Asp Val Tyr Ile Thr
        35                  40                  45

Asp Lys Thr Val Leu Asp Met Arg Ser Met Asp Phe Lys Ser Asn Ser
    50                  55                  60

Ala Val Ala Trp Ser Asn Lys Ser Asp Phe Ala Cys Ala Asn Ala Phe
65                  70                  75                  80

Asn Asn Ser Ile Ile Pro Glu Asp Thr Phe Phe Pro Ser Pro Glu Ser
                85                  90                  95

Ser Cys Asp Val Lys Leu Val Glu Lys Ser Phe Glu Thr Asp Thr Asn
            100                 105                 110

Leu Asn Phe Gln Asn Leu Ser Val Ile Gly Phe Arg Ile Leu Leu Leu
        115                 120                 125

Lys Val Ala Gly Phe Asn Leu Leu Met Thr Leu Arg Leu Trp Ser Ser
    130                 135                 140

<210> SEQ ID NO 90
<211> LENGTH: 307
<212> TYPE: PRT
<213> ORGANISM: Homo sapiens

<400> SEQUENCE: 90

Met Leu Cys Ser Leu Leu Ala Leu Leu Leu Gly Thr Phe Phe Gly Val
1               5                   10                  15

Arg Ser Gln Thr Ile His Gln Trp Pro Ala Thr Leu Val Gln Pro Val
            20                  25                  30
```

Gly Ser Pro Leu Ser Leu Glu Cys Thr Val Glu Gly Thr Ser Asn Pro
            35                  40                  45

Asn Leu Tyr Trp Tyr Arg Gln Ala Ala Gly Arg Gly Leu Gln Leu Leu
        50                  55                  60

Phe Tyr Ser Val Gly Ile Gly Gln Ile Ser Ser Glu Val Pro Gln Asn
65                  70                  75                  80

Leu Ser Ala Ser Arg Pro Gln Asp Arg Gln Phe Ile Leu Ser Ser Lys
                85                  90                  95

Lys Leu Leu Leu Ser Asp Ser Gly Phe Tyr Leu Cys Ala Trp Ser Gly
            100                 105                 110

Leu Val Ala Glu Gln Phe Phe Gly Pro Gly Thr Arg Leu Thr Val Leu
        115                 120                 125

Glu Asp Leu Lys Asn Val Phe Pro Pro Glu Val Ala Val Phe Glu Pro
130                 135                 140

Ser Glu Ala Glu Ile Ser His Thr Gln Lys Ala Thr Leu Val Cys Leu
145                 150                 155                 160

Ala Thr Gly Phe Tyr Pro Asp His Val Glu Leu Ser Trp Trp Val Asn
                165                 170                 175

Gly Lys Glu Val His Ser Gly Val Ser Thr Asp Pro Gln Pro Leu Lys
            180                 185                 190

Glu Gln Pro Ala Leu Asn Asp Ser Arg Tyr Cys Leu Ser Ser Arg Leu
        195                 200                 205

Arg Val Ser Ala Thr Phe Trp Gln Asn Pro Arg Asn His Phe Arg Cys
210                 215                 220

Gln Val Gln Phe Tyr Gly Leu Ser Glu Asn Asp Glu Trp Thr Gln Asp
225                 230                 235                 240

Arg Ala Lys Pro Val Thr Gln Ile Val Ser Ala Glu Ala Trp Gly Arg
                245                 250                 255

Ala Asp Cys Gly Phe Thr Ser Glu Ser Tyr Gln Gln Gly Val Leu Ser
            260                 265                 270

Ala Thr Ile Leu Tyr Glu Ile Leu Leu Gly Lys Ala Thr Leu Tyr Ala
        275                 280                 285

Val Leu Val Ser Ala Leu Val Leu Met Ala Met Val Lys Arg Lys Asp
        290                 295                 300

Ser Arg Gly
305

<210> SEQ ID NO 91
<211> LENGTH: 4445
<212> TYPE: DNA
<213> ORGANISM: Artificial Sequence
<220> FEATURE:
<223> OTHER INFORMATION: PTE WPRE

<400> SEQUENCE: 91
tgaaagaccc cacctgtagg tttggcaagc tagcttaagt aacgccattt tgcaaggcat     60
ggaaaataca taactgagaa tagagaagtt cagatcaagg ttaggaacag agagacagca    120
gaatatgggc caaacaggat atctgtggta agcagttcct gccccggctc agggccaaga    180
acagatggtc cccagatgcg gtcccgccct cagcagtttc tagagaacca tcagatgttt    240
ccagggtgcc ccaaggacct gaaaatgacc ctgtgcctta tttgaactaa ccaatcagtt    300
cgcttctcgc ttctgttcgc gcgcttctgc tccccgagct caataaaaga gcccacaacc    360
cctcactcag cggccgcccc gggtcgacgc taccaccatg gactcttgga ccttctgctg    420

-continued

```
cgtgagcctg tgcatcctgg tggccaagca cacagacgcc ggcgtgatcc agtcccctag    480
gcacgaggtg accgagatgg gccaggaggt gacactgcgc tgtaagccaa tctctggcca    540
caacagcctg ttttggtata gggagaccat gatgcgcggc ctggagctgc tgatctactt    600
caataacaat gtgcccatcg acgattccgg catgcctgag gatcggtttt ctgccaagat    660
gcccaatgcc agcttctcca cactgaagat ccagcctagc gagccaagag actccgccgt    720 gtattttgc cctctagcc caggcagcac cgatacacag tacttcggac caggaaccag    780
gctgacagtg ctggaggacc tgaagaacgt gttcccccct gaggtggccg tgtttgagcc    840
ctctgaggcc gagatcagcc acacccagaa ggccaccctg gtgtgcctgg caaccggctt    900
ctatcctgat cacgtggagc tgtcctggtg ggtgaacggc aaggaggtgc acagcggcgt    960
gtccacagac ccacagcccc tgaaggagca gccagccctg aatgatagcc ggtattgcct   1020
gtcctctcgg ctgagagtgt ccgccacctt ttggcagaac ccccggaatc acttcagatg   1080
tcaggtgcag ttttacgcc tgtccgagaa cgatgagtgg acccaggacc gggcaagcc    1140 tgtgacacag atcgtgtctg ccgaggcatg ggaagagca actgtggct tcacctctga   1200 gagctaccag cagggcgtgc tgagcgccac catcctgtat gagatcctgc tgggcaaggc   1260
cacactgtac gccgtcctgg tctccgctct ggtgctgatg caatggtca aagaaaaga   1320 tagtcgggga cgggccaaga gatctggcag cggcgccacc aatttcagcc tgctgaaaca   1380
ggccggcgac gtgaaagaga accctggccc catggagaag aatcccctgg ctgccccct   1440 gctgatcctg tggtttcacc tggactgcgt gtcctctatc ctgaatgtgg aacagagccc   1500
acagagcctg cacgtgcagg agggcgactc caccaacttc acatgctctt ttcctagctc   1560
caacttctac gccctgcact ggtacagaaa ggagaccgca aagtccccag aggccctgtt   1620
cgtgatgaca ctgaacggcg atgagaagaa aagggccgc atcagcgcca ccctgaatac   1680
aaaggagggc tactcctatc tgtacatcaa gggctcccag cctgaggact ctgccaccta   1740
tctgtgcgcc ctgtacaaca taacgatat gcggtttggc gccggcacca gactgacagt   1800
gaagccaaac atccagaatc cagaccccgc cgtgtatcag ctgcgggaca gcaagtctag   1860
cgataagagc gtgtgcctgt tcaccgactt tgattctcag acaaacgtga gccagtccaa   1920
ggacagcgac gtgtacatca ccgacaagac agtgctggat atgagaagca tggacttcaa   1980
gtctaacagc gccgtggcct ggtccaataa gtctgatttc gcctgcgcca atgcctttaa   2040
taactccatc atccccgagg ataccttctt tccttctcca gagtcctctt gtgacgtgaa   2100
gctggtggag aagtctttcg agaccgatac aaacctgaat tttcagaacc tgagcgtgat   2160
cggcttcagg atcctgctgc tgaaggtggc cggctttaat ctgctgatga ccctgaggct   2220
gtggagctcc cgggccaaga gatctggcag cggcgagggc agaggcagcc tgctgacctg   2280
cggcgacgtg aggagaacc ccggcccat gcgcccgaga ctgtggcttc tgctcgccgc   2340
gcaactgact gtcctgcacg gaaacagcgt gctgcagcag acaccggcct acatcaaagt   2400
gcagaccaac aagatggtca tgctgtcctg cgaggccaag atttccctct ccaacatgcg   2460
gatctattgg ttgcggcaga gacaggcgcc ttcctcggac tcccaccatg agttcttggc   2520
cctgtgggac tccgccaagg aactattca cggcgaagaa gtggaacagg agaagatcgc   2580
cgtgtttcgc gatgcctccc gctttatact gaatctgacc tccgtgaagc cgaagatag   2640 cgggatctac ttttgcatga ttgtgggctc acccgaactg accttcggga agggcactca   2700
gctgagcgtg gtggacttcc tccccactac cgccaacccc actaagaagt caaccctgaa   2760
gaagcgggtt tgcagactcc cacggccgga aacgcagaag ggtccgctgt gttccccgat   2820
```

```
caccctgggg ctccttgtgg ctggagtgct ggtccttctg gtgtcccttg gcgtcgccat    2880
tcacctctgc tgccggagaa ggagggccag actgaggttc atgaagcagc ctcagggaga    2940
ggggatcagt ggcactttcg tgccacaatg cctccatggc tactattcca acaccaccac    3000
ctcgcaaaag ctgctgaacc cctggatcct gaaaacccgg ccaagagat ctggcagcgg     3060 ccagtgcacc aactacgccc tgctgaagct ggccggcgac gtggagagca ccccggccc     3120 catggcgctt cccgtgaccg cactcctgtt gccccttgcc ctgctgttgc acgccgcacg    3180
accttcccaa ttccgggtgt cccctctgga tcgcacctgg aacctcgggg aaacggtgga    3240
gctcaagtgt caagtcctcc tgtcgaaccc gaccagcgga tgcagctggc tgttccagcc    3300
gagaggagct gccgcctcac ccaccttcct cctgtacttg agccagaaca gccgaaggc    3360 cgctgagggt ctggacaccc agcgcttctc gggcaaacgg ctgggagaca cttttgtgct    3420
gactctctcc gacttccggc gggagaacga gggctactac ttctgctctg cgctctccaa    3480
ttcaatcatg tacttctcac acttcgtgcc ggtgttcctg cctgccaagc ccaccactac    3540
tccggcaccc agacctccaa ctcccgctcc caccatcgcg tcccaacccc tttcgctgcg    3600
ccctgaagcg tgtcggcctg ctgctggagg agccgtgcat acccgcggtc tggacttcgc    3660
gtgcgacatc tacatttggg cccctttggc tggcacctgt ggagtgctgc tcctgtccct    3720
tgtgatcacc ctgtactgca accaccggaa taggcggaga gtctgcaagt gtccgcggcc    3780
tgtcgtgaag tcaggagata agccgagcct gtccgcacgc tacgtgtgaa ccggtccgca    3840
gtctgacgta cgcgtaatca acctctggat tacaaaattt gtgaaagatt gactggtatt    3900
cttaactatg ttgctccttt tacgctatgt ggatacgctg ctttaatgcc tttgtatcat    3960
gctattgctt cccgtatggc tttcattttc tcctccttgt ataaatcctg gttgctgtct    4020
ctttatgagg agttgtggcc cgttgtcagg caacgtggcg tggtgtgcac tgtgtttgct    4080
gacgcaaccc ccactggttg ggcattgcc accacctgtc agctccttc cgggactttc     4140 gctttccccc tccctattgc cacggcggaa ctcatcgccg cctgccttgc ccgctgctgg    4200 acagggctc ggctgttggg cactgacaat tccgtggtgt tgtcggggaa gctgacgtcc     4260
tttccatggc tgctcgcctg tgttgccacc tggattctgc gcgggacgtc cttctgctac    4320
gtcccttcgg ccctcaatcc agcggaccttc ccttcccgcg gcctgctgcc ggctctgcgg   4380
cctcttccgc gtcttcgcct cgccctcag acgagtcgga tctcccttg ggccgcctcc     4440 ccgcc                                                                4445
```

<210> SEQ ID NO 92
<211> LENGTH: 4445
<212> TYPE: DNA
<213> ORGANISM: Artificial Sequence
<220> FEATURE:
<223> OTHER INFORMATION: TPE WPRE

<400> SEQUENCE: 92

```
tgaaagaccc cacctgtagg tttggcaagc tagcttaagt aacgccattt tgcaaggcat     60
ggaaaataca taactgagaa tagagaagtt cagatcaagg ttaggaacag agagacagca    120
gaatatgggc caaacaggat atctgtggta agcagttcct gccccggctc agggccaaga    180
acagatggtc cccagatgcg gtcccgccct cagcagtttc tagagaacca tcagatgttt    240
ccagggtgcc ccaaggacct gaaaatgacc ctgtgcctta tttgaactaa ccaatcagtt    300
cgcttctcgc ttctgttcgc gcgcttctgc tccccgagct caataaaaga gcccacaacc    360
```

```
cctcactcag cggccgcccc gggtcgacgc taccaccatg gactcttgga ccttctgctg    420
cgtgagcctg tgcatcctgg tggccaagca cacagacgcc ggcgtgatcc agtccctag     480 gcacgaggtg accgagatgg gccaggaggt gacactgcgc tgtaagccaa tctctggcca    540
caacagcctg ttttggtata gggagaccat gatgcgcggc ctggagctgc tgatctactt    600
caataacaat gtgcccatcg acgattccgg catgcctgag gatcggtttt ctgccaagat    660
gcccaatgcc agcttctcca cactgaagat ccagcctagc gagccaagag actccgccgt    720 gtattttgc gcctctagcc caggcagcac cgatacacag tacttcggac caggaaccag     780
gctgacagtg ctggaggacc tgaagaacgt gttccccct gaggtggccg tgtttgagcc     840
ctctgaggcc gagatcagcc acacccagaa ggccaccctg tgtgcctgg caaccggctt     900 ctatcctgat cacgtggagc tgtcctggtg ggtgaacggc aaggaggtgc acagcggcgt    960
gtccacagac ccacagcccc tgaaggagca gccagccctg aatgatagcc ggtattgcct   1020
gtcctctcgg ctgagagtgt ccgccacctt ttggcagaac ccccggaatc acttcagatg   1080
tcaggtgcag ttttacggcc tgtccagaa cgatgagtgg acccaggacc gggccaagcc    1140
tgtgacacag atcgtgtctg ccgaggcatg gggaagagca gactgtggct tcacctctga   1200
gagctaccag cagggcgtgc tgagcgccac catcctgtat gagatcctgc tgggcaaggc   1260
cacactgtac gccgtcctgg tctccgctct ggtgctgatg caatggtca aagaaaaga    1320 tagtcgggga cgggccaaga gatctggcag cggcgagggc agaggcagcc tgctgacctg   1380
cggcgacgtg gaggagaacc ccggcccat ggagaagaat cccctggctg cccccctgct    1440
gatcctgtgg tttcacctgg actgcgtgtc ctctatcctg aatgtggaac agagcccaca   1500
gagcctgcac gtgcaggagg gcgactccac caacttcaca tgctcttttc ctagctccaa   1560
cttctacgcc ctgcactggt acagaaagga gaccgcaaag tccccagagg ccctgttcgt   1620
gatgacactg aacggcgatg agaagaagaa gggccgcatc agcgccaccc tgaatacaaa   1680
ggagggctac tcctatctgt acatcaaggg ctcccagcct gaggactctg ccacctatct   1740
gtgcgccctg tacaacaata cgatatgcg gtttggcgcc ggcaccagac tgacagtgaa    1800
gccaaacatc cagaatccag acccccgccgt gtatcagctg cgggacagca agtctagcga    1860
taagagcgtg tgcctgttca ccgactttga ttctcagaca aacgtgagcc agtccaagga   1920
cagcgacgtg tacatcaccg acaagacagt gctggatatg agaagcatgg acttcaagtc   1980
taacagcgcc gtggcctggt ccaataagtc tgatttcgcc tgcgccaatg cctttaataa   2040
ctccatcatc cccgaggata ccttctttcc ttctccagag tcctcttgtg acgtgaagct   2100
ggtggagaag tctttcgaga ccgatacaaa cctgaatttt cagaacctga gcgtgatcgg   2160
cttcaggatc ctgctgctga aggtggccgg ctttaatctg ctgatgaccc tgaggctgtg   2220
gagctcccgg gccaagagat ctggcagcgg cgccaccaat ttcagcctgc tgaaacaggc   2280
cggcgacgtg gaagagaacc ctggccccat gcgcccgaga ctgtggcttc tgctcgccgc   2340
gcaactgact gtcctgcacg aaacagcgt gctgcagcag acaccggcct acatcaaagt    2400
gcagaccaac aagatggtca tgctgtcctg cgaggccaag atttccctct ccaacatgcg   2460
gatctattgg ttgcggcaga acaggcgcc ttcctcggac tcccaccatg agttcttggc    2520
cctgtgggac tccgccaagg gaactattca cggcgaagaa gtgaacagg agaagatcgc    2580 cgtgtttcgc gatgcctccc gctttatact gaatctgacc tccgtgaagc ccgaagatag   2640
cgggatctac ttttgcatga ttgtgggctc acccgaactg accttcggga agggcactca   2700
gctgagcgtg gtggacttcc tccccactac cgcccaaccc actaagaagt caaccctgaa   2760
```

```
gaagcgggtt tgcagactcc cacggccgga aacgcagaag ggtccgctgt gttcccgat     2820 caccctgggg ctccttgtgg ctggagtgct ggtccttctg gtgtcccttg gcgtcgccat    2880
tcacctctgc tgccggagaa ggagggccag actgaggttc atgaagcagc ctcagggaga    2940
ggggatcagt ggcactttcg tgccacaatg cctccatggc tactattcca acaccaccac    3000
ctcgcaaaag ctgctgaacc cctggatcct gaaacccgg gccaagagat ctggcagcgg     3060
ccagtgcacc aactacgccc tgctgaagct ggccggcgac gtgagagca ccccggccc      3120 catggcgctt cccgtgaccg cactcctgtt gccccttgcc ctgctgttgc acgccgcacg    3180
accttcccaa ttccgggtgt cccctctgga tcgcacctgg aacctcgggg aaacggtgga    3240
gctcaagtgt caagtcctcc tgtcgaaccc gaccagcgga tgcagctggc tgttccagcc    3300
gagaggagct gccgcctcac ccaccttcct cctgtacttg agccagaaca agccgaaggc    3360
cgctgagggt ctggacaccc agcgcttctc gggcaaacgg ctgggagaca cttttgtgct    3420
gactctctcc gacttccggc gggagaacga gggctactac ttctgctctg cgctctccaa    3480
ttcaatcatg tacttctcac acttcgtgcc ggtgttcctg cctgccaagc ccaccactac    3540
tccggcaccc agacctccaa ctcccgctcc caccatcgcg tcccaacccc tttcgctgcg    3600
ccctgaagcg tgtcggcctg ctgctggagg agccgtgcat acccgcggtc tggacttcgc    3660
gtgcgacatc tacatttggg ccccttggc tggcacctgt ggagtgctgc tcctgtccct     3720
tgtgatcacc ctgtactgca accaccggaa taggcggaga gtctgcaagt gtccgcggcc    3780
tgtcgtgaag tcaggagata agccgagcct gtccgcacgc tacgtgtgaa ccggtccgca    3840
gtctgacgta cgcgtaatca acctctggat tacaaaattt gtgaaagatt gactggtatt    3900
cttaactatg ttgctccttt tacgctatgt ggatacgctg cttttaatgcc tttgtatcat    3960 gctattgctt cccgtatggc tttcattttc tcctccttgt ataaatcctg gttgctgtct    4020
ctttatgagg agttgtggcc cgttgtcagg caacgtggcg tggtgtgcac tgtgtttgct    4080
gacgcaaccc ccactggttg gggcattgcc accacctgtc agctcctttc cgggactttc    4140
gctttccccc tccctattgc cacggcggaa ctcatcgccg cctgccttgc ccgctgctgg    4200 acagggctc ggctgttggg cactgacaat tccgtggtgt tgtcggggaa gctgacgtcc     4260
tttccatggc tgctcgcctg tgttgccacc tggattctgc gcgggacgtc cttctgctac    4320
gtcccttcgg ccctcaatcc agcggacctt ccttcccgcg gcctgctgcc ggctctgcgg    4380
cctcttccgc gtcttcgcct tcgccctcag acgagtcgga tctcctttg gccgcctcc     4440 ccgcc                                                                4445
```

<210> SEQ ID NO 93
<211> LENGTH: 4430
<212> TYPE: DNA
<213> ORGANISM: Artificial Sequence
<220> FEATURE:
<223> OTHER INFORMATION: PTE fn WPRE

<400> SEQUENCE: 93

```
tgaaagaccc cacctgtagg tttggcaagc tagcttaagt aacgccattt tgcaaggcat      60
ggaaaataca taactgagaa tagagaagtt cagatcaagg ttaggaacag agagacagca     120
gaatatgggc caaacaggat atctgtggta agcagttcct gccccggctc agggccaaga    180
acagatggtc cccagatgcg gtcccgccct cagcagtttc tagagaacca tcagatgttt    240
ccagggtgcc ccaaggacct gaaaatgacc ctgtgcctta tttgaactaa ccaatcagtt    300
```

```
cgcttctcgc ttctgttcgc gcgcttctgc tccccgagct caataaaaga gcccacaacc    360
cctcactcag cggccgcccc gggtcgacgc taccaccatg gactcttgga ccttctgctg    420
cgtgagcctg tgcatcctgg tggccaagca cacagacgcc ggcgtgatcc agtccctag    480 gcacgaggtg accgagatgg gccaggaggt gacactgcgc tgtaagccaa tctctggcca    540
caacagcctg ttttggtata gggagaccat gatgcgcggc ctggagctgc tgatctactt    600
caataacaat gtgcccatcg acgattccgg catgcctgag gatcggtttt ctgccaagat    660
gcccaatgcc agcttctcca cactgaagat ccagcctagc gagccaagag actccgccgt    720 gtattttgc gcctctagcc caggcagcac cgatacacag tacttcggac caggaaccag    780
gctgacagtg ctggaggacc tgaagaacgt gttccccct gaggtggccg tgtttgagcc    840
ctctgaggcc gagatcagcc acacccagaa ggccaccctg gtgtgcctgg caaccggctt    900
ctatcctgat cacgtggagc tgtcctggtg ggtgaacggc aaggaggtgc acagcggcgt    960
gtccacagac ccacagcccc tgaaggagca gccagccctg aatgatagcc ggtattgcct   1020
gtcctctcgg ctgagagtgt ccgccacctt ttggcagaac cccggaatc acttcagatg   1080 tcaggtgcag ttttacggcc tgtccgagaa cgatgagtgg acccaggacc gggccaagcc   1140
tgtgacacag atcgtgtctg ccgaggcatg ggaagagca gactgtggct tcacctctga   1200
gagctaccag cagggcgtgc tgagcgccac catcctgtat gagatcctgc tgggcaaggc   1260
cacactgtac gccgtcctgg tctccgctct ggtgctgatg caatggtca aagaaaaga   1320 tagtcgggga tctggcagcg gcgccaccaa tttcagcctg ctgaaacagg ccggcgacgt   1380
ggaagagaac cctggcccca tggagaagaa tccctggct ccccctgc tgatcctgtg   1440 gtttcacctg gactgcgtgt cctctatcct gaatgtggaa cagagcccac agagcctgca   1500
cgtgcaggag ggcgactcca ccaacttcac atgctcttt cctagctcca acttctacgc   1560
cctgcactgg tacagaaagg agaccgcaaa gtccccagag gccctgttcg tgatgacact   1620
gaacggcgat gagaagaaga agggccgcat cagcgccacc ctgaatacaa aggagggcta   1680
ctcctatctg tacatcaagg gctcccagcc tgaggactct gccacctatc tgtgcgccct   1740
gtacaacaat aacgatatgc ggtttggcgc cggcaccaga ctgacagtga agccaaacat   1800
ccagaatcca gaccccgccg tgtatcagct gcgggacagc aagtctagcg ataagagcgt   1860
gtgcctgttc accgactttg attctcagac aaacgtgagc cagtccaagg acagcgacgt   1920
gtacatcacc gacaagacag tgctggatat gagaagcatg gacttcaagt ctaacagcgc   1980
cgtggcctgg tccaataagt ctgatttcgc ctgcgccaat gcctttaata actccatcat   2040
ccccgaggat accttctttc cttctccaga gtcctcttgt gacgtgaagc tggtggagaa   2100
gtctttcgag accgatacaa acctgaattt tcagaacctg agcgtgatcg gcttcaggat   2160
cctgctgctg aaggtggccg gctttaatct gctgatgacc ctgaggctgt ggagctccg   2220 ggccaagaga ggcagcggcg agggcagagg cagcctgctg acctgcggcg acgtggagga   2280 gaacccggc cccatgcgcc cgagactgtg gcttctgctc gccgcgcaac tgactgtcct   2340
gcacggaaac agcgtgctgc agcagacacc ggcctacatc aaagtgcaga ccaacaagat   2400
ggtcatgctg tcctgcgagg ccaagatttc cctctccaac atgcggatct attggttgcg   2460
gcagagacag gcgccttcct cggactccca ccatgagttc ttggccctgt gggactccgc   2520
caagggaact attcacgcg aagaagtgga acaggagaag atcgccgtgt tcgcgatgc   2580 ctcccgcttt atactgaatc tgacctccgt gaagcccgaa gatagcggga tctacttttg   2640
catgattgtg ggctcacccg aactgacctt cgggaagggc actcagctga gcgtggtgga   2700
```

```
cttcctcccc actaccgccc aacccactaa gaagtcaacc ctgaagaagc gggtttgcag    2760
actcccacgg ccggaaacgc agaagggtcc gctgtgttcc ccgatcaccc tggggctcct    2820
tgtggctgga gtgctggtcc ttctggtgtc ccttggcgtc gccattcacc tctgctgccg    2880
gagaaggagg gccagactga ggttcatgaa gcagcctcag ggagagggga tcagtggcac    2940
tttcgtgcca caatgcctcc atggctacta ttccaacacc accacctcgc aaaagctgct    3000
gaacccctgg atcctgaaaa cccgggccaa gagatctggc agcggccagt gcaccaacta    3060
cgccctgctg aagctggccg cgacgtgga gagcaacccc ggccccatgg cgcttcccgt    3120
gaccgcactc ctgttgcccc ttgccctgct gttgcacgcc gcgaccttc cccaattccg    3180 ggtgtcccct ctggatcgca cctggaacct cggggaaacg gtggagctca agtgtcaagt    3240
cctcctgtcg aacccgacca gcggatgcag ctggctgttc cagccgagag agctgccgc    3300 ctcacccacc ttcctcctgt acttgagcca gaacaagccg aaggccgctg agggtctgga    3360
cacccagcgc ttctcgggca aacgctggg agacactttt gtgctgactc tctccgactt    3420
ccggcgggag aacgagggct actacttctg ctctgcgctc tccaattcaa tcatgtactt    3480
ctcacacttc gtgccggtgt tcctgcctgc caagcccacc actactccgg cacccagacc    3540
tccaactccc gctcccacca tcgcgtccca acccctttcg ctgcgccctg aagcgtgtcg    3600
gcctgctgct ggaggagccg tgcataccc cggtctggac ttcgcgtgcg acatctacat    3660
ttgggcccct ttggctggca cctgtggagt gctgctcctg tcccttgtga tcaccctgta    3720
ctgcaaccac cggaataggc ggagagtctg caagtgtccg cggcctgtcg tgaagtcagg    3780
agataagccg agcctgtccg cacgctacgt gtgaaccggt ccgcagtctg acgtacgcgt    3840
aatcaacctc tggattacaa aatttgtgaa agattgactg gtattcttaa ctatgttgct    3900
ccttttacgc tatgtggata cgctgcttta atgcctttgt atcatgctat tgcttcccgt    3960
atggctttca ttttctcctc cttgtataaa tcctggttgc tgtctcttta tgaggagttg    4020
tggcccgttg tcaggcaacg tggcgtggtg tgcactgtgt ttgctgacgc aaccccact    4080 ggttggggca ttgccaccac ctgtcagctc ctttccggga cttttgctttt ccccctccct    4140 attgccacgg cggaactcat cgccgcctgc cttgcccgct gctggacagg gctcggctg    4200 ttgggcactg acaattccgt ggtgttgtcg gggaagctga cgtcctttcc atggctgctc    4260
gcctgtgttg ccacctggat tctgcgcggg acgtccttct gctacgtccc ttcggccctc    4320
aatccagcgg accttccttc ccgcggcctg ctgccggctc tgcggcctct tccgcgtctt    4380
cgccttcgcc ctcagacgag tcggatctcc ctttgggccg cctccccgcc               4430
```

<210> SEQ ID NO 94
<211> LENGTH: 4445
<212> TYPE: DNA
<213> ORGANISM: Artificial Sequence
<220> FEATURE:
<223> OTHER INFORMATION: PTE CD8 TCR WPRE

<400> SEQUENCE: 94

```
tgaaagaccc cacctgtagg tttggcaagc tagcttaagt aacgccattt tgcaaggcat     60
ggaaaataca taactgagaa tagagaagtt cagatcaagg ttaggaacag agagacagca    120
gaatatgggc caaacaggat atctgtggta agcagttcct gccccggctc agggccaaga    180
acagatggtc cccagatgcg gtcccgccct cagcagtttc tagagaacca tcagatgttt    240
ccagggtgcc ccaaggacct gaaaatgacc ctgtgcctta tttgaactaa ccaatcagtt    300
```

```
cgcttctcgc ttctgttcgc gcgcttctgc tccccgagct caataaaaga gcccacaacc      360
cctcactcag cggccgcccc gggtcgacgc taccaccatg cgcccgagac tgtggcttct      420
gctcgccgcg caactgactg tcctgcacgg aaacagcgtg ctgcagcaga caccggccta      480
catcaaagtg cagaccaaca agatggtcat gctgtcctgc gaggccaaga tttccctctc      540
caacatgcgg atctattggt tgcggcagag acaggcgcct tcctcggact cccaccatga      600
gttcttggcc ctgtgggact ccgccaaggg aactattcac ggcgaagaag tggaacagga      660
gaagatcgcc gtgtttcgcg atgcctcccg ctttatactg aatctgacct ccgtgaagcc      720
cgaagatagc gggatctact tttgcatgat tgtgggctca cccgaactga ccttcgggaa      780
gggcactcag ctgagcgtgg tggacttcct ccccactacc gcccaaccca ctaagaagtc      840
aaccctgaag aagcgggttt gcagactccc acggccggaa acgcagaagg gtccgctgtg      900
ttccccgatc accctggggc tccttgtggc tggagtgctg gtccttctgg tgtcccttgg      960
cgtcgccatt cacctctgct gccggagaag gagggccaga ctgaggttca tgaagcagcc     1020
tcagggagag gggatcagtg gcactttcgt gccacaatgc tccatggct actattccaa      1080 caccaccacc tcgcaaaagc tgctgaaccc ctggatcctg aaaacccggg ccaagagatc     1140
tggcagcggg gccaccaatt tcagcctgct gaaacaggcc ggcgacgtgg aagagaaccc     1200
tggccccatg gcgcttcccg tgaccgcact cctgttgccc cttgccctgc tgttgcacgc     1260
cgcacgacct tcccaattcc gggtgtcccc tctggatcgc acctggaacc tcggggaaac     1320
ggtggagctc aagtgtcaag tcctcctgtc gaacccgacc agcggatgca ctggctgtt      1380 ccagccgaga ggagctgccg cctcacccac cttcctcctg tacttgagcc agaacaagcc     1440
gaaggccgct gagggtctgg acacccagcg cttctcgggc aaacggctgg agacacttt      1500 tgtgctgact ctctccgact ccggcgggga aacagagggc tactacttct gctctgcgct     1560
ctccaattca atcatgtact tctcacactt cgtgccggtg ttcctgcctg ccaagcccac     1620
cactactccg gcacccagac ctccaactcc cgctcccacc atcgcgtccc aacccctttc     1680
gctgcgccct gaagcgtgtc ggcctgctgc tggaggagcc gtgcataccc gcggtctgga     1740
cttcgcgtgc gacatctaca tttgggcccc tttggctggc acctgtggag tgctgctcct     1800
gtcccttgtg atcaccctgt actgcaacca ccggaatagg cggagagtct gcaagtgtcc     1860
gcggcctgtc gtgaagtcag gagataagcc gagcctgtcc gcacgctacg tgcgggccaa     1920
gagatctggc agcggcgagg gcagaggcag cctgctgacc tgcggcgacg tggaggagaa     1980
ccccggcccc atggactctt ggaccttctg ctgcgtgagc ctgtgcatcc tggtggccaa     2040
gcacacagac gccggcgtga tccagtcccc taggcacgag gtgaccgaga tgggccagga     2100
ggtgacactg cgctgtaagc caatctctgg ccacaacagc ctgttttggt atagggagac     2160
catgatgcgc ggcctggagc tgctgatcta cttcaataac aatgtgccca tcgacgattc     2220
cggcatgcct gaggatcggt tttctgccaa gatgcccaat gccagcttct ccacactgaa     2280
gatccagcct agcgagccaa gagactccgc cgtgtatttt tgcgcctcta gcccaggcag     2340
caccgataca cagtacttcg gaccaggaac caggctgaca gtgctggagg acctgaagaa     2400
cgtgttcccc cctgaggtgg ccgtgtttga gccctgag gccagatca gccacaccca       2460 gaaggccacc ctggtgtgcc tggcaaccgg cttctatcct gatcacgtgg agctgtcctg     2520
gtgggtgaac ggcaaggagg tgcacagcgg cgtgtccaca gacccacagc ccctgaagga     2580
gcagccagcc ctgaatgata gccggtattg cctgtcctct cggctgagag tgtccgccac     2640
cttttggcag aaccccccgga atcacttcag atgtcaggtg cagttttacg gcctgtccga     2700
```

```
gaacgatgag tggacccagg accgggccaa gcctgtgaca cagatcgtgt ctgccgaggc    2760
atggggaaga gcagactgtg gcttcacctc tgagagctac cagcagggcg tgctgagcgc    2820
caccatcctg tatgagatcc tgctgggcaa ggccacactg tacgccgtcc tggtctccgc    2880
tctggtgctg atggcaatgg tcaaaagaaa agatagtcgg ggacgggcca agagatctgg    2940
cagcggccag tgcaccaact acgccctgct gaagctggcc ggcgacgtgg agagcaaccc    3000
cggccccatg gagaagaatc ccctggctgc ccccctgctg atcctgtggt ttcacctgga    3060
ctgcgtgtcc tctatcctga atgtggaaca gagcccacag agcctgcacg tgcaggaggg    3120
cgactccacc aacttcacat gctcttttcc tagctccaac ttctacgccc tgcactggta    3180
cagaaaggag accgcaaagt ccccagaggc cctgttcgtg atgacactga acggcgatga    3240
gaagaagaag ggccgcatca cgccaccct gaatacaaag gagggctact cctatctgta    3300
catcaagggc tcccagcctg aggactctgc cacctatctg tgcgccctgt acaacaataa    3360
cgatatgcgt tttggcgccg gcaccagact gacagtgaag ccaaacatcc agaatccaga    3420
ccccgccgtg tatcagctgc gggacagcaa gtctagcgat aagagcgtgt gcctgttcac    3480
cgactttgat tctcagacaa acgtgagcca gtccaaggac agcgacgtgt acatcaccga    3540
caagacagtg ctggatatga gaagcatgga cttcaagtct aacagcgccg tggcctggtc    3600
caataagtct gatttcgcct gcgccaatgc ctttaataac tccatcatcc ccgaggatac    3660
cttctttcct tctccagagt cctcttgtga cgtgaagctg gtggagaagt ctttcgagac    3720
cgatacaaac ctgaattttc agaacctgag cgtgatcggc ttcaggatcc tgctgctgaa    3780
ggtggccggc tttaatctgc tgatgaccct gaggctgtgg agctcctgaa ccggtccgca    3840
gtctgacgta cgcgtaatca acctctggat tacaaaattt gtgaaagatt gactggtatt    3900
cttaactatg ttgctccttt tacgctatgt ggatacgctg ctttaatgcc tttgtatcat    3960
gctattgctt cccgtatggc tttcattttc tcctccttgt ataaatcctg gttgctgtct    4020
ctttatgagg agttgtggcc cgttgtcagg caacgtggcg tggtgtgcac tgtgtttgct    4080
gacgcaaccc ccactggttg ggcattgcca ccacctgtc agctcctttc cgggactttc    4140
gctttccccc tccctattgc cacggcggaa ctcatcgccg cctgccttgc ccgctgctgg    4200 acagggctc ggctgttggg cactgacaat tccgtggtgt tgtcggggaa gctgacgtcc    4260
tttccatggc tgctcgcctg tgttgccacc tggattctgc gcgggacgtc cttctgctac    4320
gtcccttcgg ccctcaatcc agcggacctt ccttcccgcg gcctgctgcc ggctctgcgg    4380
cctcttccgc gtcttcgcct tcgccctcag acgagtcgga tctccctttg ggccgcctcc    4440
ccgcc                                                                4445
```

<210> SEQ ID NO 95
<211> LENGTH: 2849
<212> TYPE: DNA
<213> ORGANISM: Artificial Sequence
<220> FEATURE:
<223> OTHER INFORMATION: R11KE WPRE

<400> SEQUENCE: 95

```
tgaaagaccc cacctgtagg tttggcaagc tagcttaagt aacgccattt tgcaaggcat      60
ggaaaataca taactgagaa tagagaagtt cagatcaagg ttaggaacag agagacagca     120
gaatatgggc caaacaggat atctgtggta agcagttcct gccccggctc agggccaaga    180
acagatggtc cccagatgcg gtcccgccct cagcagtttc tagagaacca tcagatgttt    240
```

| | |
|---|---|
| ccagggtgcc ccaaggacct gaaaatgacc ctgtgcctta tttgaactaa ccaatcagtt | 300 |
| cgcttctcgc ttctgttcgc gcgcttctgc tccccgagct caataaaaga gcccacaacc | 360 |
| cctcactcag cggccgcccc gggtcgacgc taccaccatg gactcttgga ccttctgctg | 420 |
| cgtgagcctg tgcatcctgg tggccaagca cacagacgcc ggcgtgatcc agtcccctag | 480 |
| gcacgaggtg accgagatgg gccaggaggt gacactgcgc tgtaagccaa tctctggcca | 540 |
| caacagcctg ttttggtata gggagaccat gatgcgcggc ctggagctgc tgatctactt | 600 |
| caataacaat gtgcccatcg acgattccgg catgcctgag gatcggtttt ctgccaagat | 660 |
| gcccaatgcc agcttctcca cactgaagat ccagcctagc gagccaagag actccgccgt | 720 |
| gtattttgc gcctctagcc caggcagcac cgatacacag tacttcggac caggaaccag | 780 |
| gctgacagtg ctggaggacc tgaagaacgt gttccccct gaggtggccg tgtttgagcc | 840 |
| ctctgaggcc gagatcagcc acacccagaa ggccaccctg gtgtgcctgg caaccggctt | 900 |
| ctatcctgat cacgtggagc tgtcctggtg ggtgaacggc aaggaggtgc acagcggcgt | 960 |
| gtccacagac ccacagcccc tgaaggagca gcagccctg aatgatagcc ggtattgcct | 1020 |
| gtcctctcgg ctgagagtgt ccgccacctt ttggcagaac ccccggaatc acttcagatg | 1080 |
| tcaggtgcag ttttacggcc tgtccagaa cgatgagtgg acccaggacc gggccaagcc | 1140 |
| tgtgacacag atcgtgtctg ccgaggcatg gggaagagca gactgtggct tcacctctga | 1200 |
| gagctaccag cagggcgtgc tgagcgccac catcctgtat gagatcctgc tgggcaaggc | 1260 |
| cacactgtac gccgtcctgg tctccgctct ggtgctgatg gcaatggtca aagaaaaga | 1320 |
| tagtcgggga cggccaaga gatctggcag cggcgccacc aatttcagcc tgctgaaaca | 1380 |
| ggccggcgac gtggaagaga accctggccc catggagaag aatcccctgg ctgcccccct | 1440 |
| gctgatcctg tggtttcacc tggactgcgt gtcctctatc ctgaatgtgg aacagagccc | 1500 |
| acagagcctg cacgtgcagg agggcgactc caccaacttc acatgctctt tcctagctc | 1560 |
| caacttctac gccctgcact ggtacagaaa ggagaccgca aagtcccag aggcctgtt | 1620 |
| cgtgatgaca ctgaacggcg atgagaagaa gaagggccgc atcagcgcca ccctgaatac | 1680 |
| aaaggagggc tactcctatc tgtacatcaa gggctcccag cctgaggact ctgccaccta | 1740 |
| tctgtgcgcc ctgtacaaca ataacgatat gcggtttggc gccggcacca gactgacagt | 1800 |
| gaagccaaac atccagaatc agacccccgc cgtgtatcag ctgcgggaca gcaagtctag | 1860 |
| cgataagagc gtgtgcctgt tcaccgactt tgattctcag acaaacgtga gccagtccaa | 1920 |
| ggacagcgac gtgtacatca ccgacaagac agtgctggat atgagaagca tggacttcaa | 1980 |
| gtctaacagc gccgtggcct ggtccaataa gtctgatttc gcctgcgcca atgccttta | 2040 |
| taactccatc atccccgagg ataccttctt tccttctcca gagtcctctt gtgacgtgaa | 2100 |
| gctggtggag aagtctttcg agaccgatac aaacctgaat tttcagaacc tgagcgtgat | 2160 |
| cggcttcagg atcctgctgc tgaaggtggc cggctttaat ctgctgatga ccctgaggct | 2220 |
| gtggagctcc tgaaccggtc cgcagtctga cgtacgcgta atcaacctct ggattacaaa | 2280 |
| atttgtgaaa gattgactgg tattcttaac tatgttgctc cttttacgct atgtggatac | 2340 |
| gctgctttaa tgcctttgta tcatgctatt gcttcccgta tggctttcat tttctcctcc | 2400 |
| ttgtataaat cctggttgct gtctctttat gaggagttgt ggcccgttgt caggcaacgt | 2460 |
| ggcgtggtgt gcactgtgtt tgctgacgca accccactg gttggggcat gccaccacc | 2520 |
| tgtcagctct tttccgggac tttcgctttc ccctcccta ttgccacggc ggaactcatc | 2580 |
| gccgcctgcc ttgcccgctg ctggacaggg gctcggctgt tgggcactga caattccgtg | 2640 |

| | |
|---|---|
| gtgttgtcgg ggaagctgac gtcctttcca tggctgctcg cctgtgttgc cacctggatt | 2700 |
| ctgcgcggga cgtccttctg ctacgtccct tcggccctca atccagcgga ccttccttcc | 2760 |
| cgcggcctgc tgccggctct gcggcctctt ccgcgtcttc gccttcgccc tcagacgagt | 2820 |
| cggatctccc tttgggccgc ctccccgcc | 2849 |

<210> SEQ ID NO 96
<211> LENGTH: 2531
<212> TYPE: DNA
<213> ORGANISM: Artificial Sequence
<220> FEATURE:
<223> OTHER INFORMATION: CD8 WPRE

<400> SEQUENCE: 96

| | |
|---|---|
| tgaaagaccc cacctgtagg tttggcaagc tagcttaagt aacgccattt tgcaaggcat | 60 |
| ggaaaataca taactgagaa tagagaagtt cagatcaagg ttaggaacag agagacagca | 120 |
| gaatatgggc caaacaggat atctgtggta agcagttcct gccccggctc agggccaaga | 180 |
| acagatggtc cccagatgcg gtcccgccct cagcagtttc tagagaacca tcagatgttt | 240 |
| ccagggtgcc ccaaggacct gaaaatgacc ctgtgcctta tttgaactaa ccaatcagtt | 300 |
| cgcttctcgc ttctgttcgc gcgcttctgc tccccgagct caataaaaga gcccacaacc | 360 |
| cctcactcag cggccgcccc gggtcgacgc taccaccatg cgcccgagac tgtggcttct | 420 |
| gctcgccgcg caactgactg tcctgcacgg aaacagcgtg ctgcagcaga caccggccta | 480 |
| catcaaagtg cagaccaaca agatggtcat gctgtcctgc gaggccaaga tttccctctc | 540 |
| caacatgcgg atctattggt tgcggcagag acaggcgcct tcctcggact cccaccatga | 600 |
| gttcttggcc ctgtgggact ccgccaaggg aactattcac ggcgaagaag tgaacagga | 660 |
| gaagatcgcc gtgtttcgcg atgcctcccg ctttatactg aatctgacct ccgtgaagcc | 720 |
| cgaagatagc gggatctact tttgcatgat tgtgggctca cccgaactga ccttcgggaa | 780 |
| gggcactcag ctgagcgtgg tggacttcct ccccactacc gcccaaccca ctaagaagtc | 840 |
| aaccctgaag aagcgggttt gcagactccc acgccggaa acgcagaagg gtccgctgtg | 900 |
| ttccccgatc accctggggc tccttgtggc tggagtgctg gtccttctgg tgtcccttgg | 960 |
| cgtcgccatt cacctctgct gccgagaag gagggccaga ctgaggttca tgaagcagcc | 1020 |
| tcagggagag gggatcagtg gcactttcgt gccacaatgc tccatggct actattccaa | 1080 |
| caccaccacc tcgcaaaagc tgctgaaccc ctggatcctg aaaacccggg ccaagagatc | 1140 |
| tggcagcggc gccaccaatt tcagcctgct gaaacaggcc ggcgacgtgg aagagaaccc | 1200 |
| tggccccatg gcgcttcccg tgaccgcact cctgttgccc cttgccctgc tgttgcacgc | 1260 |
| cgcacgacct tcccaattcc gggtgtcccc tctggatcgc acctggaacc tcggggaaac | 1320 |
| ggtggagctc aagtgtcaag tcctcctgtc gaacccgacc agcggatgca gctggctgtt | 1380 |
| ccagccgaga ggagctgccg cctcacccac cttcctcctg tacttgagcc agaacaagcc | 1440 |
| gaaggccgct gagggtctgg acacccagcg cttctcgggc aaacggctgg agacactttt | 1500 |
| tgtgctgact ctctccgact ccggcgggga acgagggc tactacttct gctctgcgct | 1560 |
| ctccaattca atcatgtact ctcacactt cgtgccggtg ttcctgcctg ccaagcccac | 1620 |
| cactactccg gcacccagac ctccaactcc cgctcccacc atcgcgtccc aaccccttc | 1680 |
| gctgcgccct gaagcgtgtc ggcctgctgc tggaggagcc gtgcatacc gcggtctgga | 1740 |
| cttcgcgtgc gacatctaca tttgggcccc tttggctggc acctgtggag tgctgctcct | 1800 |

-continued

```
gtcccttgtg atcaccctgt actgcaacca ccggaatagg cggagagtct gcaagtgtcc    1860
gcggcctgtc gtgaagtcag gagataagcc gagcctgtcc gcacgctacg tgtgaaccgg    1920
tccgcagtct gacgtacgcg taatcaacct ctggattaca aaatttgtga aagattgact    1980
ggtattctta actatgttgc tccttttacg ctatgtggat acgctgcttt aatgcctttg    2040
tatcatgcta ttgcttcccg tatggctttc attttctcct ccttgtataa atcctggttg    2100
ctgtctcttt atgaggagtt gtggcccgtt gtcaggcaac gtggcgtggt gtgcactgtg    2160
tttgctgacg caaccccac tggttggggc attgccacca cctgtcagct cctttccggg    2220
actttcgctt tccccctccc tattgccacg cggaactca tcgccgcctg ccttgcccgc    2280
tgctggacag gggctcggct gttgggcact gacaattccg tggtgttgtc ggggaagctg    2340
acgtcctttc catggctgct cgcctgtgtt gccacctgga ttctgcgcgg gacgtccttc    2400
tgctacgtcc cttcggccct caatccagcg gaccttcctt cccgcggcct gctgccggct    2460
ctgcggcctc ttccgcgtct tcgccttcgc cctcagacga gtcggatctc cctttgggcc    2520
gcctccccgc c                                                        2531
```

<210> SEQ ID NO 97
<211> LENGTH: 559
<212> TYPE: PRT
<213> ORGANISM: Artificial Sequence
<220> FEATURE:
<223> OTHER INFORMATION: RD114TR

<400> SEQUENCE: 97

```
Met Lys Leu Pro Thr Gly Met Val Ile Leu Cys Ser Leu Ile Ile Val
1               5                   10                  15

Arg Ala Gly Phe Asp Asp Pro Arg Lys Ala Ile Ala Leu Val Gln Lys
            20                  25                  30

Gln His Gly Lys Pro Cys Glu Cys Ser Gly Gly Gln Val Ser Glu Ala
        35                  40                  45

Pro Pro Asn Ser Ile Gln Gln Val Thr Cys Pro Gly Lys Thr Ala Tyr
    50                  55                  60

Leu Met Thr Asn Gln Lys Trp Lys Cys Arg Val Thr Pro Lys Ile Ser
65                  70                  75                  80

Pro Ser Gly Gly Glu Leu Gln Asn Cys Pro Cys Asn Thr Phe Gln Asp
                85                  90                  95

Ser Met His Ser Ser Cys Tyr Thr Glu Tyr Arg Gln Cys Arg Arg Ile
            100                 105                 110

Asn Lys Thr Tyr Tyr Thr Ala Thr Leu Leu Lys Ile Arg Ser Gly Ser
        115                 120                 125

Leu Asn Glu Val Gln Ile Leu Gln Asn Pro Asn Gln Leu Leu Gln Ser
    130                 135                 140

Pro Cys Arg Gly Ser Ile Asn Gln Pro Val Cys Trp Ser Ala Thr Ala
145                 150                 155                 160

Pro Ile His Ile Ser Asp Gly Gly Gly Pro Leu Asp Thr Lys Arg Val
                165                 170                 175

Trp Thr Val Gln Lys Arg Leu Glu Gln Ile His Lys Ala Met Thr Pro
            180                 185                 190

Glu Leu Gln Tyr His Pro Leu Ala Leu Pro Lys Val Arg Asp Asp Leu
        195                 200                 205

Ser Leu Asp Ala Arg Thr Phe Asp Ile Leu Asn Thr Thr Phe Arg Leu
    210                 215                 220

Leu Gln Met Ser Asn Phe Ser Leu Ala Gln Asp Cys Trp Leu Cys Leu
```

```
              225                 230                 235                 240

Lys Leu Gly Thr Pro Thr Pro Leu Ala Ile Pro Thr Pro Ser Leu Thr
                        245                 250                 255

Tyr Ser Leu Ala Asp Ser Leu Ala Asn Ala Ser Cys Gln Ile Ile Pro
                        260                 265                 270

Pro Leu Leu Val Gln Pro Met Gln Phe Ser Asn Ser Ser Cys Leu Ser
                        275                 280                 285

Ser Pro Phe Ile Asn Asp Thr Glu Gln Ile Asp Leu Gly Ala Val Thr
                        290                 295                 300

Phe Thr Asn Cys Thr Ser Val Ala Asn Val Ser Ser Pro Leu Cys Ala
        305                 310                 315                 320

Leu Asn Gly Ser Val Phe Leu Cys Gly Asn Asn Met Ala Tyr Thr Tyr
                        325                 330                 335

Leu Pro Gln Asn Trp Thr Arg Leu Cys Val Gln Ala Ser Leu Leu Pro
                        340                 345                 350

Asp Ile Asp Ile Asn Pro Gly Asp Glu Pro Val Pro Ile Pro Ala Ile
                        355                 360                 365

Asp His Tyr Ile His Arg Pro Lys Arg Ala Val Gln Phe Ile Pro Leu
                        370                 375                 380

Leu Ala Gly Leu Gly Ile Thr Ala Ala Phe Thr Thr Gly Ala Thr Gly
        385                 390                 395                 400

Leu Gly Val Ser Val Thr Gln Tyr Thr Lys Leu Ser His Gln Leu Ile
                        405                 410                 415

Ser Asp Val Gln Val Leu Ser Gly Thr Ile Gln Asp Leu Gln Asp Gln
                        420                 425                 430

Val Asp Ser Leu Ala Glu Val Val Leu Gln Asn Arg Arg Gly Leu Asp
                        435                 440                 445

Leu Leu Thr Ala Glu Gln Gly Gly Ile Cys Leu Ala Leu Gln Glu Lys
                        450                 455                 460

Cys Cys Phe Tyr Ala Asn Lys Ser Gly Ile Val Arg Asn Lys Ile Arg
        465                 470                 475                 480

Thr Leu Gln Glu Glu Leu Gln Lys Arg Arg Glu Ser Leu Ala Ser Asn
                        485                 490                 495

Pro Leu Trp Thr Gly Leu Gln Gly Phe Leu Pro Tyr Leu Leu Pro Leu
                        500                 505                 510

Leu Gly Pro Leu Leu Thr Leu Leu Leu Ile Leu Thr Ile Gly Pro Cys
                        515                 520                 525

Val Phe Asn Arg Leu Val Gln Phe Val Lys Asp Arg Ile Ser Val Val
                        530                 535                 540

Gln Ala Leu Val Leu Thr Gln Gln Tyr His Gln Leu Lys Pro Leu
        545                 550                 555
```

<210> SEQ ID NO 98
<211> LENGTH: 10
<212> TYPE: PRT
<213> ORGANISM: Homo sapiens

<400> SEQUENCE: 98

```
        Tyr Leu Tyr Asp Ser Glu Thr Lys Asn Ala
        1               5                   10
```

<210> SEQ ID NO 99
<211> LENGTH: 9
<212> TYPE: PRT
<213> ORGANISM: Homo sapiens

```
<400> SEQUENCE: 99

His Leu Met Asp Gln Pro Leu Ser Val
1               5

<210> SEQ ID NO 100
<211> LENGTH: 9
<212> TYPE: PRT
<213> ORGANISM: Homo sapiens

<400> SEQUENCE: 100

Gly Leu Leu Lys Lys Ile Asn Ser Val
1               5

<210> SEQ ID NO 101
<211> LENGTH: 9
<212> TYPE: PRT
<213> ORGANISM: Homo sapiens

<400> SEQUENCE: 101

Phe Leu Val Asp Gly Ser Ser Ala Leu
1               5

<210> SEQ ID NO 102
<211> LENGTH: 10
<212> TYPE: PRT
<213> ORGANISM: Homo sapiens

<400> SEQUENCE: 102

Phe Leu Phe Asp Gly Ser Ala Asn Leu Val
1               5                   10

<210> SEQ ID NO 103
<211> LENGTH: 9
<212> TYPE: PRT
<213> ORGANISM: Homo sapiens

<400> SEQUENCE: 103

Phe Leu Tyr Lys Ile Ile Asp Glu Leu
1               5

<210> SEQ ID NO 104
<211> LENGTH: 11
<212> TYPE: PRT
<213> ORGANISM: Homo sapiens

<400> SEQUENCE: 104

Phe Ile Leu Asp Ser Ala Glu Thr Thr Thr Leu
1               5                   10

<210> SEQ ID NO 105
<211> LENGTH: 9
<212> TYPE: PRT
<213> ORGANISM: Homo sapiens

<400> SEQUENCE: 105

Ser Val Asp Val Ser Pro Pro Lys Val
1               5

<210> SEQ ID NO 106
<211> LENGTH: 8
<212> TYPE: PRT
<213> ORGANISM: Homo sapiens

<400> SEQUENCE: 106
```

Val Ala Asp Lys Ile His Ser Val
1               5

<210> SEQ ID NO 107
<211> LENGTH: 9
<212> TYPE: PRT
<213> ORGANISM: Homo sapiens

<400> SEQUENCE: 107

Ile Val Asp Asp Leu Thr Ile Asn Leu
1               5

<210> SEQ ID NO 108
<211> LENGTH: 9
<212> TYPE: PRT
<213> ORGANISM: Homo sapiens

<400> SEQUENCE: 108

Gly Leu Leu Glu Glu Leu Val Thr Val
1               5

<210> SEQ ID NO 109
<211> LENGTH: 10
<212> TYPE: PRT
<213> ORGANISM: Homo sapiens

<400> SEQUENCE: 109

Thr Leu Asp Gly Ala Ala Val Asn Gln Val
1               5                   10

<210> SEQ ID NO 110
<211> LENGTH: 10
<212> TYPE: PRT
<213> ORGANISM: Homo sapiens

<400> SEQUENCE: 110

Ser Val Leu Glu Lys Glu Ile Tyr Ser Ile
1               5                   10

<210> SEQ ID NO 111
<211> LENGTH: 9
<212> TYPE: PRT
<213> ORGANISM: Homo sapiens

<400> SEQUENCE: 111

Leu Leu Asp Pro Lys Thr Ile Phe Leu
1               5

<210> SEQ ID NO 112
<211> LENGTH: 9
<212> TYPE: PRT
<213> ORGANISM: Homo sapiens

<400> SEQUENCE: 112

Tyr Thr Phe Ser Gly Asp Val Gln Leu
1               5

<210> SEQ ID NO 113
<211> LENGTH: 9
<212> TYPE: PRT
<213> ORGANISM: Homo sapiens

<400> SEQUENCE: 113

Tyr Leu Met Asp Asp Phe Ser Ser Leu
1               5

```
<210> SEQ ID NO 114
<211> LENGTH: 9
<212> TYPE: PRT
<213> ORGANISM: Homo sapiens

<400> SEQUENCE: 114

Lys Val Trp Ser Asp Val Thr Pro Leu
1               5

<210> SEQ ID NO 115
<211> LENGTH: 11
<212> TYPE: PRT
<213> ORGANISM: Homo sapiens

<400> SEQUENCE: 115

Leu Leu Trp Gly His Pro Arg Val Ala Leu Ala
1               5                   10

<210> SEQ ID NO 116
<211> LENGTH: 11
<212> TYPE: PRT
<213> ORGANISM: Homo sapiens

<400> SEQUENCE: 116

Lys Ile Trp Glu Glu Leu Ser Val Leu Glu Val
1               5                   10

<210> SEQ ID NO 117
<211> LENGTH: 9
<212> TYPE: PRT
<213> ORGANISM: Homo sapiens

<400> SEQUENCE: 117

Leu Leu Ile Pro Phe Thr Ile Phe Met
1               5

<210> SEQ ID NO 118
<211> LENGTH: 9
<212> TYPE: PRT
<213> ORGANISM: Homo sapiens

<400> SEQUENCE: 118

Phe Leu Ile Glu Asn Leu Leu Ala Ala
1               5

<210> SEQ ID NO 119
<211> LENGTH: 11
<212> TYPE: PRT
<213> ORGANISM: Homo sapiens

<400> SEQUENCE: 119

Leu Leu Trp Gly His Pro Arg Val Ala Leu Ala
1               5                   10

<210> SEQ ID NO 120
<211> LENGTH: 9
<212> TYPE: PRT
<213> ORGANISM: Homo sapiens

<400> SEQUENCE: 120

Phe Leu Leu Glu Arg Glu Gln Leu Leu
1               5
```

```
<210> SEQ ID NO 121
<211> LENGTH: 9
<212> TYPE: PRT
<213> ORGANISM: Homo sapiens

<400> SEQUENCE: 121

Ser Leu Ala Glu Thr Ile Phe Ile Val
1               5

<210> SEQ ID NO 122
<211> LENGTH: 9
<212> TYPE: PRT
<213> ORGANISM: Homo sapiens

<400> SEQUENCE: 122

Thr Leu Leu Glu Gly Ile Ser Arg Ala
1               5

<210> SEQ ID NO 123
<211> LENGTH: 9
<212> TYPE: PRT
<213> ORGANISM: Homo sapiens

<400> SEQUENCE: 123

Lys Ile Gln Glu Ile Leu Thr Gln Val
1               5

<210> SEQ ID NO 124
<211> LENGTH: 10
<212> TYPE: PRT
<213> ORGANISM: Homo sapiens

<400> SEQUENCE: 124

Val Ile Phe Glu Gly Glu Pro Met Tyr Leu
1               5                   10

<210> SEQ ID NO 125
<211> LENGTH: 9
<212> TYPE: PRT
<213> ORGANISM: Homo sapiens

<400> SEQUENCE: 125

Ser Leu Phe Glu Ser Leu Glu Tyr Leu
1               5

<210> SEQ ID NO 126
<211> LENGTH: 9
<212> TYPE: PRT
<213> ORGANISM: Homo sapiens

<400> SEQUENCE: 126

Ser Leu Leu Asn Gln Pro Lys Ala Val
1               5

<210> SEQ ID NO 127
<211> LENGTH: 9
<212> TYPE: PRT
<213> ORGANISM: Homo sapiens

<400> SEQUENCE: 127

Gly Leu Ala Glu Phe Gln Glu Asn Val
1               5

<210> SEQ ID NO 128
<211> LENGTH: 9
```

```
<212> TYPE: PRT
<213> ORGANISM: Homo sapiens

<400> SEQUENCE: 128

Lys Leu Leu Ala Val Ile His Glu Leu
1               5

<210> SEQ ID NO 129
<211> LENGTH: 9
<212> TYPE: PRT
<213> ORGANISM: Homo sapiens

<400> SEQUENCE: 129

Thr Leu His Asp Gln Val His Leu Leu
1               5

<210> SEQ ID NO 130
<211> LENGTH: 11
<212> TYPE: PRT
<213> ORGANISM: Homo sapiens

<400> SEQUENCE: 130

Thr Leu Tyr Asn Pro Glu Arg Thr Ile Thr Val
1               5                   10

<210> SEQ ID NO 131
<211> LENGTH: 9
<212> TYPE: PRT
<213> ORGANISM: Homo sapiens

<400> SEQUENCE: 131

Lys Leu Gln Glu Lys Ile Gln Glu Leu
1               5

<210> SEQ ID NO 132
<211> LENGTH: 10
<212> TYPE: PRT
<213> ORGANISM: Homo sapiens

<400> SEQUENCE: 132

Ser Val Leu Glu Lys Glu Ile Tyr Ser Ile
1               5                   10

<210> SEQ ID NO 133
<211> LENGTH: 11
<212> TYPE: PRT
<213> ORGANISM: Homo sapiens

<400> SEQUENCE: 133

Arg Val Ile Asp Asp Ser Leu Val Val Gly Val
1               5                   10

<210> SEQ ID NO 134
<211> LENGTH: 9
<212> TYPE: PRT
<213> ORGANISM: Homo sapiens

<400> SEQUENCE: 134

Val Leu Phe Gly Glu Leu Pro Ala Leu
1               5

<210> SEQ ID NO 135
<211> LENGTH: 9
<212> TYPE: PRT
<213> ORGANISM: Homo sapiens
```

<400> SEQUENCE: 135

Gly Leu Val Asp Ile Met Val His Leu
1               5

<210> SEQ ID NO 136
<211> LENGTH: 9
<212> TYPE: PRT
<213> ORGANISM: Homo sapiens

<400> SEQUENCE: 136

Phe Leu Asn Ala Ile Glu Thr Ala Leu
1               5

<210> SEQ ID NO 137
<211> LENGTH: 9
<212> TYPE: PRT
<213> ORGANISM: Homo sapiens

<400> SEQUENCE: 137

Ala Leu Leu Gln Ala Leu Met Glu Leu
1               5

<210> SEQ ID NO 138
<211> LENGTH: 9
<212> TYPE: PRT
<213> ORGANISM: Homo sapiens

<400> SEQUENCE: 138

Ala Leu Ser Ser Ser Gln Ala Glu Val
1               5

<210> SEQ ID NO 139
<211> LENGTH: 11
<212> TYPE: PRT
<213> ORGANISM: Homo sapiens

<400> SEQUENCE: 139

Ser Leu Ile Thr Gly Gln Asp Leu Leu Ser Val
1               5                   10

<210> SEQ ID NO 140
<211> LENGTH: 9
<212> TYPE: PRT
<213> ORGANISM: Homo sapiens

<400> SEQUENCE: 140

Gln Leu Ile Glu Lys Asn Trp Leu Leu
1               5

<210> SEQ ID NO 141
<211> LENGTH: 9
<212> TYPE: PRT
<213> ORGANISM: Homo sapiens

<400> SEQUENCE: 141

Leu Leu Asp Pro Lys Thr Ile Phe Leu
1               5

<210> SEQ ID NO 142
<211> LENGTH: 9
<212> TYPE: PRT
<213> ORGANISM: Homo sapiens

<400> SEQUENCE: 142

Arg Leu His Asp Glu Asn Ile Leu Leu
1               5

<210> SEQ ID NO 143
<211> LENGTH: 9
<212> TYPE: PRT
<213> ORGANISM: Homo sapiens

<400> SEQUENCE: 143

Tyr Thr Phe Ser Gly Asp Val Gln Leu
1               5

<210> SEQ ID NO 144
<211> LENGTH: 9
<212> TYPE: PRT
<213> ORGANISM: Homo sapiens

<400> SEQUENCE: 144

Gly Leu Pro Ser Ala Thr Thr Thr Val
1               5

<210> SEQ ID NO 145
<211> LENGTH: 11
<212> TYPE: PRT
<213> ORGANISM: Homo sapiens

<400> SEQUENCE: 145

Gly Leu Leu Pro Ser Ala Glu Ser Ile Lys Leu
1               5                   10

<210> SEQ ID NO 146
<211> LENGTH: 9
<212> TYPE: PRT
<213> ORGANISM: Homo sapiens

<400> SEQUENCE: 146

Lys Thr Ala Ser Ile Asn Gln Asn Val
1               5

<210> SEQ ID NO 147
<211> LENGTH: 9
<212> TYPE: PRT
<213> ORGANISM: Homo sapiens

<400> SEQUENCE: 147

Ser Leu Leu Gln His Leu Ile Gly Leu
1               5

<210> SEQ ID NO 148
<211> LENGTH: 9
<212> TYPE: PRT
<213> ORGANISM: Homo sapiens

<400> SEQUENCE: 148

Tyr Leu Met Asp Asp Phe Ser Ser Leu
1               5

<210> SEQ ID NO 149
<211> LENGTH: 9
<212> TYPE: PRT
<213> ORGANISM: Homo sapiens

<400> SEQUENCE: 149

Leu Met Tyr Pro Tyr Ile Tyr His Val

```
1               5
```

<210> SEQ ID NO 150
<211> LENGTH: 9
<212> TYPE: PRT
<213> ORGANISM: Homo sapiens

<400> SEQUENCE: 150

```
Lys Val Trp Ser Asp Val Thr Pro Leu
1               5
```

<210> SEQ ID NO 151
<211> LENGTH: 11
<212> TYPE: PRT
<213> ORGANISM: Homo sapiens

<400> SEQUENCE: 151

```
Leu Leu Trp Gly His Pro Arg Val Ala Leu Ala
1               5                   10
```

<210> SEQ ID NO 152
<211> LENGTH: 9
<212> TYPE: PRT
<213> ORGANISM: Homo sapiens

<400> SEQUENCE: 152

```
Val Leu Asp Gly Lys Val Ala Val Val
1               5
```

<210> SEQ ID NO 153
<211> LENGTH: 9
<212> TYPE: PRT
<213> ORGANISM: Homo sapiens

<400> SEQUENCE: 153

```
Gly Leu Leu Gly Lys Val Thr Ser Val
1               5
```

<210> SEQ ID NO 154
<211> LENGTH: 9
<212> TYPE: PRT
<213> ORGANISM: Homo sapiens

<400> SEQUENCE: 154

```
Lys Met Ile Ser Ala Ile Pro Thr Leu
1               5
```

<210> SEQ ID NO 155
<211> LENGTH: 11
<212> TYPE: PRT
<213> ORGANISM: Homo sapiens

<400> SEQUENCE: 155

```
Gly Leu Leu Glu Thr Thr Gly Leu Leu Ala Thr
1               5                   10
```

<210> SEQ ID NO 156
<211> LENGTH: 9
<212> TYPE: PRT
<213> ORGANISM: Homo sapiens

<400> SEQUENCE: 156

```
Thr Leu Asn Thr Leu Asp Ile Asn Leu
1               5
```

```
<210> SEQ ID NO 157
<211> LENGTH: 9
<212> TYPE: PRT
<213> ORGANISM: Homo sapiens

<400> SEQUENCE: 157

Val Ile Ile Lys Gly Leu Glu Glu Ile
1               5

<210> SEQ ID NO 158
<211> LENGTH: 9
<212> TYPE: PRT
<213> ORGANISM: Homo sapiens

<400> SEQUENCE: 158

Tyr Leu Glu Asp Gly Phe Ala Tyr Val
1               5

<210> SEQ ID NO 159
<211> LENGTH: 11
<212> TYPE: PRT
<213> ORGANISM: Homo sapiens

<400> SEQUENCE: 159

Lys Ile Trp Glu Glu Leu Ser Val Leu Glu Val
1               5                   10

<210> SEQ ID NO 160
<211> LENGTH: 9
<212> TYPE: PRT
<213> ORGANISM: Homo sapiens

<400> SEQUENCE: 160

Leu Leu Ile Pro Phe Thr Ile Phe Met
1               5

<210> SEQ ID NO 161
<211> LENGTH: 10
<212> TYPE: PRT
<213> ORGANISM: Homo sapiens

<400> SEQUENCE: 161

Ile Ser Leu Asp Glu Val Ala Val Ser Leu
1               5                   10

<210> SEQ ID NO 162
<211> LENGTH: 10
<212> TYPE: PRT
<213> ORGANISM: Homo sapiens

<400> SEQUENCE: 162

Lys Ile Ser Asp Phe Gly Leu Ala Thr Val
1               5                   10

<210> SEQ ID NO 163
<211> LENGTH: 11
<212> TYPE: PRT
<213> ORGANISM: Homo sapiens

<400> SEQUENCE: 163

Lys Leu Ile Gly Asn Ile His Gly Asn Glu Val
1               5                   10

<210> SEQ ID NO 164
```

```
<211> LENGTH: 9
<212> TYPE: PRT
<213> ORGANISM: Homo sapiens

<400> SEQUENCE: 164

Ile Leu Leu Ser Val Leu His Gln Leu
1               5

<210> SEQ ID NO 165
<211> LENGTH: 9
<212> TYPE: PRT
<213> ORGANISM: Homo sapiens

<400> SEQUENCE: 165

Leu Asp Ser Glu Ala Leu Leu Thr Leu
1               5

<210> SEQ ID NO 166
<211> LENGTH: 13
<212> TYPE: PRT
<213> ORGANISM: Homo sapiens

<400> SEQUENCE: 166

Val Leu Gln Glu Asn Ser Ser Asp Tyr Gln Ser Asn Leu
1               5                   10

<210> SEQ ID NO 167
<211> LENGTH: 11
<212> TYPE: PRT
<213> ORGANISM: Homo sapiens

<400> SEQUENCE: 167

His Leu Leu Gly Glu Gly Ala Phe Ala Gln Val
1               5                   10

<210> SEQ ID NO 168
<211> LENGTH: 9
<212> TYPE: PRT
<213> ORGANISM: Homo sapiens

<400> SEQUENCE: 168

Ser Leu Val Glu Asn Ile His Val Leu
1               5

<210> SEQ ID NO 169
<211> LENGTH: 9
<212> TYPE: PRT
<213> ORGANISM: Homo sapiens

<400> SEQUENCE: 169

Tyr Thr Phe Ser Gly Asp Val Gln Leu
1               5

<210> SEQ ID NO 170
<211> LENGTH: 9
<212> TYPE: PRT
<213> ORGANISM: Homo sapiens

<400> SEQUENCE: 170

Ser Leu Ser Glu Lys Ser Pro Glu Val
1               5

<210> SEQ ID NO 171
<211> LENGTH: 10
<212> TYPE: PRT
```

```
<213> ORGANISM: Homo sapiens

<400> SEQUENCE: 171

Ala Met Phe Pro Asp Thr Ile Pro Arg Val
1               5                   10

<210> SEQ ID NO 172
<211> LENGTH: 9
<212> TYPE: PRT
<213> ORGANISM: Homo sapiens

<400> SEQUENCE: 172

Phe Leu Ile Glu Asn Leu Leu Ala Ala
1               5

<210> SEQ ID NO 173
<211> LENGTH: 9
<212> TYPE: PRT
<213> ORGANISM: Homo sapiens

<400> SEQUENCE: 173

Phe Thr Ala Glu Phe Leu Glu Lys Val
1               5

<210> SEQ ID NO 174
<211> LENGTH: 9
<212> TYPE: PRT
<213> ORGANISM: Homo sapiens

<400> SEQUENCE: 174

Ala Leu Tyr Gly Asn Val Gln Gln Val
1               5

<210> SEQ ID NO 175
<211> LENGTH: 9
<212> TYPE: PRT
<213> ORGANISM: Homo sapiens

<400> SEQUENCE: 175

Leu Phe Gln Ser Arg Ile Ala Gly Val
1               5

<210> SEQ ID NO 176
<211> LENGTH: 11
<212> TYPE: PRT
<213> ORGANISM: Homo sapiens

<400> SEQUENCE: 176

Ile Leu Ala Glu Glu Pro Ile Tyr Ile Arg Val
1               5                   10

<210> SEQ ID NO 177
<211> LENGTH: 9
<212> TYPE: PRT
<213> ORGANISM: Homo sapiens

<400> SEQUENCE: 177

Phe Leu Leu Glu Arg Glu Gln Leu Leu
1               5

<210> SEQ ID NO 178
<211> LENGTH: 10
<212> TYPE: PRT
<213> ORGANISM: Homo sapiens
```

```
<400> SEQUENCE: 178

Leu Leu Leu Pro Leu Glu Leu Ser Leu Ala
1               5                   10

<210> SEQ ID NO 179
<211> LENGTH: 9
<212> TYPE: PRT
<213> ORGANISM: Homo sapiens

<400> SEQUENCE: 179

Ser Leu Ala Glu Thr Ile Phe Ile Val
1               5

<210> SEQ ID NO 180
<211> LENGTH: 11
<212> TYPE: PRT
<213> ORGANISM: Homo sapiens

<400> SEQUENCE: 180

Ala Ile Leu Asn Val Asp Glu Lys Asn Gln Val
1               5                   10

<210> SEQ ID NO 181
<211> LENGTH: 9
<212> TYPE: PRT
<213> ORGANISM: Homo sapiens

<400> SEQUENCE: 181

Arg Leu Phe Glu Glu Val Leu Gly Val
1               5

<210> SEQ ID NO 182
<211> LENGTH: 9
<212> TYPE: PRT
<213> ORGANISM: Homo sapiens

<400> SEQUENCE: 182

Tyr Leu Asp Glu Val Ala Phe Met Leu
1               5

<210> SEQ ID NO 183
<211> LENGTH: 11
<212> TYPE: PRT
<213> ORGANISM: Homo sapiens

<400> SEQUENCE: 183

Lys Leu Ile Asp Glu Asp Glu Pro Leu Phe Leu
1               5                   10

<210> SEQ ID NO 184
<211> LENGTH: 9
<212> TYPE: PRT
<213> ORGANISM: Homo sapiens

<400> SEQUENCE: 184

Lys Leu Phe Glu Lys Ser Thr Gly Leu
1               5

<210> SEQ ID NO 185
<211> LENGTH: 11
<212> TYPE: PRT
<213> ORGANISM: Homo sapiens

<400> SEQUENCE: 185
```

-continued

```
Ser Leu Leu Glu Val Asn Glu Ala Ser Ser Val
1               5                   10

<210> SEQ ID NO 186
<211> LENGTH: 10
<212> TYPE: PRT
<213> ORGANISM: Homo sapiens

<400> SEQUENCE: 186

Gly Val Tyr Asp Gly Arg Glu His Thr Val
1               5                   10

<210> SEQ ID NO 187
<211> LENGTH: 10
<212> TYPE: PRT
<213> ORGANISM: Homo sapiens

<400> SEQUENCE: 187

Gly Leu Tyr Pro Val Thr Leu Val Gly Val
1               5                   10

<210> SEQ ID NO 188
<211> LENGTH: 9
<212> TYPE: PRT
<213> ORGANISM: Homo sapiens

<400> SEQUENCE: 188

Ala Leu Leu Ser Ser Val Ala Glu Ala
1               5

<210> SEQ ID NO 189
<211> LENGTH: 9
<212> TYPE: PRT
<213> ORGANISM: Homo sapiens

<400> SEQUENCE: 189

Thr Leu Leu Glu Gly Ile Ser Arg Ala
1               5

<210> SEQ ID NO 190
<211> LENGTH: 9
<212> TYPE: PRT
<213> ORGANISM: Homo sapiens

<400> SEQUENCE: 190

Ser Leu Ile Glu Glu Ser Glu Glu Leu
1               5

<210> SEQ ID NO 191
<211> LENGTH: 9
<212> TYPE: PRT
<213> ORGANISM: Homo sapiens

<400> SEQUENCE: 191

Ala Leu Tyr Val Gln Ala Pro Thr Val
1               5

<210> SEQ ID NO 192
<211> LENGTH: 10
<212> TYPE: PRT
<213> ORGANISM: Homo sapiens

<400> SEQUENCE: 192

Lys Leu Ile Tyr Lys Asp Leu Val Ser Val
1               5                   10
```

```
<210> SEQ ID NO 193
<211> LENGTH: 9
<212> TYPE: PRT
<213> ORGANISM: Homo sapiens

<400> SEQUENCE: 193

Ile Leu Gln Asp Gly Gln Phe Leu Val
1               5

<210> SEQ ID NO 194
<211> LENGTH: 9
<212> TYPE: PRT
<213> ORGANISM: Homo sapiens

<400> SEQUENCE: 194

Ser Leu Leu Asp Tyr Glu Val Ser Ile
1               5

<210> SEQ ID NO 195
<211> LENGTH: 9
<212> TYPE: PRT
<213> ORGANISM: Homo sapiens

<400> SEQUENCE: 195

Leu Leu Gly Asp Ser Ser Phe Phe Leu
1               5

<210> SEQ ID NO 196
<211> LENGTH: 10
<212> TYPE: PRT
<213> ORGANISM: Homo sapiens

<400> SEQUENCE: 196

Val Ile Phe Glu Gly Glu Pro Met Tyr Leu
1               5                   10

<210> SEQ ID NO 197
<211> LENGTH: 9
<212> TYPE: PRT
<213> ORGANISM: Homo sapiens

<400> SEQUENCE: 197

Ala Leu Ser Tyr Ile Leu Pro Tyr Leu
1               5

<210> SEQ ID NO 198
<211> LENGTH: 9
<212> TYPE: PRT
<213> ORGANISM: Homo sapiens

<400> SEQUENCE: 198

Phe Leu Phe Val Asp Pro Glu Leu Val
1               5

<210> SEQ ID NO 199
<211> LENGTH: 11
<212> TYPE: PRT
<213> ORGANISM: Homo sapiens

<400> SEQUENCE: 199

Ser Glu Trp Gly Ser Pro His Ala Ala Val Pro
1               5                   10
```

```
<210> SEQ ID NO 200
<211> LENGTH: 9
<212> TYPE: PRT
<213> ORGANISM: Homo sapiens

<400> SEQUENCE: 200

Ala Leu Ser Glu Leu Glu Arg Val Leu
1               5

<210> SEQ ID NO 201
<211> LENGTH: 9
<212> TYPE: PRT
<213> ORGANISM: Homo sapiens

<400> SEQUENCE: 201

Ser Leu Phe Glu Ser Leu Glu Tyr Leu
1               5

<210> SEQ ID NO 202
<211> LENGTH: 9
<212> TYPE: PRT
<213> ORGANISM: Homo sapiens

<400> SEQUENCE: 202

Lys Val Leu Glu Tyr Val Ile Lys Val
1               5

<210> SEQ ID NO 203
<211> LENGTH: 10
<212> TYPE: PRT
<213> ORGANISM: Homo sapiens

<400> SEQUENCE: 203

Val Leu Leu Asn Glu Ile Leu Glu Gln Val
1               5                   10

<210> SEQ ID NO 204
<211> LENGTH: 9
<212> TYPE: PRT
<213> ORGANISM: Homo sapiens

<400> SEQUENCE: 204

Ser Leu Leu Asn Gln Pro Lys Ala Val
1               5

<210> SEQ ID NO 205
<211> LENGTH: 9
<212> TYPE: PRT
<213> ORGANISM: Homo sapiens

<400> SEQUENCE: 205

Lys Met Ser Glu Leu Gln Thr Tyr Val
1               5

<210> SEQ ID NO 206
<211> LENGTH: 11
<212> TYPE: PRT
<213> ORGANISM: Homo sapiens

<400> SEQUENCE: 206

Ala Leu Leu Glu Gln Thr Gly Asp Met Ser Leu
1               5                   10

<210> SEQ ID NO 207
<211> LENGTH: 11
```

```
<212> TYPE: PRT
<213> ORGANISM: Homo sapiens

<400> SEQUENCE: 207

Val Ile Ile Lys Gly Leu Glu Glu Ile Thr Val
1               5                   10

<210> SEQ ID NO 208
<211> LENGTH: 9
<212> TYPE: PRT
<213> ORGANISM: Homo sapiens

<400> SEQUENCE: 208

Lys Gln Phe Glu Gly Thr Val Glu Ile
1               5

<210> SEQ ID NO 209
<211> LENGTH: 9
<212> TYPE: PRT
<213> ORGANISM: Homo sapiens

<400> SEQUENCE: 209

Lys Leu Gln Glu Glu Ile Pro Val Leu
1               5

<210> SEQ ID NO 210
<211> LENGTH: 9
<212> TYPE: PRT
<213> ORGANISM: Homo sapiens

<400> SEQUENCE: 210

Gly Leu Ala Glu Phe Gln Glu Asn Val
1               5

<210> SEQ ID NO 211
<211> LENGTH: 9
<212> TYPE: PRT
<213> ORGANISM: Homo sapiens

<400> SEQUENCE: 211

Asn Val Ala Glu Ile Val Ile His Ile
1               5

<210> SEQ ID NO 212
<211> LENGTH: 9
<212> TYPE: PRT
<213> ORGANISM: Homo sapiens

<400> SEQUENCE: 212

Ala Leu Ala Gly Ile Val Thr Asn Val
1               5

<210> SEQ ID NO 213
<211> LENGTH: 12
<212> TYPE: PRT
<213> ORGANISM: Homo sapiens

<400> SEQUENCE: 213

Asn Leu Leu Ile Asp Asp Lys Gly Thr Ile Lys Leu
1               5                   10

<210> SEQ ID NO 214
<211> LENGTH: 10
<212> TYPE: PRT
<213> ORGANISM: Homo sapiens
```

```
<400> SEQUENCE: 214

Val Leu Met Gln Asp Ser Arg Leu Tyr Leu
1               5                   10

<210> SEQ ID NO 215
<211> LENGTH: 9
<212> TYPE: PRT
<213> ORGANISM: Homo sapiens

<400> SEQUENCE: 215

Lys Val Leu Glu His Val Val Arg Val
1               5

<210> SEQ ID NO 216
<211> LENGTH: 9
<212> TYPE: PRT
<213> ORGANISM: Homo sapiens

<400> SEQUENCE: 216

Leu Leu Trp Gly Asn Leu Pro Glu Ile
1               5

<210> SEQ ID NO 217
<211> LENGTH: 9
<212> TYPE: PRT
<213> ORGANISM: Homo sapiens

<400> SEQUENCE: 217

Ser Leu Met Glu Lys Asn Gln Ser Leu
1               5

<210> SEQ ID NO 218
<211> LENGTH: 9
<212> TYPE: PRT
<213> ORGANISM: Homo sapiens

<400> SEQUENCE: 218

Lys Leu Leu Ala Val Ile His Glu Leu
1               5

<210> SEQ ID NO 219
<211> LENGTH: 10
<212> TYPE: PRT
<213> ORGANISM: Homo sapiens

<400> SEQUENCE: 219

Ala Leu Gly Asp Lys Phe Leu Leu Arg Val
1               5                   10

<210> SEQ ID NO 220
<211> LENGTH: 11
<212> TYPE: PRT
<213> ORGANISM: Homo sapiens

<400> SEQUENCE: 220

Phe Leu Met Lys Asn Ser Asp Leu Tyr Gly Ala
1               5                   10

<210> SEQ ID NO 221
<211> LENGTH: 10
<212> TYPE: PRT
<213> ORGANISM: Homo sapiens

<400> SEQUENCE: 221
```

Lys Leu Ile Asp His Gln Gly Leu Tyr Leu
1               5                   10

<210> SEQ ID NO 222
<211> LENGTH: 12
<212> TYPE: PRT
<213> ORGANISM: Homo sapiens

<400> SEQUENCE: 222

Gly Pro Gly Ile Phe Pro Pro Pro Pro Gln Pro
1               5                   10

<210> SEQ ID NO 223
<211> LENGTH: 9
<212> TYPE: PRT
<213> ORGANISM: Homo sapiens

<400> SEQUENCE: 223

Ala Leu Asn Glu Ser Leu Val Glu Cys
1               5

<210> SEQ ID NO 224
<211> LENGTH: 9
<212> TYPE: PRT
<213> ORGANISM: Homo sapiens

<400> SEQUENCE: 224

Gly Leu Ala Ala Leu Ala Val His Leu
1               5

<210> SEQ ID NO 225
<211> LENGTH: 9
<212> TYPE: PRT
<213> ORGANISM: Homo sapiens

<400> SEQUENCE: 225

Leu Leu Leu Glu Ala Val Trp His Leu
1               5

<210> SEQ ID NO 226
<211> LENGTH: 9
<212> TYPE: PRT
<213> ORGANISM: Homo sapiens

<400> SEQUENCE: 226

Ser Ile Ile Glu Tyr Leu Pro Thr Leu
1               5

<210> SEQ ID NO 227
<211> LENGTH: 9
<212> TYPE: PRT
<213> ORGANISM: Homo sapiens

<400> SEQUENCE: 227

Thr Leu His Asp Gln Val His Leu Leu
1               5

<210> SEQ ID NO 228
<211> LENGTH: 9
<212> TYPE: PRT
<213> ORGANISM: Homo sapiens

<400> SEQUENCE: 228

Ser Leu Leu Met Trp Ile Thr Gln Cys

```
1               5
```

<210> SEQ ID NO 229
<211> LENGTH: 11
<212> TYPE: PRT
<213> ORGANISM: Homo sapiens

<400> SEQUENCE: 229

```
Phe Leu Leu Asp Lys Pro Gln Asp Leu Ser Ile
1               5                   10
```

<210> SEQ ID NO 230
<211> LENGTH: 10
<212> TYPE: PRT
<213> ORGANISM: Homo sapiens

<400> SEQUENCE: 230

```
Tyr Leu Leu Asp Met Pro Leu Trp Tyr Leu
1               5                   10
```

<210> SEQ ID NO 231
<211> LENGTH: 9
<212> TYPE: PRT
<213> ORGANISM: Homo sapiens

<400> SEQUENCE: 231

```
Gly Leu Leu Asp Cys Pro Ile Phe Leu
1               5
```

<210> SEQ ID NO 232
<211> LENGTH: 9
<212> TYPE: PRT
<213> ORGANISM: Homo sapiens

<400> SEQUENCE: 232

```
Val Leu Ile Glu Tyr Asn Phe Ser Ile
1               5
```

<210> SEQ ID NO 233
<211> LENGTH: 11
<212> TYPE: PRT
<213> ORGANISM: Homo sapiens

<400> SEQUENCE: 233

```
Thr Leu Tyr Asn Pro Glu Arg Thr Ile Thr Val
1               5                   10
```

<210> SEQ ID NO 234
<211> LENGTH: 9
<212> TYPE: PRT
<213> ORGANISM: Homo sapiens

<400> SEQUENCE: 234

```
Ala Val Pro Pro Pro Ser Ser Val
1               5
```

<210> SEQ ID NO 235
<211> LENGTH: 9
<212> TYPE: PRT
<213> ORGANISM: Homo sapiens

<400> SEQUENCE: 235

```
Lys Leu Gln Glu Glu Leu Asn Lys Val
1               5
```

```
<210> SEQ ID NO 236
<211> LENGTH: 11
<212> TYPE: PRT
<213> ORGANISM: Homo sapiens

<400> SEQUENCE: 236

Lys Leu Met Asp Pro Gly Ser Leu Pro Pro Leu
1               5                   10

<210> SEQ ID NO 237
<211> LENGTH: 9
<212> TYPE: PRT
<213> ORGANISM: Homo sapiens

<400> SEQUENCE: 237

Ala Leu Ile Val Ser Leu Pro Tyr Leu
1               5

<210> SEQ ID NO 238
<211> LENGTH: 9
<212> TYPE: PRT
<213> ORGANISM: Homo sapiens

<400> SEQUENCE: 238

Phe Leu Leu Asp Gly Ser Ala Asn Val
1               5

<210> SEQ ID NO 239
<211> LENGTH: 10
<212> TYPE: PRT
<213> ORGANISM: Homo sapiens

<400> SEQUENCE: 239

Ala Leu Asp Pro Ser Gly Asn Gln Leu Ile
1               5                   10

<210> SEQ ID NO 240
<211> LENGTH: 9
<212> TYPE: PRT
<213> ORGANISM: Homo sapiens

<400> SEQUENCE: 240

Ile Leu Ile Lys His Leu Val Lys Val
1               5

<210> SEQ ID NO 241
<211> LENGTH: 9
<212> TYPE: PRT
<213> ORGANISM: Homo sapiens

<400> SEQUENCE: 241

Val Leu Leu Asp Thr Ile Leu Gln Leu
1               5

<210> SEQ ID NO 242
<211> LENGTH: 9
<212> TYPE: PRT
<213> ORGANISM: Homo sapiens

<400> SEQUENCE: 242

His Leu Ile Ala Glu Ile His Thr Ala
1               5

<210> SEQ ID NO 243
```

```
<211> LENGTH: 9
<212> TYPE: PRT
<213> ORGANISM: Homo sapiens

<400> SEQUENCE: 243

Ser Met Asn Gly Gly Val Phe Ala Val
1               5

<210> SEQ ID NO 244
<211> LENGTH: 9
<212> TYPE: PRT
<213> ORGANISM: Homo sapiens

<400> SEQUENCE: 244

Met Leu Ala Glu Lys Leu Leu Gln Ala
1               5

<210> SEQ ID NO 245
<211> LENGTH: 9
<212> TYPE: PRT
<213> ORGANISM: Homo sapiens

<400> SEQUENCE: 245

Tyr Met Leu Asp Ile Phe His Glu Val
1               5

<210> SEQ ID NO 246
<211> LENGTH: 11
<212> TYPE: PRT
<213> ORGANISM: Homo sapiens

<400> SEQUENCE: 246

Ala Leu Trp Leu Pro Thr Asp Ser Ala Thr Val
1               5                   10

<210> SEQ ID NO 247
<211> LENGTH: 9
<212> TYPE: PRT
<213> ORGANISM: Homo sapiens

<400> SEQUENCE: 247

Gly Leu Ala Ser Arg Ile Leu Asp Ala
1               5

<210> SEQ ID NO 248
<211> LENGTH: 9
<212> TYPE: PRT
<213> ORGANISM: Homo sapiens

<400> SEQUENCE: 248

Ala Leu Ser Val Leu Arg Leu Ala Leu
1               5

<210> SEQ ID NO 249
<211> LENGTH: 9
<212> TYPE: PRT
<213> ORGANISM: Homo sapiens

<400> SEQUENCE: 249

Ser Tyr Val Lys Val Leu His His Leu
1               5

<210> SEQ ID NO 250
<211> LENGTH: 9
<212> TYPE: PRT
```

<213> ORGANISM: Homo sapiens

<400> SEQUENCE: 250

Val Tyr Leu Pro Lys Ile Pro Ser Trp
1               5

<210> SEQ ID NO 251
<211> LENGTH: 9
<212> TYPE: PRT
<213> ORGANISM: Homo sapiens

<400> SEQUENCE: 251

Asn Tyr Glu Asp His Phe Pro Leu Leu
1               5

<210> SEQ ID NO 252
<211> LENGTH: 9
<212> TYPE: PRT
<213> ORGANISM: Homo sapiens

<400> SEQUENCE: 252

Val Tyr Ile Ala Glu Leu Glu Lys Ile
1               5

<210> SEQ ID NO 253
<211> LENGTH: 12
<212> TYPE: PRT
<213> ORGANISM: Homo sapiens

<400> SEQUENCE: 253

Val His Phe Glu Asp Thr Gly Lys Thr Leu Leu Phe
1               5                   10

<210> SEQ ID NO 254
<211> LENGTH: 9
<212> TYPE: PRT
<213> ORGANISM: Homo sapiens

<400> SEQUENCE: 254

Val Leu Ser Pro Phe Ile Leu Thr Leu
1               5

<210> SEQ ID NO 255
<211> LENGTH: 9
<212> TYPE: PRT
<213> ORGANISM: Homo sapiens

<400> SEQUENCE: 255

His Leu Leu Glu Gly Ser Val Gly Val
1               5

<210> SEQ ID NO 256
<211> LENGTH: 3658
<212> TYPE: DNA
<213> ORGANISM: Artificial Sequence
<220> FEATURE:
<223> OTHER INFORMATION: CD8aCD4Fusion.TCR.WPRE

<400> SEQUENCE: 256

| | | | | |
|---|---|---|---|---|
| tgaaagaccc cacctgtagg tttggcaagc tagcttaagt aacgccattt tgcaaggcat | | | | 60 |
| ggaaaataca taactgagaa tagagaagtt cagatcaagg ttaggaacag agagacagca | | | | 120 |
| gaatatgggc caaacaggat atctgtggta agcagttcct gccccggctc agggccaaga | | | | 180 |
| acagatggtc cccagatgcg gtcccgccct cagcagtttc tagagaacca tcagatgttt | | | | 240 |

```
ccagggtgcc ccaaggacct gaaaatgacc ctgtgcctta tttgaactaa ccaatcagtt    300
cgcttctcgc ttctgttcgc gcgcttctgc tccccgagct caataaaaga gcccacaacc    360
cctcactagc ggccgccccg ggtcgacgct accaccatgg cgcttcccgt gaccgcactc    420
ctgttgcccc ttgccctgct gttgcacgcc gcacgacctt cccaattccg ggtgtcccct    480
ctggatcgca cctggaacct cggggaaacg gtggagctca agtgtcaagt cctcctgtcg    540
aacccgacca gcggatgcag ctggctgttc agccgagag gagctgccgc ctcacccacc    600
ttcctcctgt acttgagcca gaacaagccg aaggccgctg agggtctgga cacccagcgc    660
ttctcgggca acggctggg agacacttt gtgctgactc tctccgactt ccggcgggag    720
aacgagggct actacttctg ctctgcgctc tccaattcaa tcatgtactt ctcacacttc    780
gtgccggtgt tcctgcctgc caagcccacc actactccgg cacccagacc tccaactccc    840
gctcccacca tcgcgtccca accccttccg ctgcgccctg aagcgtgtcg gcctgctgct    900
ggaggagccg tgcatacccg cggtctggac ttcgcgtgcg acatggccct gattgtgctg    960
gggggcgtcg ccggcctcct gcttttcatt gggctaggca tcttcttctg tgtcaggtgc   1020
cggcaccgaa ggcgccaagc agagcggatg tctcagatca agagactcct cagtgagaag   1080
aagacctgcc agtgtcctca ccggtttcag aagacatgta gccccattcg gccaagaga    1140
tctggcagcg cgccaccaa tttcagcctg ctgaaacagg ccggcgacgt ggaagagaac   1200
cctggcccca tggactcttg gaccttctgc tgcgtgagcc tgtgcatcct ggtggccaag   1260
cacacagacg ccggcgtgat ccagtcccct aggcacgagg tgaccgagat gggccaggag   1320
gtgacactgc gctgtaagcc aatctctggc cacaacagcc tgttttggta tagggagacc   1380
atgatgcgcg gcctggagct gctgatctac ttcaataaca atgtgcccat cgacgattcc   1440
ggcatgcctg aggatcggtt ttctgccaag atgcccaatg ccagcttctc cacactgaag   1500
atccagccta gcgagccaag agactccgcc gtgtatttt gcgcctctag cccaggcagc   1560
accgatacac agtacttcgg accaggaacc aggctgacag tgctggagga cctgaagaac   1620
gtgttccccc ctgaggtggc cgtgtttgag ccctctgagg ccgagatcag ccacacccag   1680
aaggccaccc tggtgtgcct ggcaaccggc ttctatcctg atcacgtgga gctgtcctgg   1740
tgggtgaacg gcaaggaggt gcacagcggc gtgtccacag acccacagcc cctgaaggag   1800
cagccagccc tgaatgatag ccggtattgc ctgtcctctc ggctgagagt gtccgccacc   1860
ttttggcaga accccggaa tcacttcaga tgtcaggtgc agttttacgg cctgtccgag   1920
aacgatgagt ggacccagga ccgggccaag cctgtgacac agatcgtgtc tgccgaggca   1980
tggggaagag cagactgtgg cttcacctct gagagctacc agcagggcgt gctgagcgcc   2040
accatcctgt atgagatcct gctgggcaag gccacactgt acgccgtcct ggtctccgct   2100
ctggtgctga tggcaatggt caaaagaaaa gatagtcggg acgggccaa gagatctggc   2160
agcggcgagg gcagaggcag cctgctgacc tgcggcgacg tggaggagaa ccccggcccc   2220
atggagaaga atcccctggc tgcccccctg ctgatcctgt ggtttcacct ggactgcgtg   2280
tcctctatcc tgaatgtgga acagagccca cagagcctgc acgtgcagga gggcgactcc   2340
accaacttca catgctcttt tcctagctcc aacttctacg ccctgcactg gtacagaaag   2400
gagaccgcaa agtccccaga ggccctgttc gtgatgacac tgaacggcga tgagaagaag   2460
aagggccgca tcgcgccac cctgaataca aaggagggct actcctatct gtacatcaag   2520
ggctcccagc ctgaggactc tgccacctat ctgtgcgccc tgtacaacaa taacgatatg   2580
```

```
cggtttggcg ccggcaccag actgacagtg aagccaaaca tccagaatcc agaccccgcc    2640
gtgtatcagc tgcgggacag caagtctagc gataagagcg tgtgcctgtt caccgacttt    2700
gattctcaga caaacgtgag ccagtccaag gacagcgacg tgtacatcac cgacaagaca    2760
gtgctggata tgagaagcat ggacttcaag tctaacagcg ccgtggcctg gtccaataag    2820
tctgatttcg cctgcgccaa tgcctttaat aactccatca tccccgagga taccttcttt    2880
ccttctccag agtcctcttg tgacgtgaag ctggtggaga gtctttcga gaccgataca     2940
aacctgaatt ttcagaacct gagcgtgatc ggcttcagga tcctgctgct gaaggtggcc    3000
ggctttaatc tgctgatgac cctgaggctg tggagctcct gaaccggtcc gcagtctgac    3060
gtacgcgtaa tcaacctctg gattacaaaa tttgtgaaag attgactggt attcttaact    3120
atgttgctcc ttttacgcta tgtggatacg ctgctttaat gcctttgtat catgctattg    3180
cttcccgtat ggctttcatt ttctcctcct tgtataaatc ctggttgctg tctctttatg    3240
aggagttgtg gcccgttgtc aggcaacgtg gcgtggtgtg cactgtgttt gctgacgcaa    3300
cccccactgg ttggggcatt gccaccacct gtcagctcct ttccgggact ttcgctttcc    3360
ccctccctat tgccacggcg gaactcatcg ccgcctgcct tgcccgctgc tggacagggg    3420
ctcggctgtt gggcactgac aattccgtgg tgttgtcggg gaagctgacg tccttcccat    3480
ggctgctcgc ctgtgttgcc acctggattc tgcgcgggac gtccttctgc tacgtccctt    3540
cggccctcaa tccagcggac cttccttccc gcggcctgct gccggctctg cggcctcttc    3600
cgcgtcttcg ccttcgccct cagacgagtc ggatctccct ttgggccgcc tccccgcc     3658

<210> SEQ ID NO 257
<211> LENGTH: 3622
<212> TYPE: DNA
<213> ORGANISM: Artificial Sequence
<220> FEATURE:
<223> OTHER INFORMATION: CD8bCD4Fusion.TCR.WPRE

<400> SEQUENCE: 257
tgaaagaccc cacctgtagg tttggcaagc tagcttaagt aacgccattt tgcaaggcat      60
ggaaaataca taactgagaa tagagaagtt cagatcaagg ttaggaacag agagacagca    120
gaatatgggc caaacaggat atctgtggta agcagttcct gccccggctc agggccaaga    180
acagatggtc cccagatgcg gtcccgccct cagcagtttc tagagaacca tcagatgttt    240
ccagggtgcc ccaaggacct gaaaatgacc ctgtgcctta tttgaactaa ccaatcagtt    300
cgcttctcgc ttctgttcgc gcgcttctgc tccccgagct caataaaaga gcccacaacc    360
cctcactagc ggccgccccg gtcgacgcta ccaccatgc gcccgagact gtggcttctg    420
ctcgccgcgc aactgactgt cctgcacgga acagcgtgc tgcagcagac accggcctac    480
atcaaagtgc agaccaacaa gatggtcatg ctgtcctgcg aggccaagat tccctctcc    540
aacatgcgga tctattggtt gcggcagaga caggcgcctt cctcggactc ccaccatgag    600
ttcttggccc tgtgggactc cgccaaggga actattcacg gcgaagaagt ggaacaggag    660
aagatcgccg tgtttcgcga tgcctcccgc tttatactga atctgacctc cgtgaagccc    720
gaagatagcg gatctacttt tgcatgatt gtgggctcac ccgaactgac cttcgggaag    780
ggcactcagc tgagcgtggt ggacttcctc cccactaccg cccaacccac taagaagtca    840
accctgaaga gcgggttttg cagactccca cggccgaaa cgcagaaggg tccgctgtgt    900
tccccgatgg ccctgattgt gctgggggc gtcgccggcc tcctgctttt cattgggcta    960
ggcatcttct tctgtgtcag gtgccggcac cgaaggcgcc aagcagagcg gatgtctcag   1020
```

```
atcaagagac tcctcagtga gaagaagacc tgccagtgtc ctcaccggtt tcagaagaca    1080
tgtagcccca ttcgggccaa gagatctggc agcggcgcca ccaatttcag cctgctgaaa    1140
caggccggcg acgtggaaga gaaccctggc cccatggact cttggacctt ctgctgcgtg    1200
agcctgtgca tcctggtggc caagcacaca gacgccggcg tgatccagtc ccctaggcac    1260
gaggtgaccg agatgggcca ggaggtgaca ctgcgctgta agccaatctc tggccacaac    1320
agcctgtttt ggtataggga gaccatgatg cgcggcctgg agctgctgat ctacttcaat    1380
aacaatgtgc ccatcgacga ttccggcatg cctgaggatc ggttttctgc caagatgccc    1440
aatgccagct tctccacact gaagatccag cctagcgagc aagagactc cgccgtgtat    1500
ttttgcgcct ctagcccagg cagcaccgat acacagtact tcggaccagg aaccaggctg    1560
acagtgctgg aggacctgaa gaacgtgttc cccctgagg tggccgtgtt tgagccctct    1620
gaggccgaga tcagccacac ccagaaggcc accctggtgt gcctggcaac cggcttctat    1680
cctgatcacg tggagctgtc ctggtgggtg aacggcaagg aggtgcacag cggcgtgtcc    1740
acagacccac agccctgaa ggagcagcca gccctgaatg atagccggta ttgcctgtcc    1800
tctcggctga gagtgtccgc caccttttgg cagaaccccc ggaatcactt cagatgtcag    1860
gtgcagtttt acgcctgtc cgagaacgat gagtggaccc aggaccgggc caagcctgtg    1920
acacagatcg tgtctgccga ggcatgggga agagcagact gtggcttcac ctctgagagc    1980
taccagcagg gcgtgctgag cgccaccatc ctgtatgaga tcctgctggg caaggccaca    2040
ctgtacgccg tcctggtctc cgctctggtg ctgatggcaa tggtcaaaag aaaagatagt    2100
cggggacggg ccaagagatc tggcagcggc gagggcagag gcagcctgct gacctgcggc    2160
gacgtggagg agaaccccgg ccccatggag aagaatcccc tggctgcccc cctgctgatc    2220
ctgtggtttc acctggactg cgtgtcctct atcctgaatg tggaacagag cccacagagc    2280
ctgcacgtgc aggagggcga ctccaccaac ttcacatgct cttttcctag ctccaacttc    2340
tacgccctgc actggtacag aaaggagacc gcaaagtccc cagaggccct gttcgtgatg    2400
acactgaacg gcgatgagaa gaagaaggc gccatcagcg ccaccctgaa tacaaaggag    2460
ggctactcct atctgtacat caagggctcc cagcctgagg actctgccac ctatctgtgc    2520
gccctgtaca caataacga tatgcggttt ggcgccggca ccagactgac agtgaagcca    2580
aacatccaga tccagacccc cgccgtgtat cagctgcggg acagcaagtc tagcgataag    2640
agcgtgtgcc tgttcaccga ctttgattct cagacaaacg tgagccagtc caaggacagc    2700
gacgtgtaca tcaccgacaa gacagtgctg gatatgagaa gcatggactt caagtctaac    2760
agcgccgtgg cctggtccaa taagtctgat ttcgcctgcg ccaatgcctt taataactcc    2820
atcatccccg aggatacctt ctttccttct ccagagtcct cttgtgacgt gaagctggtg    2880
gagaagtctt tcgagaccga tacaaacctg aattttcaga acctgagcgt gatcggcttc    2940
aggatcctgc tgctgaaggt ggccggcttt aatctgctga tgaccctgag gctgtgggc    3000
tcctgaaccg gtccgcagtc tgacgtacgc gtaatcaacc tctggattac aaaatttgtg    3060
aaagattgac tggtattctt aactatgttg ctccttttac gctatgtgga tacgctgctt    3120
taatgccttt gtatcatgct attgcttccc gtatggcttt cattttctcc tccttgtata    3180
aatcctggtt gctgtctctt tatgaggagt tgtggcccgt tgtcaggcaa cgtggcgtgg    3240
tgtgcactgt gtttgctgac gcaacccccca ctggttgggg cattgccacc acctgtcagc    3300
tcctttccgg gactttcgct ttccccctcc ctattgccac ggcggaactc atcgccgcct    3360
```

```
gccttgcccg ctgctggaca ggggctcggc tgttgggcac tgacaattcc gtggtgttgt    3420
cggggaagct gacgtccttt ccatggctgc tcgcctgtgt tgccacctgg attctgcgcg    3480
ggacgtcctt ctgctacgtc ccttcggccc tcaatccagc ggaccttcct tcccgcggcc    3540
tgctgccggc tctgcggcct cttccgcgtc ttcgccttcg ccctcagacg agtcggatct    3600 cccttttgggc cgcctccccg cc                                           3622

<210> SEQ ID NO 258
<211> LENGTH: 3595
<212> TYPE: DNA
<213> ORGANISM: Artificial Sequence
<220> FEATURE:
<223> OTHER INFORMATION: CD8bCD8aFusion.TCR.WPRE

<400> SEQUENCE: 258
tgaaagaccc cacctgtagg tttggcaagc tagcttaagt aacgccattt tgcaaggcat      60
ggaaaataca taactgagaa tagagaagtt cagatcaagg ttaggaacag agagacagca     120
gaatatgggc caaacaggat atctgtggta agcagttcct gccccggctc agggccaaga    180
acagatggtc cccagatgcg gtcccgccct cagcagtttc tagagaacca tcagatgttt    240
ccagggtgcc ccaaggacct gaaaatgacc ctgtgcctta tttgaactaa ccaatcagtt    300
cgcttctcgc ttctgttcgc gcgcttctgc tccccgagct caataaaaga gcccacaacc    360
cctcactagc ggccgccccg ggtcgacgct accaccatgc cccgagact gtggcttctg    420 ctcgccgcgc aactgactgt cctgcacgga acagcgtgc tgcagcagac accggcctac    480
atcaaagtgc agaccaacaa gatggtcatg ctgtcctgcg aggccaagat ttccctctcc    540
aacatgcgga tctattggtt gcggcagaga caggcgcctt cctcggactc ccaccatgag    600
ttcttggccc tgtgggactc cgccaaggga actattcacg gcgaagaagt ggaacaggag    660
aagatcgccg tgtttcgcga tgcctcccgc tttatactga atctgacctc cgtgaagccc    720
gaagatagcg ggatctactt ttgcatgatt gtgggctcac ccgaactgac cttcgggaag    780
ggcactcagc tgagcgtggt ggacttcctc cccactaccg cccaacccac taagaagtca    840
accctgaaga gcgggttttg cagactccca cggccgaaaa cgcagaaggg tccgctgtgt    900
tccccgatct acatttgggc ccctttggct ggcacctgtg gagtgctgct cctgtccctt    960
gtgatcaccc tgtactgcaa ccaccggaat aggcggagag tctgcaagtg tccgcggcct   1020
gtcgtgaagt caggagataa gccgagcctg tccgcacgct acgtgcgggc caagagatct   1080
ggcagcggcg ccaccaattt cagcctgctg aaacaggccg cgacgtggga agagaaccct   1140
ggccccatgg actcttggac cttctgctgc gtgagcctgt gcatcctggt ggccaagcac   1200
acagacgccg gcgtgatcca gtcccctagg cacgaggtga ccgagatggg ccaggaggtg   1260
acactgcgct gtaagccaat ctctggccac aacagcctgt tttggtatag ggagaccatg   1320
atgcgcggcc tggagctgct gatctacttc aataacaatg tgcccatcga cgattccggc   1380
atgcctgagg atcggttttc tgccaagatg cccaatgcca gcttctccac actgaagatc   1440
cagcctagcg agccaagaga ctccgccgtg tattttgcg cctctagccc aggcagcacc   1500
gatacacagt acttcggacc aggaaccagg ctgacagtgc tggaggacct gaagaacgtg   1560 ttccccctg aggtggccgt gttgagccc tctgaggccg agatcagcca cacccagaag   1620
gccaccctgg tgtgcctggc aaccggcttc tatcctgatc acgtggagct gtcctggtgg   1680
gtgaacggca aggaggtgca cagcggcgtg tccacagacc cacagcccct gaaggagcag   1740
ccagccctga atgatagccg gtattgcctg tcctctcggc tgagagtgtc cgccaccttt   1800
```

```
tggcagaacc cccggaatca cttcagatgt caggtgcagt tttacggcct gtccgagaac    1860
gatgagtgga cccaggaccg ggccaagcct gtgacacaga tcgtgtctgc cgaggcatgg    1920
ggaagagcag actgtggctt cacctctgag agctaccagc agggcgtgct gagcgccacc    1980
atcctgtatg agatcctgct gggcaaggcc acactgtacg ccgtcctggt ctccgctctg    2040
gtgctgatgg caatggtcaa agaaaagat agtcggggac gggccaagag atctggcagc     2100
ggcgagggca gaggcagcct gctgacctgc ggcgacgtgg aggagaaccc cggccccatg    2160
gagaagaatc ccctggctgc ccccctgctg atcctgtggt tcacctggga ctgcgtgtcc    2220
tctatcctga atgtggaaca gagcccacag agcctgcacg tgcaggaggg cgactccacc    2280
aacttcacat gctcttttcc tagctccaac ttctacgccc tgcactggta cagaaaggag    2340
accgcaaagt ccccagaggc cctgttcgtg atgacactga acggcgatga agaagaag     2400 ggccgcatca gcgccaccct gaatacaaag gagggctact cctatctgta catcaagggc    2460
tcccagcctg aggactctgc cacctatctg tgcgccctgt acaacaataa cgatatgcgg    2520
tttggcgccg gcaccagact gacagtgaag ccaaacatcc agaatccaga ccccgccgtg    2580
tatcagctgc gggacagcaa gtctagcgat aagagcgtgt gcctgttcac cgactttgat    2640
tctcagacaa acgtgagcca gtccaaggac agcgacgtgt acatcaccga caagacagtg    2700
ctggatatga agcatgga cttcaagtct aacagcgccg tggcctggtc caataagtct     2760
gatttcgcct gcgccaatgc ctttaataac tccatcatcc ccgaggatac cttctttcct    2820
tctccagagt cctcttgtga cgtgaagctg gtggagaagt cttcgagac cgatacaaac     2880 ctgaattttc agaacctgag cgtgatcggc ttcaggatcc tgctgctgaa ggtggccggc    2940
tttaatctgc tgatgacccct gaggctgtgg agctcctgaa ccggtccgca gtctgacgta   3000
cgcgtaatca acctctggat tacaaaattt gtgaaagatt gactggtatt cttaactatg    3060
ttgctccttt tacgctatgt ggatacgctg ctttaatgcc tttgtatcat gctattgctt    3120
cccgtatggc tttcattttc tcctccttgt ataaatcctg gttgctgtct ctttatgagg    3180
agttgtggcc cgttgtcagg caacgtggcg tggtgtgcac tgtgtttgct gacgcaaccc    3240
ccactggttg gggcattgcc accacctgtc agctcctttc cgggactttc gctttccccc    3300
tccctattgc cacggcggaa ctcatcgccg cctgccttgc ccgctgctgg acagggctc     3360 ggctgttggg cactgacaat tccgtggtgt tgtcggggaa gctgacgtcc tttccatggc    3420
tgctcgcctg tgttgccacc tggattctgc gcgggacgtc cttctgctac gtcccttcgg    3480
ccctcaatcc agcggacctt ccttcccgcg gcctgctgcc ggctctgcgg cctcttccgc    3540
gtcttcgcct cgccctcag acgagtcgga tctccctttg ggccgcctcc ccgcc          3595
```

<210> SEQ ID NO 259
<211> LENGTH: 5091
<212> TYPE: DNA
<213> ORGANISM: Artificial Sequence
<220> FEATURE:
<223> OTHER INFORMATION: PGK.CD8.EF1a.TCR

<400> SEQUENCE: 259

```
tcacacgtag cgtgcggaca ggctcggctt atctcctgac ttcacgacag gccgcggaca     60
cttgcagact ctccgcctat tccggtggtt gcagtacagg gtgatcacaa gggacaggag    120
cagcactcca caggtgccag ccaaagggc ccaaatgtag atgtcgcacg cgaagtccag      180
accgcgggta tgcacggctc ctccagcagc aggccgacac gcttcagggc gcagcgaaag    240
```

```
gggttgggac gcgatggtgg gagcgggagt tggaggtctg ggtgccggag tagtggtggg      300
cttggcaggc aggaacaccg gcacgaagtg tgagaagtac atgattgaat tggagagcgc      360
agagcagaag tagtagccct cgttctcccg ccggaagtcg gagagagtca gcacaaaagt      420
gtctcccagc cgtttgcccg agaagcgctg ggtgtccaga ccctcagcgg ccttcggctt      480
gttctggctc aagtacagga ggaaggtggg tgaggcggca gctcctctcg gctggaacag      540
ccagctgcat ccgctggtcg ggttcgacag gaggacttga cacttgagct ccaccgtttc      600
cccgaggttc caggtgcgat ccagagggga cacccggaat tgggaaggtc gtgcggcgtg      660
caacagcagg gcaaggggca acaggagtgc ggtcacggga agcgccatgg ggccagggtt      720
ctcttccacg tcgccggcct gtttcagcag gctgaaattg gtggcgccgc tgccagatct      780
cttggcccgg gttttcagga tccagggggtt cagcagcttt tgcgaggtgg tggtgttgga      840
atagtagcca tggaggcact gtggcacgaa agtgccactg atcccctctc cctgaggctg      900
cttcatgaac ctcagtctgg ccctccttct ccggcagcag aggtgaatgg cgacgccaag      960
ggacaccaga aggaccagca ctccagccac aaggagcccc agggtgatcg gggaacacag     1020
cggacccttc tgcgtttccg gccgtgggag tctgcaaacc cgcttcttca gggttgactt     1080
cttagtgggt tgggcggtag tggggaggaa gtccaccacg ctcagctgag tgcccttccc     1140
gaaggtcagt tcgggtgagc ccacaatcat gcaaaagtag atcccgctat cttcgggctt     1200
cacggaggtc agattcagta taaagcggga ggcatcgcga aacacggcga tcttctcctg     1260
ttccacttct tcgccgtgaa tagttccctt ggcggagtcc cacagggcca agaactcatg     1320
gtgggagtcc gaggaaggcg cctgtctctg ccgcaaccaa tagatccgca tgttggagag     1380
ggaaatcttg gcctcgcagg acagcatgac catcttgttg gtctgcactt tgatgtaggc     1440
cggtgtctgt tgcagcacgc tgtttccgtg caggacagtc agttgcgcgg cgagcagaag     1500
ccacagtctc gggcgcatgg tggtagcgtc gacccggggc ggccgctcga aaggcccgga     1560
gatgaggaag aggagaacag cgcggcagac gtgcgctttt gaagcgtgca gaatgccggg     1620
cctccggagg accttcgggc gcccgccccg cccctgagcc cgcccctgag cccgcccccg     1680
gacccacccc ttcccagcct ctgagcccag aaagcgaagg agcaaagctg ctattggccg     1740
ctgccccaaa ggcctacccg cttccagtgc tcagcggtgc tgtccatctg cacgagacta     1800
gtgagacgtg ctacttccat ttgtcacgtc ctgcacgacg cgagctgcgg ggcgggggg      1860 aacttcctga ctaggggagg agtagaaggt ggcgcgaagg ggccaccaaa gaacggagcc     1920
ggttggcgcc taccggtgga tgtggaatgt gtgcgaggcc agaggccact tgtgtagcgc     1980
caagtgccca gcggggctgc taaagcgcat gctccagact gccttgggaa aagcgcctcc     2040
cctacccgct ccggtgcccg tcagtgggca gagcgcacat cgcccacagt ccccgagaag     2100 ttgggggggag gggtcggcaa ttgaaccggt gcctagagaa ggtggcgcgg ggtaaactgg     2160
gaaagtgatg tcgtgtactg gctccgcctt tttcccgagg gtgggggaga accgtatata     2220
agtgcagtag tcgccgtgaa cgttcttttt cgcaacgggt tgccgccag aacacaggta      2280 agtgccgtgt gtggttcccg cgggcctggc ctctttacgg ttatggccc ttgcgtgcct      2340 tgaattactt ccacgcccct ggctgcagta cgtgattctt gatcccgagc ttcgggttgg     2400
aagtgggtgg gagagttcga ggccttgcgc ttaaggagcc ccttcgcctc gtgcttgagt     2460
tgaggcctgg cctgggcgct ggggccgccg cgtgcgaatc tggtggcacc ttcgcgcctg     2520
tctcgctgct ttcgataagt ctctagccat ttaaaatttt tgatgacctg ctgcgacgct     2580
ttttttctgg caagatagtc ttgtaaatgc gggccaagat ctgcacactg gtatttcggt     2640
```

-continued

```
ttttggggcc gcgggcggcg acggggcccg tgcgtcccag cgcacatgtt cggcgaggcg    2700
gggcctgcga gcgcggccac cgagaatcgg acggggtag tctcaagctg gccggcctgc    2760
tctggtgcct ggcctcgcgc cgccgtgtat cgccccgccc tgggcggcaa ggctggcccg    2820
gtcggcacca gttgcgtgag cggaaagatg gccgcttccc ggccctgctg cagggagctc    2880
aaaatggagg acgcggcgct cgggagagcg ggcgggtgag tcacccacac aaaggaaaag    2940
ggcctttccg tcctcagccg tcgcttcatg tgactccacg gagtaccggg cgccgtccag    3000
gcacctcgat tagttctcga gcttttggag tacgtcgtct ttaggttggg gggaggggtt    3060
ttatgcgatg gagtttcccc acactgagtg ggtggagact gaagttaggc cagcttggca    3120
cttgatgtaa ttctccttgg aatttgccct ttttgagttt ggatcttggt tcattctcaa    3180
gcctcagaca gtggttcaaa gttttttct tccatttcag gtgtcgtgaa gcggccgccc    3240
cgggtcgacg ctaccaccat ggactcttgg accttctgct gcgtgagcct gtgcatcctg    3300
gtggccaagc acacagacgc cggcgtgatc cagtcccta ggcacgaggt gaccgagatg    3360
ggccaggagg tgacactgcg ctgtaagcca atctctggcc acaacagcct gttttggtat    3420
agggagacca tgatgcgcgg cctggagctg ctgatctact tcaataacaa tgtgcccatc    3480
gacgattccg gcatgcctga ggatcggttt tctgccaaga tgcccaatgc cagcttctcc    3540
acactgaaga tccagcctag cgagccaaga gactccgccg tgtatttttg cgcctctagc    3600 ccagcagca ccgatacaca gtacttcgga ccaggaacca ggctgacagt gctggaggac    3660
ctgaagaacg tgttccccc tgaggtggcc gtgtttgagc cctctgaggc cgagatcagc    3720
cacacccaga aggccaccct ggtgtgcctg gcaaccggct tctatcctga tcacgtggag    3780
ctgtcctggt gggtgaacgg caaggagtg cacagcggcg tgtccacaga cccacagccc    3840
ctgaaggagc agccagccct gaatgatagc cggtattgcc tgtcctctcg gctgagagtg    3900
tccgccacct tttggcagaa cccccggaat cacttcagat gtcaggtgca gttttacggc    3960
ctgtccgaga acgatgagtg gacccaggac cgggccaagc ctgtgacaca gatcgtgtct    4020
gccgaggcat ggggaagagc agactgtggc ttcacctctg agagctacca gcagggcgtg    4080
ctgagcgcca ccatcctgta tgagatcctg ctgggcaagg ccacactgta cgccgtcctg    4140
gtctccgctc tggtgctgat ggcaatggtc aaaagaaaag atagtcgggg acgggccaag    4200
agatctggca gcggcgaggg cagaggcagc ctgctgacct cgggcgacgt ggaggagaac    4260
cccggcccca tggagaagaa tccctggct gccccctgc tgatcctgtg gtttcacctg    4320
gactgcgtgt cctctatcct gaatgtggaa cagagcccac agagcctgca cgtgcaggag    4380
ggcgactcca ccaacttcac atgctctttt cctagctcca acttctacgc cctgcactgg    4440
tacagaaagg agaccgcaaa gtccccagag gccctgttcg tgatgacact gaacggcgat    4500
gagaagaaga agggccgcat cagcgccacc ctgaatacaa aggagggcta ctcctatctg    4560
tacatcaagg gctcccagcc tgaggactct gccacctatc tgtgcgccct gtacaacaat    4620
aacgatatgc ggtttggcgc cggcaccaga ctgacagtga agccaaacat ccagaatcca    4680
gaccccgccg tgtatcagct gcgggacagc aagtctagcg ataagagcgt gtgcctgttc    4740
accgactttg attctcagac aaacgtgagc cagtccaagg acagcgacgt gtacatcacc    4800
gacaagacag tgctggatat gagaagcatg gacttcaagt ctaacagcgc cgtggcctgg    4860
tccaataagt ctgatttcgc ctgcgccaat gcctttaata actccatcat ccccgaggat    4920
accttctttc cttctccaga gtcctcttgt gacgtgaagc tggtggagaa gtctttcgag    4980
```

| accgatacaa acctgaattt tcagaacctg agcgtgatcg gcttcaggat cctgctgctg | 5040 |

| aaggtggccg gctttaatct gctgatgacc ctgaggctgt ggagctcctg a | 5091 |

<210> SEQ ID NO 260
<211> LENGTH: 5091
<212> TYPE: DNA
<213> ORGANISM: Artificial Sequence
<220> FEATURE:
<223> OTHER INFORMATION: PGK.TCR.EF1a.CD8

<400> SEQUENCE: 260

| tcaggagctc cacagcctca gggtcatcag cagattaaag ccggccacct tcagcagcag | 60 |

| gatcctgaag ccgatcacgc tcaggttctg aaaattcagg tttgtatcgg tctcgaaaga | 120 |

| cttctccacc agcttcacgt cacaagagga ctctggagaa ggaaagaagg tatcctcggg | 180 |

| gatgatggag ttattaaagg cattggcgca ggcgaaatca gacttattgg accaggccac | 240 |

| ggcgctgtta gacttgaagt ccatgcttct catatccagc actgtcttgt cggtgatgta | 300 |

| cacgtcgctg tccttggact ggctcacgtt tgtctgagaa tcaaagtcgg tgaacaggca | 360 |

| cacgctctta tcgctagact tgctgtcccg cagctgatac acggcggggt ctggattctg | 420 |

| gatgtttggc ttcactgtca gtctggtgcc ggcgccaaac cgcatatcgt tattgttgta | 480 |

| cagggcgcac agataggtgg cagagtcctc aggctgggag cccttgatgt acagatagga | 540 |

| gtagccctcc tttgtattca gggtggcgct gatgcgccc ttcttcttct catcgccgtt | 600 |

| cagtgtcatc acgaacaggg cctctgggga ctttgcggtc tcctttctgt accagtgcag | 660 |

| ggcgtagaag ttggagctag gaaaagagca tgtgaagttg gtggagtcgc cctcctgcac | 720 |

| gtgcaggctc tgtgggctct gttccacatt caggatagag acacgcagt ccaggtgaaa | 780 |

| ccacaggatc agcaggggg cagccagggg attcttctcc atggggccgg ggttctcctc | 840 |

| cacgtcgccg caggtcagca ggctgcctct gccctcgccg ctgccagatc tcttggcccg | 900 |

| tccccgacta tctttctttt tgaccattgc catcagcacc agagcggaga ccaggacggc | 960 |

| gtacagtgtg gccttgccca gcaggatctc atacaggatg gtggcgctca gcacgccctg | 1020 |

| ctggtagctc tcagaggtga agccacagtc tgctcttccc catgcctcgg cagacacgat | 1080 |

| ctgtgtcaca ggcttggccc ggtcctgggt ccactcatcg ttctcggaca ggccgtaaaa | 1140 |

| ctgcacctga catctgaagt gattccgggg gttctgccaa aggtggcgg acactctcag | 1200 |

| ccgagaggac aggcaatacc ggctatcatt cagggctggc tgctccttca ggggctgtgg | 1260 |

| gtctgtggac acgccgctgt gcacctcctt gccgttcacc caccaggaca gctccacgtg | 1320 |

| atcaggatag aagccggttg ccaggcacac cagggtggcc ttctgggtgt ggctgatctc | 1380 |

| ggcctcagag ggctcaaaca cggccacctc agggggggaac acgttcttca ggtcctccag | 1440 |

| cactgtcagc ctggttcctg gtccgaagta ctgtgtatcg gtgctgcctg gctagaggc | 1500 |

| gcaaaaatac acggcggagt ctcttggctc gctaggctgg atcttcagtg tggagaagct | 1560 |

| ggcattgggc atcttggcag aaaaccgatc ctcaggcatg ccggaatcgt cgatgggcac | 1620 |

| attgttattg aagtagatca gcagctccag gccgcgcatc atggtctccc tataccaaaa | 1680 |

| caggctgttg tggccagaga ttggcttaca gcgcagtgtc acctcctggc ccatctcggt | 1740 |

| cacctcgtgc ctaggggact ggatcacgcc ggcgtctgtg tgcttggcca ccaggatgca | 1800 |

| caggctcacg cagcagaagg tccaagagtc catggtggta gcgtcgaccc ggggcggccg | 1860 |

| ctcgaaaggc ccggagatga ggaagaggag aacagcgcgg cagacgtgcg cttttgaagc | 1920 |

| gtgcagaatg ccgggcctcc ggaggacctt cgggcgcccg ccccgcccct gagcccgccc | 1980 |

```
ctgagcccgc ccccggaccc acccttccc agcctctgag cccagaaagc gaaggagcaa    2040
agctgctatt ggccgctgcc ccaaaggcct acccgcttcc agtgctcagc ggtgctgtcc    2100
atctgcacga gactagtgag acgtgctact tccatttgtc acgtcctgca cgacgcgagc    2160
tgcggggcgg gggggaactt cctgactagg ggaggagtag aaggtggcgc gaaggggcca    2220
ccaaagaacg gagccggttg gcgcctaccg gtggatgtgg aatgtgtgcg aggccagagg    2280
ccacttgtgt agccgccaagt gcccagcggg gctgctaaag cgcatgctcc agactgcctt    2340
gggaaaagcg cctcccctac ccgctccggt gcccgtcagt gggcagagcg cacatcgccc    2400
acagtccccg agaagttggg gggaggggtc ggcaattgaa ccgtgcccta gagaaggtgg    2460
cgcggggtaa actgggaaag tgatgtcgtg tactggctcc gcctttttcc cgagggtggg    2520
ggagaaccgt atataagtgc agtagtcgcc gtgaacgttc tttttcgcaa cgggtttgcc    2580
gccagaacac aggtaagtgc cgtgtgtggt tcccgcgggc ctggcctctt tacgggttat    2640
ggcccttgcg tgccttgaat tacttccacg ccctggctg cagtacgtga ttcttgatcc    2700
cgagcttcgg gttggaagtg ggtgggagag ttcgaggcct tgcgcttaag gagccccttc    2760
gcctcgtgct tgagttgagg cctggcctgg gcgctgggc cgccgcgtgc gaatctggtg    2820
gcaccttcgc gcctgtctcg ctgctttcga taagtctcta gccatttaaa attttttgatg    2880 acctgctgcg acgctttttt tctggcaaga tagtcttgta aatgcgggcc aagatctgca    2940
cactggtatt tcggtttttg gggccgcggg cggcgacggg gcccgtgcgt cccagcgcac    3000
atgttcggcg aggcggggcc tgcgagcgcg gccaccgaga atcggacggg ggtagtctca    3060
agctggccgg cctgctctgg tgcctggcct cgcgccgccg tgtatcgccc cgccctgggc    3120
ggcaaggctg gccggtcgg caccagttgc gtgagcggaa agatggccgc ttccggccc    3180 tgctgcaggg agctcaaaat ggaggacgcg gcgctcggga gagcgggcgg gtgagtcacc    3240
cacacaaagg aaaagggcct ttccgtcctc agccgtcgct tcatgtgact ccacggagta    3300
ccgggcgccg tccaggcacc tcgattagtt ctcgagcttt tggagtacgt cgtctttagg    3360
ttggggggag gggttttatg cgatggagtt tccccacact gagtgggtgg agactgaagt    3420
taggccagct tggcacttga tgtaattctc cttggaattt gcccttttttg agtttggatc    3480 ttggttcatt ctcaagcctc agacagtggt tcaaagttttt tttcttccat ttcaggtgtc    3540
gtgaagcggc cgccccgggt cgacgctacc accatgcgcc cgagactgtg gcttctgctc    3600
gccgcgcaac tgactgtcct gcacggaaac agcgtgctgc agcagacacc ggcctacatc    3660
aaagtgcaga ccaacaagat ggtcatgctg tcctgcgagg ccaagattc cctctccaac    3720 atgcggatct attggttgcg gcagagacag gcgccttcct cggactccca ccatgagttc    3780
ttggccctgt gggactccgc caaggaact attcacggcg aagaagtgga acaggagaag    3840
atcgccgtgt ttcgcgatgc ctcccgcttt atactgaatc tgacctccgt gaagcccgaa    3900
gatagcggga tctacttttg catgattgtg ggctcacccg aactgacctt cgggaagggc    3960
actcagctga gcgtggtgga cttcctcccc actaccgccc aacccactaa gaagtcaacc    4020
ctgaagaagc gggtttgcag actcccacgg ccggaaacgc agaagggtcc gctgtgttcc    4080
ccgatcaccc tggggctcct tgtggctgga gtgctggtc ttctggtgtc ccttggcgtc    4140
gccattcacc tctgctgccg gagaaggagg ccagactga ggttcatgaa gcagcctcag    4200
ggagagggga tcagtggcac tttcgtgcca cagtgcctcc atggctacta ttccaacacc    4260
accacctcgc aaaagctgct gaacccctgg atcctgaaaa cccgggccaa gagatctggc    4320
```

| | |
|---|---|
| agcggcgcca ccaatttcag cctgctgaaa caggccggcg acgtggaaga gaaccctggc | 4380 |
| cccatggcgc ttcccgtgac cgcactcctg ttgccccttg ccctgctgtt gcacgccgca | 4440 |
| cgaccttccc aattccgggt gtcccctctg gatcgcacct ggaacctcgg ggaaacggtg | 4500 |
| gagctcaagt gtcaagtcct cctgtcgaac ccgaccagcg gatgcagctg gctgttccag | 4560 |
| ccgagaggag ctgccgcctc acccaccttc ctcctgtact tgagccagaa caagccgaag | 4620 |
| gccgctgagg gtctggacac ccagcgcttc tcgggcaaac ggctgggaga cacttttgtg | 4680 |
| ctgactctct ccgacttccg gcgggagaac gagggctact acttctgctc tgcgctctcc | 4740 |
| aattcaatca tgtacttctc acacttcgtg ccggtgttcc tgcctgccaa gcccaccact | 4800 |
| actccggcac ccagacctcc aactcccgct cccaccatcg cgtcccaacc cctttcgctg | 4860 |
| cgccctgaag cgtgtcggcc tgctgctgga ggagccgtgc atacccgcgg tctggacttc | 4920 |
| gcgtgcgaca tctacatttg ggcccctttg gctggcacct gtggagtgct gctcctgtcc | 4980 |
| cttgtgatca ccctgtactg caaccaccgg aataggcgga gagtctgcaa gtgtccgcgg | 5040 |
| cctgtcgtga agtcaggaga taagccgagc ctgtccgcac gctacgtgtg a | 5091 |

<210> SEQ ID NO 261
<211> LENGTH: 2749
<212> TYPE: DNA
<213> ORGANISM: Artificial Sequence
<220> FEATURE:
<223> OTHER INFORMATION: NFAT.IL12

<400> SEQUENCE: 261

| | |
|---|---|
| gtcgaccgtg gaggaaaaac tgtttcatac agaaggcgtg gaggaaaaac tgtttcatac | 60 |
| agaaggcgtg gaggaaaaac tgtttcatac agaaggcgtg gaggaaaaac tgtttcatac | 120 |
| agaaggcgtg gaggaaaaac tgtttcatac agaaggcgtg gaggaaaaac tgtttcatac | 180 |
| agaaggcgca ttttgacacc cccataatat ttttccagaa ttaacagtat aaattgcatc | 240 |
| tcttgttcaa gagttcccta tcactctctt taatcactac tcacagtaac ctcaactcct | 300 |
| gcccaagctt ggcattccgg tactgttggt aaagccacca tgtgtcacca gcagttggtc | 360 |
| atctcttggt tttcccctggt ttttctggca tctcccctcg tggccatatg ggaactgaag | 420 |
| aaagatgttt atgtcgtaga attggattgg tatccggatg cccctggaga aatggtggtc | 480 |
| ctcacctgtg acacccctga agaagatggt atcacctgga ccttggacca gagcagtgag | 540 |
| gtcttaggct ctggcaaaac cctgaccatc caagtcaaag agtttggaga tgctggccag | 600 |
| tacacctgtc acaaaggagg cgaggttcta agcattcgc tcctgctgct tcacaaaaag | 660 |
| gaagatggaa tttggtccac tgatattta aaggaccaga agaacccaa aataagacc | 720 |
| tttctaagat gcgaggccaa gaattattct ggacgtttca cctgctggtg gctgacgaca | 780 |
| atcagtactg atttgacatt cagtgtcaaa agcagcagag gctcttctga ccccaagggg | 840 |
| gtgacgtgcg gagctgctac actctctgca gagagagtca gagggacaa caaggagtat | 900 |
| gagtactcag tggagtgcca ggaggacagt gcctgcccag ctgctgagga gagtctgccc | 960 |
| attgaggtca tggtggatgc cgttcacaag ctcaagtatg aaaactacac cagcagcttc | 1020 |
| ttcatcaggg acatcatcaa acctgacccca cccaagaact gcagctgaa gccattaaag | 1080 |
| aattctcggc aggtggaggt cagctgggag taccctgaca cctggagtac tccacattcc | 1140 |
| tacttctccc tgacattctg cgttcaggtc agggcaaga gcaagagaga aaagaaagat | 1200 |
| agagtcttca cggacaagac ctcagccacg gtcatctgcc gcaaacaagc cagcattagc | 1260 |
| gtgcgggccc aggaccgcta ctatagctca tcttggagcg agtgggcatc tgtgccctgc | 1320 |

```
agtggcggcg gcggcagcgg cggcggcggc agcggcggcg gcggcagcat gtggcccct    1380 gggtcagcct cccagccacc gccctcacct gccgcggcca caggtctgca tccagcggct    1440
cgccctgtgt ccctgcagtg ccggctcagc atgtgtccag cgcgcagcct cctccttgtg    1500
gctaccctgg tcctcctgga ccacctcagt ttggccagaa acctccccgt ggccactcca    1560
gacccaggaa tgttcccatg ccttcaccac tcccaaaacc tgctgagggc cgtcagcaac    1620
atgctccaga aggccagaca aactctagaa ttttacccct tgcacttctga agagattgat    1680 catgaagata tcacaaaaga taaaaccagc acagtggagg cctgtttacc attggaatta    1740
accaagaatg agagttgcct aaattccaga gagacctctt tcataactaa tgggagttgc    1800
ctggcctcca gaaagacctc tttttatgatg gccctgtgcc ttagtagtat ttatgaagac    1860
ttgaagatgt accaggtgga gttcaagacc atgaatgcaa agcttctgat ggatcctaag    1920
aggcagatct ttctagatca aaacatgctg gcagttattg atgagctgat gcaggccctg    1980
aatttcaaca gtgagactgt gccacaaaaa tcctcccttg aagaaccgga ttttataaaa    2040
actaaaatca agctctgcat acttcttcat gctttcagaa ttcgggcagt gactattgat    2100
agagtgatga gctatctgaa tgcttcctag tgaaccggtc cgcagtctga cgtacgcgta    2160
atcaacctct ggattacaaa atttgtgaaa gattgactgg tattcttaac tatgttgctc    2220
cttttacgct atgtggatac gctgctttaa tgcctttgta tcatgctatt gcttcccgta    2280
tggctttcat tttctcctcc ttgtataaat cctggttgct gtctctttat gaggagttgt    2340
ggcccgttgt caggcaacgt ggcgtggtgt gcactgtgtt tgctgacgca accccactg     2400 gttgggcat tgccaccacc tgtcagctcc tttccgggac tttcgctttc ccctcccta    2460 ttgccacggc ggaactcatc gccgcctgcc ttgcccgctg ctggacaggg gctcggctgt    2520
tgggcactga caattccgtg tgtgttgtcgg ggaagctgac gtccttttcca tggctgctcg    2580 cctgtgttgc cacctggatt ctgcgcggga cgtccttctg ctacgtccct tcggccctca    2640
atccagcgga ccttccttcc cgcggcctgc tgccggctct gcggcctctt ccgcgtcttc    2700
gccttcgccc tcagacgagt cggatctccc tttgggccgc ctccccgcc                2749
```

<210> SEQ ID NO 262
<211> LENGTH: 5048
<212> TYPE: DNA
<213> ORGANISM: Artificial Sequence
<220> FEATURE:
<223> OTHER INFORMATION: CD69pro.IL12

<400> SEQUENCE: 262

```
tttatgatag catagtagcc cagaccccgg cctaccttaa aattctatat ggtacatttg      60
ctattttcac accattatct ttgagagtag tctccaaaaa tgttgtatat ggataagtct     120
ggaattaatt taggtaaagt actcagacat ggttaagcgt tatatctcat ctttaatata     180
gctcttcttt tattctctta tgtattttac tttcagaaac agtcaggttt tcagagtcc      240 aagcttgtgt gtacacaagc actatctttt accttcactg tctcaagtca aaagaagaa      300 aatgccagct cacactttcc aagctcattt tttgtgtttc agatgttcca ttgaagagga    360
aagttagaaa gttcaaagac ttgaagagga cagaaggttg gaaagtgttt aaaactggaa    420 atccccgtt tactcatggt taccttcatt gacccttac ggtaaacaat tcaaaaacac    480
aaaggcacct gcaggttaaa aataaatttt accaatttgt gtaatttgca ttaatttgag     540
agaggatgat gtattctaaa ttgaagtttt gattcacaag aagattaaaa gccattcaga    600
```

| | | | | | |
|---|---|---|---|---|---|
| aacctaattc | acccactgaa | aggaaaaaaa | aaaaaagaga | gatgagcagt | ttgtctccgg | 660 |
| aaattgtctt | aggtcggaag | tctgtggtcc | ctgttcacat | gtacccaaaa | gcatcctgct | 720 |
| gctgcagctg | tctgataagc | acagagtacc | ccaccttctc | tgcacacttt | gcatctagct | 780 |
| catattacct | catctttact | tcctttctga | cgtctcaccc | tggattctac | atataaggtc | 840 |
| acacaggaag | gaaagctgca | ttgagttttg | gtgtcctgaa | agacttttgc | caaccttgtc | 900 |
| cccgcactaa | tttctctaag | cctcggctat | actattttct | cagctacacg | atgaaatgtg | 960 |
| aatgataatt | tctgccctaa | aaatatcact | taatttttta | acatatcatt | tatgaaagaa | 1020 |
| gacacataaa | atgtctccct | gaagagtgag | tcggttaaag | ggagagcgag | acatgcaggg | 1080 |
| agatggaaaa | agaatctttt | agagaaaaag | taaaagccct | gtagtggtag | gatgcttggc | 1140 |
| attttttaagg | aggaggtttc | tgtcagagag | gatactgaat | aataggaaaa | atgataagag | 1200 |
| aggtaaccag | gggccatatt | atgtataaag | cattctcaac | tattaggtct | ttggatttta | 1260 |
| cggtacattt | gataggaagc | ctttcaaagt | gcagtggggg | gaggagttaa | acacttcacc | 1320 |
| aaaatcatat | gaattaatta | taaaacaatg | gttctagctg | ctatgtggaa | aagggactaa | 1380 |
| gaaattgact | gaaaaatagg | atggaagcaa | agggagcttt | tagggccaac | atgtacctct | 1440 |
| ttgtgtctta | ggtagacaaa | tgcatctaat | ggtccaacta | acttctctag | atgataactt | 1500 |
| ccaacccacc | tatgcataaa | atttaacgtc | tttattctaa | ataagtgata | ttaataataa | 1560 |
| aatttggggc | accaagatta | ttaatcagag | tggtattttg | atttccctcc | ttaaatcacc | 1620 |
| atacatagct | ttctgcattc | atcttgcgtt | gactgtcatt | acttgtctga | gtgagactga | 1680 |
| taccacagcg | atgttttaaa | taataatcat | acctcaaaag | actgaagtct | cagaggtatc | 1740 |
| tgaagagaat | aacctagagc | acaggggag | aattgaagga | gctgttactg | aggtgacata | 1800 |
| aaagcagtct | aaatgacagt | aaaatgtgac | aagaaaatta | gcaggaaaca | aatgaaacag | 1860 |
| ataatttaag | ataaacaatt | ttagagcata | gcaaggaagt | tccagaccac | aagctttctg | 1920 |
| tttcctgcat | tcttacttct | tactacgtga | tacatctagt | caccagggaa | gaagcgaatg | 1980 |
| acacacttcc | aaaaaccaat | tcgtagcttt | ctaaataaaa | cccttcaag | ctggagagag | 2040 |
| atccatgagc | atagagatct | taaaattcat | gttcagcaat | aaatcctggg | gccccagaca | 2100 |
| gtgtcaggtg | cataggggt | gttcagtaaa | tatcagttaa | atgtatgcat | aaatcgataa | 2160 |
| acgggattcc | tggaaaatac | tacactctcc | ttctccaaat | tatcttcatc | tcaaagacag | 2220 |
| gaacctctaa | cttttaattc | tttacttaga | ttatgctgtc | tcctaaactg | tttatgtttt | 2280 |
| ctagaaattt | aaggcaggat | gtctcagagt | ctgggaaaat | cccactttcc | tcctgctaca | 2340 |
| ccttacagtt | gtgagaaagc | acatttcaga | caacagggaa | aacccatact | tcaccacaac | 2400 |
| aacacactat | acattgtctg | gtccactgga | gcataaatta | agagaaaca | atgtagtcaa | 2460 |
| gcaagtaggc | ggcaagagga | aggggcgga | gacatcatca | gggagtataa | actctgagat | 2520 |
| gcctcagagc | ctcacagact | caacaagagc | tccagcaaag | actttcactg | tagcttgact | 2580 |
| tgacctgaga | ttaactaggg | aatcttgaca | gcggccgccc | cgggtcgacg | ctaccaccat | 2640 |
| gtgtcaccag | cagttggtca | tctcttggtt | ttccctggtt | tttctggcat | ctcccctcgt | 2700 |
| ggccatatgg | gaactgaaga | agatgtttta | tgtcgtagaa | ttggattggt | atccggatgc | 2760 |
| ccctggagaa | atggtggtcc | tcacctgtga | caccctgaa | gaagatggta | tcacctggac | 2820 |
| cttggaccag | agcagtgagg | tcttaggctc | tggcaaaacc | ctgaccatcc | aagtcaaaga | 2880 |
| gtttggagat | gctggccagt | acacctgtca | caaaggaggc | gaggtctaa | gccattcgct | 2940 |
| cctgctgctt | cacaaaaagg | aagatggaat | ttggtccact | gatattttaa | aggaccagaa | 3000 |

```
agaacccaaa aataagacct ttctaagatg cgaggccaag aattattctg gacgtttcac    3060
ctgctggtgg ctgacgacaa tcagtactga tttgacattc agtgtcaaaa gcagcagagg    3120
ctcttctgac ccccaagggg tgacgtgcgg agctgctaca ctctctgcag agagagtcag    3180
aggggacaac aaggagtatg agtactcagt ggagtgccag gaggacagtg cctgcccagc    3240
tgctgaggag agtctgccca ttgaggtcat ggtggatgcc gttcacaagc tcaagtatga    3300
aaactacacc agcagcttct tcatcaggga catcatcaaa cctgacccac caagaaactt    3360
gcagctgaag ccattaaaga attctcggca ggtggaggtc agctgggagt accctgacac    3420
ctggagtact ccacattcct acttctccct gacattctgc gttcaggtcc agggcaagag    3480
caagagagaa aagaaagata gagtcttcac ggacaagacc tcagccacgg tcatctgccg    3540
caaacaagcc agcattagcg tgcgggccca ggaccgctac tatagctcat cttggagcga    3600
gtgggcatct gtgccctgca gtggcggcgg cggcagcggc ggcggcggca gcggcggcgg    3660
cggcagcatg tggccccctg gtcagcctc ccagccaccg ccctcacctg ccgcggccac    3720
aggtctgcat ccagcggctc gccctgtgtc cctgcagtgc cggctcagca tgtgtccagc    3780
gcgcagcctc ctccttgtgg ctaccctggt cctcctggac cacctcagtt tggccagaaa    3840
cctccccgtg gccactccag acccaggaat gttcccatgc cttcaccact cccaaaacct    3900
gctgagggcc gtcagcaaca tgctccagaa ggccagacaa actctagaat tttacccttg    3960
cacttctgaa gagattgatc atgaagatat cacaaaagat aaaaccagca cagtggaggc    4020
ctgtttacca ttggaattaa ccaagaatga gagttgccta aattccagag agacctcttt    4080
cataactaat gggagttgcc tggcctccag aaagacctct tttatgatgg ccctgtgcct    4140
tagtagtatt tatgaagact tgaagatgta ccaggtggag ttcaagacca tgaatgcaaa    4200
gcttctgatg gatcctaaga ggcagatctt tctagatcaa acatgctggc agttattga    4260 tgagctgatg caggccctga atttcaacag tgagactgtg ccacaaaaat cctcccttga    4320
agaaccggat ttttataaaa ctaaaatcaa gctctgcata cttcttcatg ctttcagaat    4380
tcgggcagtg actattgata gagtgatgag ctatctgaat gcttcctagt gaaccggtcc    4440
gcagtctgac gtacgcgtaa tcaacctctg gattacaaaa tttgtgaaag attgactggt    4500
attcttaact atgttgctcc ttttacgcta tgtggatacg ctgctttaat gcctttgtat    4560
catgctattg cttcccgtat ggctttcatt ttctcctcct tgtataaatc ctggttgctg    4620
tctctttatg aggagttgtg gcccgttgtc aggcaacgtg gcgtggtgtg cactgtgttt    4680
gctgacgcaa cccccactgg ttggggcatt gccaccacct gtcagctcct ttccgggact    4740
ttcgctttcc ccctccctat tgccacggcg gaactcatcg ccgcctgcct tgcccgctgc    4800
tggacagggg ctcggctgtt gggcactgac aattccgtgg tgttgtcggg gaagctgacg    4860
tcctttccat ggctgctcgc ctgtgttgcc acctggattc tgcgcgggac gtccttctgc    4920
tacgtccctt cggccctcaa tccagcggac cttccttccc gcggcctgct gccggctctg    4980
cggcctcttc cgcgtcttcg ccttcgccct cagacgagtc ggatctccct ttgggccgcc    5040
tccccgcc                                                            5048
```

<210> SEQ ID NO 263
<211> LENGTH: 1540
<212> TYPE: DNA
<213> ORGANISM: Artificial Sequence
<220> FEATURE:
<223> OTHER INFORMATION: NFAT.IL18.var1

<400> SEQUENCE: 263

```
gtcgaccgtg gaggaaaaac tgtttcatac agaaggcgtg gaggaaaaac tgtttcatac      60
agaaggcgtg gaggaaaaac tgtttcatac agaaggcgtg gaggaaaaac tgtttcatac     120
agaaggcgtg gaggaaaaac tgtttcatac agaaggcgtg gaggaaaaac tgtttcatac     180
agaaggcgca ttttgacacc cccataatat ttttccagaa ttaacagtat aaattgcatc     240
tcttgttcaa gagttcccta tcactctctt taatcactac tcacagtaac ctcaactcct     300
gcccaagctt ggcattccgg tactgttggt aaagccacca tggctgctga accagtagaa     360
gacaattgca tcaactttgt ggcaatgaaa tttattgaca atacgcttta ctttatagct     420
gaagatgatg aaaacctgga atcagattac tttggcaagc ttgaatctaa attatcagtc     480
ataagaaatt tgaatgacca agttctcttc attgaccaag gaaatcggcc tctatttgaa     540
gatatgactg attctgactg tagagataat gcaccccgga ccatatttat tataagtatg     600
tataaagata gccagcctag aggtatggct gtaactatct ctgtgaagtg tgagaaaatt     660
tcaactctct cctgtgagaa caaaattatt tcctttaagg aaatgaatcc tcctgataac     720
atcaaggata caaaaagtga catcatattc tttcagagaa gtgtcccagg acatgataat     780
aagatgcaat ttgaatcttc atcatacgaa ggatactttc tagcttgtga aaagagaga      840
gacctttta aactcatttt gaaaaaagag gatgaattgg gggatagatc tataatgttc       900
actgttcaaa acgaagacta gtgaaccggt ccgcagtctg acgtacgcgt aatcaacctc      960
tggattacaa aatttgtgaa agattgactg gtattcttaa ctatgttgct ccttttacgc    1020
tatgtggata cgctgcttta atgcctttgt atcatgctat tgcttcccgt atggctttca    1080
ttttctcctc cttgtataaa tcctggttgc tgtctcttta tgaggagttg tggcccgttg    1140
tcaggcaacg tggcgtggtg tgcactgtgt ttgctgacgc aaccccccact ggttggggca    1200
ttgccaccac ctgtcagctc ctttccggga ctttcgcttt cccctccct attgccacgg      1260
cggaactcat cgccgcctgc cttgcccgct gctggacagg ggctcggctg ttgggcactg    1320
acaattccgt ggtgttgtcg gggaagctga cgtccttcc atggctgctc gcctgtgttg      1380
ccacctggat tctgcgcggg acgtccttct gctacgtccc ttcggccctc aatccagcgg    1440
accttccttc ccgcggcctg ctgccggctc tgcggcctct tccgcgtctt cgccttcgcc    1500
ctcagacgag tcggatctcc ctttgggccg cctccccgcc                          1540
```

<210> SEQ ID NO 264
<211> LENGTH: 3839
<212> TYPE: DNA
<213> ORGANISM: Artificial Sequence
<220> FEATURE:
<223> OTHER INFORMATION: CD69pro.IL18.var1

<400> SEQUENCE: 264

```
tttatgatag catagtagcc cagaccccgg cctaccttaa aattctatat ggtacatttg      60
ctattttcac accattatct ttgagagtag tctccaaaaa tgttgtatat ggataagtct     120
ggaattaatt taggtaaagt actcagacat ggttaagcgt tatatctcat ctttaatata     180
gctcttcttt tattctctta tgtattttac tttcagaaac agtcaggttt tcagagtcc     240
aagcttgtgt gtacacaagc actatctttt accttcactg tctcaagtca aaagaagaa      300
aatgccagct cacactttcc aagctcattt tttgtgtttc agatgttcca ttgaagagga    360
aagttagaaa gttcaaagac ttgaagagga cagaaggttg aaagtgttt aaaactggaa      420
atccccgtt tactcatggt taccttcatt gacccttac ggtaaacaat tcaaaaacac       480
```

```
aaaggcacct gcaggttaaa aataaatttt accaatttgt gtaatttgca ttaatttgag      540
agaggatgat gtattctaaa ttgaagtttt gattcacaag aagattaaaa gccattcaga      600
aacctaattc acccactgaa aggaaaaaaa aaaaagaga  gatgagcagt ttgtctccgg      660
aaattgtctt aggtcggaag tctgtggtcc ctgttcacat gtacccaaaa gcatcctgct      720
gctgcagctg tctgataagc acagagtacc ccaccttctc tgcacacttt gcatctagct      780
catattacct catctttact tcctttctga cgtctcaccc tggattctac atataaggtc      840
acacaggaag gaaagctgca ttgagttttg gtgtcctgaa agactttgc  caaccttgtc      900 cccgcactaa tttctctaag cctcggctat actattttct cagctacacg atgaaatgtg      960
aatgataatt tctgccctaa aaatatcact taattttta  acatatcatt tatgaaagaa     1020
gacacataaa atgtctccct gaagagtgag tcggttaaag ggagagcgag acatgcaggg     1080
agatggaaaa agaatctttt agagaaaaag taaaagccct gtagtggtag gatgcttggc     1140 attttaagg  aggaggtttc tgtcagagag gatactgaat aataggaaaa atgataagag     1200
aggtaaccag gggccatatt atgtataaag cattctcaac tattaggtct ttggatttta     1260
cggtacattt gataggaagc cttcaaagt  gcagtggggg gaggagttaa acacttcacc     1320
aaaatcatat gaattaatta taaaacaatg gttctagctg ctatgtggaa aagggactaa     1380
gaaattgact gaaaaatagg atggaagcaa agggagcttt tagggccaac atgtacctct     1440
ttgtgtctta ggtagacaaa tgcatctaat ggtccaacta acttctctag atgataactt     1500
ccaacccacc tatgcataaa atttaacgtc tttattctaa ataagtgata ttaataataa     1560
aatttggggc accaagatta ttaatcagag tggtattttg atttccctcc ttaaatcacc     1620
atacatagct ttctgcattc atcttgcgtt gactgtcatt acttgtctga gtgagactga     1680
taccacagcg atgttttaaa taataatcat acctcaaaag actgaagtct cagaggtatc     1740
tgaagagaat aacctagagc acaggggag  aattgaagga gctgttactg aggtgacata     1800
aaagcagtct aaatgacagt aaaatgtgac aagaaaatta gcaggaaaca aatgaaacag     1860
ataatttaag ataaacaatt ttagagcata gcaaggaagt tccagaccac aagctttctg     1920
tttcctgcat tcttacttct tactacgtga tacatctagt caccagggaa gaagcgaatg     1980
acacacttcc aaaaaccaat tcgtagcttt ctaaataaaa ccctttcaag ctggagagag     2040
atccatgagc atagagatct taaaattcat gttcagcaat aaatcctggg gccccagaca     2100
gtgtcaggtg cataggggt  gttcagtaaa tatcagttaa atgtatgcat aaatcgataa     2160
acgggattcc tggaaaatac tacactctcc ttctccaaat tatcttcatc tcaaagacag     2220
gaacctctaa ctttaattc tttacttaga ttatgctgtc tcctaaactg tttatgtttt     2280
ctagaaattt aaggcaggat gtctcagagt ctgggaaaat cccactttcc tcctgctaca     2340
ccttacagtt gtgagaaagc acatttcaga caacagggaa acccatact  tcaccacaac     2400 aacacactat acattgtctg gtccactgga gcataaatta agagaaaaca atgtagtcaa     2460
gcaagtaggc ggcaagagga aggggcgga  gacatcatca gggagtataa actctgagat     2520
gcctcagagc ctcacagact caacaagagc tccagcaaag actttcactg tagcttgact     2580
tgacctgaga ttaactaggg aatcttgaca gcggccgccc cgggtcgacg ctaccaccat     2640
ggctgctgaa ccagtagaag acaattgcat caactttgtg gcaatgaaat ttattgacaa     2700
tacgctttac tttatagctg aagatgatga aaacctggaa tcagattact ttggcaagct     2760
tgaatctaaa ttatcagtca taagaaattt gaatgaccaa gttctcttca ttgaccaagg     2820
```

```
aaatcggcct ctatttgaag atatgactga ttctgactgt agagataatg caccccggac   2880
catatttatt ataagtatgt ataaagatag ccagcctaga ggtatggctg taactatctc   2940
tgtgaagtgt gagaaaattt caactctctc ctgtgagaac aaaattattt cctttaagga   3000
aatgaatcct cctgataaca tcaaggatac aaaaagtgac atcatattct ttcagagaag   3060
tgtcccagga catgataata agatgcaatt tgaatcttca tcatacgaag gatactttct   3120
agcttgtgaa aaagagagag acctttttaa actcattttg aaaaagagg atgaattggg    3180 ggatagatct ataatgttca ctgttcaaaa cgaagactag tgaaccggtc cgcagtctga   3240
cgtacgcgta atcaacctct ggattacaaa atttgtgaaa gattgactgg tattcttaac   3300
tatgttgctc cttttacgct atgtggatac gctgctttaa tgcctttgta tcatgctatt   3360
gcttcccgta tggctttcat tttctcctcc ttgtataaat cctggttgct gtctctttat   3420
gaggagttgt ggcccgttgt caggcaacgt ggcgtggtgt gcactgtgtt tgctgacgca   3480 accccccactg gttggggcat tgccaccacc tgtcagctcc tttccgggac tttcgctttc   3540
cccctcccta ttgccacggc ggaactcatc gccgcctgcc ttgcccgctg ctggacaggg   3600
gctcggctgt tgggcactga caattccgtg gtgttgtcgg ggaagctgac gtcctttcca   3660
tggctgctcg cctgtgttgc cacctggatt ctgcgcggga cgtccttctg ctacgtccct   3720
tcggccctca atccagcgga ccttccttcc cgcggcctgc tgccggctct gcggcctctt   3780
ccgcgtcttc gccttcgccc tcagacgagt cggatctccc tttgggccgc ctccccgcc    3839

<210> SEQ ID NO 265
<211> LENGTH: 607
<212> TYPE: DNA
<213> ORGANISM: Artificial Sequence
<220> FEATURE:
<223> OTHER INFORMATION: WPREmut1

<400> SEQUENCE: 265
cagtctgacg tacgcgtaat caacctctgg attacaaaat tgtgaaaga ttgactggta      60 ttcttaacta tgttgctcct tttacgctat gtggatacgc tgctttaatg cctttgtatc    120
atgctattgc ttcccgtatg gctttcattt tctcctcctt gtataaatcc tggttgctgt    180
ctctttatga ggagttgtgg cccgttgtca ggcaacgtgg cgtggtgtgc actgtgtttg    240
ctgacgcaac cccccactgg tggggcattg ccaccacctg tcagctcctt ccgggactt    300 tcgctttccc cctccctatt gccacggcgg aactcatcgc cgcctgcctt gcccgctgct    360
ggacaggggc tcggctgttg gcactgaca attccgtggt ggttgtcgggg aaatcatcgt    420 cctttccttg gctgctcgcc tgtgttgcca cctggattct gcgcgggacg tccttctgct    480 acgtccttc ggccctcaat ccagcggacc ttccttcccg cggcctgctg ccggctctgc    540
ggcctcttcc gcgtcttcgc cttcgccctc agacgagtcg gatctccctt tgggccgcct   600
ccccgcc                                                              607

<210> SEQ ID NO 266
<211> LENGTH: 581
<212> TYPE: DNA
<213> ORGANISM: Artificial Sequence
<220> FEATURE:
<223> OTHER INFORMATION: WPREmut2

<400> SEQUENCE: 266
gagcatctta ccgccattta tacccatatt tgttctgttt tcttgatttt gggtatacat     60
ttaaatgtta ataaaacaaa atggtggggc aatcatttac attttttggg atatgtaatt    120
```

```
actagttcag gtgtattgcc acaagacaaa cttgttaaga aactttcccg ttatttacgc    180
tctgttcctg ttaatcaacc tctggattac aaaatttgtg aaagattgac tgatattctt    240
aactttgttg ctccttttac gctgtgtgga tttgctgctt tattgcctct gtatcttgct    300
attgcttccc gtacggcttt cgttttctcc tccttgtata aatcctggtt gctgtctctt    360
tttgaggagt tgtggcccgt tgtccgtcaa cgtggcgtgg tgtgctctgt gtttgctgac    420 gcaacccca ctggctgggg cattgccacc acctgtcaac tcctttctgg gactttcgct     480
ttccccctcc cgatcgccac ggcagaactc atcgccgcct gccttgcccg ctgctggaca    540
ggggctaggt tgctgggcac tgataattcc gtggtgttgt c                        581
```